US010717704B2

(12) United States Patent
Martinez et al.

(10) Patent No.: US 10,717,704 B2
(45) Date of Patent: Jul. 21, 2020

(54) INHIBITORS OF CREATINE TRANSPORT AND USES THEREOF

(71) Applicant: Rgenix, Inc., New York, NY (US)

(72) Inventors: Eduardo J. Martinez, Bryn Mawr, PA (US); Sohail F. Tavazoie, New York, NY (US)

(73) Assignee: Rgenix, Inc., New York, NY (US)

( * ) Notice: Subject to any disclaimer, the term of this patent is extended or adjusted under 35 U.S.C. 154(b) by 0 days.

(21) Appl. No.: 16/389,008

(22) Filed: Apr. 19, 2019

(65) Prior Publication Data

US 2019/0315680 A1    Oct. 17, 2019

Related U.S. Application Data

(62) Division of application No. 15/307,178, filed as application No. PCT/US2015/028633 on Apr. 30, 2015, now Pat. No. 10,308,597.

(Continued)

(51) Int. Cl.
| | |
|---|---|
| *A61K 31/7105* | (2006.01) |
| *A61K 31/704* | (2006.01) |
| *A61K 31/337* | (2006.01) |
| *A61K 31/155* | (2006.01) |
| *A61K 31/53* | (2006.01) |
| *A61K 31/7068* | (2006.01) |
| *A61K 45/06* | (2006.01) |
| *A61K 31/397* | (2006.01) |
| *A61K 31/40* | (2006.01) |
| *A61K 31/4168* | (2006.01) |
| *A61K 31/4402* | (2006.01) |
| *A61K 31/4427* | (2006.01) |
| *A61K 31/505* | (2006.01) |
| *C07C 279/14* | (2006.01) |
| *C07C 279/16* | (2006.01) |
| *C07C 313/34* | (2006.01) |
| *C07F 9/48* | (2006.01) |
| *C07F 9/09* | (2006.01) |
| *C07F 9/24* | (2006.01) |
| *C07F 9/38* | (2006.01) |
| *C07F 9/40* | (2006.01) |
| *A61K 31/00* | (2006.01) |
| *C07D 213/76* | (2006.01) |
| *C07C 257/14* | (2006.01) |
| *C07C 259/14* | (2006.01) |

(Continued)

(52) U.S. Cl.
CPC ........... *C07C 279/14* (2013.01); *A61K 31/00* (2013.01); *A61K 31/155* (2013.01); *A61K 31/337* (2013.01); *A61K 31/397* (2013.01); *A61K 31/40* (2013.01); *A61K 31/4168* (2013.01); *A61K 31/4402* (2013.01); *A61K 31/4427* (2013.01); *A61K 31/505* (2013.01); *A61K 31/53* (2013.01); *A61K 31/704* (2013.01); *A61K 31/7068* (2013.01); *A61K 31/7105* (2013.01); *A61K 45/06* (2013.01); *C07C 257/14* (2013.01); *C07C 259/14* (2013.01); *C07C 275/70* (2013.01); *C07C 279/16* (2013.01); *C07C 279/26* (2013.01); *C07C 279/36* (2013.01); *C07C 281/16* (2013.01); *C07C 281/18* (2013.01); *C07C 309/15* (2013.01); *C07C 313/34* (2013.01); *C07D 205/04* (2013.01); *C07D 205/08* (2013.01); *C07D 207/16* (2013.01); *C07D 207/22* (2013.01); *C07D 213/74* (2013.01); *C07D 213/76* (2013.01); *C07D 231/12* (2013.01); *C07D 233/26* (2013.01); *C07D 233/46* (2013.01); *C07D 233/52* (2013.01); *C07D 233/64* (2013.01); *C07D 233/88* (2013.01); *C07D 239/06* (2013.01); *C07D 239/14* (2013.01); *C07D 249/08* (2013.01); *C07D 249/14* (2013.01); *C07D 253/06* (2013.01); *C07D 257/08* (2013.01); *C07D 295/32* (2013.01); *C07D 401/04* (2013.01); *C07D 405/04* (2013.01); *C07D 487/04* (2013.01); *C07F 9/097* (2013.01); *C07F 9/2458* (2013.01); *C07F 9/3808* (2013.01); *C07F 9/4006* (2013.01); *C07F 9/48* (2013.01); *C07F 9/568* (2013.01); *C07F 9/572* (2013.01); *C07F 9/6506* (2013.01); *C07H 19/06* (2013.01); *C07B 2200/05* (2013.01); *C07C 2601/02* (2017.05); *C07C 2601/04* (2017.05)

(58) Field of Classification Search
CPC .................................................... C07C 279/14
USPC .......................................................... 514/49
See application file for complete search history.

(56) References Cited

U.S. PATENT DOCUMENTS

| | | |
|---|---|---|
| 5,321,030 A | 6/1994 | Kaddurah-Daouk et al. |
| 5,324,731 A | 6/1994 | Kaddurah-Daouk et al. |

(Continued)

FOREIGN PATENT DOCUMENTS

| | | | |
|---|---|---|---|
| CN | 14341450 A | * | 2/2015 |
| WO | WO-90/009192 A1 | | 8/1990 |

(Continued)

OTHER PUBLICATIONS

Chinese Patent CN104341450A to Fu et al. (2015) (English translation of the Specification).*

(Continued)

*Primary Examiner* — Yong L Chu
(74) *Attorney, Agent, or Firm* — Clark & Elbing LLP

(57) ABSTRACT

This invention relates to compounds that inhibit creatine transport and/or creatine kinase, pharmaceutical compositions including such compounds, and methods of utilizing such compounds and compositions for the treatment of cancer.

14 Claims, 7 Drawing Sheets

Specification includes a Sequence Listing.

Related U.S. Application Data

(60) Provisional application No. 61/986,723, filed on Apr. 30, 2014.

(51) Int. Cl.

| | |
|---|---|
| C07C 279/26 | (2006.01) |
| C07C 279/36 | (2006.01) |
| C07C 281/16 | (2006.01) |
| C07C 281/18 | (2006.01) |
| C07D 231/12 | (2006.01) |
| C07C 309/15 | (2006.01) |
| C07D 233/26 | (2006.01) |
| C07D 233/46 | (2006.01) |
| C07D 233/52 | (2006.01) |
| C07D 233/64 | (2006.01) |
| C07D 233/88 | (2006.01) |
| C07D 401/04 | (2006.01) |
| C07D 239/06 | (2006.01) |
| C07D 405/04 | (2006.01) |
| C07D 239/14 | (2006.01) |
| C07D 249/08 | (2006.01) |
| C07D 249/14 | (2006.01) |
| C07D 253/06 | (2006.01) |
| C07D 257/08 | (2006.01) |
| C07D 487/04 | (2006.01) |
| C07D 205/04 | (2006.01) |
| C07D 207/16 | (2006.01) |
| C07D 207/22 | (2006.01) |
| C07D 295/32 | (2006.01) |
| C07F 9/568 | (2006.01) |
| C07F 9/572 | (2006.01) |
| C07F 9/6506 | (2006.01) |
| C07C 275/70 | (2006.01) |
| C07D 205/08 | (2006.01) |
| C07D 213/74 | (2006.01) |
| C07H 19/06 | (2006.01) |

(56) References Cited

U.S. PATENT DOCUMENTS

| | | |
|---|---|---|
| 5,576,316 A | 11/1996 | Cohn |
| 5,955,617 A | 9/1999 | Larsen et al. |
| 5,994,577 A | 11/1999 | Larsen et al. |
| 5,998,457 A | 12/1999 | Kaddurah-Daouk |
| 6,518,299 B1 | 2/2003 | Chand et al. |
| 9,040,497 B2 | 5/2015 | Tavazoie et al. |
| 2011/0111066 A1 | 5/2011 | Ferguson et al. |
| 2012/0258925 A1 | 10/2012 | Aggen et al. |

FOREIGN PATENT DOCUMENTS

| | | |
|---|---|---|
| WO | WO-92/008456 A2 | 5/1992 |
| WO | WO-94/016687 A1 | 8/1994 |
| WO | WO-97/013507 A1 | 4/1997 |
| WO | WO-2014/071067 A2 | 5/2014 |
| WO | WO-2016/176636 A1 | 11/2016 |
| WO | WO-2017/035331 A1 | 3/2017 |

OTHER PUBLICATIONS

Schafer et al. Drug Discovery Today, 2008, 13 (21/22), 913-916.*
Horig et al. Journal of Translational Medicine 2004, 2(44), p. 1-8.*
Cutsem et al., New England J of Medicine, (2009), v.360, p. 1408-1417.*
Compound (CAS RN 1348115-72-9), entering STN Chemical database and accessible to public on Dec. 4, 2011.
Dodd et al., "Selective Amino Acid Substitutions Convert the Creatine Transporter to a gamma-Aminobutyric Acid Transporter," J Biol Chem. 282(21):15528-33 (2007).
Dodd et al., "Substituted cysteine accessibility of the third transmembrane domain of the creatine transporter: defining a transport pathway," J Biol Chem. 280(38):32649-54 (2005).
Extended European Search Report for European Patent Application No. 15786453.9, dated Dec. 6, 2017 (11 pages).
Fitch et al., "Inhibition of Creatine and Phosphocreatine Accumulation in Skeletal Muscle and Heart," Metabolism. 29(7):686-90 (1980).
International Preliminary Report on Patentability for International Application Patent No. PCT/US2015/028633, dated Nov. 1, 2016 (5 pages).
International Search Report and Written Opinion for International Application No.: PCT/US15/28633, dated Aug. 4, 2015 (11 pages).
Juaristi et al., "Enantioselective synthesis of beta-amino acids. 4. 1,2 asymmetric induction in the alkylation of 1-Benzoyl-3,6(S)-dimethylperhydropyrimidin-4-one. Preparation of the like and unlike stereoisomers of 2-Methyl-and 2-Benzyl-3(S)-aminobutanoic acid," J Org Chem. 58(8):2282-5 (1993).
Kalinoski et al., "Specific L-arginine taste receptor sites in the catfish, Ictalurus punctatus: biochemical and neurophysiological characterization," Brain Res. 488(1-2):163-73 (1989).
Lal et al., "A practical synthesis of free and protected guanidino acids from amino acids," Tetrahedron Lett. 37(14):2483-6 (1996).
Larsen et al., "Synthesis and Biological Activity of Analogues of the Antidiabetic/Antiobesity Agent 3-guanidinopropionic Acid: Discovery of a Novel Aminoguanidinoacetic Acid Antidiabetic Agent," J Med Chem. 44(8):1217-30 (2001).
Marenich et al., "Quantitative antidiabetic activity prediction for the class of guanidino-and aminoguanidinopropionic acid analogs based on electron-conformational studies," J Chem lnf Model. 48(3):556-68 (2008).
Martin et al., "Specific targeting of tumor cells by the creatine analog cyclocreatine," Int J Oncol. 9(5):993-9 (1996).
McLaughlin et al., "Specificity of creatine kinase for guanidino substrates. Kinetic and Proton nuclear magnetic relaxation rate studies," J Biol Chem. 247(13):4382-8 (1972).
Meffert et al., "Elevated creatine kinase activity in primary hepatocellular carcinoma," BMC Gastroenterol. 5:9 (2005) (7 pages).
Rendina et al., "The design and synthesis of inhibitors of dethiobiotin synthetase as potential herbicides," Pestic Sci. 55(3):236-47 (1999).
Vaillancourt et al., "Synthesis and Biological Activity of Aminoguanidine and Diaminoguanidine Analogues of the Antidiabetic/Antiobesity Agent 3-Guanidinopropionic Acid," J Med Chem. 44(8):1231-48 (2001).

* cited by examiner

INHIBITORS OF CREATINE TRANSPORT AND USES THEREOF

REFERENCE TO A SEQUENCE LISTING

This application contains a Sequence Listing in computer readable form. The computer readable form is incorporated herein by reference.

BACKGROUND OF THE INVENTION

Creatine is synthesized in the liver and kidney and transported throughout the body to tissues with high energy demands through an active transport system. Creatine is used by the body during times of increased energy demands to rapidly resynthesize ATP from ADP through the anaerobic conversion of phosphorylated creatine (phosphocreatine) to creatine in a reversible reaction by the enzyme creatine kinase. In times of low energy demands, excess ATP can be utilized to convert creatine to phosphocreatine. Increased expression of creatine kinase promotes metastasis by enhancing the survival of disseminated cancer cells in the liver where they encounter hepatic hypoxia. Increased expression of creatine kinase results in production of excess phosphocreatine which may be used as an energetic store for generating ATP needed to endure hepatic hypoxia. Inhibition of the phosphocreatine system through inhibition of creatine uptake and/or creatine kinase in cancer cells is thus a therapeutic target for the treatment of cancer and/or metastasis.

SUMMARY OF THE INVENTION

This invention features compounds that inhibit creatine transport and/or creatine kinase, pharmaceutical compositions including the compounds of the invention, and methods of utilizing those compositions for inhibition of creatine transport and/or creatine kinase (e.g., for the treatment of cancer).

Accordingly, in a first aspect the invention features a compound having the structure of Formula I:

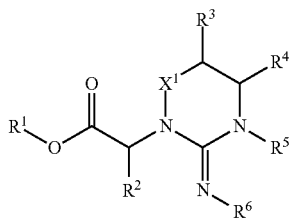

Formula I wherein $X^1$ is absent, NH, or $CH_2$;
$R^1$ is hydrogen, optionally substituted $C_1$-$C_6$ alkyl, or optionally substituted $C_6$-$C_{10}$ aryl $C_1$-$C_6$ alkyl;
$R^2$, $R^3$, and $R^4$ are independently hydrogen or optionally substituted $C_1$-$C_6$ alkyl; and
$R^5$ and $R^6$ are hydrogen or $NH_2$;
wherein if $R^5$ and $R^6$ are both hydrogen or $R^5$ is $NH_2$ and $R^6$ is hydrogen then $R^2$ is optionally substituted $C_1$-$C_6$ alkyl, or a pharmaceutically acceptable salt thereof.

In some embodiments, $R^1$ is hydrogen. In other embodiments, $R^3$ and $R^4$ are hydrogen. In certain embodiments, $R^2$ is hydrogen or optionally substituted $C_1$-$C_6$ alkyl (e.g., methyl, ethyl, isopropyl, propyl, isobutyl, or optionally substituted $C_1$-$C_6$ haloalkyl such as, trifluoromethyl.

In some embodiments, $R^5$ and $R^6$ are both hydrogen and $R^2$ is optionally substituted $C_1$-$C_6$ alkyl (e.g., methyl, ethyl, isopropyl, or isobutyl).

In other embodiments, $R^5$ and $R^6$ are both $NH_2$. In certain embodiments, $R^2$ is hydrogen. In some embodiments, $R^2$ is optionally substituted $C_1$-$C_6$ alkyl (e.g., methyl or isopropyl).

In other embodiments, $R^5$ is $NH_2$, $R^6$ is hydrogen, and $R^2$ is optionally substituted $C_1$-$C_6$ alkyl (e.g., methyl or isopropyl).

In certain embodiments, $R^5$ is hydrogen and $R^6$ is $NH_2$. In some embodiments, $R^2$ is hydrogen. In other embodiments, $R^2$ is optionally substituted $C_1$-$C_6$ alkyl (e.g., methyl or isopropyl).

In certain embodiments, $X^1$ is absent. In some embodiments, $X^1$ is $CH_2$. In other embodiments, $X^1$ is $NH_2$.

In certain embodiments, the compound is a compound of Table 1 (e.g., compound 225, 229, 230, 234, or 235).

TABLE 1

Selected Phosphocreatine System Inhibitors

| Compound Number | Structure | Compound Name |
|---|---|---|
| 225 | 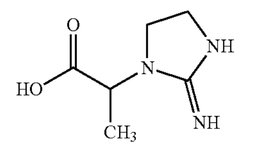 | 2-(2-iminoimidazolidin-1-yl)propanoic acid |
| 226 | 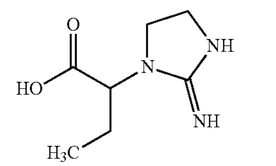 | 2-(2-iminoimidazolidin-1-yl)butanoic acid |
| 227 | 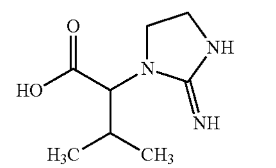 | 2-(2-iminoimidazolidin-1-yl)-3-methylbutanoic acid |
| 228 | 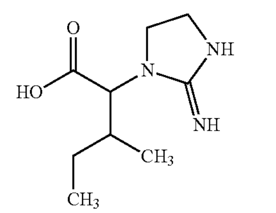 | 2-(2-iminoimidazolidin-1-yl)-3-methylpentanoic acid |
| 229 | 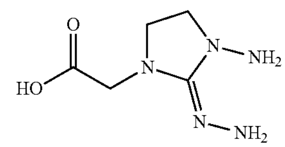 [SMILES: N/N=C1\N(N)CCN1CC(=O)O] | 2-[3-amino-2-hydrazinylidene-imidazolidin-1-yl]acetic acid |
| 230 | 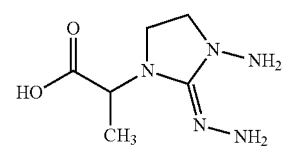 | 2-[3-amino-2-hydrazinylideneimidazolidin-1-yl]propanoic acid |

TABLE 1-continued

Selected Phosphocreatine System Inhibitors

| Compound Number | Structure | Compound Name |
|---|---|---|
| 231 | 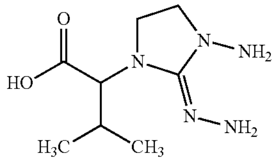 | 2-[3-amino-2-hydrazinylideneimidazolidin-1-yl]-3-methylbutanoic acid |
| 232 | 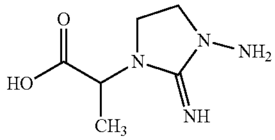 | 2-(3-amino-2-iminoimidazolidin-1-yl)propanoic acid |
| 233 | 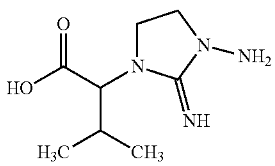 | 2-(3-amino-2-iminoimidazolidin-1-yl)-3-methylbutanoic acid |
| 234 | 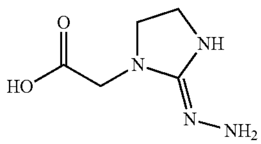 [SMILES: N/N=C1\NCCN1CC(=O)O] | 2-[2-hydrazinylideneimidazolidin-1-yl]acetic acid |
| 235 | 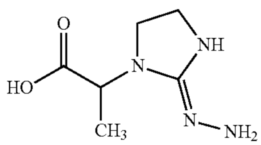 | 2-[2-hydrazinylideneimidazolidin-1-yl]propanoic acid |
| 236 | 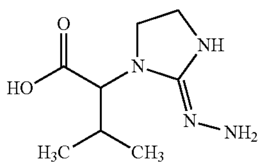 | 2-[2-hydrazinylideneimidazolidin-1-yl]-3-methylbutanoic acid |

In some embodiments, the compound is a compound of Table 2 (e.g., compound 237, 238, 241, 242, 244, 245, 247, or 248).

TABLE 2

Selected Phosphocreatine System Inhibitors

| Compound Number | Structure | Compound Name |
|---|---|---|
| 237 | | 2-(2-imino-1,3-diazinan-1-yl)propanoic acid |
| 238 | 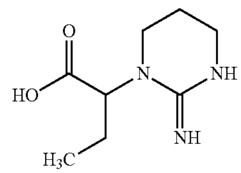 | 2-(2-imino-1,3-diazinan-1-yl)butanoic acid |
| 239 | 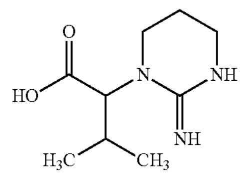 | 2-(2-imino-1,3-diazinan-1-yl)-3-methylbutanoic acid |
| 240 | 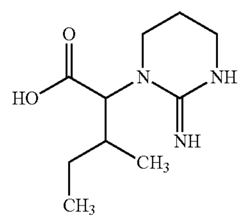 | 2-(2-imino-1,3-diazinan-1-yl)-3-methylpentanoic acid |
| 241 | 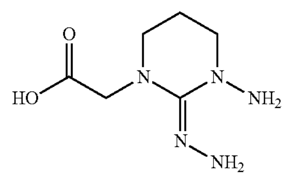 [SMILES: N/N=C1\N(N)CCCN1CC(=O)O] | 2-[3-amino-2-hydrazinylidene-1,3-diazinan-1-yl]acetic acid |
| 242 | 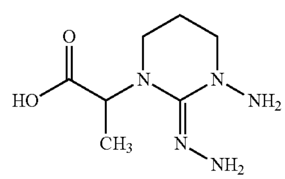 | 2-[3-amino-2-hydrazinylidene-1,3-diazinan-1-yl]propionic acid |
| 243 | 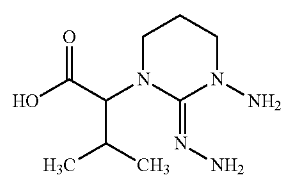 | 2-[3-amino-2-hydrazinylidene-1,3-diazinan-1-yl]-3-methylbutanoic acid |
| 244 | 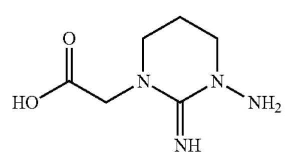 [SMILES: N=C1N(N)CCCN1CC(=O)O] | 2-(3-amino-2-imino-1,3-diazinan-1-yl)acetic acid |
| 245 | 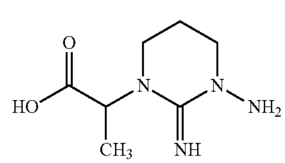 | 2-(3-amino-2-imino-1,3-diazinan-1-yl)propanoic acid |

TABLE 2-continued

Selected Phosphocreatine System Inhibitors

| Compound Number | Structure | Compound Name |
|---|---|---|
| 246 | 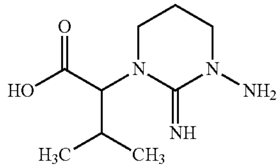 | 2-(3-amino-2-imino-1,3-diazinan-1-yl)-3-methylbutanoic acid |
| 247 | 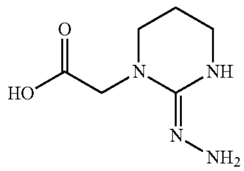 [SMILES: N/N=C1\NCCCN1CC(=O)O] | 2-[2-hydrazinylidene-1,3-diazinan-1-yl]acetic acid |
| 248 | 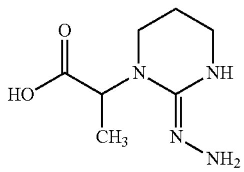 | 2-[2-hydrazinylidene-1,3-diazinan-1-yl]propanoic acid |
| 249 | 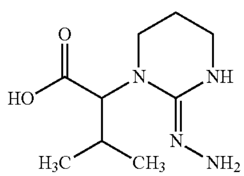 | 2-[2-hydrazinylidene-1,3-diazinan-1-yl]-3-methylbutanoic acid |

In other embodiments, the compound is a compound of Table 3 (e.g., compound 250 or 251).

TABLE 3

Selected Phosphocreatine System Inhibitors

| Compound Number | Structure | Compound Name |
|---|---|---|
| 250 | 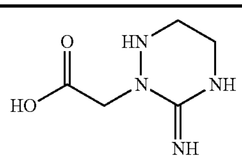 | 2-(3-imino-1,2,4-triazinan-2-yl)acetic acid |
| 251 | 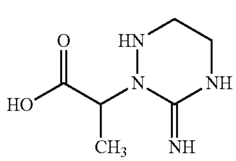 | 2-(3-imino-1,2,4-triazinan-2-yl)propanoic acid |
| 252 | 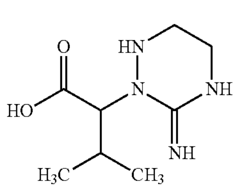 | 2-(3-imino-1,2,4-triazinan-2-yl)-3-methylbutanoic acid |

In another aspect, the invention features a compound having the structure of Formula II:

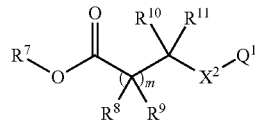

Formula II wherein $Q^1$ is optionally substituted amidino or optionally substituted 2-pyridyl;
$X^2$ is S or $NR^{12}$;
m is 0 or 1;
$R^7$ is hydrogen, optionally substituted $C_1$-$C_6$ alkyl, or optionally substituted $C_6$-$C_{10}$ aryl $C_1$-$C_6$ alkyl;
$R^8$ and $R^9$ are independently hydrogen, deuterium, halo, hydroxyl, $NH_2$, optionally substituted $C_1$-$C_6$ alkyl, or $R^8$ or $R^9$ can combine with $R^{10}$ or $R^{11}$ to form an optionally substituted $C_3$-$C_6$ cycloalkyl ring or with $R^{12}$ to form an optionally substituted $C_3$-$C_6$ heterocycle;
$R^{10}$ and $R^{11}$ are independently hydrogen, deuterium, optionally substituted $C_1$-$C_6$ alkyl, or $R^{10}$ or $R^{11}$ can combine with $R^8$ or $R^9$ to form an optionally substituted $C_3$-$C_6$ cycloalkyl ring;
$R^{12}$ is hydrogen, optionally substituted $C_1$-$C_6$ alkyl, or $R^{12}$ can combine with $R^8$ or $R^9$ to form an optionally substituted $C_3$-$C_6$ heterocycle, and wherein if $R^9$ is halo then $R^8$ is halo or optionally substituted $C_1$-$C_6$ alkyl, or a pharmaceutically acceptable salt thereof.

In some embodiments, if $Q^1$ is optionally substituted 2-pyridyl then $R^{12}$ is hydrogen, In some embodiments, $R^7$ is hydrogen. In other embodiments, m is 1. In certain embodiments, $R^9$ is hydrogen, deuterium, or halo (e.g., fluoro). In some embodiments, $R^{11}$ is hydrogen or deuterium.

In other embodiments, $R^8$ and $R^{10}$ combine to form an optionally substituted $C_3$-$C_6$ cycloalkyl ring (e.g., cyclopropyl or cyclobutyl). In certain embodiments, $R^{10}$ and $R^{11}$ are deuterium. In other embodiments, $R^8$ and $R^9$ are deuterium. In some embodiments, both $R^8$ and $R^9$ are halo (e.g., fluoro).

In other embodiments, $R^{10}$ is optionally substituted $C_1$-$C_6$ alkyl (e.g., optionally substituted $C_1$-$C_6$ haloalkyl such as, trifluoromethyl).

In certain embodiments, $R^8$ is $NH_2$. In some embodiments, $R^{10}$ is optionally substituted $C_1$-$C_6$ alkyl (e.g., methyl).

In other embodiments, $Q^1$ is optionally substituted amidino (e.g.,

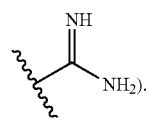

$NH_2$).

In certain embodiments, $X^2$ is $NR^{12}$. In some embodiments, $R^8$ and $R^{12}$ combine to form an optionally substituted $C_3$-$C_6$ heterocycle (e.g., azetidine). In other embodiments, $R^{12}$ is hydrogen. In certain embodiments, $X^2$ is S.

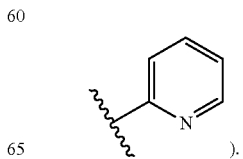

).

In some embodiments, $Q^1$ is optionally substituted 2-pyridyl (e.g., In other embodiments, $X^2$ is $NR^{12}$ and $R^{12}$ is hydrogen.

In some embodiments, the compound has the structure of Formula II:

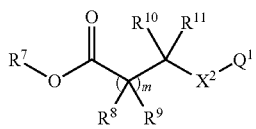

Formula II wherein $Q^1$ is optionally substituted amidino or optionally substituted 2-pyridyl;

$X^2$ is S or $NR^{12}$;

m is 1 or 2;

$R^7$ is hydrogen, optionally substituted $C_1$-$C_6$ alkyl, or optionally substituted $C_6$-$C_{10}$ aryl $C_1$-$C_6$ alkyl;

$R^8$ and $R^9$ are independently hydrogen, deuterium, halo, hydroxyl, $NH_2$, optionally substituted $C_1$-$C_3$ alkyl, or $R^8$ and $R^9$ combine with the atoms to which they are attached to form an optionally substituted $C_3$-$C_6$ cycloalkyl ring; or $R^8$ or $R^9$ combine with $R^{10}$ or $R^{11}$ with the atoms to which they are attached to form an optionally substituted $C_3$-$C_4$ cycloalkyl ring; or $R^8$ or $R^9$ combine with $R^{12}$ with the atoms to which they are attached to form an optionally substituted $C_3$-$C_5$ heterocycle;

$R^{10}$ and $R^{11}$ are independently hydrogen, deuterium, optionally substituted $C_1$-$C_4$ alkyl, optionally substituted $C_2$-$C_6$ alkenyl, optionally substituted $C_2$-$C_6$ alkynyl or $R^{10}$ and $R^{11}$ combine with the atoms to which they are attached to form an optionally substituted $C_3$-$C_6$ cycloalkyl ring; or $R^{10}$ or $R^{11}$ combine with $R^8$ or $R^9$ with the atoms to which they are attached to form an optionally substituted $C_3$-$C_4$ cycloalkyl ring; or $R^{10}$ or $R^{11}$ combine with $R^{12}$ with the atoms to which they are attached to form an optionally substituted $C_3$-$C_5$ heterocycle;

$R^{12}$ is hydrogen, optionally substituted $C_1$-$C_6$ alkyl, or $R^{12}$ combines with $R^8$, $R^9$, $R^{10}$, or $R^{11}$ with the atoms to which they are attached to form an optionally substituted $C_3$-$C_5$ heterocycle, wherein if $Q^1$ is optionally substituted 2-pyridyl and $R^8$ is optionally substituted $C_1$-$C_3$ alkyl, halo, or hydroxyl then at least one of $R^{10}$ and $R^{11}$ are independently deuterium, optionally substituted $C_2$-$C_6$ alkenyl, optionally substituted $C_2$-$C_6$ alkynyl or $R^{10}$ and $R^{11}$ combine with the atoms to which they are attached to form an optionally substituted $C_3$-$C_6$ cycloalkyl ring; or $R^{10}$ or $R^{11}$ combine with $R^9$ with the atoms to which they are attached to form an optionally substituted $C_3$-$C_4$ cycloalkyl ring; or $R^{10}$ or $R^{11}$ combine with $R^{12}$ with the atoms to which they are attached to form an optionally substituted $C_3$-$C_5$ heterocycle;

wherein if $Q^1$ is optionally substituted 2-pyridyl and $R^{10}$ is optionally substituted $C_1$-$C_4$ alkyl then at least one of $R^8$ and $R^9$ are independently deuterium, hydroxyl, $NH_2$, optionally substituted $C_1$-$C_3$ alkyl, or $R^8$ and $R^9$ combine with the atoms to which they are attached to form an optionally substituted $C_3$-$C_6$ cycloalkyl ring; or $R^8$ or $R^9$ combine with $R^{11}$ with the atoms to which they are attached to form an optionally substituted $C_3$-$C_4$ cycloalkyl ring; or $R^8$ or $R^9$ combine with $R^{12}$ with the atoms to which they are attached to form an optionally substituted $C_3$-$C_5$ heterocycle;

wherein if m is 1 and $R^8$ is hydrogen, fluoro, hydroxyl, or methyl then at least one of $R^9$, $R^{10}$, and $R^{11}$ is not hydrogen;

wherein if m is 1 and $R^{10}$ is methyl then at least one of $R^8$, $R^9$, and $R^{11}$ is not hydrogen;

wherein if m is 1 and $R^8$ is $NH_2$ and $R^{10}$ is hydrogen, methyl, or —$CH_2CH_2OH$ then at least one of $R^9$ or $R^{11}$ is not hydrogen;

or a pharmaceutically acceptable salt thereof.

In some embodiments, if $Q^1$ is optionally substituted 2-pyridyl then $R^{12}$ is hydrogen, In another aspect, the invention features a compound having the structure of Formula V:

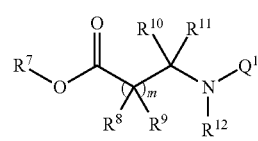

Formula V wherein $Q^1$ is optionally substituted amidino or optionally substituted 2-pyridyl;

m is 1 or 2;

$R^7$ is hydrogen, optionally substituted $C_1$-$C_6$ alkyl, or optionally substituted $C_6$-$C_{10}$ aryl $C_1$-$C_6$ alkyl;

$R^8$ and $R^9$ are independently hydrogen, deuterium, halo, hydroxyl, $NH_2$, optionally substituted $C_1$-$C_3$ alkyl, or $R^8$ and $R^9$ combine with the atoms to which they are attached to form an optionally substituted $C_3$-$C_6$ cycloalkyl ring; or $R^8$ or $R^9$ combine with $R^{10}$ or $R^{11}$ with the atoms to which they are attached to form an optionally substituted $C_3$-$C_4$ cycloalkyl ring; or $R^8$ or $R^9$ combine with $R^{12}$ with the atoms to which they are attached to form an optionally substituted $C_3$-$C_5$ heterocycle;

$R^{10}$ and $R^{11}$ are independently hydrogen, deuterium, optionally substituted $C_1$-$C_4$ alkyl, optionally substituted $C_2$-$C_6$ alkenyl, optionally substituted $C_2$-$C_6$ alkynyl or $R^{10}$ and $R^{11}$ combine with the atoms to which they are attached to form an optionally substituted $C_3$-$C_6$ cycloalkyl ring; or $R^{10}$ or $R^{11}$ combine with $R^8$ or $R^9$ with the atoms to which they are attached to form an optionally substituted $C_3$-$C_4$ cycloalkyl ring; or $R^{10}$ or $R^{11}$ combine with $R^{12}$ with the atoms to which they are attached to form an optionally substituted $C_3$-$C_4$ heterocycle;

$R^{12}$ is hydrogen, optionally substituted $C_1$-$C_6$ alkyl, or $R^{12}$ combines with $R^8$ or $R^9$ with the atoms to which they are attached to form an optionally substituted $C_3$-$C_5$ heterocycle, or $R^{12}$ combines with $R^{10}$ or $R^{11}$ with the atoms to which they are attached to form an optionally substituted $C_3$-$C_4$ heterocycle wherein if m is 1 and $R^8$ is hydrogen, halo, hydroxyl, or methyl then at least one of $R^9$, $R^{10}$, and $R^{11}$ is not hydrogen;

wherein if m is 1 and $R^{10}$ is methyl then at least one of $R^8$, $R^9$, and $R^{11}$ is not hydrogen;

wherein if m is 1 and $R^8$ is $NH_2$ and $R^{10}$ is hydrogen, methyl, or —$CH_2CH_2OH$ then at least one of $R^9$ or $R^{11}$ is not hydrogen;

wherein if m is 1, $R^8$ is halo, and $R^{10}$ is optionally substituted $C_1$-$C_4$ alkyl then at least one of $R^9$ and $R^{10}$ is not hydrogen;

or a pharmaceutically acceptable salt thereof.

In some embodiments, $R^7$ is hydrogen. In other embodiments $Q^1$ is optionally substituted amidino (e.g., $Q^1$ is

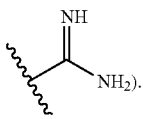

In some embodiments, $Q^1$ is optionally substituted 2-pyridyl (e.g., 2-pyridyl).

In some embodiments, $R^8$ combines with $R^{10}$ with the atoms to which they are attached to form an optionally substituted $C_3$-$C_4$ cycloalkyl ring. In some embodiments, the compound has the structure of Formula VI:

Formula VI

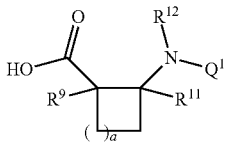

wherein a is 0 or 1.

In other embodiments, the compound has the structure of Formula VII:

Formula VII

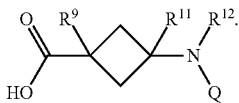

In some embodiments, $R^9$ is hydrogen, hydroxyl, or $NH_2$. In other embodiments, $R^{11}$ is hydrogen.

In some embodiments, m is 1 and $R^{10}$ is deuterium, optionally substituted $C_1$-$C_4$ alkyl, optionally substituted $C_2$-$C_6$ alkenyl, optionally substituted $C_2$-$C_6$ alkynyl, or $R^{10}$ and $R^{11}$ combine with the atoms to which they are attached to form an optionally substituted $C_3$-$C_6$ cycloalkyl ring.

In other embodiments, $R^{10}$ is deuterium. In some embodiments, $R^{11}$ is deuterium. In other embodiments, $R^8$ and $R^9$ are both deuterium. In some embodiments, $R^{10}$ is optionally substituted $C_1$-$C_4$ alkyl, optionally substituted $C_2$-$C_6$ alkenyl, optionally substituted $C_2$-$C_6$ alkynyl. In other embodiments, $R^{10}$ is methyl, ethyl, n-propyl, iso-propyl, —$CD_3$, —$CF_3$, —$CH_2F$, —$CHF_2$, —$CH=CH_2$, or —C≡CH. In some embodiments, $R^{11}$ is hydrogen or methyl. In other embodiments, $R^8$ is hydrogen. In some embodiments, $R^9$ is hydrogen, $NH_2$, or methyl. In other embodiments, $R^{10}$ and $R^{11}$ combine with the atoms to which they are attached to form an optionally substituted $C_3$-$C_6$ cycloalkyl ring (e.g., an optionally substituted $C_3$-$C_4$ cycloalkyl ring such as cyclopropyl or cyclobutyl). In some embodiments, $R^8$ and $R^9$ are both hydrogen.

In other embodiments, $R^8$ is halo, optionally substituted $C_1$-$C_3$ alkyl, or $R^8$ and $R^9$ combine with the atoms to which they are attached to form an optionally substituted $C_3$-$C_6$ cycloalkyl ring. In some embodiments, $R^8$ is halo (e.g., fluoro). In other embodiments, $R^9$ is halo (e.g., fluoro). In some embodiments, $R^8$ is optionally substituted $C_1$-$C_3$ alkyl (e.g., methyl). In other embodiments, $R^9$ is optionally substituted $C_1$-$C_3$ alkyl (e.g., methyl). In some embodiments, $R^8$ and $R^9$ combine with the atoms to which they are attached to form an optionally substituted $C_3$-$C_6$ cycloalkyl ring (e.g., an optionally substituted $C_3$-$C_4$ cycloalkyl ring such as cyclopropyl or cyclobutyl). In some embodiments, $R^{10}$ and $R^{11}$ are both hydrogen.

In certain embodiments of the compounds of Formula V, $R^{12}$ is hydrogen.

In some embodiments, $R^{12}$ combines with $R^8$ with the atoms to which they are attached to form an optionally substituted $C_3$-$C_5$ heterocycle (e.g., an optionally substituted $C_4$-$C_5$ heterocycle).

In some embodiments, the compound has the structure of Formula VIII:

Formula VIII

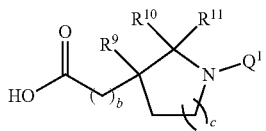

wherein b and c are each, independently, 0 or 1.

In some embodiments, $R^{10}$ is hydrogen or optionally substituted $C_1$-$C_4$ alkyl (e.g., methyl). In other embodiments, $R^{11}$ is hydrogen. In some embodiments, $R^9$ is hydrogen, halo (e.g., fluoro), hydroxyl, $NH_2$, optionally substituted $C_1$-$C_3$ alkyl (e.g., methyl).

In other embodiments, $R^{12}$ combines with $R^{10}$ with the atoms to which they are attached to form an optionally substituted $C_3$-$C_4$ heterocycle.

In some embodiments, the compound has the structure of Formula IX:

Formula IX

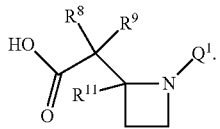

In some embodiments, $R^{11}$ is hydrogen. In other embodiments, $R^8$ and $R^9$ are both hydrogen.

In certain embodiments of any of the compounds of Formula V, $Q^1$ is

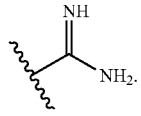 [SMILES: *C(=N)N]

In some embodiments, the compound of Formula II or Formula V is any one of compounds 253-262 or 327-385 in Table 4.

In some embodiments, the compound of Formula II or Formula V is any one of compounds 263-274 or 386-436 in Table 5.

In another aspect the invention features a compound selected from any one of compounds 253-262 and 327-385 in Table 4. In some embodiments, the compound is any one of compounds 258, 327-338, 340, 343-348, 351-352, 366-367, 369-370, 372-375, and 379-385 in Table 4.

TABLE 4

Selected Phosphocreatine System Inhibitors

| Compound Number | Structure | Compound Name |
|---|---|---|
| 253 | 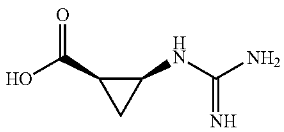 | cis-2-carbamimidamidocyclopropane-1-carboxylic acid |
| 254 | 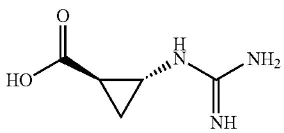 | trans-2-carbamimidamidocyclopropane-1-carboxylic acid |
| 255 | 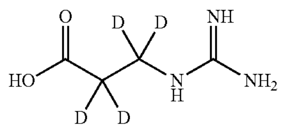 [SMILES: [2H]C([2H])(NC(=N)N)C([2H])([2H])C(=O)O] | 3-carbamimidamido($^2$H)propanoic acid |
| 256 | 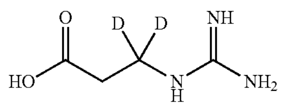 [SMILES: [2H]C([2H])(CC(=O)O)NC(=N)N] | 3-carbamimidamido(3,3-$^2$H$_2$)propanoic acid |
| 257 | 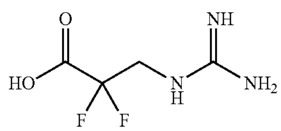 [SMILES: N=C(N)NCC(F)(F)C(=O)O] | 3-carbamimidamido-2,2-difluoropropanoic acid |
| 258 | 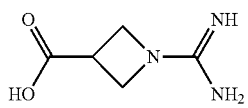 | 1-carbamimidoylazetidine-3-carboxylic acid |
| 259 | 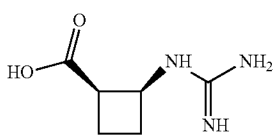 [SMILES: N=C(N)N[C@H]1CC[C@H]1C(=O)O] | cis-2-carbamimidamidocyclobutane-1-carboxylic acid |
| 260 | 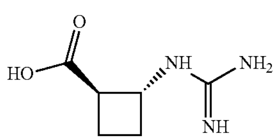 [SMILES: N=C(N)N[C@@H]1CC[C@H]1C(=O)O] | trans-2-carbamimidamidocyclobutane-1-carboxylic acid |
| 261 | 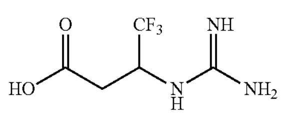 [SMILES: N=C(N)NC(CC(=O)O)C(F)(F)F] | 3-guanidino-4,4,4-trifluorobutanoic acid |
| 262 | 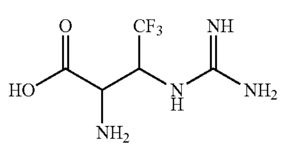 [SMILES: N=C(N)NC(C(N)C(=O)O)C(F)(F)F] | 2-amino-3-guanidino-4,4,4-trifluorobutanoic acid |
| 327 | 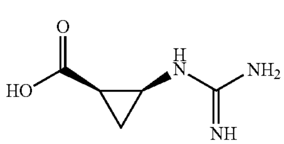 | (1R,2S)-2-carbamimidamidocyclopropane-1-carboxylic acid |

TABLE 4-continued

Selected Phosphocreatine System Inhibitors

| Compound Number | Structure | Compound Name |
|---|---|---|
| 328 | 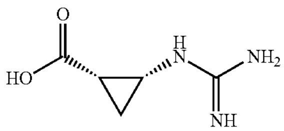 | (1S,2R)-2-carbamimidamidocyclopropane-1-carboxylic acid |
| 329 | 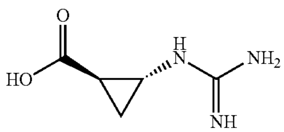 | (1R,2R)-2-carbamimidamidocyclopropane-1-carboxylic acid |
| 330 | 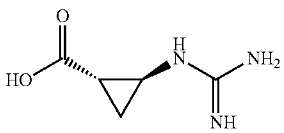 | (1S,2S)-2-carbamimidamidocyclopropane-1-carboxylic acid |
| 331 | 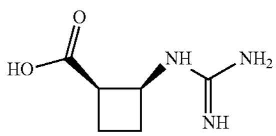 [SMILES: N=C(N)N[C@H]1CC[C@H]1C(=O)O] | (1R,2S)-2-carbamimidamidocyclobutane-1-carboxylic acid |
| 332 | 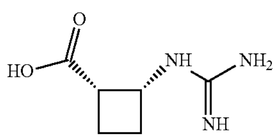 [SMILES: N=C(N)N[C@@H]1CC[C@@H]1C(=O)O] | (1S,2R)-2-carbamimidamidocyclobutane-1-carboxylic acid |
| 333 | 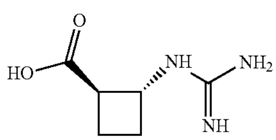 [SMILES: N=C(N)N[C@@H]1CC[C@H]1C(=O)O] | (1R,2R)-2-carbamimidamidocyclobutane-1-carboxylic acid |
| 334 | 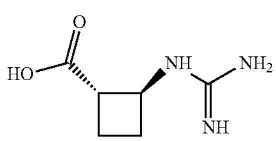 [SMILES: N=C(N)N[C@H]1CC[C@@H]1C(=O)O] | (1S,2S)-2-carbamimidamidocyclobutane-1-carboxylic acid |
| 335 | 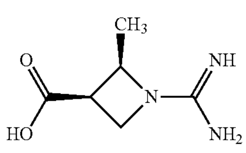 | (2R,3R)-1-carbamimidoyl-2-methylazetidine-3-carboxylic acid |
| 336 | 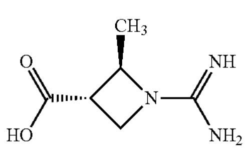 | (2R,3S)-1-carbamimidoyl-2-methylazetidine-3-carboxylic acid |
| 337 | 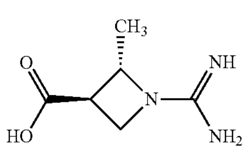 | (2S,3R)-1-carbamimidoyl-2-methylazetidine-3-carboxylic acid |

TABLE 4-continued

Selected Phosphocreatine System Inhibitors

| Compound Number | Compound Name |
|---|---|
| 338 | (2S,3S)-1-carbamimidoyl-2-methylazetidine-3-carboxylic acid |
| 339 | 1-carbamimidoyl-3-hydroxyazetidine-3-carboxylic acid |
| 340 | 3-amino-1-carbamimidoylazetidine-3-carboxylic acid |
| 341 | 1-carbamimidoyl-3-fluoroazetidine-3-carboxylic acid |
| 342 | 1-carbamimidoyl-3-methylazetidine-3-carboxylic acid |
| 343 | (S)-3-guanidino-4,4,4-trifluorobutanoic acid |
| 344 | (R)-3-guanidino-4,4,4-trifluorobutanoic acid |
| 345 | (2S,3S)-2-amino-3-carbamimidamido-4,4,4-trifluorobutanoic acid |
| 346 | (2S,3R)-2-amino-3-carbamimidamido-4,4,4-trifluorobutanoic acid |
| 347 | (2R,3R)-2-amino-3-carbamimidamido-4,4,4-trifluorobutanoic acid |
| 348 | (2R,3S)-2-amino-3-carbamimidamido-4,4,4-trifluorobutanoic acid |

TABLE 4-continued

Selected Phosphocreatine System Inhibitors

| Compound Number | Structure | Compound Name |
|---|---|---|
| 349 | 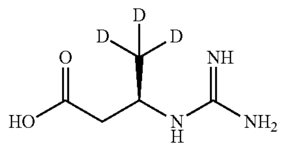 [SMILES: [2H]C([2H])([2H])[C@H](CC(=O)O)NC(=N)N] | (3R)-3-carbamimidamido(4,4,4-$^2$H$_3$) butanoic acid |
| 350 | 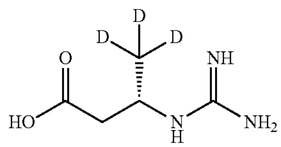 [SMILES: [2H]C([2H])([2H])[C@@H](CC(=O)O)NC(=N)N] | (3S)-3-carbamimidamido(4,4,4-$^2$H$_3$) butanoic acid |
| 351 | 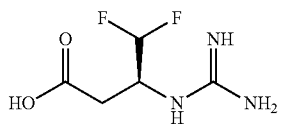 [SMILES: N=C(N)N[C@@H](CC(=O)O)C(F)F] | (3S)-3-carbamimidamido-4,4-difluorobutanoic acid |
| 352 | 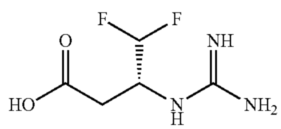 [SMILES: N=C(N)N[C@H](CC(=O)O)C(F)F] | (3R)-3-carbamimidamido-4,4-difluorobutanoic acid |
| 353 | 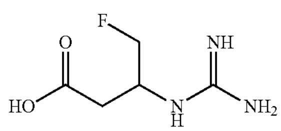 [SMILES: N=C(N)NC(CF)CC(=O)O] | 3-carbamimidamido-4-fluorobutanoic acid |
| 354 | 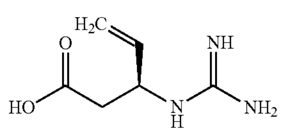 | (3S)-3-carbamimidamidopent-4-enoic acid |
| 355 | 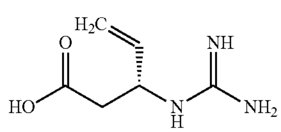 | (3R)-3-carbamimidamidopent-4-enoic acid |
| 356 | 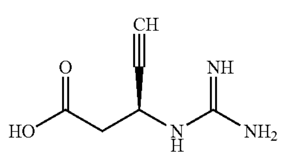 | (3S)-3-carbamimidamidopent-4-ynoic acid |
| 357 | 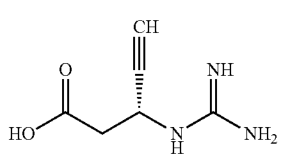 | (3R)-3-carbamimidamidopent-4-ynoic acid |
| 358 | 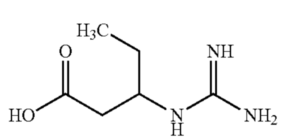 | 3-carbamimidamidopentanoic acid |

TABLE 4-continued

Selected Phosphocreatine System Inhibitors

| Compound Number | Structure | Compound Name |
|---|---|---|
| 359 | 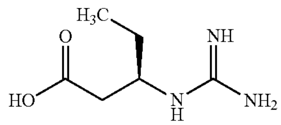 | (3R)-3-carbamimidamidopentanoic acid |
| 360 | 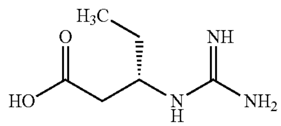 | (3S)-3-carbamimidamidopentanoic acid |
| 361 | 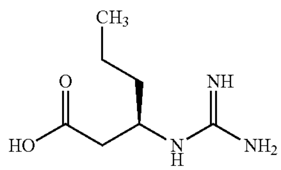 | (3R)-3-carbamimidamidohexanoic acid |
| 362 | 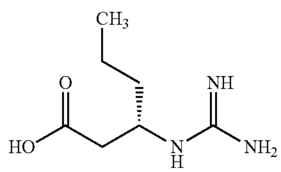 | (3S)-3-carbamimidamidohexanoic acid |
| 363 | 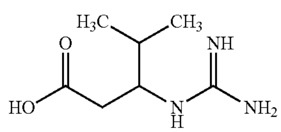 | 3-carbamimidamido-4-methylpentanoic acid |
| 364 | 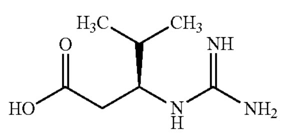 | (3S)-3-carbamimidamido-4-methylpentanoic acid |
| 365 | 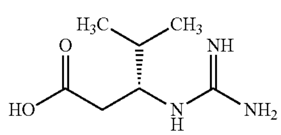 | (3R)-3-carbamimidamido-4-methylpentanoic acid |
| 366 | 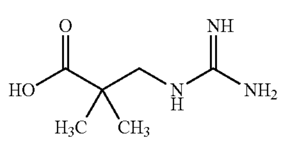 | 3-carbamimidamido-2,2-dimethylpropanoic acid |
| 367 | 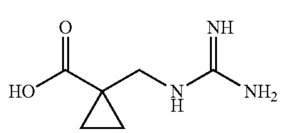 [SMILES: N=C(N)NCC1(C(=O)O)CC1] | 1-(carbamimidamidomethyl)cyclopropane-1-carboxylic acid |
| 368 | 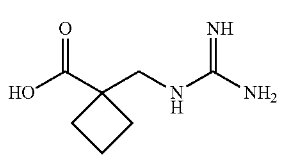 [SMILES: N=C(N)NCC1(C(=O)O)CCC1] | 1-(carbamimidamidomethyl)cyclobutane-1-carboxylic acid |

TABLE 4-continued

Selected Phosphocreatine System Inhibitors

| Compound Number | Structure | Compound Name |
|---|---|---|
| 369 | 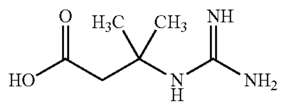 | 3-carbamimidamido-3-methylbutanoic acid |
| 370 | 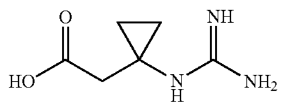 [SMILES: N=C(N)NC1(CC(=O)O)CC1] | 2-(1-carbamimidamidocyclopropyl)acetic acid |
| 371 | 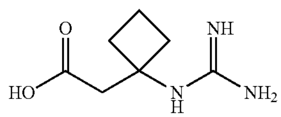 [SMILES: N=C(N)NC1(CC(=O)O)CCC1] | 2-(1-carbamimidamidocyclobutyl)acetic acid |
| 372 | 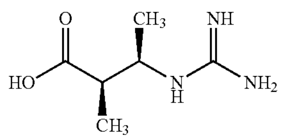 | (2R,3R)-3-carbamimidamido-2-methylbutanoic acid |
| 373 | 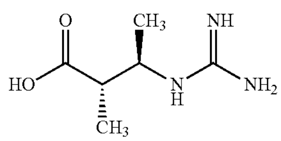 | (2S,3R)-3-carbamimidamido-2-methylbutanoic acid |
| 374 | 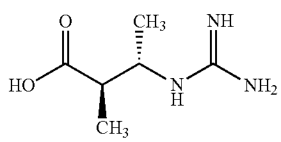 | (2R,3S)-3-carbamimidamido-2-methylbutanoic acid |
| 375 | 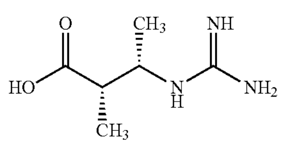 | (2S,3S)-3-carbamimidamido-2-methylbutanoic acid |
| 376 | 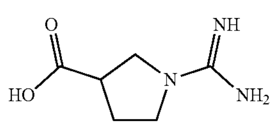 [SMILES: N=C(N)N1CCC(C(=O)O)C1] | 1-carbamimidoylpyrrolidine-3-carboxylic acid |
| 377 | 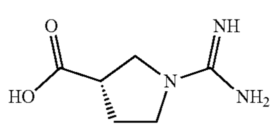 [SMILES: N=C(N)N1CC[C@H](C(=O)O)C1] | (3S)-1-carbamimidoylpyrrolidine-3-carboxylic acid |
| 378 | 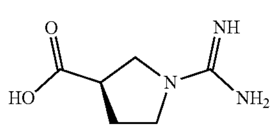 [SMILES: N=C(N)N1CC[C@@H](C(=O)O)C1] | (3R)-1-carbamimidoylpyrrolidine-3-carboxylic acid |
| 379 | 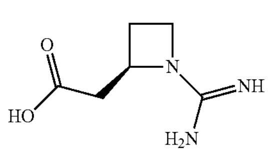 [SMILES: N=C(N)N1CC[C@@H]1CC(=O)O] | 2-[(2R)-1-carbamimidoylazetidin-2-yl]acetic acid |

TABLE 4-continued

Selected Phosphocreatine System Inhibitors

| Compound Number | Structure | Compound Name |
|---|---|---|
| 380 | 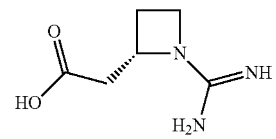 [SMILES: N=C(N)N1CC[C@H]1CC(=O)O] | 2-[(2S)-1-carbamimidoylazetidin-2-yl]acetic acid |
| 381 | 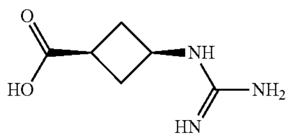 [SMILES: N=C(N)N[C@H]1C[C@@H](C(=O)O)C1] | cis-3-carbamimidamidocyclobutane-1-carboxylic acid |
| 382 | 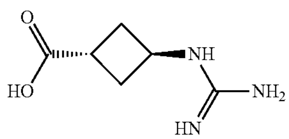 [SMILES: N=C(N)N[C@H]1C[C@H](C(=O)O)C1] | trans-3-carbamimidamidocyclobutane-1-carboxylic acid |
| 383 | 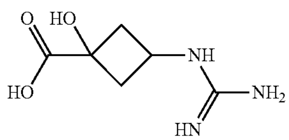 [SMILES: N=C(N)NC1CC(O)(C(=O)O)C1] | 3-carbamimidamido-1-hydroxycyclobutane-1-carboxylic acid |
| 384 | 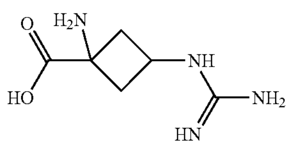 [SMILES: N=C(N)NC1CC(N)(C(=O)O)C1] | 1-amino-3-carbamimidamidocyclobutane-1-carboxylic acid |
| 385 | 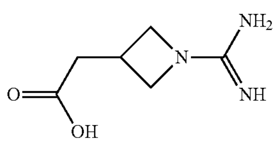 [SMILES: N=C(N)N1CC(CC(=O)O)C1] | 2-(1-carbamimidoylazetidin-3-yl)acetic acid |

In another aspect, the invention features a compound selected from any one of compounds 263-274 and 386-436 in Table 5.

TABLE 5

Selected Phosphocreatine System Inhibitors

| Compound Number | Structure | Compound Name |
|---|---|---|
| 263 | | (2S)-2-amino-3-[(pyridin-2-yl)amino]propanoic acid |
| 264 | | (2S,3S)-2-amino-3-[(pyridin-2-yl)amino]butanoic acid |
| 265 | 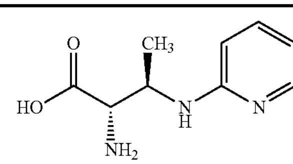 | (2S,3R)-2-amino-3-[(pyridin-2-yl)amino]butanoic acid |
| 266 | 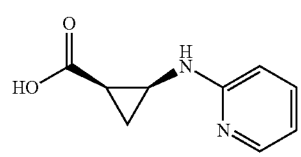 [SMILES: O=C(O)[C@@H]1C[C@@H]1Nc1ccccn1] | cis-2-[(pyridin-2-yl)amino]cyclopropane-1-carboxylic acid |
| 267 | 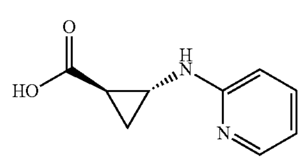 [SMILES: O=C(O)[C@@H]1C[C@H]1Nc1ccccn1] | trans-2-[(pyridin-2-yl)amino]cyclopropane-1-carboxylic acid |

TABLE 5-continued

Selected Phosphocreatine System Inhibitors

| Compound Number | Structure | Compound Name |
|---|---|---|
| 268 | 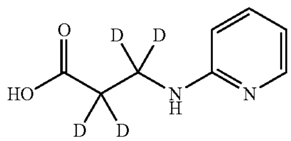 [SMILES: [2H]C([2H])(Nc1ccccn1)C([2H])([2H])C(=O)O] | 3-[(pyridin-2-yl)amino]($^2$H$_4$) propanoic acid |
| 269 | 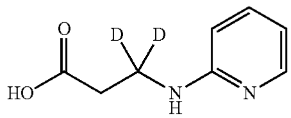 [SMILES: [2H]C([2H])(CC(=O)O)Nc1ccccn1] | 3-[(pyridin-2-yl)amino](3,3-$^2$H$_2$) propanoic acid |
| 270 | 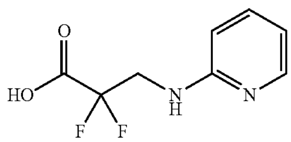 [SMILES: O=C(O)C(F)(F)CNc1ccccn1] | 2,2-difluoro-3-[(pyridin-2-yl)amino] propanoic acid |
| 271 | 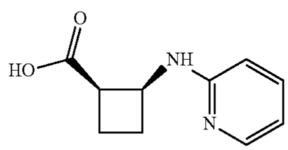 [SMILES: O=C(O)[C@@H]1CC[C@@H]1Nc1ccccn1] | cis-2-[(pyridin-2-yl)amino] cyclobutane-1-carboxylic acid |
| 272 | 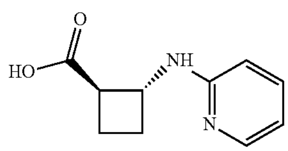 [SMILES: O=C(O)[C@@H]1CC[C@H]1Nc1ccccn1] | trans-2-[(pyridin-2-yl)amino] cyclobutane-1-carboxylic acid |
| 273 | 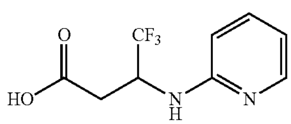 [SMILES: O=C(O)CC(Nc1ccccn1)C(F)(F)F] | 4,4,4-trifluoro-3-[(pyridine-2-yl)amino] butanoic acid |
| 274 | 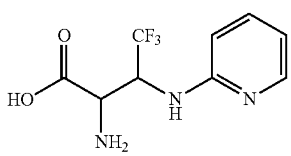 [SMILES: NC(C(=O)O)C(Nc1ccccn1)C(F)(F)F] | 2-amino-4,4,4-trifluoro-3-[(pyridine-2-yl)amino]butanoic acid |
| 386 | 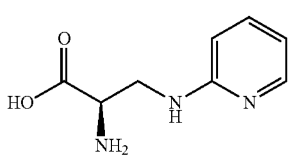 [SMILES: N[C@H](CNc1ccccn1)C(=O)O] | (2R)-2-amino-3-[(pyridin-2-yl)amino] propanoic acid |
| 387 | 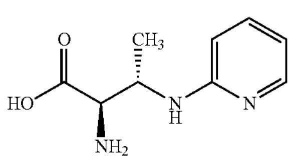 | (2R,3S)-2-amino-3-[(pyridin-2-yl)amino] butanoic acid |
| 388 | 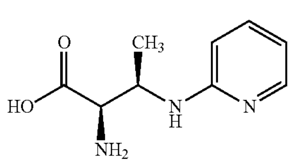 | (2R,3R)-2-amino-3-[(pyridin-2-yl)amino] butanoic acid |
| 389 | | (1R,2S)-2-[(pyridin-2-yl)amino] cyclopropane-1-carboxylic acid |
| 390 | | (1S,2R)-2-[(pyridin-2-yl)amino] cyclopropane-1-carboxylic acid |
| 391 | | (1R,2R)-2-[(pyridin-2-yl)amino] cyclopropane-1-carboxylic acid |
| 392 | | (1S,2S)-2-[(pyridin-2-yl)amino] cyclopropane-1-carboxylic acid |
| 393 | | (1R,2S)-2-[(pyridin-2-yl)amino] cyclobutane-1-carboxylic acid |
| 394 | | (1S,2R)-2-[(pyridin-2-yl)amino]cyclobutane-1-carboxylic acid |
| 395 | | (1R,2R)-2-[(pyridin-2-yl)amino]cyclobutane-1-carboxylic acid |
| 396 | | (1S,2S)-2-[(pyridin-2-yl)amino]cyclobutane-1-carboxylic acid |
| 397 | | (2R,3R)-2-methyl-1-(pyridin-2-yl)azetidine-3-carboxylic acid |

TABLE 5-continued

Selected Phosphocreatine System Inhibitors

| Compound Number | Structure | Compound Name |
|---|---|---|
| 398 | 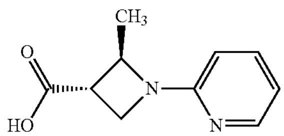 | (2R,3S)-2-methyl-1-(pyridin-2-yl)azetidine-3-carboxylic acid |
| 399 | 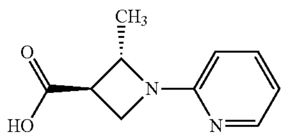 | (2S,3R)-2-methyl-1-(pyridin-2-yl)azetidine-3-carboxylic acid |
| 400 | 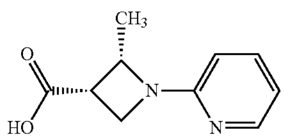 | (2S,3S)-2-methyl-1-(pyridin-2-yl)azetidine-3-carboxylic acid |
| 401 | 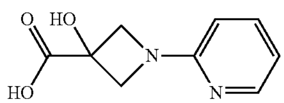 [SMILES: O=C(O)C1(O)CN(c2ccccn2)C1] | 3-hydroxy-1-(pyridin-2-yl)azetidine-3-carboxylic acid |
| 402 | 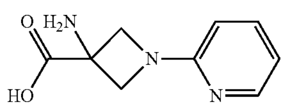 | 3-amino-1-(pyridin-2-yl)azetidine-3-carboxylic acid |
| 403 | 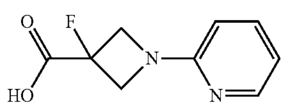 | 3-fluoro-1-(pyridin-2-yl)azetidine-3-carboxylic acid |
| 404 | 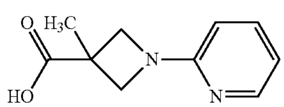 [SMILES: NC1(C(=O)O)CN(c2ccccn2)C1] | 3-methyl-1-(pyridin-2-yl)azetidine-3-carboxylic acid |
| 405 | 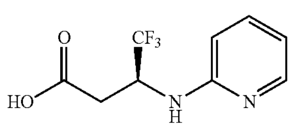 | (3S)-4,4,4-trifluoro-3-[(pyridin-2-yl)amino]butanoic acid |
| 406 | 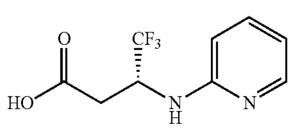 [SMILES: O=C(O)C[C@@H](Nc1ccccn1)C(F)(F)F] | (3R)-4,4,4-trifluoro-3-[(pyridin-2-yl)amino]butanoic acid |
| 407 | 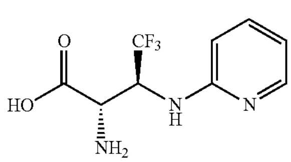 [SMILES: N[C@H](C(=O)O)[C@H](Nc1ccccn1)C(F)(F)F] | (2S,3S)-2-amino-4,4,4-trifluoro-3-[(pyridin-2-yl)amino]butanoic acid |
| 408 | 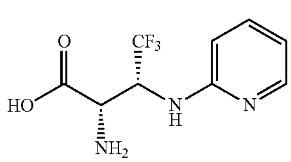 | (2S,3R)-2-amino-4,4,4-trifluoro-3-[(pyridin-2-yl)amino]butanoic acid |
| 409 | | (2R,3R)-2-amino-4,4,4-trifluoro-3-[(pyridin-2-yl)amino]butanoic acid |
| 410 | | (2R,3S)-2-amino-4,4,4-trifluoro-3-[(pyridin-2-yl)amino]butanoic acid |
| 411 | | (3R)-3-[(pyridin-2-yl)amino](4,4,4-$^2H_3$)butanoic acid |
| 412 | | (3S)-3-[(pyridin-2-yl)amino](4,4,4-$^2H_3$)butanoic acid |
| 413 | | (3S)-4,4-difluoro-3-[(pyridin-2-yl)amino]butanoic acid |
| 414 | | (3R)-4,4-difluoro-3-[(pyridin-2-yl)amino]butanoic acid |
| 415 | | 4-fluoro-3-[(pyridin-2-yl)amino]butanoic acid |
| 416 | | (3S)-3-[(pyridin-2-yl)amino]pent-4-enoic acid |
| 417 | | (3R)-3-[(pyridin-2-yl)amino]pent-4-enoic acid |
| 418 | | (3S)-3-[(pyridin-2-yl)amino]pent-4-ynoic acid |

TABLE 5-continued

Selected Phosphocreatine System Inhibitors

| Compound Number | Compound Name |
|---|---|
| 419 | (3R)-3-[(pyridin-2-yl)amino]pent-4-ynoic acid |
| 420 | (3R)-3-[(pyridin-2-yl)amino]pentanoic acid |
| 421 | (3S)-3-[(pyridin-2-yl)amino]pentanoic acid |
| 422 | 2,2-dimethyl-3-[(pyridin-2-yl)amino]propanoic acid |
| 423 | 1-{[(pyridin-2-yl)amino]methyl}cyclopropane-1-carboxylic acid |
| 424 | 1-{[(pyridin-2-yl)amino]methyl}cyclobutane-1-carboxylic acid |
| 425 | 3-methyl-3-[(pyridin-2-yl)amino]butanoic acid |
| 426 | 2-{1-[(pyridin-2-yl)amino]cyclopropyl}acetic acid |
| 427 | 2-{1-[(pyridin-2-yl)amino]cyclobutyl}acetic acid |
| 428 | (2R,3R)-2-methyl-3-[(pyridin-2-yl)amino]butanoic acid |
| 429 | (2S,3R)-2-methyl-3-[(pyridin-2-yl)amino]butanoic acid |
| 430 | (2R,3S)-2-methyl-3-[(pyridin-2-yl)amino]butanoic acid |
| 431 | (2S,3S)-2-methyl-3-[(pyridin-2-yl)amino]butanoic acid |
| 432 | 2-[(2R)-1-(pyridin-2-yl)azetidin-2-yl]acetic acid |
| 433 | 2-[(2S)-1-(pyridin-2-yl)azetidin-2-yl]acetic acid |
| 434 | cis-3-[(pyridin-2-yl)amino]cyclobutane-1-carboxylic acid |
| 435 | trans-3-[(pyridin-2-yl)amino]cyclobutane-1-carboxylic acid |
| 436 | 1-hydroxy-3-[(pyridin-2-yl)amino]cyclobutane-1-carboxylic acid |

In another aspect, the invention features a compound selected from any one of compounds 275-286 in Table 6.

TABLE 6

Selected Phosphocreatine System Inhibitors

| Compound Number | Structure | Compound Name |
|---|---|---|
| 275 | 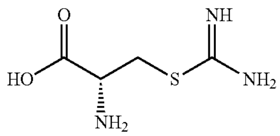 | (2R)-2-amino-3-(carbamimidoylsulfanyl)propanoic acid |
| 276 | 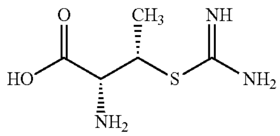 | (2S,3S)-2-amino-3-(carbamimidoylsulfanyl)butanoic acid |
| 277 | 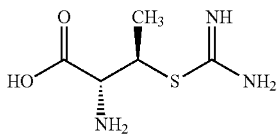 | (2S,3R)-2-amino-3-(carbamimidoylsulfanyl)butanoic acid |
| 278 | 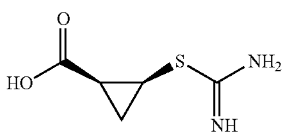 | cis-2-(carbamimidoylsulfanyl)cyclopropane-1-carboxylic acid |
| 279 | 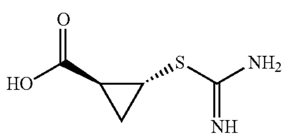 | trans-2-(carbamimidoylsulfanyl)cyclopropane-1-carboxylic acid |
| 280 | 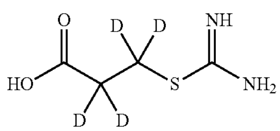 [SMILES: [2H]C([2H])(SC(=N)N)C([2H])([2H])C(=O)O] | 3-(carbamimidoylsulfanyl)(2,2-$^2$H$_4$)propanoic acid |
| 281 | 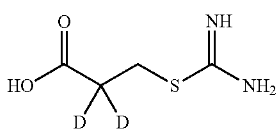 [SMILES: [2H]C([2H])(CSC(=N)N)C(=O)O] | 3-(carbamimidoylsulfanyl)(2,2-$^2$H)propanoic acid |
| 282 | 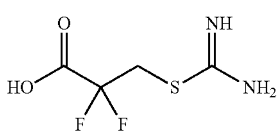 [SMILES: N=C(N)SCC(F)(F)C(=O)O] | 3-(carbamimidoylsulfanyl)-2,2-difluoropropanoic acid |
| 283 | 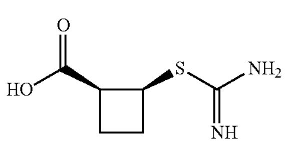 [SMILES: N=C(N)S[C@H]1CC[C@H]1C(=O)O] | cis-2-(carbamimidoylsulfanyl)cyclobutane-1-carboxylic acid |
| 284 | 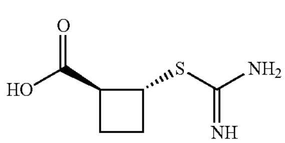 | trans-2-(carbamimidoylsulfanyl)cyclobutane-1-carboxylic acid |
| 285 | 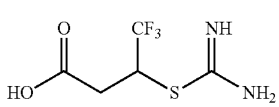 | 3-(carbamimidoylsulfanyl)-4,4,4-trifluorobutanoic acid |

TABLE 6-continued

Selected Phosphocreatine System Inhibitors

| Compound Number | Structure | Compound Name |
|---|---|---|
| 286 | 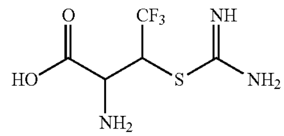 | 2-amino-3-(carbamimidoylsulfanyl)-4,4,4-trifluorobutanoic acid |

In another aspect, the invention features a compound of Table 7 that is substantially enantiomerically pure.

TABLE 7

Selected Phosphocreatine System Inhibitors

| Compound Number | Structure | Compound Name |
|---|---|---|
| 219 | 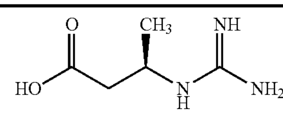 | (3R)-3-carbamimidamidobutanoic acid |
| 220 | 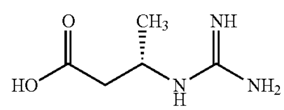 | (3S)-3-carbamimidamidobutanoic acid |
| 221 | 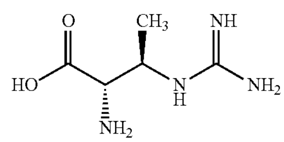 | (2S,3R)-2-amino-3-carbamimidamidobutanoic acid |
| 222 | 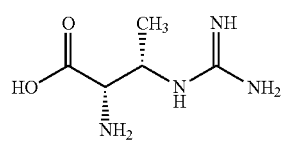 | (2S,3S)-2-amino-3-carbamimidamidobutanoic acid |
| 437 | 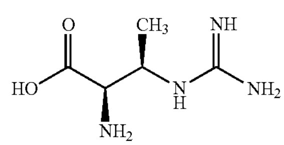 | (2R,3R)-2-amino-3-carbamimidamidobutanoic acid |
| 438 | 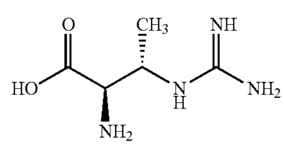 | (2R,3S)-2-amino-3-carbamimidamidobutanoic acid |
| 439 | 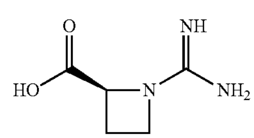 | (2S)-1-carbamimidoylazetidine-2-carboxylic acid |
| 440 | 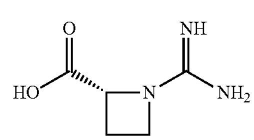 | (2R)-1-carbamimidoylazetidine-2-carboxylic acid |

TABLE 7-continued

Selected Phosphocreatine System Inhibitors

| Compound Number | Structure | Compound Name |
|---|---|---|
| 223 | 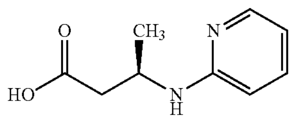 | (3R)-3-[(pyridin-2-yl)amino]butanoic acid |
| 224 | 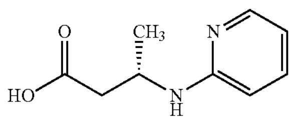 | (3S)-3-[(pyridin-2-yl)amino]butanoic acid |
| 441 | 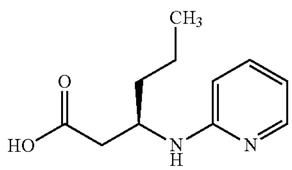 | (3R)-3-[(pyridin-2-yl)amino]hexanoic acid |
| 442 | 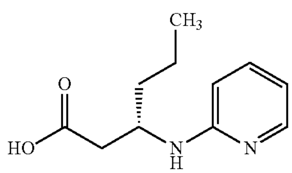 | (3S)-4-methyl-3-[(pyridin-2-yl)amino]pentanoic acid |
| 443 | 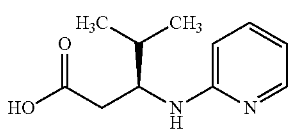 | (3S)-4-methyl-3-[(pyridin-2-yl)amino]pentanoic acid |
| 444 | 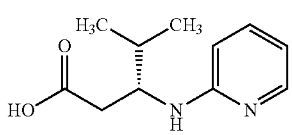 | (3R)-4-methyl-3-[(pyridin-2-yl)amino]pentanoic acid |
| 445 | 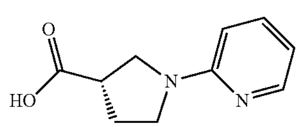 [SMILES: O=C(O)[C@H]1CCN(c2ccccn2)C1] | (3S)-1-(pyridin-2-yl)pyrrolidine-3-carboxylic acid |
| 446 | 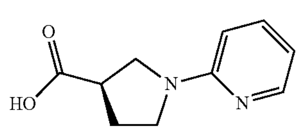 [SMILES: O=C(O)[C@@H]1CCN(c2ccccn2)C1] | (3R)-1-(pyridin-2-yl)pyrrolidine-3-carboxylic acid |

In another aspect, the invention features a compound having the structure:

A-B          Formula III wherein A is a inhibitor of creatine transport and/or creatine kinase comprising an amidino group;

B has the structure:

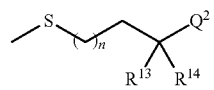

Formula IV wherein n is 0 or 1;

$Q^2$ is hydroxyl, optionally substituted amino, or —$SO_2OH$; and $R^{13}$ and $R^{14}$ are independently hydrogen, —$CO_2H$, or combine to form C=O;

wherein B is conjugated to A at one of the amidino nitrogens, or a pharmaceutically acceptable salt thereof.

In some embodiments, $R^{14}$ is hydrogen. In other embodiments, $R^{13}$ is –$CO_2H$. In certain embodiments, $R^{13}$ is hydrogen. In some embodiments, $R^{13}$ and $R^{14}$ combine to form C=O. In other embodiments, n is 0. In certain embodiments, n is 1. In some embodiments, $Q^2$ is optionally substituted amino (e.g., —$NH_2$ or

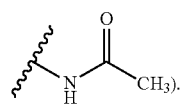

In other embodiments, $Q^2$ is hydroxyl. In certain embodiments, $Q^2$ is —$SO_2OH$.

In some embodiments, B has the structure:

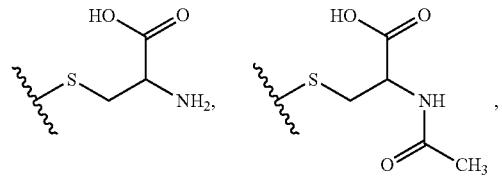

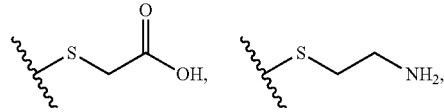

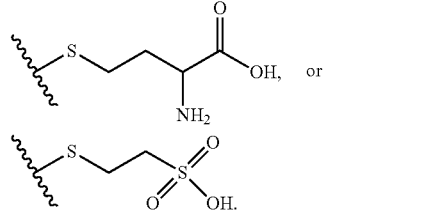

In other embodiments, A has the structure of any of the foregoing compounds.

In another aspect, the invention features a compound selected from any one of compounds 1-218 or 323-326 in Table 8.

TABLE 8

Selected Phosphocreatine System Inhibitors

| Compound Number | Structure | Compound Name |
|---|---|---|
| 1 | 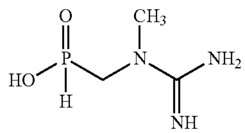 | (1-methylguanidinomethyl)phosphinic acid |
| 2 | 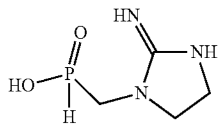 | [(2-iminoimidazolidin-1-yl)methyl]phosphinic acid |
| 3 | 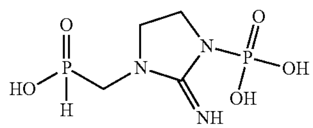 [SMILES: N=C1N(C[PH](=O)O)CCN1P(=O)(O)O] | [(2-imino-3-(phosphono)imidazolidin-1-yl)methyl]phosphinic acid |
| 4 | 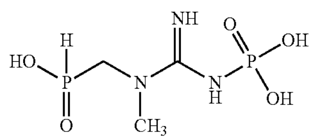 | {1-methyl-3-(phosphono)guanidinomethyl} phosphinic acid |
| 5 | 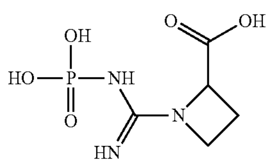 [SMILES: N=C(NP(=O)(O)O)N1CCC1C(=O)O] | 1-(N-phosphonocarbamimidoyl)azetidine-2-carboxylic acid |
| 6 | 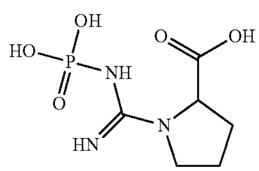 [SMILES: N=C(NP(=O)(O)O)N1CCCC1C(=O)O] | 1-(N-phosphonocarbamimidoyl)pyrrolidine-2-carboxylic acid |
| 7 | 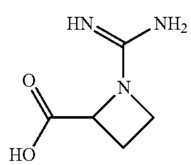 | 1-carbamimidoylazetidine-2-carboxylic acid |
| 8 | 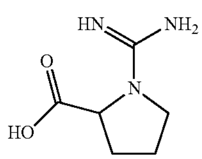 [SMILES: N=C(N)N1CCCC1C(=O)O] | 1-carbamimidoylpyrrolidine-2-carboxylic acid |
| 9 | 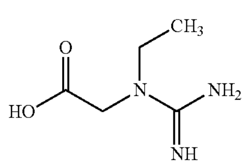 | 2-(1-ethylguanidino)acetic acid |
| 10 | 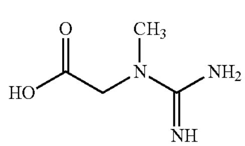 | 2-(1-methylguanidino)acetic acid (Creatine) |

TABLE 8-continued

Selected Phosphocreatine System Inhibitors

| Compound Number | Structure | Compound Name |
|---|---|---|
| 11 | 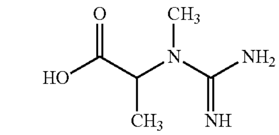 | 2-(1-methylguanidino)propanoic acid |
| 12 | 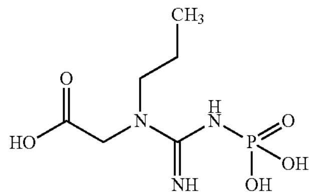 | 2-(3-phosphono-1-propylguanidino)acetic acid |
| 13 | 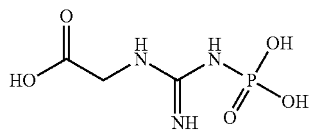 [SMILES: N=C(NCC(=O)O)NP(=O)(O)O] | 2-(1-phosphonocarbamimidamido)acetic acid |
| 14 | 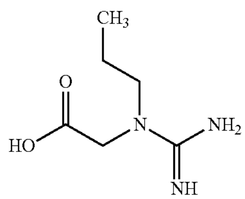 | 2-(1-propylguanidino)acetic acid |
| 15 | 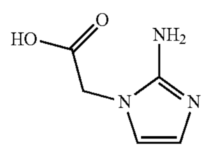 | 2-(2-amino-1H-imidazol-1-yl)acetic acid |
| 16 | 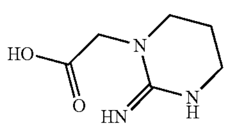 [SMILES: N=C1NCCCN1CC(=O)O] | 2-(2-imino-1,3-diazinan-1-yl)acetic acid (1-Carboxymethyl-2-iminohexahydropyrimidine) |
| 17 | 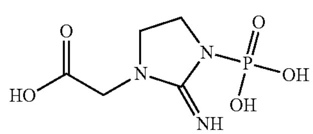 [SMILES: N=C1N(CC(=O)O)CCN1P(=O)(O)O] | 2-(2-imino-3-phosphonoimidazolidin-1-yl)acetic acid (N-Phosphoryl Cyclocreatine) |
| 18 | 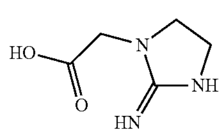 | 2-(2-iminoimidazolidin-1-yl)acetic acid (Cyclocreatine) |
| 19 | 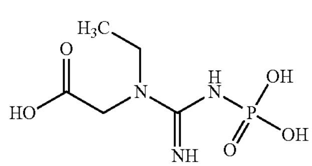 | 2-(3-phosphono-1-ethylguanidino)acetic acid |

TABLE 8-continued

Selected Phosphocreatine System Inhibitors

| Compound Number | Structure | Compound Name |
| --- | --- | --- |
| 20 | 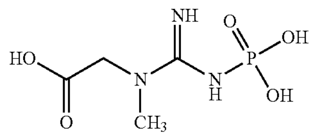 | 2-(3-phosphono-1-methylguanidino)acetic acid (N-Phosphoryl Creatine) |
| 21 | 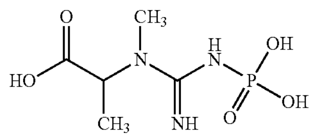 | 2-(3-phosphono-1-methylguanidino)propionic acid |
| 22 | 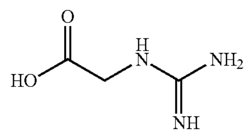 | 2-carbamimidamidoacetic acid (Guanidinoacetic acid) |
| 23 | 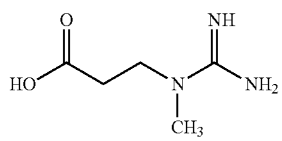 | 3-(1-methylguanidino)propanoic acid (Homocreatine) |
| 24 | 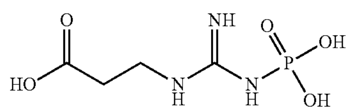 [SMILES: N=C(NCCC(=O)O)NP(=O)(O)O] | 3-(3-phosphonoguanidino)propionic acid |
| 25 | 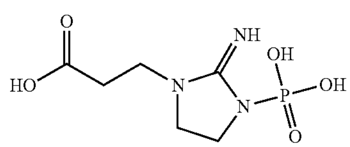 [SMILES: N=C1N(CCC(=O)O)CCN1P(=O)(O)O] | 3-(2-imino-3-phosphonoimidazolidin-1-yl)propanoic acid (N-Phosphoryl Homocyclocreatine) |
| 26 | 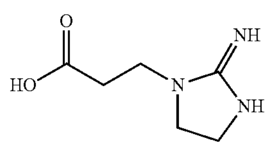 [SMILES: N=C1NCCN1CCC(=O)O] | 3-(2-iminoimidazolidin-1-yl)propanoic acid (Homocyclocreatine) |
| 27 | 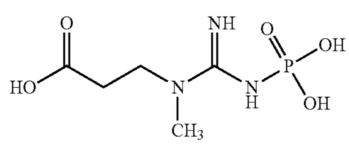 | 3-(3-phosphono-1-methylguanidino)propionic acid (Phosohomocreatine) |
| 28 | 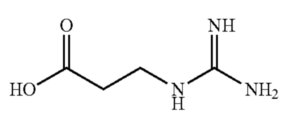 | 3-carbamimidamidopropanoic acid (β-Guandinopropionic acid; β-GPA) |
| 29 | 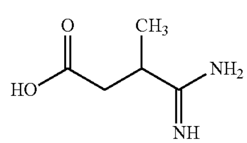 | 3-carbamimidoyl-3-methylpropanoic acid (Carbocreatine) |
| 30 | 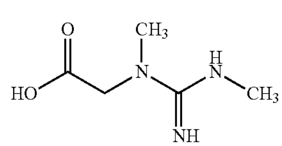 | 2-(1,3-dimethylguanidino)acetic acid |

TABLE 8-continued

Selected Phosphocreatine System Inhibitors

| Compound Number | Structure | Compound Name |
|---|---|---|
| 31 | 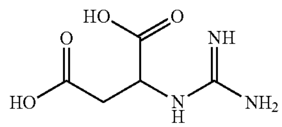 [SMILES: N=C(N)NC(CC(=O)O)C(=O)O] | 2-carbamimidamidobutanedioic acid |
| 32 | 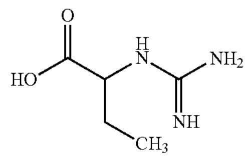 | 2-carbamimidamidobutanoic acid |
| 33 | 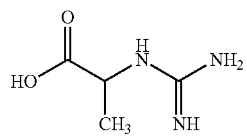 | 2-carbamimidamidopropanoic acid |
| 34 | 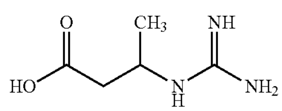 | 3-carbamimidamidobutanoic acid (β-DL-Guanidinobutanoicic acid; β-GBA) |
| 35 | 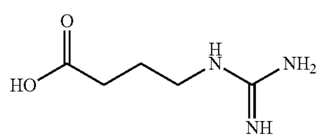 | 4-carbamimidamidobutanoic acid |
| 36 | 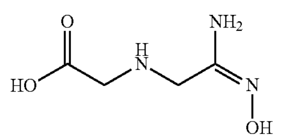 | 2-({[N''-hydroxycarbamimidoyl]methyl}amino) acetic acid |
| 37 | 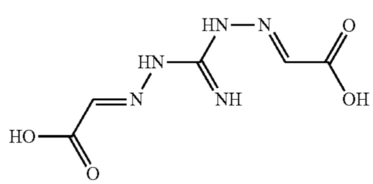 [SMILES: N=C(N/N=C/C(=O)O)N/N=C/C(=O)O] | 2-({3-[(carboxymethylidene)amino]guanidino} imino)acetic acid |
| 38 | 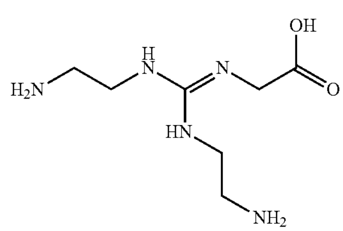 [SMILES: NCCNC(=NCC(=O)O)NCCN] | 2-({bis[(2-aminoethyl)amino]methylidene}amino) acetic acid |
| 39 | 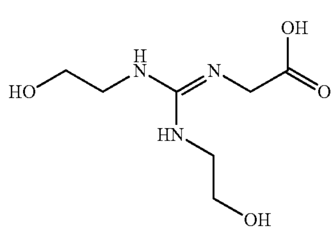 [SMILES: O=C(O)CN=C(NCCO)NCCO] | 2-({bis[(2-hydroxyethyl)amino]methylidene}amino) acetic acid |

TABLE 8-continued

Selected Phosphocreatine System Inhibitors

| Compound Number | Structure | Compound Name |
| --- | --- | --- |
| 40 | 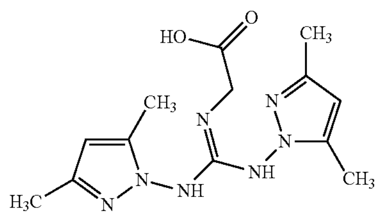 | 2-({bis[(3,5-dimethyl-1H-pyrazol-1-yl)amino]methylidene}amino)acetic acid |
| 41 | 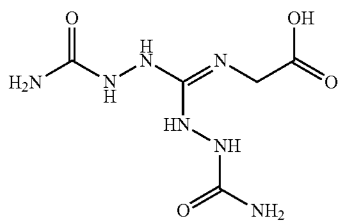 [SMILES: NC(=O)NNC(=NCC(=O)O)NNC(N)=O] | 2-({bis[(carbamoylamino)amino]methylidene}amino)acetic acid |
| 42 | 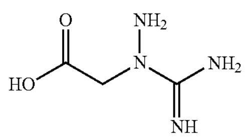 | 2-(1-aminoguanidino)acetic acid |
| 43 | 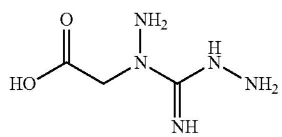 | 2-(1,3-diaminoguanidino)acetic acid |
| 44 | 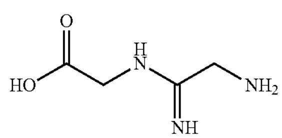 | 2-{N-(2-amino)ethanimidamido}acetic acid |
| 45 | 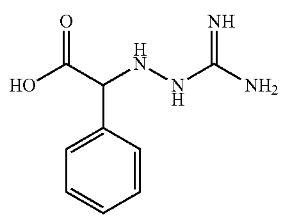 [SMILES: N=C(N)NNC(C(=O)O)c1ccccc1] | 2-(carbamimidamidoamino)-2-phenylacetic acid |
| 46 | 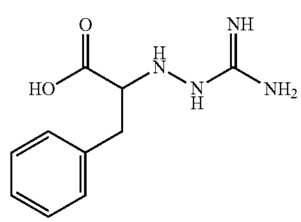 [SMILES: N=C(N)NNC(Cc1ccccc1)C(=O)O] | 2-(carbamimidamidoamino)-3-phenylpropanoic acid |
| 47 | 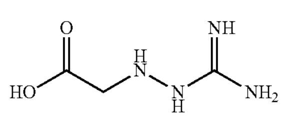 | 2-(carbamimidamidoamino)acetic acid |

TABLE 8-continued

Selected Phosphocreatine System Inhibitors

| Compound Number | Structure | Compound Name |
|---|---|---|
| 48 | 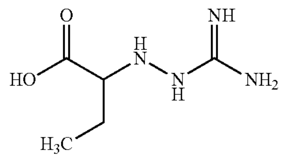 | 2-(carbamimidamidoamino)butanoic acid |
| 49 | 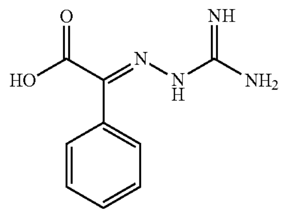 [SMILES: N=C(N)N/N=C(/C(=O)O)c1ccccc1] | 2-(carbamimidamidoimino)-2-phenylacetic acid |
| 50 | 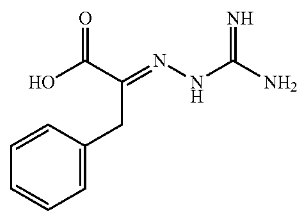 [SMILES: N=C(N)N/N=C(\Cc1ccccc1)C(=O)O] | 2-(carbamimidamidoimino)-3-phenylpropanoic acid |
| 51 | 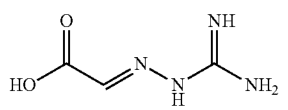 | 2-(carbamimidamidoimino)acetic acid |
| 52 | 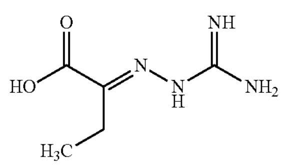 | 2-(carbamimidamidoimino)butanoic acid |
| 53 | 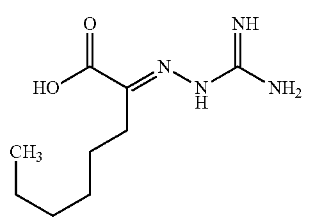 | 2-(carbamimidamidoimino)octanoic acid |
| 54 | 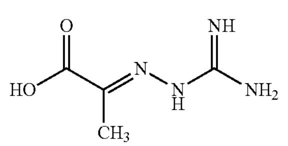 | 2-(carbamimidamidoimino)propanoic acid |
| 55 | 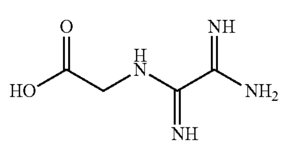 | 2-(N-carbamimidoylimidamido)acetic acid |
| 56 | 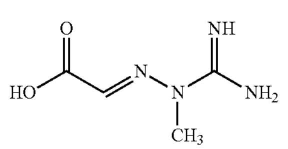 | 2-[(1-methylguanidino)imino]acetic acid |

TABLE 8-continued

Selected Phosphocreatine System Inhibitors

| Compound Number | Structure | Compound Name |
|---|---|---|
| 57 | 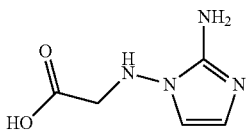 [SMILES: Nc1nccn1NCC(=O)O] | 2-[(2-amino-1H-imidazol-1-yl)amino]acetic acid |
| 58 | 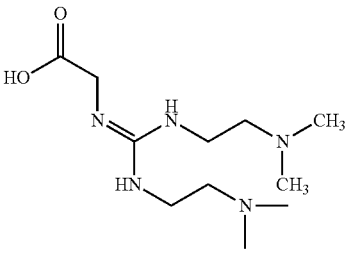 [SMILES: CN(C)CCNC(=NCC(=O)O)NCCN(C)C] | 2-[(2,10-dimethyl-2,5,7,10-tetraazaundecan-6-ylidene)amino]acetic acid |
| 59 | 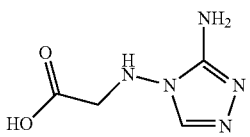 [SMILES: Nc1nncn1NCC(=O)O] | 2-[(3-amino-4H-1,2,4-triazol-4-yl)amino]acetic acid |
| 60 | 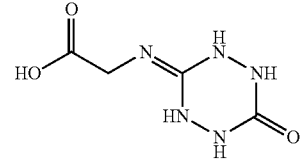 | 2-[(6-oxo-1,2,4,5-tetrazinan-3-ylidene)amino]acetic acid |
| 61 | 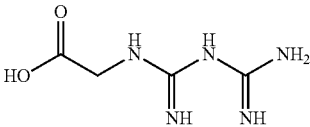 [SMILES: N=C(N)NC(=N)NCC(=O)O] | 2-(biguanide)acetic acid |
| 62 | 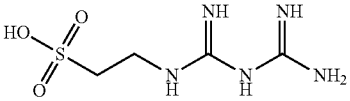 [SMILES: N=C(N)NC(=N)NCCS(=O)(=O)O] | 2-(biguanide)ethane-1-sulfonic acid |
| 63 | 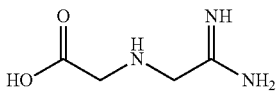 | 2-[(carbamimidoylmethyl)amino]acetic acid |
| 64 | 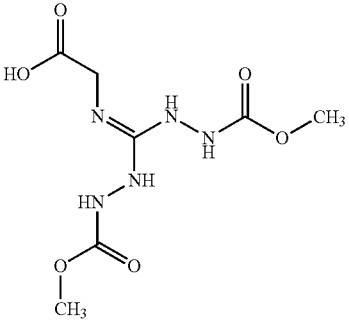 [SMILES: COC(=O)NNC(=NCC(=O)O)NNC(=O)OC] | 2-[(di{[(methoxycarbonyl)amino]amino}methylidene)amino]acetic acid |

TABLE 8-continued

Selected Phosphocreatine System Inhibitors

| Compound Number | Structure | Compound Name |
| --- | --- | --- |
| 65 | 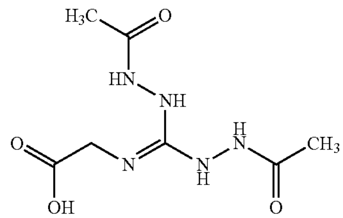 [SMILES: CC(=O)NNC(=NCC(=O)O)NNC(C)=O] | 2-[(di{[(acetyl)amino]amino}methylidene)amino]acetic acid |
| 66 | 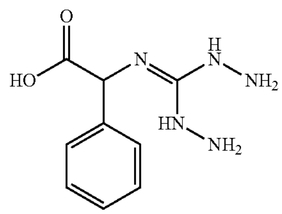 [SMILES: NNC(=NC(C(=O)O)c1ccccc1)NN] | 2-[(dihydrazinylmethylidene)amino]-2-phenylacetic acid |
| 67 | 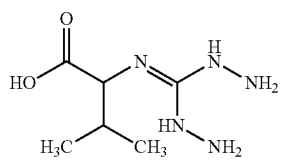 | 2-[(dihydrazinylmethylidene)amino]-3-methylbutanoic acid |
| 68 | 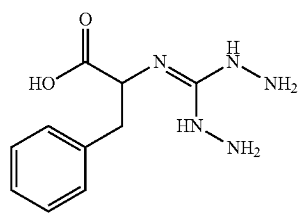 [SMILES: NNC(=NC(Cc1ccccc1)C(=O)O)NN] | 2-[(dihydrazinylmethylidene)amino]-3-phenylpropanoic acid |
| 69 | 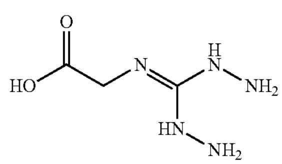 | 2-[(dihydrazinylmethylidene)amino]acetic acid |
| 70 | 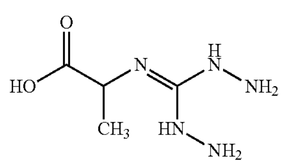 | 2-[(dihydrazinylmethylidene)amino]propanoic acid |
| 71 | 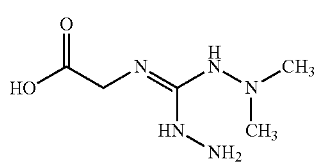 | 2-[[(2,2-dimethylhydrazin-1-yl)(hydrazinyl)methylidene]amino]acetic acid |
| 72 | 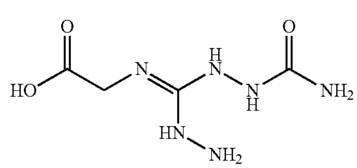 [SMILES: NN/C(=N\CC(=O)O)NNC(N)=O] | 2-[{[(carbamoylamino)amino]hydrazinyl)methylidene}amino]acetic acid |

TABLE 8-continued

Selected Phosphocreatine System Inhibitors

| Compound Number | Structure | Compound Name |
|---|---|---|
| 73 | 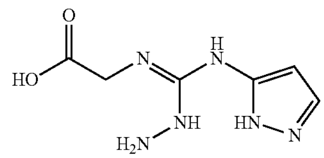 [SMILES: NN/C(=N\CC(=O)O)Nc1ccn[nH]1] | 2-[{hydrazinyl[(1H-pyrazol-5-yl)amino]methylidene}amino]acetic acid |
| 74 | 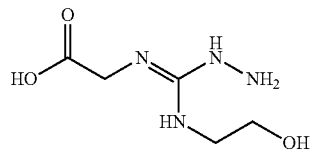 [SMILES: NN/C(=N/CC(=O)O)NCCO] | 2-[{hydrazinyl[(2-hydroxyethyl)amino]methylidene}amino]acetic acid |
| 75 | 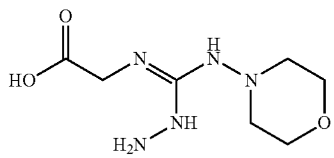 [SMILES: NN/C(=N\CC(=O)O)NN1CCOCC1] | 2-[{hydrazinyl[(morpholin-4-yl)amino]methylidene}amino]acetic acid |
| 76 | 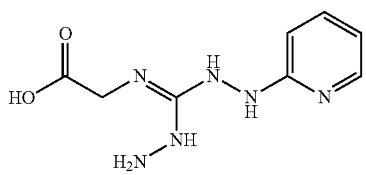 [SMILES: NN/C(=N\CC(=O)O)NNc1ccccn1] | 2-[{hydrazinyl[2-(pyridin-2-yl)hydrazin-1-yl]methylidene}amino]acetic acid |
| 77 | 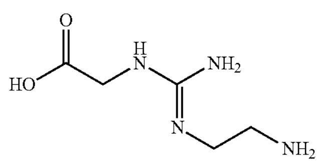 [SMILES: NCC/N=C(\N)NCC(=O)O] | 2-[2-(2-aminoethyl)carbamimidamido]acetic acid |
| 78 | 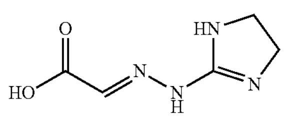 [SMILES: O=C(O)/C=N/NC1=NCCN1] | 2-[2-(4,5-dihydro-1H-imidazol-2-yl)hydrazin-1-ylidene]acetic acid |
| 79 | 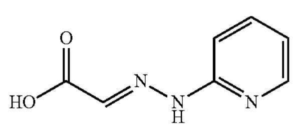 [SMILES: O=C(O)/C=N/Nc1ccccn1] | 2-[2-(pyridin-2-yl)hydrazin-1-ylidene]acetic acid |
| 80 | 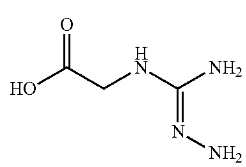 | 2-[2-aminocarbamimidamido]acetic acid |
| 81 | 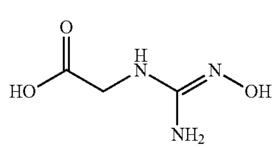 | 2-[2-hydroxycarbamimidamido]acetic acid |
| 82 | 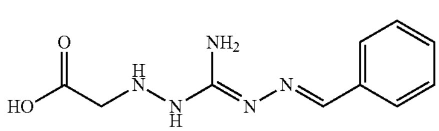 [SMILES: N/C(=N\N=C\c1ccccc1)NNCC(=O)O] | 2-{[2-[(phenylmethylidene)amino]carbamimidamido]amino}acetic acid |

TABLE 8-continued

Selected Phosphocreatine System Inhibitors

| Compound Number | Structure | Compound Name |
|---|---|---|
| 83 | 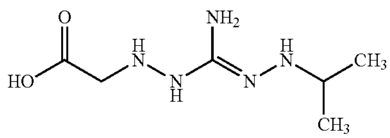 | 2-{[2-[(propan-2-yl)amino]carbamimidamido]amino} acetic acid |
| 84 | 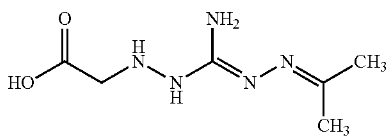 | 2-{[2-[(propan-2-ylidene)amino]carbamimidamido]amino} acetic acid |
| 85 | 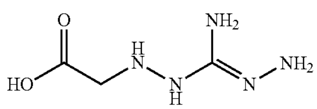 | 2{[2-aminocarbamimidamido]amino}acetic acid |
| 86 | 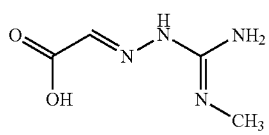 | 2{[2-methylcarbamimidamido]imino}acetic acid |
| 87 | 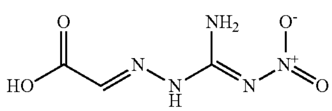 [SMILES: N/C(=N\[N+](=O)[O-])N/N=C/C(=O)O] | 2-{[2-nitrocarbamimidamido]imino}acetic acid |
| 88 | 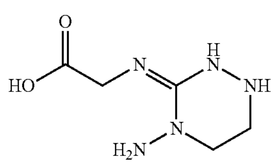 [SMILES: NN1CCNN/C1=N/CC(=O)O] | 2-{[4-amino-1,2,4-triazinan-3-ylidene]amino}acetic acid |
| 89 | 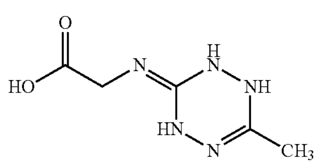 | 2-{[6-methyl-1,2,3,4-tetrahydro-1,2,4,5-tetrazin-3-ylidene]amino}acetic acid |
| 90 | 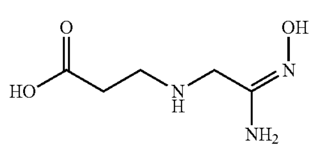 [SMILES: N/C(CNCCC(=O)O)=N/O] | 3-({[N'-hydroxycarbamimidoyl]methyl}amino) propanoic acid |
| 91 | 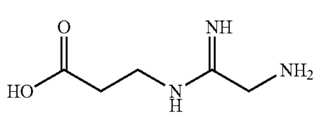 | 3-{N-(2-amino)ethanimidamido}propanoic acid |
| 92 | 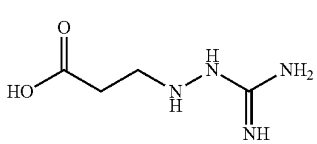 | 3-(carbamimidamidoamino)propanoic acid |

TABLE 8-continued

Selected Phosphocreatine System Inhibitors

| Compound Number | Structure | Compound Name |
|---|---|---|
| 93 | 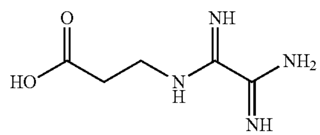 [SMILES: N=C(N)C(=N)NCCC(=O)O] | 3-(N-carbamimidoylimidamido)propanoic acid |
| 94 | 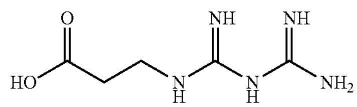 [SMILES: N=C(N)NC(=N)NCCC(=O)O] | 3-(biguanide)propanoic acid |
| 95 | 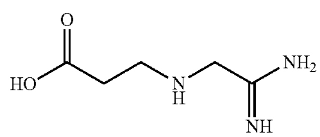 | 3-[(carbamimidoylmethyl)amino]propanoic acid |
| 96 | 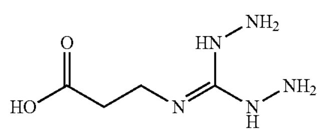 [SMILES: NNC(=NCCC(=O)O)NN] | 3-[(dihydrazinylmethylidene)amino]propanoic acid |
| 97 | 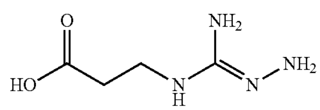 | 3-[2-aminocarbamimidamido]propanoic acid |
| 98 | 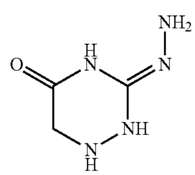 | 3-hydrazinylidene-1,2,4-triazinan-5-one |
| 99 | 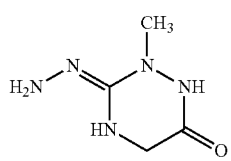 | 3-hydrazinylidene-2-methyl-1,2,4-triazinan-6-one |
| 100 | 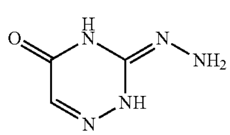 | 3-hydrazinylidene-2,3,4,5-tetrahydro-1,2,4-triazin-5-one |
| 101 | 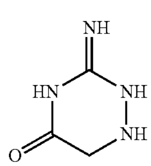 | 3-imino-1,2,4-triazinan-5-one |
| 102 | 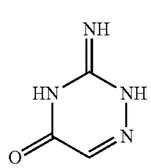 | 3-imino-2,3,4,5-tetrahydro-1,2,4-triazin-5-one |

TABLE 8-continued

Selected Phosphocreatine System Inhibitors

| Compound Number | Structure | Compound Name |
|---|---|---|
| 103 | 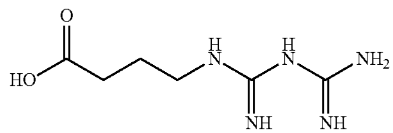 [SMILES: N=C(N)NC(=N)NCCCC(=O)O] | 4-(biguanide)butanoic acid |
| 104 | 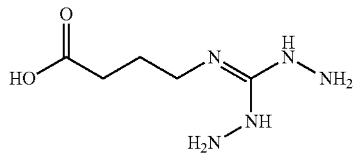 [SMILES: NNC(=NCCCC(=O)O)NN] | 4-[(dihydrazinylmethylidene)amino]butanoic acid |
| 105 | 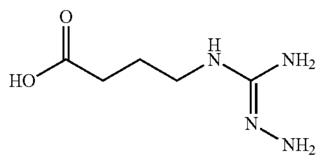 [SMILES: N/N=C(\N)NCCCC(=O)O] | 4-[2-aminocarbamimidamido]butanoic acid |
| 107 | 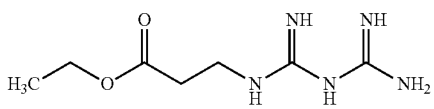 | ethyl 3-(biguanide)propanoate |
| 108 | 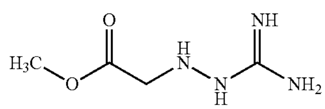 | methyl 2-(carbamimidamidoamino)acetate |
| 109 | 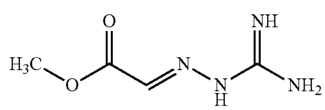 | methyl 2-(carbamimidamidoimino)acetate |
| 110 | 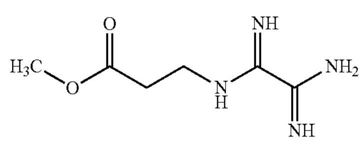 | methyl 3-(N-carbamimidoylimidamido)propanoate |
| 111 | 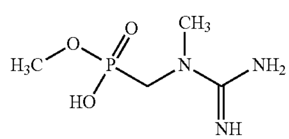 | methoxy(1-methylcarbamimidamidomethyl)phosphinic acid |
| 112 | 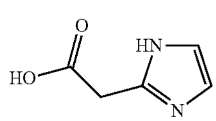 | 2-(1H-imidazol-2-yl)acetic acid |
| 113 | 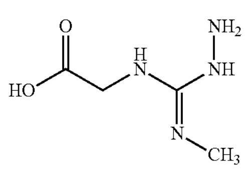 | 2-[1-amino-2-methylguanidino]acetic acid |
| 114 | 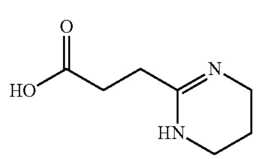 [SMILES: O=C(O)CCC1=NCCCN1] | 3-(1,4,5,6-tetrahydropyrimidin-2-yl)propanoic acid |

TABLE 8-continued

Selected Phosphocreatine System Inhibitors

| Compound Number | Structure | Compound Name |
|---|---|---|
| 115 | 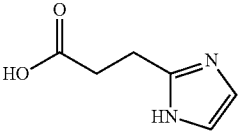 | 3-(1H-imidazol-2-yl)propanoic acid |
| 116 | 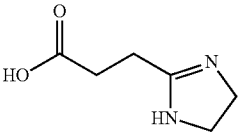 | 3-(4,5-dihydro-1H-imidazol-2-yl)propanoic acid |
| 117 | 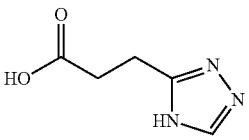 | 3-(4H-1,2,4-triazol-3-yl)propanoic acid |
| 118 | 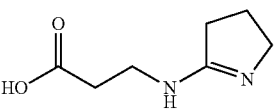 [SMILES: O=C(O)CCNC1=NCCC1] | 3-[(3,4-dihydro-2H-pyrrol-5-yl)amino]propanoic acid |
| 119 | 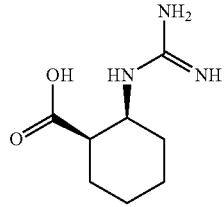 [SMILES: N=C(N)N[C@H]1CCCC[C@H]1C(=O)O] | (1R,2S)-2-carbamimidamidocyclohexane-1-carboxylic acid |
| 120 | 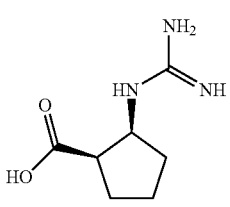 [SMILES: N=C(N)N[C@H]1CCC[C@H]1C(=O)O] | (1R,2S)-2-carbamimidamidocyclopentane-1-carboxylic acid |
| 121 | 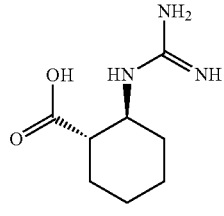 [SMILES: N=C(N)N[C@H]1CCCC[C@@H]1C(=O)O] | (1S,2S)-2-carbamimidamidocyclohexane-1-carboxylic acid |
| 122 | 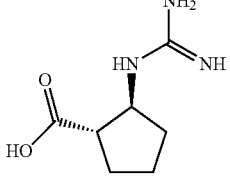 | (1S,2S)-2-carbamimidamidocyclopentane-1-carboxylic acid |
| 123 | 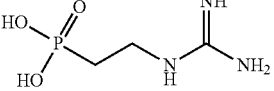 | (2-carbamimidamidoethyl)phosphonic acid |

TABLE 8-continued

Selected Phosphocreatine System Inhibitors

| Compound Number | Structure | Compound Name |
|---|---|---|
| 124 | 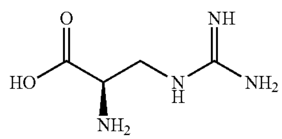 | (2R)-2-amino-3-carbamimidamidopropanoic acid |
| 125 | 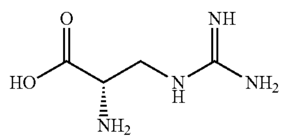 | (2S)-2-amino-3-carbamimidamidopropanoic acid |
| 126 | 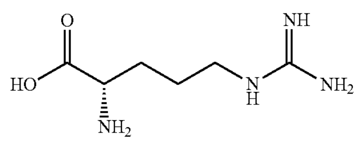 [SMILES: N=C(N)NCCC[C@H](N)C(=O)O] | (2S)-2-amino-5-carbamimidamidopentanoic acid (L-Arg) |
| 127 | 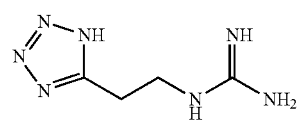 [SMILES: N=C(N)NCCc1nnn[nH]1] | 1-[2-(1H-1,2,3,4-tetrazol-5-yl)ethyl]guanidine |
| 128 | 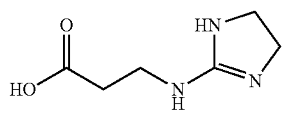 [SMILES: O=C(O)CCNC1=NCCN1] | 3-[(4,5-dihydro-1H-imidazol-2-yl)amino]propanoic acid |
| 129 | 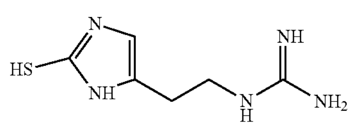 [SMILES: N=C(N)NCCc1cnc(S)[nH]1] | 1-[2-(2-sulfanyl-1H-imidazol-5-yl)ethyl]guanidine |
| 130 | 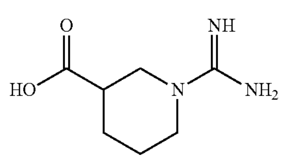 [SMILES: N=C(N)N1CCCC(C(=O)O)C1] | 1-carbamimidoylpiperidine-3-carboxylic acid |
| 131 | 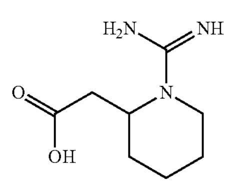 [SMILES: N=C(N)N1CCCCC1CC(=O)O] | 2-(1-carbamimidoylpiperidin-2-yl)acetic acid |
| 132 | 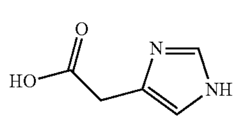 | 2-(1H-imidazol-4-yl)acetic acid |
| 133 | 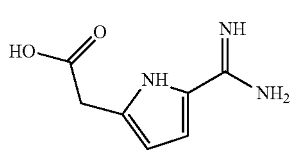 [SMILES: N=C(N)c1ccc(CC(=O)O)[nH]1] | 2-(5-carbamimidoyl-1H-pyrrol-2-yl)acetic acid |

TABLE 8-continued

Selected Phosphocreatine System Inhibitors

| Compound Number | Structure | Compound Name |
|---|---|---|
| 134 | 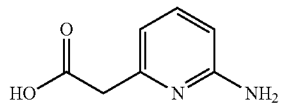 [SMILES: Nc1cccc(CC(=O)O)n1] | 2-(6-aminopyridin-2-yl)acetic acid |
| 135 | 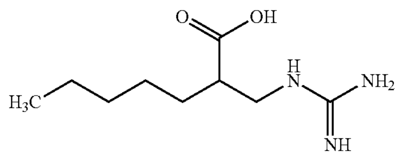 | 2-(carbamimidamidomethyl)heptanoic acid |
| 136 | 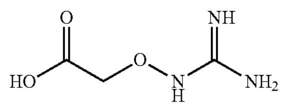 | 2-(carbamimidamidooxy)acetic acid |
| 137 | 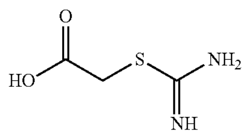 | 2-(carbamimidoylsulfanyl)acetic acid |
| 138 | 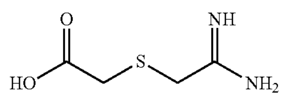 | 2-[(carbamimidoylmethyl)sulfanyl] acetic acid |
| 139 | 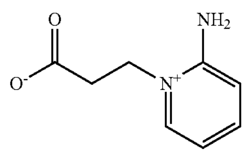 [SMILES: Nc1cccc[n+]1CCC(=O)[O-]] | 2-amino-1-(2-carboxylatoethyl)pyridin-1-ium |
| 140 | 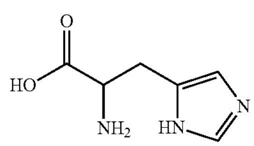 [SMILES: NC(Cc1cnc[nH]1)C(=O)O] | 2-amino-3-(1H-imidazol-5-yl)propanoic acid |
| 141 | 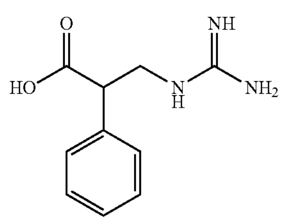 [SMILES: N=C(N)NCC(C(=O)O)c1ccccc1] | 2-phenyl-3-carbamimidamidopropanoic acid |
| 142 | 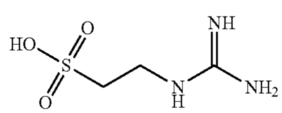 | 2-carbamimidamidoethane-1-sulfonic acid |
| 143 | 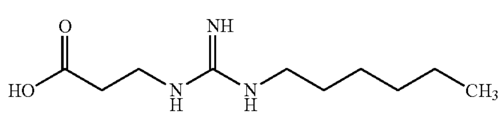 | 3-(3-hexylguanidino)propanoic acid |
| 144 | 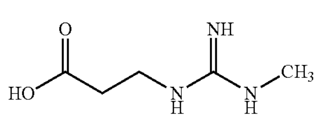 | 3-(3-methylguanidino)propanoic acid |

TABLE 8-continued

Selected Phosphocreatine System Inhibitors

| Compound Number | Structure | Compound Name |
|---|---|---|
| 145 | 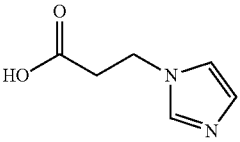 | 3-(1H-imidazol-1-yl)propanoic acid |
| 147 | 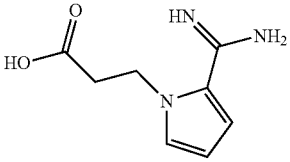 [SMILES: N=C(N)c1cccn1CCC(=O)O] | 3-(2-carbamimidoyl-1H-pyrrol-1-yl)propanoic acid |
| 148 | 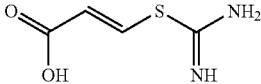 | (E)-3-(carbamimidoylsulfanyl)prop-2-enoic acid |
| 149 | 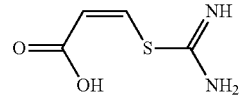 | (Z)-3-(carbamimidoylsulfanyl)prop-2-enoic acid |
| 150 | 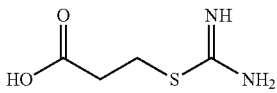 | 3-(carbamimidoylsulfanyl)propanoic acid |
| 151 | 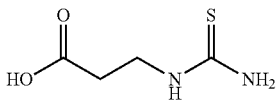 | 3-(carbamothioylamino)propanoic acid |
| 152 | 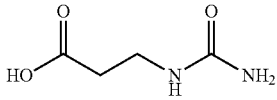 | 3-(carbamoylamino)propanoic acid |
| 153 | 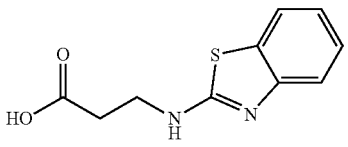 [SMILES: O=C(O)CCNc1nc2ccccc2s1] | 3-[(1,3-benzothiazol-2-yl)amino]propanoic acid |
| 154 | 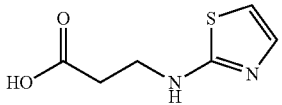 [SMILES: O=C(O)CCNc1nccs1] | 3-[(1,3-thiazol-2-yl)amino]propanoic acid |
| 155 | 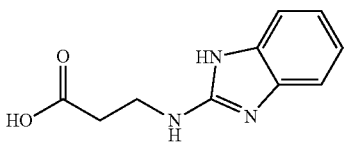 [SMILES: O=C(O)CCNc1nc2ccccc2[nH]1] | 3-[(1H-1,3-benzodiazol-2-yl)amino]propanoic acid |
| 156 | 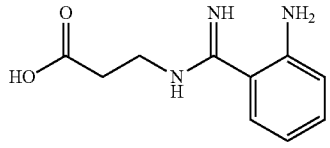 [SMILES: N=C(NCCC(=O)O)c1ccccc1N] | 3-[N-(2-aminobenzene-1-carbamimido)]propanoic acid |

TABLE 8-continued

Selected Phosphocreatine System Inhibitors

| Compound Number | Structure | Compound Name |
|---|---|---|
| 157 | 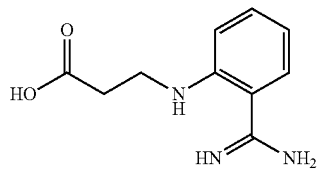 [SMILES: N=C(N)c1ccccc1NCCC(=O)O] | 3-[(2-carbamimidoylphenyl)amino]propanoic acid |
| 158 | 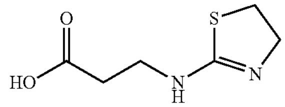 [SMILES: O=C(O)CCNC1=NCCS1] | 3-[(4,5-dihydro-1,3-thiazol-2-yl)amino]propanoic acid |
| 159 | 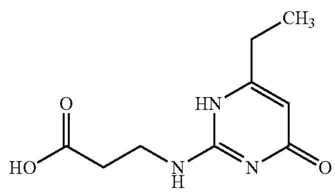 | 3-[(6-ethyl-4-oxo-1,4-dihydropyrimidin-2-yl)amino]propanoic acid |
| 160 | 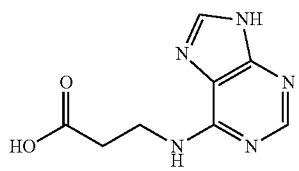 [SMILES: O=C(O)CCNc1ncnc2[nH]cnc12] | 3-[(9H-purin-6-yl)amino]propanoic acid |
| 161 | 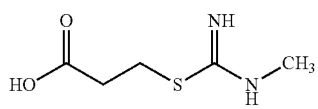 | 3-[(N-methylcarbamimidoyl)sulfanyl]propanoic acid |
| 162 | 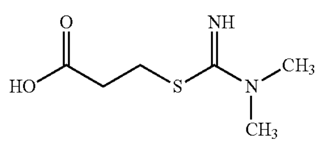 | 3-[(N,N-dimethylcarbamimidoyl)sulfanyl]propanoic acid |
| 163 | 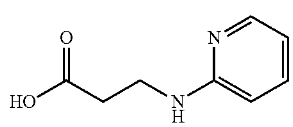 [SMILES: O=C(O)CCNc1ccccn1] | 3-[(pyridin-2-yl)amino]propanoic acid |
| 164 | 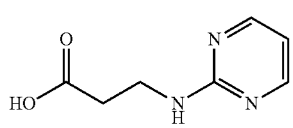 [SMILES: O=C(O)CCNc1ncccn1] | 3-[(pyrimidin-2-yl)amino]propanoic acid |
| 165 | 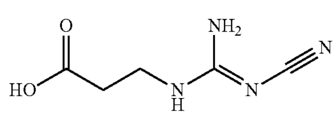 [SMILES: N#C/N=C(\N)NCCC(=O)O] | 3-[2-cyanocarbamimidamido]propanoic acid |
| 166 | 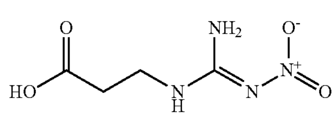 [SMILES: N/C(=N\[N+](=O)[O-])NCCC(=O)O] | 3-[2-nitrocarbamimidamido]propanoic acid |
| 167 | 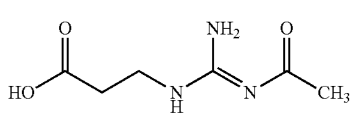 | 3-{[(acetylimino)(amino)methyl]amino}propanoic acid |

TABLE 8-continued

Selected Phosphocreatine System Inhibitors

| Compound Number | Structure | Compound Name |
| --- | --- | --- |
| 168 | 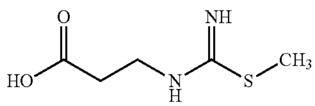 | 3-{[(methylsulfanyl)methanimidoyl]amino}propanoic acid |
| 169 | 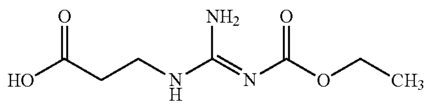 | 3-{[amino[(ethoxycarbonyl)imino]methyl]amino}propanoic acid |
| 173 | 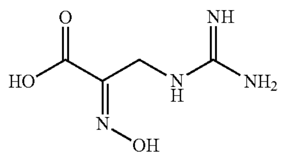 [SMILES: N=C(N)NC/C(=N\O)C(=O)O] | 3-carbamimidamido-2-(hydroxyimino)propanoic acid |
| 174 | 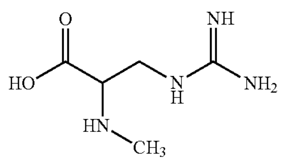 | 3-carbamimidamido-2-(methylamino)propanoic acid |
| 175 | 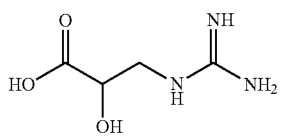 | 3-carbamimidamido-2-hydroxypropanoic acid |
| 176 | 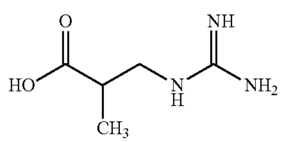 | 3-carbamimidamido-2-methylpropanoic acid |
| 177 | 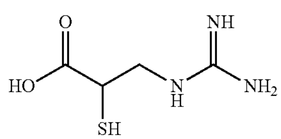 | 3-carbamimidamido-2-sulfanylpropanoic acid |
| 178 | 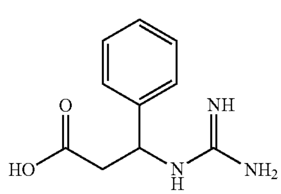 [SMILES: N=C(N)NC(CC(=O)O)c1ccccc1] | 3-carbamimidamido-3-phenylpropanoic acid |
| 179 | 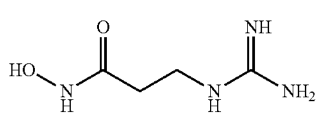 | 3-carbamimidamido-N-hydroxypropanamide |
| 180 | 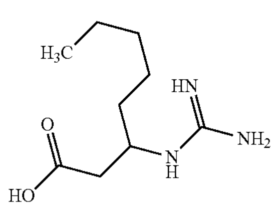 | 3-carbamimidamidooctanoic acid |

TABLE 8-continued

Selected Phosphocreatine System Inhibitors

| Compound Number | Structure | Compound Name |
|---|---|---|
| 181 | 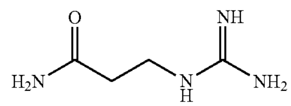 | 3-carbamimidamidopropanamide |
| 182 | 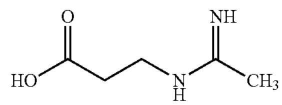 | 3-ethanimidamidopropanoic acid |
| 183 | 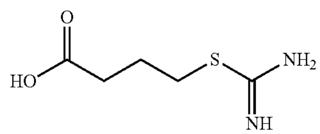 | 4-(carbamimidoylsulfanyl)butanoic acid |
| 184 | 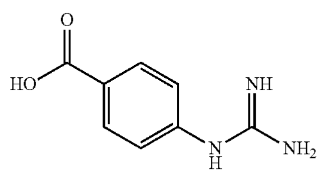 [SMILES: N=C(N)Nc1ccc(C(=O)O)cc1] | 4-carbamimidamidobenzoic acid |
| 185 | 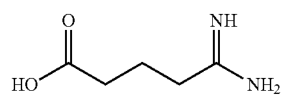 | 4-carbamimidoylbutanoic acid |
| 186 | 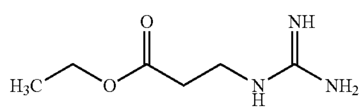 | ethyl 3-guanidinopropanoate |
| 187 | 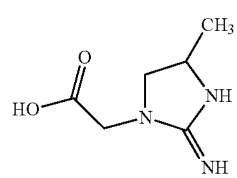 | 2-(2-imino-4-methylimidazolidin-1-yl)acetic acid |
| 188 | 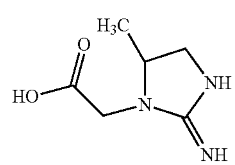 | 2-(2-imino-5-methylimidazolidin-1-yl)acetic acid |
| 189 | 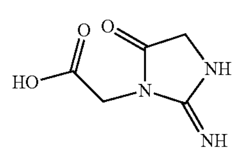 | 2-(2-imino-5-oxoimidazolidin-1-yl)acetic acid |
| 190 | 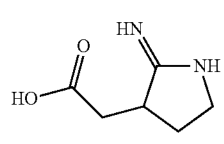 | 2-(2-iminopyrrolidin-3-yl)acetic acid |

TABLE 8-continued

Selected Phosphocreatine System Inhibitors

| Compound Number | Structure | Compound Name |
| --- | --- | --- |
| 191 | 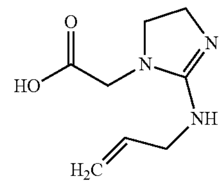 | 2-{2-[(prop-2-en-1-yl)amino]-4,5-dihydro-1H-imidazol-1-yl}acetic acid |
| 192 | 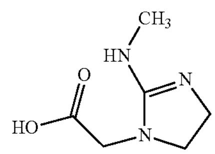 | 2-[2-(methylamino)-4,5-dihydro-1H-imidazol-1-yl]acetic acid |
| 193 | 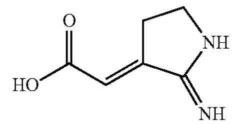 | 2-[2-iminopyrrolidin-3-ylidene]acetic acid |
| 194 | 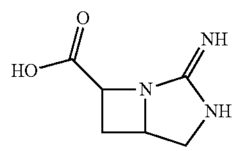 | 2-imino-1,3-diazabicyclo[3.2.0]heptane-7-carboxylic acid |
| 195 | 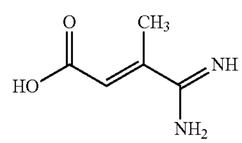 | 3-carbamimidoyl-3-methylprop-2-enoic acid |
| 196 | 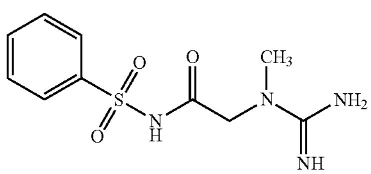 [SMILES: CN(CC(=O)NS(=O)(=O)c1ccccc1)C(=N)N] | N-(benzenesulfonyl)-2-(1-methylguanidino)acetamide |
| 197 | 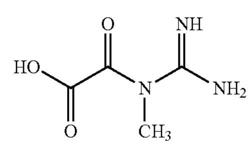 | [carbamimidoyl(methyl)carbamoyl]formic acid |
| 198 | 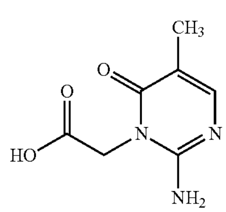 | 2-(2-amino-5-methyl-6-oxo-1,6-dihydropyrimidin-1-yl)acetic acid |
| 199 | 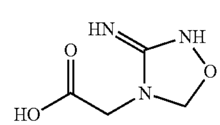 | 2-(3-imino-1,2,4-oxadiazolidin-4-yl)acetic acid |

TABLE 8-continued

Selected Phosphocreatine System Inhibitors

| Compound Number | Structure | Compound Name |
|---|---|---|
| 200 | 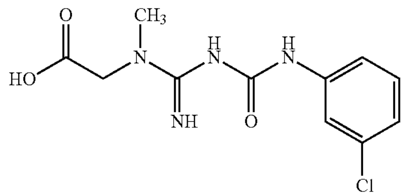 [SMILES: CN(CC(=O)O)C(=N)NC(=O)Nc1cccc(Cl)c1] | 2-[({[(3-chlorophenyl)carbamoyl]amino}methanimidoyl)(methyl)amino]acetic acid |
| 201 | 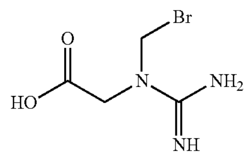 | 2-[1-(bromomethyl)guanidino]acetic acid |
| 202 | 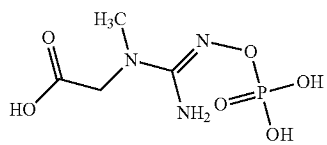 | 2-[1-methyl-2-(phosphonooxy)guanidino]acetic acid |
| 203 | 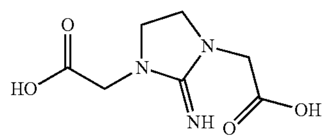 [SMILES: N=C1N(CC(=O)O)CCN1CC(=O)O] | 2-[3-(carboxymethyl)-2-iminoimidazolidin-1-yl]acetic acid |
| 204 | 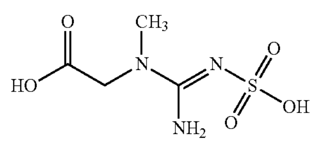 | 2-{[amino(sulfoimino)methyl](methyl)amino}acetic acid |
| 205 | 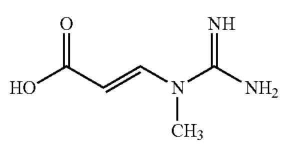 | 3-(1-methylguanidino)prop-2-enoic acid |
| 206 | 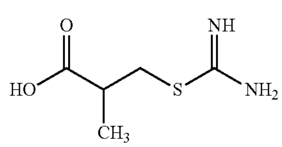 | 3-(carbamimidoylsulfanyl)-2-methylpropanoic acid |
| 207 | 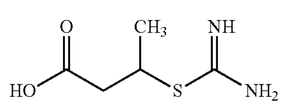 | 3-(carbamimidoylsulfanyl)butanoic acid |
| 209 | 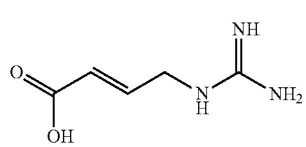 | 4-carbamimidamidobut-2-enoic acid |
| 210 | 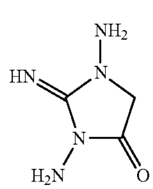 | 1,3-diamino-2-iminoimidazolidin-4-one |

TABLE 8-continued

Selected Phosphocreatine System Inhibitors

| Compound Number | Structure | Compound Name |
|---|---|---|
| 211 | 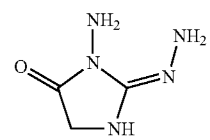 | 3-amino-2-hydrazinylideneimidazolidin-4-one |
| 212 | 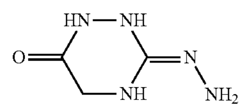 | 3-hydrazinylidene-1,2,4-triazinan-6-one |
| 213 | 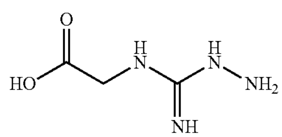 | 2-(3-aminoguanidino)acetic acid |
| 214 | 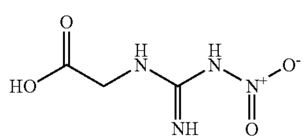 [SMILES: N=C(NCC(=O)O)N[N+](=O)[O-]] | 2-(3-nitroguanidino)acetic acid |
| 215 | 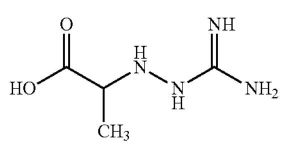 | 2-(carbamimidamidoamino)propanoic acid |
| 216 | 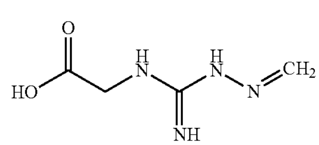 | 2-[3-(methylideneamino)guanidino]acetic acid |
| 217 | 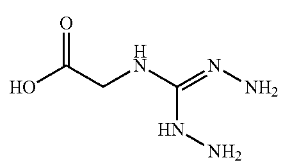 | 2-[1,2-diaminoguanidino]acetic acid |
| 218 | 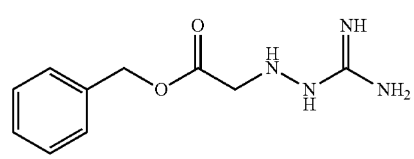 [SMILES: N=C(N)NNCC(=O)OCc1ccccc1] | benzyl 2-(carbamimidamidoamino)acetate |
| 323 | 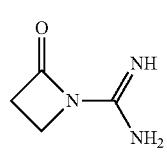 | 2-oxoazetidine-1-carboximidamide |

TABLE 8-continued

Selected Phosphocreatine System Inhibitors

| Compound Number | Structure | Compound Name |
|---|---|---|
| 325 | 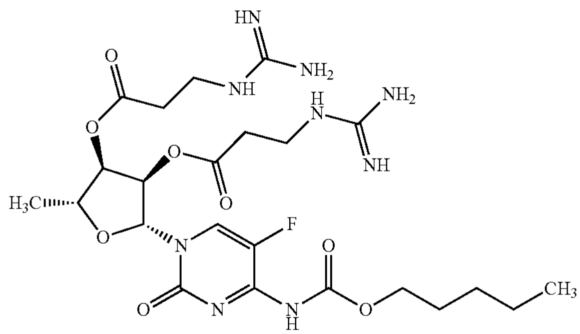 [SMILES: CCCCCOC(=O)Nc1nc(=O)n([C@@H]2O[C@H](C)[C@@H](OC(=O)CCNC(=N)N)[C@H]2OC(=O)CCNC(=N)N)cc1F] | (2R,3R,4R,5R)-4-[(3-carbamimidamidopropanoyl)oxy]-5-(5-fluoro-2-oxo-4-{[(pentyloxy)carbonyl]amino}-1,2-dihydropyrimidin-1-yl)-2-methyloxolan-3-yl 3-carbamimidamidopropanoate |
| 326 | 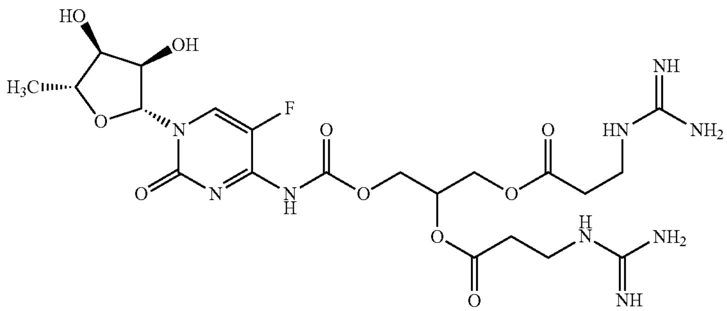 [SMILES: C[C@H]1O[C@@H](n2cc(F)c(NC(=O)OCC(COC(=O)CCNC(=N)N)OC(=O)CCNC(=N)N)nc2=O)[C@H](O)[C@@H]1O] | 1-[(3-carbamimidamidopropanoyl)oxy]-3-[({1-[(2R,3R,4S,5R)-3,4-dihydroxy-5-methyloxolan-2-yl]-5-fluoro-2-oxo-1,2-dihydropyrimidin-4-yl}carbamoyl)oxy]propan-2-yl 3-carbamimidamidopropanoate |
| 324 | 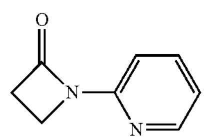 [SMILES: O=C1CCN1c1ccccn1] | 1-(pyridin-2-yl)azetidin-2-one |
| 447 | 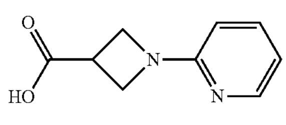 [SMILES: O=C(O)C1CN(c2ccccn2)C1] | 1-(pyridin-2-yl)azetidine-3-carboxylic acid |
| 448 | 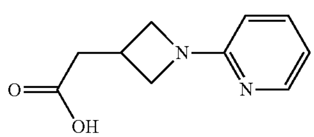 [SMILES: O=C(O)CC1CN(c2ccccn2)C1] | 2-[1-(pyridin-2-yl)azetidin-3-yl]acetic acid |

In another aspect, the invention features a compound selected from any one of compounds 287-298 in Table 9.

TABLE 9

Selected Phosphocreatine System Inhibitors

| Compound Number | Structure | Compound Name |
|---|---|---|
| 287 | 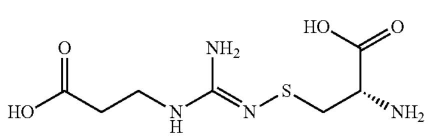 [SMILES: N/C(=N\SC[C@@H](N)C(=O)O)NCCC(=O)O] | (2S)-2-amino-3-{[{amino[(2-carboxyethyl)amino]methylidene}amino]sulfanyl}propanoic acid |

TABLE 9-continued

Selected Phosphocreatine System Inhibitors

| Compound Number | Structure | Compound Name |
|---|---|---|
| 288 | 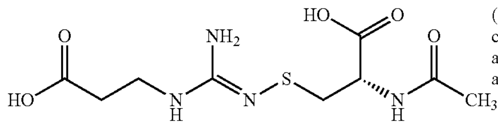 [SMILES: CC(=O)N[C@H](CS/N=C(\N)NCCC(=O)O)C(=O)O] | (2S)-3-{[{amino[(2-carboxyethyl)amino]methylidene}amino]sulfanyl}-2-acetamidopropanoic acid |
| 289 | 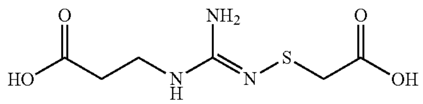 [SMILES: N/C(=N\SCC(=O)O)NCCC(=O)O] | 3-[2-[(carboxymethyl)sulfanyl]carbamimidamido]propanoic acid |
| 290 | 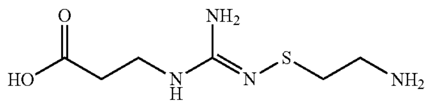 [SMILES: NCCS/N=C(\N)NCCC(=O)O] | 3-[2-[(2-aminoethyl)sulfanyl]carbamimidamido]propanoic acid |
| 291 | 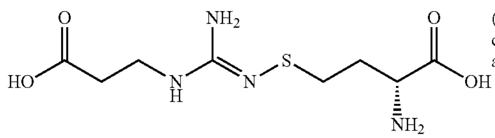 | (2R)-2-amino-4-{[{amino[(2-carboxyethyl)amino]methylidene}amino]sulfanyl}butanoic acid |
| 292 | 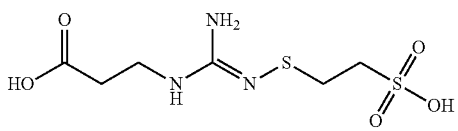 [SMILES: N/C(=N\SCCS(=O)(=O)O)NCCC(=O)O] | 3-[2-[(2-sulfoethyl)sulfanyl]carbamimidamido]propanoic acid |
| 293 | 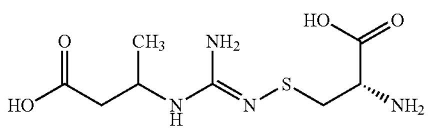 [SMILES: CC(CC(=O)O)N/C(N)=N/SC[C@@H](N)C(=O)O] | 3-[2-{[(2S)-2-amino-2-carboxyethyl]sulfanyl}carbamimidamido]butanoic acid |
| 294 | 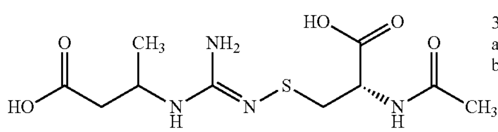 [SMILES: CC(=O)N[C@H](CS/N=C(\N)NC(C)CC(=O)O)C(=O)O] | 3-[2-{[(2S)-2-carboxy-2-acetamidoethyl]sulfanyl}carbamimidamido]butanoic acid |
| 295 | 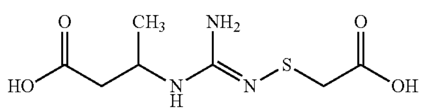 | 3-[2-[(carboxymethyl)sulfanyl]carbamimidamido]butanoic acid |
| 296 | 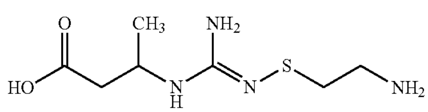 | 3-[2-[(2-aminoethyl)sulfanyl]carbamimidamido]butanoic acid |
| 297 | 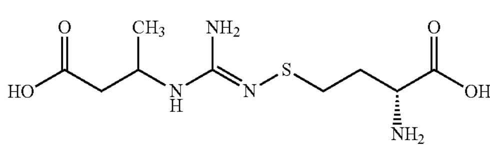 [SMILES: CC(CC(=O)O)N/C(N)=N/SCC[C@@H](N)C(=O)O] | (2R)-2-amino-4-{[{amino[(1-carboxypropan-2-yl)amino]methylidene}amino]sulfanyl}butanoic acid |
| 298 | 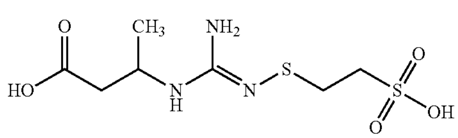 [SMILES: CC(CC(=O)O)N/C(N)=N/SCCS(=O)(=O)O] | 3-[2-[(2-sulfoethyl)sulfanyl]carbamimidamido]butanoic acid |

In another aspect, the invention features a compound selected from any one of compounds 299-322 in Table 10.

TABLE 10

Selected Phosphocreatine System Inhibitors

| Compound Number | Structure | Compound Name |
|---|---|---|
| 299 | 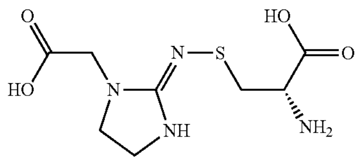 [SMILES: N[C@H](CS/N=C1\NCCN1CC(=O)O)C(=O)O] | (2S)-2-amino-3-({[1-(carboxymethyl)imidazolidin-2-ylidene]amino}sulfanyl)propanoic acid |
| 300 | 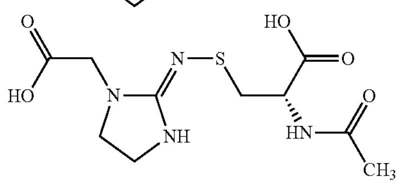 | (2S)-3-({[1-(carboxymethyl)imidazolidin-2-ylidene]amino}sulfanyl)-2-acetamidopropanoic acid |
| 301 | 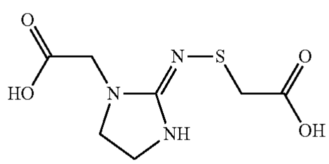 [SMILES: O=C(O)CS/N=C1\NCCN1CC(=O)O] | 2-({[1-(carboxymethyl)imidazolidin-2-ylidene]amino}sulfanyl)acetic acid |
| 302 | 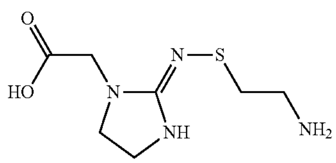 [SMILES: NCCS/N=C1\NCCN1CC(=O)O] | 2-[2-{[(2-aminoethyl)sulfanyl]imino}imidazolidin-1-yl]acetic acid |
| 303 | 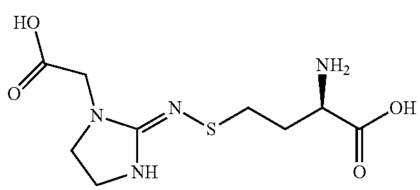 [SMILES: N[C@H](CCS/N=C1\NCCN1CC(=O)O)C(=O)O] | (2R)-2-amino-4-({[1-(carboxymethyl)imidazolidin-2-ylidene]amino}sulfanyl)butanoic acid |
| 304 | 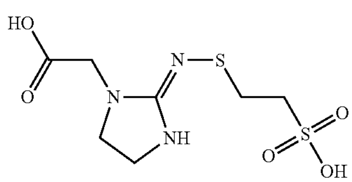 [SMILES: O=C(O)CN1CCN/C1=N\SCCS(=O)(=O)O] | 2-[2-{[(2-sulfoethyl)sulfanyl]imino}imidazolidin-1-yl]acetic acid |
| 305 | 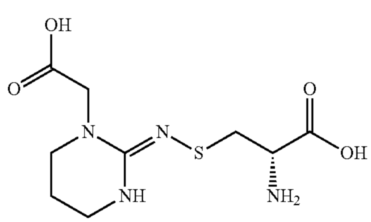 [SMILES: N[C@H](CS/N=C1\NCCCN1CC(=O)O)C(=O)O] | (2S)-2-amino-3-({[1-(carboxymethyl)-1,3-diazinan-2-ylidene]amino}sulfanyl)propanoic acid |
| 306 | 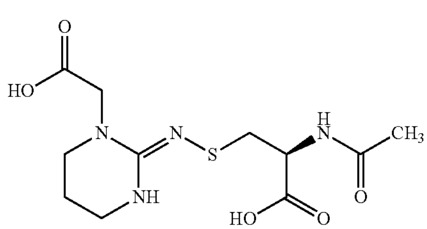 [SMILES: CC(=O)N[C@H](CS/N=C1\NCCCN1CC(=O)O)C(=O)O] | (2S)-3-({[1-(carboxymethyl)-1,3-diazinan-2-ylidene]amino}sulfanyl)-2-acetamidopropanoic acid |

TABLE 10-continued

Selected Phosphocreatine System Inhibitors

| Compound Number | Structure | Compound Name |
| --- | --- | --- |
| 307 | 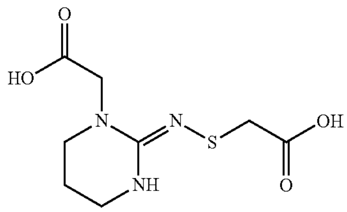 [SMILES: O=C(O)CS/N=C1\NCCCN1CC(=O)O] | 2-({[1-(carboxymethyl)-1,3-diazinan-2-ylidene]amino}sulfanyl)acetic acid |
| 308 | 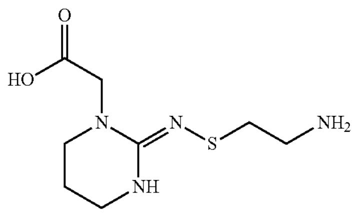 [SMILES: NCCS/N=C1\NCCCN1CC(=O)O] | 2-[2-{[(2-aminoethyl)sulfanyl]imino}-1,3-diazinan-1-yl]acetic acid |
| 309 | 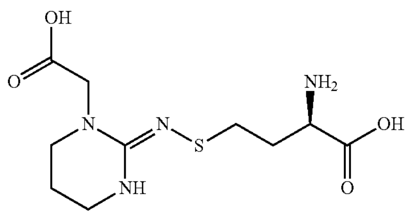 [SMILES: N[C@H](CCS/N=C1\NCCCN1CC(=O)O)C(=O)O] | (2R)-2-amino-4-({[1-(carboxymethyl)-1,3-diazinan-2-ylidene]amino}sulfanyl)butanoic acid |
| 310 | 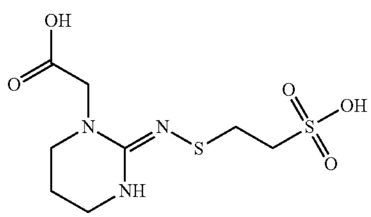 [SMILES: O=C(O)CN1CCCN/C1=N\SCCS(=O)(=O)O] | 2-[2-{[(2-sulfoethyl)sulfanyl]imino}-1,3-diazinan-1-yl]acetic acid |
| 311 | 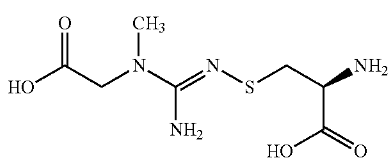 [SMILES: CN(CC(=O)O)/C(N)=N/SC[C@@H](N)C(=O)O] | (2S)-2-amino-3-{[{amino[(carboxymethyl)(methyl)amino]methylidene}amino]sulfanyl}propanoic acid |
| 312 | 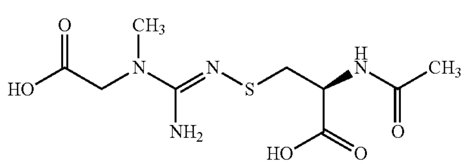 [SMILES: CC(=O)N[C@H](CS/N=C(\N)N(C)CC(=O)O)C(=O)O] | (2S)-3-{[{amino[(carboxymethyl)(methyl)amino]methylidene}amino]sulfanyl}-2-acetamidopropanoic acid |
| 313 | 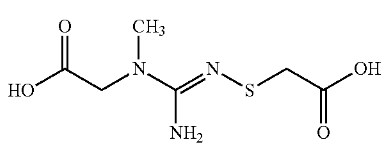 | 2-{[{[(carboxymethyl)(methyl)amino](amino)methylidene}amino]sulfanyl}acetic acid |
| 314 | 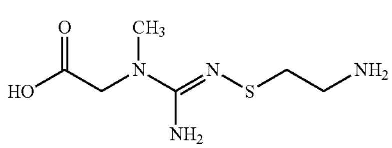 | 2-[2-[(2-aminoethyl)sulfanyl]-1-methylguanidino]acetic acid |

TABLE 10-continued

Selected Phosphocreatine System Inhibitors

| Compound Number | Structure | Compound Name |
|---|---|---|
| 315 | 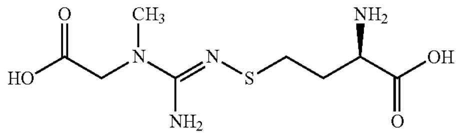 [SMILES: CN(CC(=O)O)/C(N)=N/SCC[C@@H](N)C(=O)O] | (2R)-2-amino-4-{[{amino[(carboxymethyl)(methyl)amino]methylidene}amino]sulfanyl}butanoic acid |
| 316 | 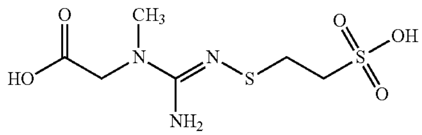 [SMILES: CN(CC(=O)O)/C(N)=N/SCCS(=O)(=O)O] | 2-[1-methyl-2-[(2-sulfoethyl)sulfanyl]guanidino]acetic acid |
| 317 | 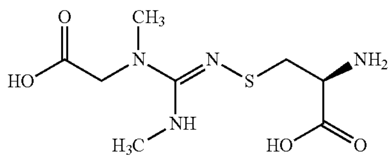 [SMILES: CN/C(=N\SC[C@@H](N)C(=O)O)N(C)CC(=O)O] | (2S)-2-amino-3-{[{[(carboxymethyl)(methyl)amino](methylamino)methylidene}amino]sulfanyl}propanoic acid |
| 318 | 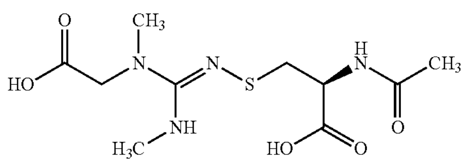 [SMILES: CN/C(=N\SC[C@@H](NC(C)=O)C(=O)O)N(C)CC(=O)O] | (2S)-3-{[{[(carboxymethyl)(methyl)amino](methylamino)methylidene}amino]sulfanyl}-2-acetamidopropanoic acid |
| 319 | 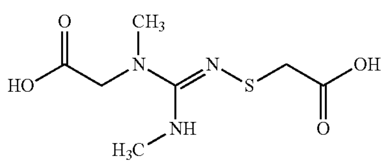 | 2-{[{[(carboxymethyl)(methyl)amino](methylamino)methylidene}amino]sulfanyl}acetic acid |
| 320 | 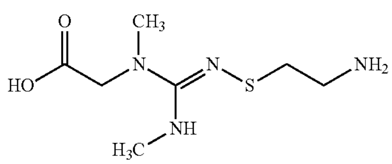 | 2-[2-[(2-aminoethyl)sulfanyl]-1,3-dimethylguanidino]acetic acid |
| 321 | 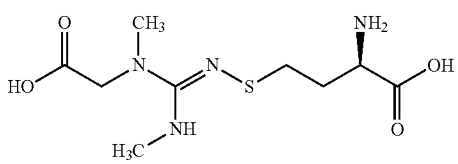 [SMILES: CN/C(=N\SCC[C@@H](N)C(=O)O)N(C)CC(=O)O] | (2R)-2-amino-4-{[{[(carboxymethyl)(methyl)amino](methylamino)methylidene}amino]sulfanyl}butanoic acid |
| 322 | 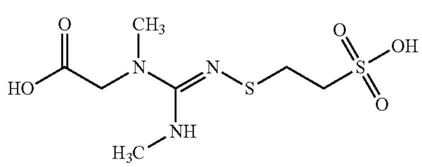 [SMILES: CN/C(=N\SCCS(=O)(=O)O)N(C)CC(=O)O] | 2-[1,3-dimethyl-2-[(2-sulfoethyl)sulfanyl]guanidino]acetic acid |

In another aspect, the invention features a composition comprising any of the foregoing compounds and a pharmaceutically acceptable excipient. In some embodiments, the composition is a pharmaceutical composition. In some embodiments, the creatine transport inhibitor or creatine kinase inhibitor in the composition is substantially enantiomerically pure.

In another aspect, the invention features a method for treating cancer (e.g., gastrointestinal cancer such as, esophageal cancer, stomach cancer, pancreatic cancer, liver cancer, gallbladder cancer, colorectal cancer, anal cancer, mucosa-associated lymphoid tissue cancer, gastrointestinal stromal tumors, cancers of the biliary tree, and gastrointestinal carcioid tumor), comprising administering to a subject in need thereof, any of the foregoing compounds in an amount sufficient to treat said cancer. In some embodiments, the compound is any of the foregoing compounds of Formula I, Formula II, or Formula III. In other embodiments, the compound is any compound of any one of Tables 1-11 (e.g., a compound of any one of Tables 1-7, 9 or 10).

TABLE 11

Selected Phosphocreatine System Inhibitors

| Compound Number | Structure | Compound Name |
|---|---|---|
| 106 | 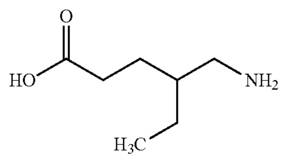 | 5-amino-4-(aminomethyl)pentanoic acid |
| 146 | 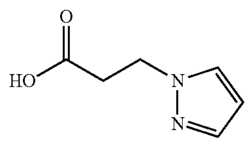 | 3-(1H-pyrazol-1-yl)propanoic acid |
| 170 | 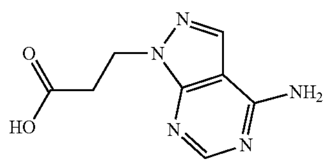 [SMILES: Nc1ncnc2c1cnn2CCC(=O)O] | 3-{4-amino-1H-pyrazolo[3,4-d]pyrimidin-1-yl}propanoic acid |
| 171 | 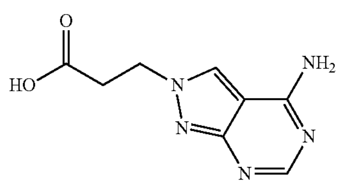 [SMILES: Nc1ncnc2nn(CCC(=O)O)cc12] | 3-{4-amino-2H-pyrazolo[3,4-d]pyrimidin-2-yl}propanoic acid |
| 172 | 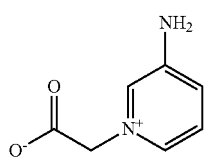 [SMILES: Nc1ccc[n+](CC(=O)[O-])c1] | 3-amino-1-(carboxylatomethyl)pyridin-1-ium |
| 208 | 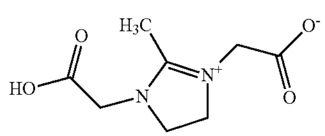 | 3-(carboxylatomethyl)-1-(carboxymethyl)-2-methyl-4,5-dihydro-1H-imidazol-3-ium |

In another aspect, the invention features a method of slowing the spread of a migrating cancer, including administering to a subject in need thereof, an inhibitor of creatine transport and/or creatine kinase in an amount sufficient to slow the spread of said migrating cancer. In some embodiments, the method comprises the suppression of metastatic colonization of said migrating cancer in the liver of said subject. In some embodiments, the migrating cancer is metastatic cancer (e.g., including cells exhibiting migration, invasion of migrating cells, endothelial recruitment, and/or angiogenesis). In other embodiments, the migrating cancer spreads via seeding the surface of the peritoneal, pleural, pericardial, or subarachnoid spaces. In certain embodiments, the migrating cancer spreads via the lymphatic system. In some embodiments, the migrating cancer spreads hematogenously. In other embodiments, the migrating cancer is a cell migration cancer (e.g., a non-metastatic cell migration cancer such as, ovarian cancer, mesothelioma, or primary lung cancer).

In another aspect, the invention features a method for inhibiting proliferation or growth of cancer stem cells or cancer initiating cells, including contacting the cell with an inhibitor of creatine transport and/or creatine kinase in an amount sufficient to inhibit proliferation or growth of said cell.

In another aspect, the invention features a method of reducing the rate of tumor seeding of a cancer including administering to a subject in need thereof an inhibitor of creatine transport and/or creatine kinase in an amount sufficient to reduce tumor seeding.

In another aspect, the invention features a method of reducing or treating metastatic nodule-forming of cancer including administering to a subject in need thereof an inhibitor of creatine transport and/or creatine kinase in an amount sufficient to treat said metastatic nodule-forming of cancer.

In another aspect, the invention features a method of treating metastatic cancer in a subject in need thereof. The method includes: (a) providing a subject identified to have, or to be at risk of having, metastatic cancer on the basis of the expression level of miR-483-5p and/or miR-551a is below a predetermined reference value or the expression level of CKB and/or SLC6a8 is above a predetermined reference value; and (b) administering to said subject an effective amount of any of the foregoing compounds.

In another aspect, the invention features a method for treating metastatic cancer in a subject in need thereof, comprising contacting creatine transport channel SLC6a8 with any of the foregoing compounds in an amount effective to suppress metastatic colonization of said cancer.

In some embodiments of any of the foregoing methods, the cancer is breast cancer, colon cancer, renal cell cancer, non-small cell lung cancer, hepatocellular carcinoma, gastric cancer, ovarian cancer, pancreatic cancer, esophageal cancer, prostate cancer, sarcoma, or melanoma. In other embodiments of any of the foregoing methods the cancer is gastrointestinal cancer such as, esophageal cancer, stomach cancer, pancreatic cancer, liver cancer, gallbladder cancer, colorectal cancer, anal cancer, mucosa-associated lymphoid tissue cancer, gastrointestinal stromal tumors, cancers of the biliary tree, and gastrointestinal carcioid tumor.

In certain embodiments of any of the foregoing methods, the method includes administration of any of the foregoing compositions. In some embodiments of any of the foregoing methods, the method includes administration of a composition including a creatine transport inhibitor or creatine kinase inhibitor that is substantially enantiomerically pure.

In other embodiments of any of the foregoing methods, the cancer is a drug resistant cancer (e.g., the cancer is resistant to vemurafenib, dacarbazine, a CTLA4 inhibitor, a BRAF inhibitor, a MEK inhibitor, a PD1 inhibitor, or a PDL1 inhibitor).

In other embodiments of any of the foregoing methods, the method further includes administering an antiproliferative (e.g., capecitabine, gemcitabine, fluorouracil, FOLFOX (5-FU, leucovorin, and Eloxatin), FOLFIRI (5-FU, leucovorin, and Camptosar), EOX (Epirubicin, Oxaliplatinum, and Xeloda), Taxotere, Erbitux, Zaltrap, Vectibix, Ramucirumab, Tivozanib, Stivarga, CRS-207, a PD-1 or PDL-1 antibody (e.g., nivolumab, pembrolizumab, MED14736, or MPDL3280A), and therapies that target CDK4/6, EGFR, PARP), wherein any of the foregoing compounds and the antiproliferative are administered in an amount that together, is sufficient to slow the progression of migrating cancer. In certain embodiments, any of the foregoing compounds and the antiproliferative are administered within 28 days of each other in amounts that together are effective to treat the subject.

In certain embodiments of any of the foregoing methods, the inhibitor of creatine transport and/or creatine kinase is any of the foregoing compounds of Formula I, Formula II, Formula III, or Formula V. In other embodiments, the compound is any compound of any one of Tables 1-11 or a pharmaceutically acceptable salt thereof (e.g., a compound of any one of Tables 1-7, 9 or 10). In some embodiments, the compound is any compound of Table 4 or a pharmaceutically acceptable salt thereof.

In some embodiments, of any of the foregoing methods, the inhibitor of creatine transport and/or creatine kinase is any one of compounds 7-9, 11, 15, 16, 28, 29, 30, 32, 33, 34, 43, 47, 48, 51, 52, 54, 67, 69, 70, 79, 80, 85, 124, 132, 149, 150, 187, 188, 190, 192-195, 199, 210-213, 215, 217, 324, 447, or 448 or a pharmaceutically acceptable salt thereof. In other embodiments, of any of the foregoing methods, the inhibitor of creatine transport and/or creatine kinase is any one of compounds 16, 28, 29, 33, 34, 43, 47, 85, 124, 149, 150, 210-213, 215, 217, 324, 447, or 448 or a pharmaceutically acceptable salt thereof. In certain embodiments of any of the foregoing methods, the inhibitor of creatine transport and/or creatine kinase is any one of compounds 26, 28, 34, 92, 96, 124, 125, 149, 150, 161, 163, 207, 324, 447 or 448 or a pharmaceutically acceptable salt thereof. In certain embodiments of any of the foregoing methods, the inhibitor of creatine transport and/or creatine kinase is any one of compounds 28, 34, 124, 149, or 150 or a pharmaceutically acceptable salt thereof. In some embodiments of any of the foregoing methods, the inhibitor of creatine transport and/or creatine kinase is compound 34, a stereoisomer thereof, and/or a pharmaceutically acceptable salt thereof. In some embodiments of any of the foregoing methods, the inhibitor of creatine transport and/or creatine kinase is any one of compounds 219-224, or a pharmaceutically acceptable salt thereof.

Chemical Terms

As used herein, the term "compound," is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins and C=N double bonds can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. Herein a phrase of the form "optionally substituted X" (e.g., optionally substituted alkyl) is intended to be equivalent to "X, wherein X is optionally substituted" (e.g., "alkyl, wherein the alkyl is optionally substituted"). It is not intended to mean that the feature "X" (e.g., alkyl) per se is optional.

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 7, from 1 to 11, or from 1 to 21 carbons. In some embodiments, the alkyl group is further substituted with 1, 2, 3, or 4 substituents as described herein.

Non-limiting examples of optionally substituted acyl groups include, alkoxycarbonyl, alkoxycarbonylacyl, arylalkoxycarbonyl, aryloyl, carbamoyl, carboxyaldehyde, (heterocyclyl) imino, and (heterocyclyl)oyl:

The "alkoxycarbonyl" group, which as used herein, represents an alkoxy, as defined herein, attached to the parent molecular group through a carbonyl atom (e.g., —C(O)—OR, where R is H or an optionally substituted $C_{1-6}$, $C_{1-10}$, or $C_{1-20}$ alkyl group). Exemplary unsubstituted alkoxycarbonyl include from 1 to 21 carbons (e.g., from 1 to 11 or from 1 to 7 carbons). In some embodiments, the alkoxy group is further substituted with 1, 2, 3, or 4 substituents as described herein.

The "alkoxycarbonylacyl" group, which as used herein, represents an acyl group, as defined herein, that is substituted with an alkoxycarbonyl group, as defined herein (e.g., —C(O)-alkyl-C(O)—OR, where R is an optionally substituted $C_{1-6}$, $C_{1-10}$, or $C_{1-20}$ alkyl group). Exemplary unsubstituted alkoxycarbonylacyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ acyl, $C_{1-10}$ alkoxycarbonyl-$C_{1-10}$ acyl, or $C_{1-20}$ alkoxycarbonyl-$C_{1-20}$ acyl). In some embodiments, each alkoxy and alkyl group is further independently substituted with 1, 2, 3, or 4 substituents, as described herein (e.g., a hydroxy group) for each group.

The "arylalkoxycarbonyl" group, which as used herein, represents an arylalkoxy group, as defined herein, attached to the parent molecular group through a carbonyl (e.g., —C(O)—O-alkyl-aryl). Exemplary unsubstituted arylalkoxy groups include from 8 to 31 carbons (e.g., from 8 to 17 or from 8 to 21 carbons, such as $C_{6-10}$ aryl-$C_{1-6}$ alkoxycarbonyl, $C_{6-10}$ alkoxy-carbonyl, or $C_{6-10}$ aryl-$C_{1-20}$ alkoxy-carbonyl). In some embodiments, the arylalkoxycarbonyl group can be substituted with 1, 2, 3, or 4 substituents as defined herein.

The "aryloyl" group, which as used herein, represents an aryl group, as defined herein, that is attached to the parent molecular group through a carbonyl group. Exemplary unsubstituted aryloyl groups are of 7 to 11 carbons. In some embodiments, the aryl group can be substituted with 1, 2, 3, or 4 substituents as defined herein.

The "carbamoyl" group, which as used herein, represents —C(O)—N($R^{N1}$)$_2$, where the meaning of each $R^{N1}$ is found in the definition of "amino" provided herein.

The "carboxaldehyde" group, which as used herein, represents an acyl group having the structure —CHO.

The "(heterocyclyl) imino" group, which as used herein, represents a heterocyclyl group, as defined herein, attached to the parent molecular group through an imino group. In some embodiments, the heterocyclyl group can be substituted with 1, 2, 3, or 4 substituent groups as defined herein.

The "(heterocyclyl)oyl" group, which as used herein, represents a heterocyclyl group, as defined herein, attached to the parent molecular group through a carbonyl group. In some embodiments, the heterocyclyl group can be substituted with 1, 2, 3, or 4 substituent groups as defined herein.

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, and neopentyl, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N($R^{N1}$)$_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy, optionally substituted with an O-protecting group; (9) nitro; (10) oxo (e.g., carboxaldehyde or acyl); (11) $C_{1-7}$ spirocyclyl; (12) thioalkoxy; (13) thiol; (14) —CO$_2$$R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO$_2$R$^{D'}$, where R$^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —SO$_2$NR$^{E'}$R$^{F'}$, where each of R$^{E'}$ and R$^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —NR$^{H'}$C(O)R$^{H'}$, wherein R$^{H'}$ is selected from the group consisting of (a1) hydrogen and (b1) $C_{1-6}$ alkyl, and R$^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —NR$^{J'}$C(O)OR$^{K'}$, wherein R$^{J'}$ is selected from the group consisting of (a1) hydrogen and (b1) $C_{1-6}$ alkyl, and R$^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, and isopropylene. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, or $C_{2-20}$ alkylene). In some embodiments, the alkylene can be further substituted with 1, 2, 3, or 4 substituent groups as defined herein for an alkyl group.

Non-limiting examples of optionally substituted alkyl and alkylene groups include acylaminoalkyl, acyloxyalkyl, alkoxyalkyl, alkoxycarbonylalkyl, alkylsulfinyl, alkylsulfinylalkyl, aminoalkyl, carbamoylalkyl, carboxyalkyl, carboxyaminoalkyl, haloalkyl, hydroxyalkyl, perfluoroalkyl, and sulfoalkyl:

The "acylaminoalkyl" group, which as used herein, represents an acyl group, as defined herein, attached to an amino group that is in turn attached to the parent molecular group through an alkylene group, as defined herein (i.e., -alkyl-N($R^{N1}$)—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylaminoalkyl groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkylene group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The "acyloxyalkyl" group, which as used herein, represents an acyl group, as defined herein, attached to an oxygen atom that in turn is attached to the parent molecular group though an alkylene group (i.e., -alkyl-O—C(O)—R, where R is H or an optionally substituted $C_{1-6}$, $C_{1-10}$, or $C_{1-20}$ alkyl group). Exemplary unsubstituted acyloxyalkyl groups include from 1 to 21 carbons (e.g., from 1 to 7 or from 1 to 11 carbons). In some embodiments, the alkylene group is, independently, further substituted with 1, 2, 3, or 4 substituents as described herein.

The "alkoxyalkyl" group, which as used herein, represents an alkyl group that is substituted with an alkoxy group. Exemplary unsubstituted alkoxyalkyl groups include between 2 to 40 carbons (e.g., from 2 to 12 or from 2 to 20 carbons, such as $C_{1-6}$ alkoxy-$C_{1-6}$ alkyl, $C_{1-10}$ alkoxy-$C_{1-10}$ alkyl, or $C_{1-20}$ alkoxy-$C_{1-20}$ alkyl). In some embodiments, the alkyl and the alkoxy each can be further substituted with 1, 2, 3, or 4 substituent groups as defined herein for the respective group.

The "alkoxycarbonylalkyl" group, which as used herein, represents an alkyl group, as defined herein, that is substituted with an alkoxycarbonyl group, as defined herein (e.g., -alkyl-C(O)—OR, where R is an optionally substituted $C_{1-20}$, $C_{1-10}$, or $C_{1-6}$ alkyl group). Exemplary unsubstituted alkoxycarbonylalkyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkyl, $C_{1-10}$ alkoxycarbonyl-$C_{1-10}$ alkyl, or $C_{1-20}$ alkoxycarbonyl-$C_{1-20}$ alkyl). In some embodiments, each alkyl and alkoxy group is further independently substituted with 1, 2, 3, or 4 substituents as described herein (e.g., a hydroxy group).

The "alkylsulfinylalkyl" group, which as used herein, represents an alkyl group, as defined herein, substituted with an alkylsulfinyl group. Exemplary unsubstituted alkylsulfinylalkyl groups are from 2 to 12, from 2 to 20, or from 2 to 40 carbons. In some embodiments, each alkyl group can be further substituted with 1, 2, 3, or 4 substituent groups as defined herein.

The "aminoalkyl" group, which as used herein, represents an alkyl group, as defined herein, substituted with an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "carbamoylalkyl" group, which as used herein, represents an alkyl group, as defined herein, substituted with a carbamoyl group, as defined herein. The alkyl group can be further substituted with 1, 2, 3, or 4 substituent groups as described herein.

The "carboxyalkyl" group, which as used herein, represents an alkyl group, as defined herein, substituted with a carboxy group, as defined herein. The alkyl group can be further substituted with 1, 2, 3, or 4 substituent groups as described herein, and the carboxy group can be optionally substituted with one or more O-protecting groups.

The "carboxyaminoalkyl" group, which as used herein, represents an aminoalkyl group, as defined herein, substituted with a carboxy, as defined herein. The carboxy, alkyl, and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group, and/or an O-protecting group).

The "haloalkyl" group, which as used herein, represents an alkyl group, as defined herein, substituted with a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —$CF_3$), —$CHF_2$, —$CH_2F$, —$CCl_3$, —$CH_2CH_2Br$, —$CH_2CH(CH_2CH_2Br)CH_3$, and —$CHlCH_3$. In some embodiments, the haloalkyl group can be further substituted with 1, 2, 3, or 4 substituent groups as described herein for alkyl groups.

The "hydroxyalkyl" group, which as used herein, represents an alkyl group, as defined herein, substituted with one to three hydroxy groups, with the proviso that no more than one hydroxy group may be attached to a single carbon atom of the alkyl group, and is exemplified by hydroxymethyl and dihydroxypropyl. In some embodiments, the hydroxyalkyl group can be substituted with 1, 2, 3, or 4 substituent groups (e.g., O-protecting groups) as defined herein for an alkyl.

The "perfluoroalkyl" group, which as used herein, represents an alkyl group, as defined herein, where each hydrogen radical bound to the alkyl group has been replaced by a fluoride radical. Perfluoroalkyl groups are exemplified by trifluoromethyl, pentafluoroethyl.

The "sulfoalkyl" group, which as used herein, represents an alkyl group, as defined herein, substituted with a sulfo group of —$SO_3H$. In some embodiments, the alkyl group can be further substituted with 1, 2, 3, or 4 substituent groups as described herein, and the sulfo group can be further substituted with one or more O-protecting groups (e.g., as described herein).

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, and 2-butenyl. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

Non-limiting examples of optionally substituted alkenyl groups include, alkoxycarbonylalkenyl, aminoalkenyl, and hydroxyalkenyl:

The "alkoxycarbonylalkenyl" group, which as used herein, represents an alkenyl group, as defined herein, that is substituted with an alkoxycarbonyl group, as defined herein (e.g., -alkenyl-C(O)—OR, where R is an optionally substituted $C_{1-20}$, $C_{1-10}$, or $C_{1-6}$ alkyl group). Exemplary unsubstituted alkoxycarbonylalkenyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkenyl, $C_{1-10}$ alkoxycarbonyl-$C_{2-10}$ alkenyl, or $C_{1-20}$ alkoxycarbonyl-$C_{2-20}$ alkenyl). In some embodiments, each alkyl, alkenyl, and alkoxy group is further independently substituted with 1, 2, 3, or 4 substituents as described herein (e.g., a hydroxy group).

The "aminoalkenyl" group, which as used herein, represents an alkenyl group, as defined herein, substituted with an amino group, as defined herein. The alkenyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "hydroxyalkenyl" group, which as used herein, represents an alkenyl group, as defined herein, substituted with one to three hydroxy groups, with the proviso that no more than one hydroxy group may be attached to a single carbon atom of the alkyl group, and is exemplified by dihydroxypropenyl, and hydroxyisopentenyl. In some embodiments, the hydroxyalkenyl group can be substituted with 1, 2, 3, or 4 substituent groups (e.g., O-protecting groups) as defined herein for an alkyl.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, and 1-propynyl. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

Non-limiting examples of optionally substituted alkynyl groups include alkoxycarbonylalkynyl, aminoalkynyl, and hydroxyalkynyl:

The "alkoxycarbonylalkynyl" group, which as used herein, represents an alkynyl group, as defined herein, that is substituted with an alkoxycarbonyl group, as defined herein (e.g., -alkynyl-C(O)—OR, where R is an optionally substituted $C_{1-20}$, $C_{1-10}$, or $C_{1-6}$ alkyl group). Exemplary unsubstituted alkoxycarbonylalkynyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkynyl, $C_{1-10}$ alkoxycarbonyl-$C_{2-10}$ alkynyl, or $C_{1-20}$ alkoxycarbonyl-$C_{2-20}$ alkynyl). In some embodiments, each alkyl, alkynyl, and alkoxy group is further independently substituted with 1, 2, 3, or 4 substituents as described herein (e.g., a hydroxy group).

The "aminoalkynyl" group, which as used herein, represents an alkynyl group, as defined herein, substituted with an amino group, as defined herein. The alkynyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "hydroxyalkynyl" group, which as used herein, represents an alkynyl group, as defined herein, substituted with one to three hydroxy groups, with the proviso that no more than one hydroxy group may be attached to a single carbon atom of the alkyl group. In some embodiments, the hydroxyalkynyl group can be substituted with 1, 2, 3, or 4 substituent groups (e.g., O-protecting groups) as defined herein for an alkyl.

The term "amidino," as used herein, represents a group with the structure

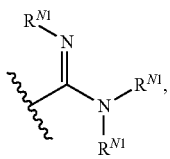

wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. Non-limiting examples of optionally substituted amidino groups include guanidino, 2-amino-imidazoyl, 2-iminoimidazolidino, 2-imino-1,3-diazinan-1-yl, 3-amino-1,2,4-triazol-4-yl, imidazol-2yl, 1,4,5,6-tetrahydropyrimidin-2-yl, 1,2,4-triazol-3-yl, 5-amino-3,4-dihydro-pyrrol-5-yl, imidazol-1-yl, carbamimidoylsulfanyl, carbamoylamino, carbamothioylamino, 2-amino-1,3-benzothiazol-2-yl, 2-amino-1,3-thiazol-2-yl, 2-amino-1,3-benzodiazol-2-yl, and 2-aminopyridyl.

The term "amino," as used herein, represents —$N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. The amino groups of the invention can be an unsubstituted amino (i.e., —$NH_2$) or a substituted amino (i.e., —$N(R^{N1})_2$). In a preferred embodiment, amino is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each $R^{N2}$ can be H, $C_{1-20}$ alkyl (e.g., $C_{1-6}$ alkyl), or $C_{6-10}$ aryl.

Non-limiting examples of optionally substituted amino groups include acylamino and carbamyl:

The "acylamino" group, which as used herein, represents an acyl group, as defined herein, attached to the parent molecular group though an amino group, as defined herein (i.e., —N($R^{N1}$)—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}{}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The "carbamyl" group, which as used herein, refers to a carbamate group having the structure —$NR^{N1}$C(=O)OR or —OC(=O)N($R^{N1}$)$_2$, where the meaning of each $R^{N1}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "amino acid," as described herein, refers to a molecule having a side chain, an amino group, and an acid group (e.g., a carboxy group of —$CO_2H$ or a sulfo group of —$SO_3H$), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —$NH_2$) or a substituted amino (i.e., —N($R^{N1}$)$_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxyaldehyde or acyl); (11) $C_{1-7}$ spirocyclyl; (12) thioalkoxy; (13) thiol; (14) —$CO_2R^{A'}$, where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}$$(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —C(O)$NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —$SO_2R^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —$SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)$R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}$$(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —$NR^{H'}C(O)R^{I'}$, wherein $R^{H'}$ is selected from the group consisting of (a1) hydrogen and (b1) $C_{1-6}$ alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —$NR^{J'}C(O)OR^{K'}$, wherein is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}$$(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, and indenyl, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) alkyl, (b) $C_{6-10}$ aryl, and (c) alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "arylalkyl" group, which as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as $C_{1-6}$ alk-$C_{6-10}$ aryl, $C_{1-10}$ alk-$C_{6-10}$ aryl, or $C_{1-20}$ alk-$C_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "azido" represents an —$N_3$ group, which can also be represented as —N=N=N.

The term "bicyclic," as used herein, refer to a structure having two rings, which may be aromatic or non-aromatic. Bicyclic structures include spirocyclyl groups, as defined herein, and two rings that share one or more bridges, where such bridges can include one atom or a chain including two, three, or more atoms. Exemplary bicyclic groups include a bicyclic carbocyclyl group, where the first and second rings are carbocyclyl groups, as defined herein; a bicyclic aryl groups, where the first and second rings are aryl groups, as defined herein; bicyclic heterocyclyl groups, where the first ring is a heterocyclyl group and the second ring is a carbocyclyl (e.g., aryl) or heterocyclyl (e.g., heteroaryl) group; and bicyclic heteroaryl groups, where the first ring is a heteroaryl group and the second ring is a carbocyclyl (e.g., aryl) or heterocyclyl (e.g., heteroaryl) group. In some embodiments, the bicyclic group can be substituted with 1, 2, 3, or 4 substituents as defined herein for cycloalkyl, heterocyclyl, and aryl groups.

The term "boranyl," as used herein, represents —$B(R^{B1})_3$, where each $R^{B1}$ is, independently, selected from the group consisting of H and optionally substituted alkyl. In some embodiments, the boranyl group can be substituted with 1, 2, 3, or 4 substituents as defined herein for alkyl.

The terms "carbocyclic" and "carbocyclyl," as used herein, refer to an optionally substituted $C_{3-12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "carbonyl," as used herein, represents a C(O) group, which can also be represented as C=O.

The term "carboxy," as used herein, means —$CO_2H$.

The term "cyano," as used herein, represents an —CN group.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, and bicycle heptyl. When the cycloalkyl group includes one carbon-carbon double bond, the cycloalkyl group can be referred to as a "cycloalkenyl" group. Exemplary cycloalkenyl groups include cyclopentenyl, and cyclohexenyl. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "cycloalkylalkyl" group, which as used herein, represents a cycloalkyl group, as defined herein, attached to the parent molecular group through an alkylene group, as defined herein (e.g., an alkylene group of from 1 to 4, from 1 to 6, from 1 to 10, or form 1 to 20 carbons). In some embodiments, the alkylene and the cycloalkyl each can be further substituted with 1, 2, 3, or 4 substituent groups as defined herein for the respective group.

The term "diastereomer," as used herein means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo," as used herein, represents a halogen selected from bromine, chlorine, iodine, or fluorine.

The term "heteroalkyl," as used herein, refers to an alkyl group, as defined herein, in which one or two of the constituent carbon atoms have each been replaced by nitrogen, oxygen, or sulfur. In some embodiments, the heteroalkyl group can be further substituted with 1, 2, 3, or 4 substituent groups as described herein for alkyl groups. The terms "heteroalkenyl" and heteroalkynyl," as used herein refer to alkenyl and alkynyl groups, as defined herein, respectively, in which one or two of the constituent carbon atoms have each been replaced by nitrogen, oxygen, or sulfur. In some embodiments, the heteroalkenyl and heteroalkynyl groups can be further substituted with 1, 2, 3, or 4 substituent groups as described herein for alkyl groups.

Non-limiting examples of optionally substituted heteroalkyl, heteroalkenyl, and heteroalkynyl groups include acyloxy, alkenyloxy, alkoxy, alkoxyalkoxy, alkoxycarbonylalkoxy, alkynyloxy, aminoalkoxy, arylalkoxy, carboxyalkoxy, cycloalkoxy, haloalkoxy, (heterocyclyl)oxy, perfluoroalkoxy, thioalkoxy, and thioheterocyclylalkyl:

The "acyloxy" group, which as used herein, represents an acyl group, as defined herein, attached to the parent molecular group though an oxygen atom (i.e., —O—C(O)—R, where R is H or an optionally substituted $C_{1-6}$, $C_{1-10}$, or $C_{1-20}$ alkyl group). Exemplary unsubstituted acyloxy groups include from 1 to 21 carbons (e.g., from 1 to 7 or from 1 to 11 carbons). In some embodiments, the alkyl group is further substituted with 1, 2, 3, or 4 substituents as described herein.

The "alkenyloxy" group, which as used here, represents a chemical substituent of formula —OR, where R is a $C_{2-20}$ alkenyl group (e.g., $C_{2-6}$ or $C_{2-10}$ alkenyl), unless otherwise specified. Exemplary alkenyloxy groups include ethenyloxy, and propenyloxy. In some embodiments, the alkenyl group can be further substituted with 1, 2, 3, or 4 substituent groups as defined herein (e.g., a hydroxy group).

The "alkoxy" group, which as used herein, represents a chemical substituent of formula —OR, where R is a $C_{1-20}$ alkyl group (e.g., $C_{1-6}$ or $C_{1-10}$ alkyl), unless otherwise specified. Exemplary alkoxy groups include methoxy, ethoxy, propoxy (e.g., n-propoxy and isopropoxy), and t-butoxy. In some embodiments, the alkyl group can be further substituted with 1, 2, 3, or 4 substituent groups as defined herein (e.g., hydroxy or alkoxy).

The "alkoxyalkoxy" group, which as used herein, represents an alkoxy group that is substituted with an alkoxy group. Exemplary unsubstituted alkoxyalkoxy groups include between 2 to 40 carbons (e.g., from 2 to 12 or from 2 to 20 carbons, such as $C_{1-6}$ alkoxy-$C_{1-6}$ alkoxy, $C_{1-10}$ alkoxy-$C_{1-10}$ alkoxy, or $C_{1-20}$ alkoxy-$C_{1-20}$ alkoxy). In some embodiments, the each alkoxy group can be further substituted with 1, 2, 3, or 4 substituent groups as defined herein.

The "alkoxycarbonylalkoxy" group, which as used herein, represents an alkoxy group, as defined herein, that is substituted with an alkoxycarbonyl group, as defined herein (e.g., —O-alkyl-C(O)—OR, where R is an optionally substituted $C_{1-6}$, $C_{1-10}$, or $C_{1-20}$ alkyl group). Exemplary unsubstituted alkoxycarbonylalkoxy include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkoxy, $C_{1-10}$ alkoxycarbonyl-$C_{1-10}$ alkoxy, or $C_{1-20}$ alkoxycarbonyl-$C_{1-20}$ alkoxy). In some embodiments, each alkoxy group is further independently substituted with 1, 2, 3, or 4 substituents, as described herein (e.g., a hydroxy group).

The "alkynyloxy" group, which as used herein, represents a chemical substituent of formula —OR, where R is a $C_{2-20}$ alkynyl group (e.g., $C_{2-6}$ or $C_{2-10}$ alkynyl), unless otherwise specified. Exemplary alkynyloxy groups include ethynyloxy, and propynyloxy. In some embodiments, the alkynyl group can be further substituted with 1, 2, 3, or 4 substituent groups as defined herein (e.g., a hydroxy group).

The "aminoalkoxy" group, which as used herein, represents an alkoxy group, as defined herein, substituted with an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy).

The "arylalkoxy" group, which as used herein, represents an alkaryl group, as defined herein, attached to the parent molecular group through an oxygen atom. Exemplary unsubstituted arylalkoxy groups include from 7 to 30 carbons (e.g., from 7 to 16 or from 7 to 20 carbons, such as $C_{6-10}$ aryl-$C_{1-6}$ alkoxy, $C_{6-10}$ aryl $C_{1-10}$ alkoxy, or $C_{6-10}$ aryl-$C_{1-20}$ alkoxy). In some embodiments, the arylalkoxy group can be substituted with 1, 2, 3, or 4 substituents as defined herein.

The "aryloxy" group, which as used herein, represents a chemical substituent of formula —OR', where R' is an aryl group of 6 to 18 carbons, unless otherwise specified. In some embodiments, the aryl group can be substituted with 1, 2, 3, or 4 substituents as defined herein.

The "carboxyalkoxy" group, which as used herein, represents an alkoxy group, as defined herein, substituted with a carboxy group, as defined herein. The alkoxy group can be further substituted with 1, 2, 3, or 4 substituent groups as described herein for the alkyl group, and the carboxy group can be optionally substituted with one or more O-protecting groups.

The "cycloalkoxy" group, which as used herein, represents a chemical substituent of formula —OR, where R is a $C_{3-8}$ cycloalkyl group, as defined herein, unless otherwise specified. The cycloalkyl group can be further substituted with 1, 2, 3, or 4 substituent groups as described herein. Exemplary unsubstituted cycloalkoxy groups are from 3 to 8 carbons. In some embodiment, the cycloalkyl group can be further substituted with 1, 2, 3, or 4 substituent groups as described herein.

The "haloalkoxy" group, which as used herein, represents an alkoxy group, as defined herein, substituted with a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —$COF_3$), —$OCHF_2$, —$OCH_2F$, —$OCCl_3$, —$OCH_2CH_2Br$, —$OCH_2CH(CH_2CH_2Br)CH_3$, and —$OCHICH_3$. In some embodiments, the haloalkoxy group can be further substituted with 1, 2, 3, or 4 substituent groups as described herein for alkyl groups.

The "(heterocyclyl)oxy" group, which as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The "perfluoroalkoxy" group, which as used herein, represents an alkoxy group, as defined herein, where each hydrogen radical bound to the alkoxy group has been replaced by a fluoride radical. Perfluoroalkoxy groups are exemplified by trifluoromethoxy and pentafluoroethoxy.

The "alkylsulfinyl" group, which as used herein, represents an alkyl group attached to the parent molecular group through an —S(O)— group. Exemplary unsubstituted alkylsulfinyl groups are from 1 to 6, from 1 to 10, or from 1 to 20 carbons. In some embodiments, the alkyl group can be further substituted with 1, 2, 3, or 4 substituent groups as defined herein.

The "thioarylalkyl" group, which as used herein, represents a chemical substituent of formula —SR, where R is an arylalkyl group. In some embodiments, the arylalkyl group can be further substituted with 1, 2, 3, or 4 substituent groups as described herein.

The "thioalkoxy" group as used herein, represents a chemical substituent of formula —SR, where R is an alkyl group, as defined herein. In some embodiments, the alkyl group can be further substituted with 1, 2, 3, or 4 substituent groups as described herein.

The "thioheterocyclylalkyl" group, which as used herein, represents a chemical substituent of formula —SR, where R is an heterocyclylalkyl group. In some embodiments, the heterocyclylalkyl group can be further substituted with 1, 2, 3, or 4 substituent groups as described herein.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heteroarylalkyl" refers to a heteroaryl group, as defined herein, attached to the parent molecular group through an alkylene group, as defined herein. Exemplary unsubstituted heteroarylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Heteroarylalkyl groups are a subset of heterocyclylalkyl groups.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, and benzothienyl. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, and benzothienyl, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl(e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

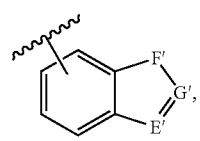

where

E' is selected from the group consisting of —N— and —CH—; F' is selected from the group consisting of —N=CH—, —NH—CH$_2$—, —NH—C(O)—, —NH—, —CH=N—, —CH$_2$—NH—, —C(O)—NH—, —CH=CH—, —CH$_2$—, —CH$_2$CH$_2$—, —CH$_2$O—, —OCH$_2$-, —O—, and —S—; and G' is selected from the group consisting of —CH— and —N—. Any of the heterocyclyl groups mentioned herein may be optionally substituted with one, two, three, four or five substituents independently selected from the group consisting of: (1) C$_{1-7}$ acyl (e.g., carboxyaldehyde); (2) C$_{1-20}$ alkyl (e.g., C$_{1-6}$ alkyl, C$_{1-6}$ alkoxy-C$_{1-6}$ alkyl, C$_{1-6}$ alkylsulfinyl-C$_{1-6}$ alkyl, amino-C$_{1-6}$ alkyl, azido-C$_{1-6}$ alkyl, (carboxyaldehyde)-C$_{1-6}$ alkyl, halo-C$_{1-6}$ alkyl (e.g., perfluoroalkyl), hydroxy-C$_{1-6}$ alkyl, nitro-C$_{1-6}$ alkyl, or C$_{1-6}$ thioalkoxy-C$_{1-6}$ alkyl); (3) C$_{1-20}$ alkoxy (e.g., C$_{1-6}$ alkoxy, such as perfluoroalkoxy); (4) C$_{1-6}$ alkylsulfinyl; (5) C$_{6-10}$ aryl; (6) amino; (7) C$_{1-6}$ alk-C$_{6-10}$ aryl; (8) azido; (9) C$_{3-8}$ cycloalkyl; (10) C$_{1-6}$ alk-C$_{3-8}$ cycloalkyl; (11) halo; (12) C$_{1-12}$ heterocyclyl (e.g., C$_{2-12}$ heteroaryl); (13) (C$_{1-12}$ heterocyclyl)oxy; (14) hydroxy; (15) nitro; (16) C$_{1-20}$ thioalkoxy (e.g., C$_{1-6}$ thioalkoxy); (17) —(CH$_2$)$_q$CO$_2$R$^{A'}$, where q is an integer from zero to four, and R$^{A'}$ is selected from the group consisting of (a) C$_{1-6}$ alkyl, (b) C$_{6-10}$ aryl, (c) hydrogen, and (d) C$_{1-6}$ alk-C$_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) C$_{1-6}$ alkyl, (c) C$_{6-10}$ aryl, and (d) C$_{1-6}$ alk-C$_{6-10}$ aryl; (19) —(CH$_2$)$_q$SO$_2$R$^{D'}$, where q is an integer from zero to four and where R$^{D'}$ is selected from the group consisting of (a) C$_{1-6}$ alkyl, (b) C$_{6-10}$ aryl, and (c) C$_{1-6}$ alk-C$_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) C$_{1-6}$ alkyl, (c) C$_{6-10}$ aryl, and (d) C$_{1-6}$ alk-C$_{6-10}$ aryl; (21) thiol; (22) C$_{6-10}$ aryloxy; (23) C$_{3-8}$ cycloalkoxy; (24) arylalkoxy; (25) C$_{1-6}$ alk-C$_{1-12}$ heterocyclyl (e.g., C$_{1-6}$ alk-C$_{1-12}$ heteroaryl); (26) oxo; (27) (C$_{1-12}$ heterocyclyl) imino; (28) C$_{2-20}$ alkenyl; and (29) C$_{2-20}$ alkynyl. In some embodiments, each of these groups can be further substituted as described herein. For example, the alkylene group of a C$_1$-alkaryl or a C$_1$-alkheterocyclyl can be further substituted with an oxo group to afford the respective aryloyl and (heterocyclyl)oyl substituent group.

The "heterocyclylalkyl" group, which as used herein, represents a heterocyclyl group, as defined herein, attached to the parent molecular group through an alkylene group, as defined herein. Exemplary unsubstituted heterocyclylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as C$_{1-6}$ alk-C$_{1-12}$ heterocyclyl, alk-C$_{1-12}$ heterocyclyl, or C$_{1-20}$ alk-C$_{1-12}$ heterocyclyl). In some embodiments, the alkylene and the heterocyclyl each can be further substituted with 1, 2, 3, or 4 substituent groups as defined herein for the respective group.

The term "hydrocarbon," as used herein, represents a group consisting only of carbon and hydrogen atoms.

The term "hydroxy," as used herein, represents an —OH group. In some embodiments, the hydroxy group can be substituted with 1, 2, 3, or 4 substituent groups (e.g., O-protecting groups) as defined herein for an alkyl.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, alkaryl groups such as benzyl, triphenylmethyl, and benzyloxymethyl, and silyl groups, such as trimethylsilyl. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," 3$^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, and pivaloyl; optionally substituted arylcarbonyl groups, such as benzoyl; silyl groups, such as trimethylsilyl (TMS), tert-butyldimethylsilyl (TBDMS), tri-iso-propylsilyloxymethyl (TOM), and triisopropylsilyl (TIPS); ether-forming groups with the hydroxyl, such methyl, methoxymethyl, tetrahydropyranyl, benzyl, p-methoxybenzyl, and trityl; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, and methyloxycarbonyl; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, and 3-methyl-2-butenoxycarbonyl; haloalkoxycarbonyls, such as 2-chloroethoxycarbonyl, 2-chloroethoxycarbonyl, and 2,2,2-trichloroethoxycarbonyl; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, and fluorenylmethyloxycarbonyl; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, and 2-chloro-4-nitrophenoxycarbonyl); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, and 1,3-dioxolane; acylal groups; and dithiane groups, such as 1,3-dithianes, and 1,3-dithiolane); carboxylic acid-protecting groups (e.g., ester groups, such as methyl ester, benzyl ester, t-butyl ester, and orthoesters; and oxazoline groups.

Exemplary O- and N-protecting groups include: Acetyl (Ac); Acylals; Benzoyl (Bz); Benzyl (Bn, Bnl); Benzyl esters; Carbamate; Carbobenzyloxy (Cbz); Dimethoxytrityl, [bis-(4-methoxyphenyl)phenylmethyl] (DMT); Dithianes; Ethoxyethyl ethers (EE); Methoxymethyl ether (MOM); Methoxytrityl [(4-methoxyphenyl)diphenylmethyl], (MMT); Methyl Ethers; Methyl (Me); Methyl esters; Methylthiomethyl ether; Orthoesters; Oxazoline; Pivaloyl (Piv); Phthalimido; p-Methoxybenzyl carbonyl (Moz or MeOZ); p-Methoxybenzyl (PMB); Propargyl alcohols; Silyl groups (e.g., trimethylsilyl (TMS), tert-butyldimethylsilyl (TBDMS), tri-iso-propylsilyloxymethyl (TOM) and triisopropylsilyl (TIPS)); Silyl esters; tert-Butyl esters; tert-Butyloxycarbonyl (Boc or tBoc); Tetrahydropyranyl (THP); Tosyl (Ts or Tos); Trimethylsilylethoxymethyl (SEM); Trityl (triphenylmethyl, Tr); β-Methoxyethoxymethyl ether (MEM); (4-Nitrophenyl)sulfonyl or (4-nitrophenyl)(dioxido)-lambda(6)-sulfanyl) (Nosyl); 2-Cyanoethyl; 2-Nitrophenylsulfenyl (Nps); 3,4-Dimethoxybenzyl (DMPM); and 9-Fluorenylmethyloxycarbonyl (FMOC)

The term "oxo" as used herein, represents =O.

The prefix "perfluoro," as used herein, represents anyl group, as defined herein, where each hydrogen radical bound to the alkyl group has been replaced by a fluoride radical. For example, perfluoroalkyl groups are exemplified by trifluoromethyl, and pentafluoroethyl.

The term "protected hydroxyl," as used herein, refers to an oxygen atom bound to an O-protecting group.

The term "spirocyclyl," as used herein, represents a $C_{2-7}$ alkylene diradical, both ends of which are bonded to the same carbon atom of the parent group to form a spirocyclic group, and also a $C_{1-6}$ heteroalkylene diradical, both ends of which are bonded to the same atom. The heteroalkylene radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the invention may be optionally substituted with 1, 2, 3, or 4 substituents provided herein as optional substituents for cycloalkyl and/or heterocyclyl groups.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfonyl," as used herein, represents an —S(O)$_2$— group.

The term "thiol," as used herein represents an —SH group.

Definitions

The term "cancer" refers to any cancer caused by the proliferation of malignant neoplastic cells, such as tumors, neoplasms, carcinomas, sarcomas, leukimias, and lymphomas.

"Cell migration" as used in this application involves the invasion by the cancer cells into the surrounding tissue and the crossing of the vessel wall to exit the vasculature in distal organs of the cancer cell.

By "cell migration cancers" is meant cancers that migrate by invasion by the cancer cells into the surrounding tissue and the crossing of the vessel wall to exit the vasculature in distal organs of the cancer cell.

As used herein, "drug resistant cancer" refers to any cancer that is resistant to an antiproliferative in Table 11.

As used herein, "metastatic nodule" refers to an aggregation of tumor cells in the body at a site other than the site of the original tumor.

As used herein, "metastatic tumor" refers to a tumor or cancer in which the cancer cells forming the tumor have a high potential to or have begun to, metastasize, or spread from one location to another location or locations within a subject, via the lymphatic system or via haematogenous spread, for example, creating secondary tumors within the subject. Such metastatic behavior may be indicative of malignant tumors. In some cases, metastatic behavior may be associated with an increase in cell migration and/or invasion behavior of the tumor cells.

Examples of cancers that can be defined as metastatic include but are not limited to non-small cell lung cancer, breast cancer, ovarian cancer, colorectal cancer, biliary tract cancer, bladder cancer, brain cancer including glioblastomas and medullablastomas, cervical cancer, choriocarcinoma, endometrial cancer, esophageal cancer, gastric cancer, hematological neoplasms, multiple myeloma, leukemia, intraepithelial neoplasms, liver cancer, lymphomas, neuroblastomas, oral cancer, pancreatic cancer, prostate cancer, sarcoma, skin cancer including melanoma, basocellular cancer, squamous cell cancer, testicular cancer, stromal tumors, germ cell tumors, thyroid cancer, and renal cancer.

As used herein, "migrating cancer" refers to a cancer in which the cancer cells forming the tumor migrate and subsequently grow as malignant implants at a site other than the site of the original tumor. The cancer cells migrate via seeding the surface of the peritoneal, pleural, pericardial, or subarachnoid spaces to spread into the body cavities; via invasion of the lymphatic system through invasion of lymphatic cells and transport to regional and distant lymph nodes and then to other parts of the body; via haematogenous spread through invasion of blood cells; or via invasion of the surrounding tissue. Migrating cancers include metastatic tumors and cell migration cancers, such as ovarian cancer, mesothelioma, and primary lung cancer, each of which is characterized by cellular migration.

"Non-metastatic cell migration cancer" as used herein refers to cancers that do not migrate via the lymphatic system or via haematogenous spread.

"Proliferation" as used in this application involves reproduction or multiplication of similar forms (cells) due to constituting (cellular) elements.

As used herein, "slowing the spread of metastasis" refers to reducing or stopping the formation of new loci; or reducing, stopping, or reversing the tumor load.

As used herein, "slowing the spread of migrating cancer" refers to reducing or stopping the formation of new loci; or reducing, stopping, or reversing the tumor load.

As used herein "substantially enantiomerically pure," refers to a composition (e.g., a pharmaceutical composition) wherein greater 85% (e.g., greater than 90%, greater than 95%, up to and including 100%, i.e., within the limits of detection) of the molecules of creatine transport inhibitor or creatine kinase inhibitor in the composition have the same chirality sense.

As used herein, and as well understood in the art, "to treat" a condition or "treatment" of the condition (e.g., the conditions described herein such as cancer) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

As used herein, "tumor seeding" refers to the spillage of tumor cell clusters and their subsequent growth as malignant implants at a site other than the site of the original tumor.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

Mice were euthanized 28 days after injection and livers excised for bioluminescent imaging and gross histology. c) Liver metastasis in mice injected with 5×10⁵ PANC1 pancreatic cancer cells transduced with a shRNA targeting SLC6a8. Metastatic progression was monitored by bioluminescent imaging and mice were euthanized as described above. Error bars represent the s.e.m; all P values are based on one-sided Student's t-tests. *P<0.05; P<0.001; *P<0.0001.

Figure 4:
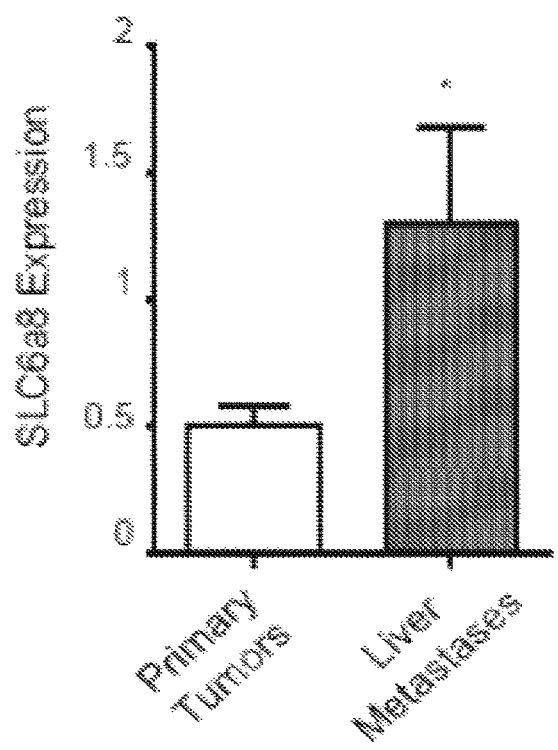

FIG. 4 is a diagram showing that SLC6a8 is up-regulated in liver metastases compared to primary tumors. Expression of SLC6a8 in 36 primary tumors and 30 liver metastases were quantified by quantitative real-time PCR. Error bars represent the s.e.m; all P values are based on one-sided Student's t-tests. *P<0.05.

Figure 5:
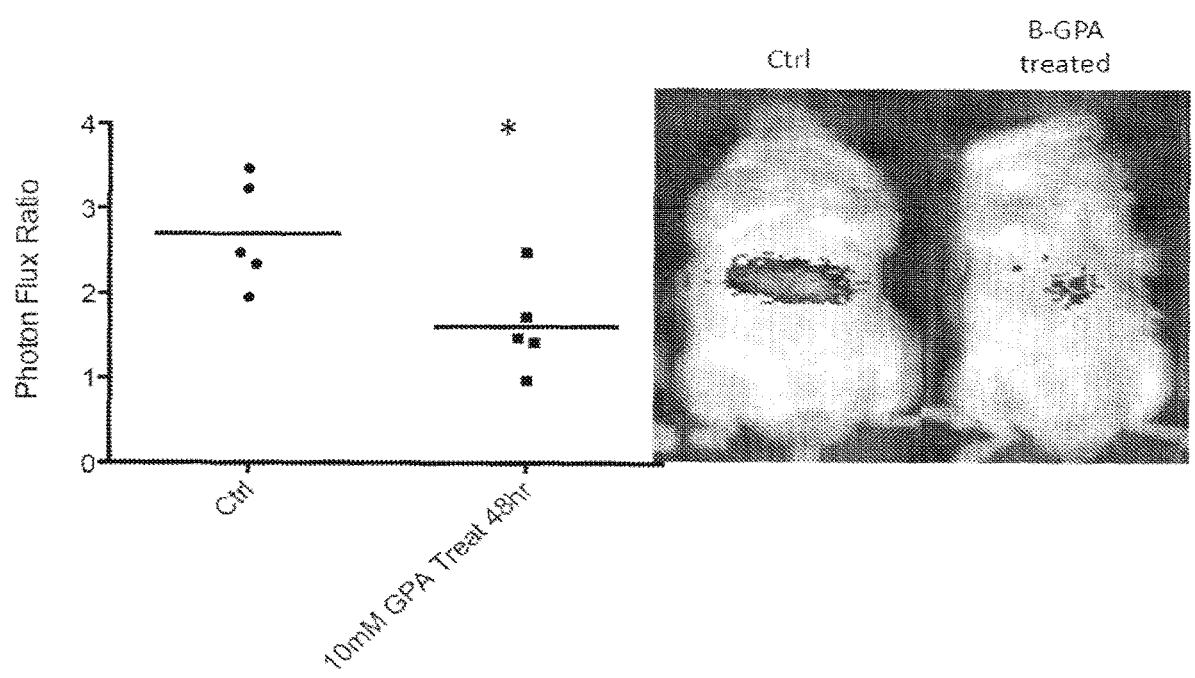

FIG. 5 is a diagram and a photograph showing that β-GPA treatment suppresses survival of disseminated PANC1 pancreatic cancer cells in the liver in vivo. Bioluminescence imaging of immunodeficient mice injected with 5×10⁵ PANC1 cells with and without 10 mM β-GPA-pre-treatment for 48 hr. Mice were imaged on day 1 after injection and signal was normalized to day zero. P values are based on one-sided Student's t-tests. *P<0.05.

Figure 6:
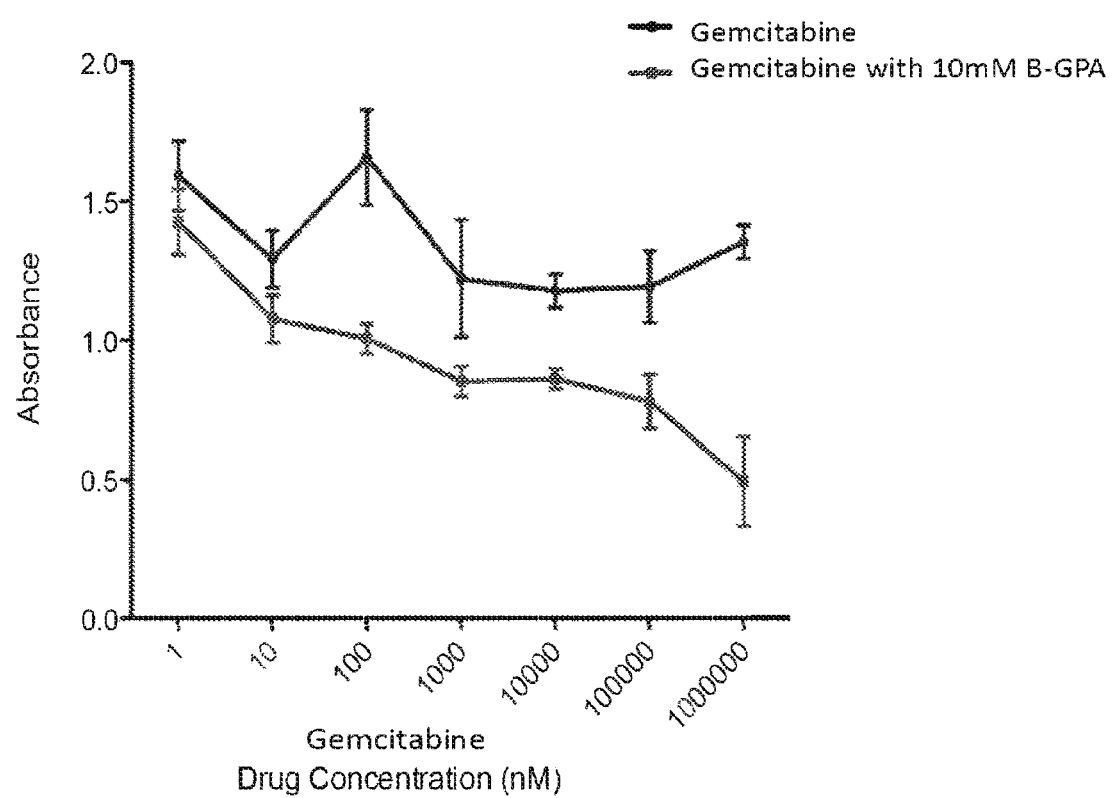

FIG. 6 is a diagram showing that β-GPA enhances the cytotoxicity of Gemcitabine on PANC1 pancreatic cancer cells. Cell viability of PANC1 pancreatic cancer cells after treatment with escalating doses of Gemcitabine alone or escalating doses of Gemcitabine in combination with 10 mM β-GPA. Cell viability was assayed using the WST-1 reagent. Error bars represent standard error of the mean.

Figure 7:
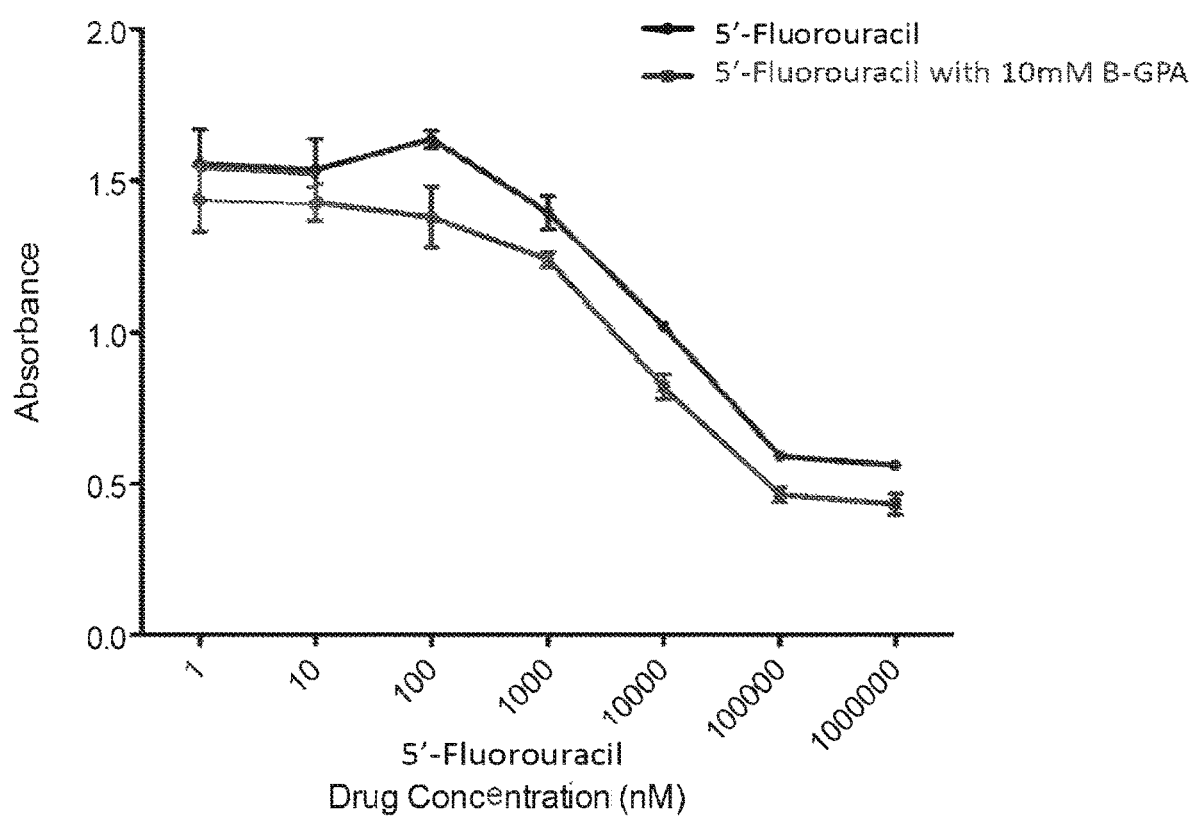

FIG. 7 is a diagram showing that β-GPA enhances the cytotoxicity of 5'-fluorouracil on LS-LvM3b colorectal cancer cells. Cell viability of Ls-LvM3b cells after treatment with escalating doses of 5'-Fluorouracil alone or escalating doses of 5'-Fluorouracil in combination with 10 mM β-GPA. Cell viability was assayed using the WST-1 reagent. Error bars represent standard error of the mean.

DETAILED DESCRIPTION OF THE INVENTION

The present invention features methods for preventing or reducing aberrant proliferation, differentiation, or survival of cells. For example, compounds of the invention may be useful in reducing the risk of, or preventing, tumors from increasing in size or from reaching a metastatic state. The subject compounds may be administered to halt the progression or advancement of cancer. In addition, the instant invention includes use of the subject compounds to reduce the risk of, or prevent, a recurrence of cancer.

Compounds

The invention features compounds useful in the treatment of cancer. Exemplary compounds described herein include compounds having a structure according to Formulae I-III as described herein:

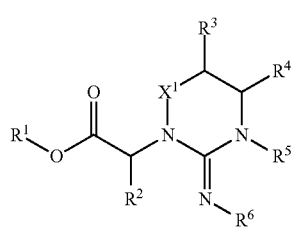

Formula I wherein $X^1$ is absent, NH, or $CH_2$;
$R^1$ is hydrogen, optionally substituted $C_1$-$C_6$ alkyl, or optionally substituted $C_6$-$C_{10}$ aryl $C_1$-$C_6$ alkyl;
$R^2$, $R^3$, and $R^4$ are independently hydrogen or optionally substituted $C_1$-$C_6$ alkyl; and
$R^5$ and $R^6$ are hydrogen or $NH_2$;
wherein if $R^5$ and $R^6$ are both hydrogen or $R^5$ is $NH_2$ and $R^6$ is hydrogen then $R^2$ is optionally substituted $C_1$-$C_6$ alkyl, or a pharmaceutically acceptable salt thereof;

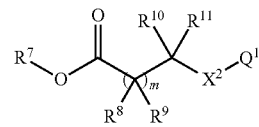

Formula II wherein $Q^1$ is optionally substituted amidino or optionally substituted 2-pyridyl;
$X^2$ is S or $NR^{12}$;
m is 0 or 1;
$R^7$ is hydrogen, optionally substituted $C_1$-$C_6$ alkyl, or optionally substituted $C_6$-$C_{10}$ aryl $C_1$-$C_6$ alkyl;
$R^8$ and $R^9$ are independently hydrogen, deuterium, halo, hydroxyl, $NH_2$, optionally substituted $C_1$-$C_6$ alkyl, or $R^8$ or $R^9$ can combine with $R^{10}$ or $R^{11}$ to form an optionally substituted $C_3$-$C_6$ cycloalkyl ring or with $R^{12}$ to form an optionally substituted $C_3$-$C_6$ heterocycle;
$R^{10}$ and $R^{11}$ are independently hydrogen, deuterium, optionally substituted $C_1$-$C_6$ alkyl, or $R^{10}$ or $R^{11}$ can combine with $R^8$ or $R^9$ to form an optionally substituted $C_3$-$C_6$ cycloalkyl ring;
$R^{12}$ is hydrogen, optionally substituted $C_1$-$C_6$ alkyl, or $R^{12}$ can combine with $R^8$ or $R^9$ to form an optionally substituted $C_3$-$C_6$ heterocycle, and
wherein if $R^9$ is halo then $R^8$ is halo or optionally substituted $C_1$-$C_6$ alkyl,
or a pharmaceutically acceptable salt thereof;

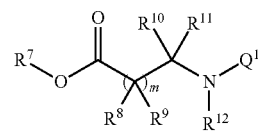

Formula V wherein a is optionally substituted amidino or optionally substituted 2-pyridyl;
m is 1 or 2;
$R^7$ is hydrogen, optionally substituted $C_1$-$C_6$ alkyl, or optionally substituted $C_6$-$C_{10}$ aryl $C_1$-$C_6$ alkyl;
$R^8$ and $R^9$ are independently hydrogen, deuterium, halo, hydroxyl, $NH_2$, optionally substituted $C_1$-$C_3$ alkyl, or $R^8$ and $R^9$ combine with the atoms to which they are attached to form an optionally substituted $C_3$-$C_6$ cycloalkyl ring; or $R^8$ or $R^9$ combine with $R^{10}$ or $R^{11}$ with the atoms to which they are attached to form an optionally substituted $C_3$-$C_4$ cycloalkyl ring; or $R^8$ or $R^9$ combine with $R^{12}$ with the atoms to which they are attached to form an optionally substituted $C_3$-$C_5$ heterocycle;
$R^{10}$ and $R^{11}$ are independently hydrogen, deuterium, optionally substituted $C_1$-$C_4$ alkyl, optionally substituted $C_2$-$C_6$ alkenyl, optionally substituted $C_2$-$C_6$ alkynyl or $R^{10}$ and $R^{11}$ combine with the atoms to which they are attached to form an optionally substituted $C_3$-$C_6$ cycloalkyl ring; or $R^{10}$ or $R^{11}$ combine with $R^8$ or $R^9$ with the atoms to which they are attached to form an optionally substituted $C_3$-$C_4$ cycloalkyl ring; or $R^{10}$ or $R^{11}$ combine with $R^{12}$ with the atoms to which they are attached to form an optionally substituted $C_3$-$C_4$ heterocycle;

$R^{12}$ is hydrogen, optionally substituted $C_1$-$C_6$ alkyl, or $R^{12}$ combines with $R^8$ or $R^9$ with the atoms to which they are attached to form an optionally substituted $C_3$-$C_5$ heterocycle, or $R^{12}$ combines with $R^{10}$ or $R^{11}$ with the atoms to which they are attached to form an optionally substituted $C_3$-$C_4$ heterocycle wherein if m is 1 and $R^8$ is hydrogen, halo, hydroxyl, or methyl then at least one of $R^9$, $R^{10}$, and $R^{11}$ is not hydrogen;

wherein if m is 1 and $R^{10}$ is methyl then at least one of $R^8$, $R^9$, and $R^{11}$ is not hydrogen;

wherein if m is 1 and $R^8$ is $NH_2$ and $R^{10}$ is hydrogen, methyl, or —$CH_2CH_2OH$ then at least one of $R^9$ or $R^{11}$ is not hydrogen;

wherein if m is 1, $R^8$ is halo, and $R^{10}$ is optionally substituted $C_1$-$C_4$ alkyl then at least one of $R^9$ and $R^{10}$ is not hydrogen;

or a pharmaceutically acceptable salt thereof; and

A-B      Formula III wherein A is a inhibitor of creatine transport and/or creatine kinase comprising an amidino group;

B has the structure:

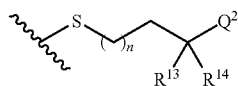

Formula IV wherein n is 0 or 1;

$Q^2$ is hydroxyl, optionally substituted amino, or —$SO_2OH$; and $R^{13}$ and $R^{14}$ are independently hydrogen, —$CO_2H$, or combine to form C=0;

wherein B is conjugated to A at one of the amidino nitrogens, or a pharmaceutically acceptable salt thereof.

Other embodiments (e.g., Compounds 1-326 of Tables 1-11) as well as exemplary methods for the synthesis of these compounds are described herein.

Utility and Administration

The compounds described herein (e.g., a compound according to Formulae I-IX or any of Compounds 1-448 of Tables 1-11) are useful in the methods of the invention and, while not bound by theory, are believed to exert their desirable effects through their ability to inhibit creatine transport and/or creatine kinase. The compounds described herein (e.g., a compound according to Formulae I-IX or any of Compounds 1-448 of Tables 1-11) can also be used for the treatment of certain conditions such as cancer.

Creatine helps supply energy to all cells in the body by increasing formation of ATP. It is taken up by tissues with high energy demands through an active transport system. The conversion of ADP to ATP by phosphate transfer from phosphocreatine is catylzed by creatine kinase. Some of the functions associated with the phosphocreatine system include efficient regeneration of energy in the form of ATP in cells with fluctuating and high energy demand, energy transport to different parts of the cell, phosphoryl transport activity, ion transport regulation, and involvement in signal transduction pathways.

Creatine kinase has been shown to have elevated levels in certain tumor types. These tumor types may utilize the increased expression of creatine kinase to prevent apoptosis under hypoxic or hypoglycemic conditions. Malignant cancers with poor prognosis have also been shown to overexpress creatine kinases, which may be related to high energy turnover and failure to eliminate cancer cells by apoptosis. Inhibtion of the active transport of creatine into cancer cells may reverse these trends and result in inhibition of the cancer and/or metastasis.

Treatment Methods

As disclosed herein, inhibition of creatine transport and/or creatine kinase suppresses metastasis. The phosphocreatine system promotes metastasis by enhancing the survival of disseminated cancer cells in the liver by acting as an energetic store for ATP generation to endure hepatic hypoxia. Inhibition of creatine transport into cancer cells limits the amount of phosphocreatine available to use in the production of ATP. Inhibition of creatine kinase inhibits the production of ATP through conversion of phosphocreatine to creatine.

Typical vascularized tumors that can be treated with the method include solid tumors, particularly carcinomas, which require a vascular component for the provision of oxygen and nutrients. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas.

Treating cancer can result in a reduction in size or volume of a tumor. For example, after treatment, tumor size is reduced by 5% or greater (e.g., 10%, 20%, 30%, 40%, 50%, 60%, 70%, 80%, 90% or greater) relative to its size prior to treatment. Size of a tumor may be measured by any reproducible means of measurement. The size of a tumor may be measured as a diameter of the tumor or by any reproducible means of measurement.

Treating cancer may further result in a decrease in number of tumors. For example, after treatment, tumor number is reduced by 5% or greater (e.g., 10%, 20%, 30%, 40%, 50%, 60%, 70%, 80%, 90% or greater) relative to number prior to treatment. Number of tumors may be measured by any reproducible means of measurement. The number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic noduless may be measured by any reproducible means of measurement. The number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with the compound of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with the compound of the invention. A decrease in the mortality rate of a population may also be measured, for example, by calculating for a population the average number of disease-related deaths per unit time following completion of a first round of treatment with the compound of the invention.

Compositions

Within the scope of this invention is a composition that contains a suitable carrier and one or more of the therapeutic agents described above. The composition can be a pharmaceutical composition that contains a pharmaceutically acceptable carrier, a dietary composition that contains a dietarily acceptable suitable carrier, or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, sodium lauryl sulfate, and D&C Yellow #10.

As used herein, the term "pharmaceutically acceptable salt" refers to those salts which are, within the scope of sound medical judgment, suitable for use in contact with the tissues of humans and lower animals without undue toxicity, irritation, or allergic response, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts, include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Representative alkali or alkaline earth metal salts include sodium, lithium, potassium, calcium, and magnesium. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutical compositions of the present invention additionally include a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, and lubricants, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, diastearoyl phosphatidylethanolamine (DSPE) and its pegylated esters, such as DSPE-PEG750 and, DSPE-PEG2000, phosphatidic acid, phosphatidyl glycerol and phosphatidyl serine. Commercial grades of lecithin which are preferred include those which are available under the trade name Phosal® or Phospholipon® and include Phosal 53 MCT, Phosal 50 PG, Phosal 75 SA, Phospholipon 90H, Phospholipon 90G and Phospholipon 90 NG; soy-phosphatidylcholine (SoyPC) and DSPE-PEG2000 are particularly preferred; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The above-described composition, in any of the forms described above, can be used for treating melanoma, or any other disease or condition described herein. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment. A pharmaceutical composition of this invention can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally include one or more excipients or diluents. In some preferred embodiments, the topical formulations include a material that would enhance absorption or penetration of the active agent(s) through the skin or other affected areas.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, or allergic response. The carrier enables an active agent and optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition.

Combination Therapies

In some embodiments, the pharmaceutical composition may further include an additional compound having antiproliferative activity. The additional compound having antiproliferative activity can be selected from a group of antiproliferative agents including those shown in Table 12.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

By "antiproliferative agent" is meant any antiproliferative agent, including those antiproliferative agents listed in Table 12, any of which can be used in combination with a creatine transport and/or creatine kinase inhibitor to treat the medical conditions recited herein. Antiproliferative agents also include organo-platine derivatives, naphtoquinone and benzoquinone derivatives, chrysophanic acid and anthroquinone derivatives thereof.

TABLE 12

| Alkylating agents | Busulfan | Chlorambucil |
|---|---|---|
| | dacarbazine | procarbazine |
| | ifosfamide | altretamine |
| | hexamethylmelamine | estramustine phosphate |

TABLE 12-continued

| | | |
|---|---|---|
| | thiotepa | mechlorethamine |
| | decarbazine | streptozocin |
| | lomustine | temozolomide |
| | cyclophosphamide | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | SM-11355 (Sumitomo) |
| | ZD-0473 (AnorMED) | AP-5280 (Access) |
| | oxaliplatin | cisplatin |
| | carboplatin | |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | J-107088 (Merck & Co) |
| | rebeccamycin analogue (Exelixis) | BNP-1350 (BioNumerik) |
| | BBR-3576 (Novuspharma) | CKD-602 (Chong Kun Dang) |
| | rubitecan (SuperGen) | KW-2170 (Kyowa Hakko) |
| | irinotecan (CPT-11) | hydroxycamptothecin (SN-38) |
| | topotecan | |
| Antitumor antibiotics | valrubicin | azonafide |
| | therarubicin | anthrapyrazole |
| | idarubicin | oxantrazole |
| | rubidazone | losoxantrone |
| | plicamycin | MEN-10755 (Menarini) |
| | porfiromycin | GPX-100 (Gem Pharmaceuticals) |
| | mitoxantrone (novantrone) | Epirubicin |
| | amonafide | mitoxantrone |
| | | doxorubicin |
| Antimitotic agents | colchicine | E7010 (Abbott) |
| | vinblastine | PG-TXL (Cell Therapeutics) |
| | vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | ZD 6126 (AstraZeneca) |
| | T 138067 (Tularik) | AZ10992 (Asahi) |
| | cryptophycin 52 (Eli Lilly) | IDN-5109 (Indena) |
| | vinflunine (Fabre) | AVLB (Prescient NeuroPharma) |
| | auristatin PE (Teikoku Hormone) | azaepothilone B (BMS) |
| | BMS 247550 (BMS) | BNP-7787 (BioNumerik) |
| | BMS 184476 (BMS) | CA-4 prodrug (OXiGENE) |
| | BMS 188797 (BMS) | dolastatin-10 (NIH) |
| | taxoprexin (Protarga) | CA-4 (OXiGENE) |
| | SB 408075 (GlaxoSmithKline) | docetaxel |
| | Vinorelbine | vincristine |
| | Trichostatin A | paclitaxel |
| Aromatase inhibitors | aminoglutethimide | YM-511 (Yamanouchi) |
| | atamestane (BioMedicines) | formestane |
| | letrozole | exemestane |
| | anastrazole | |
| Thymidylate synthase inhibitors | pemetrexed (Eli Lilly) | nolatrexed (Eximias) |
| | ZD-9331 (BTG) | CoFactor ™ (BioKeys) |
| DNA antagonists | trabectedin (PharmaMar) | edotreotide (Novartis) |
| | glufosfamide (Baxter International) | mafosfamide (Baxter International) |
| | albumin + 32P (Isotope Solutions) | apaziquone (Spectrum Pharmaceuticals) |
| | thymectacin (NewBiotics) | O6 benzyl guanine (Paligent) |
| Farnesyltransferase inhibitors | arglabin (NuOncology Labs) | tipifarnib (Johnson & Johnson) |
| | lonafarnib (Schering-Plough) | perillyl alcohol (DOR BioPharma) |
| | BAY-43-9006 (Bayer) | |

TABLE 12-continued

| | | |
|---|---|---|
| Pump inhibitors | CBT-1 (CBA Pharma) | zosuquidar trihydrochloride (Eli Lilly) |
| | tariquidar (Xenova) | biricodar dicitrate (Vertex) |
| | MS-209 (Schering AG) | |
| Histone | tacedinaline (Pfizer) | pivaloyloxymethyl butyrate (Titan) |
| acetyltransferase | SAHA (Aton Pharma) | depsipeptide (Fujisawa) |
| inhibitors | MS-275 (Schering AG) | |
| Metalloproteinase | Neovastat (Aeterna Laboratories) | CMT-3 (CollaGenex) |
| inhibitors | marimastat (British Biotech) | BMS-275291 (Celltech) |
| Ribonucleoside | gallium maltolate (Titan) | tezacitabine (Aventis) |
| reductase inhibitors | triapine (Vion) | didox (Molecules for Health) |
| TNF alpha | virulizin (Lorus Therapeutics) | revimid (Celgene) |
| agonists/antagonists | CDC-394 (Celgene) | |
| Endothelin A | atrasentan (Abbott) | YM-598 (Yamanouchi) |
| receptor antagonist | ZD-4054 (AstraZeneca) | |
| Retinoic acid | fenretinide (Johnson & Johnson) | alitretinoin (Ligand) |
| receptor agonists | LGD-1550 (Ligand) | |
| Immuno-modulators | interferon | dexosome therapy (Anosys) |
| | oncophage (Antigenics) | pentrix (Australian Cancer |
| | GMK (Progenics) | Technology) |
| | adenocarcinoma vaccine (Biomira) | ISF-154 (Tragen) |
| | CTP-37 (AVI BioPharma) | cancer vaccine (Intercell) |
| | IRX-2 (Immuno-Rx) | norelin (Biostar) |
| | PEP-005 (Peplin Biotech) | BLP-25 (Biomira) |
| | synchrovax vaccines (CTL Immuno) | MGV (Progenics) |
| | melanoma vaccine (CTL Immuno) | ß-alethine (Dovetail) |
| | p21 RAS vaccine (GemVax) | CLL therapy (Vasogen) |
| | MAGE-A3 (GSK) | Ipilimumab (BMS), |
| | nivolumab (BMS) | CM-10 (cCam Biotherapeutics) |
| | abatacept (BMS) | MPDL3280A (Genentech) |
| | pembrolizumab | MEDI4736 |
| Hormonal and | estrogens | dexamethasone |
| antihormonal agents | conjugated estrogens | prednisone |
| | ethinyl estradiol | methylprednisolone |
| | chlortrianisen | prednisolone |
| | idenestrol | aminoglutethimide |
| | hydroxyprogesterone caproate | leuprolide |
| | medroxyprogesterone | octreotide |
| | testosterone | mitotane |
| | testosterone propionate; | P-04 (Novogen) |
| | fluoxymesterone | 2-methoxyestradiol (EntreMed) |
| | methyltestosterone | arzoxifene (Eli Lilly) |
| | diethylstilbestrol | tamoxifen |
| | megestrol | toremofine |
| | bicalutamide | goserelin |
| | flutamide | Leuporelin |
| | nilutamide | bicalutamide |
| Photodynamic | talaporfin (Light Sciences) | Pd-bacteriopheophorbide (Yeda) |
| agents | Theralux (Theratechnologies) | lutetium texaphyrin (Pharmacyclics) |
| | motexafin gadolinium | hypericin |
| | (Pharmacyclics) | |
| Kinase Inhibitors | imatinib (Novartis) | EKB-569 (Wyeth) |
| | leflunomide (Sugen/Pharmacia) | kahalide F (PharmaMar) |
| | ZD1839 (AstraZeneca) | CEP-701 (Cephalon) |
| | erlotinib (Oncogene Science) | CEP-751 (Cephalon) |
| | canertinib (Pfizer) | MLN518 (Millenium) |
| | squalamine (Genaera) | PKC412 (Novartis) |
| | SU5416 (Pharmacia) | Phenoxodiol (Novogen) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (ImClone) |
| | trastuzumab (Genentech) | Tyrphostins |
| | OSI-774 (Tarceva ™) | Gefitinib (Iressa) |
| | CI-1033 (Pfizer) | PTK787 (Novartis) |
| | SU11248 (Pharmacia) | EMD 72000 (Merck) |
| | RH3 (York Medical) | Emodin |
| | Genistein | Radicinol |
| | Radicinol | Vemurafenib (B-Raf enzyme |
| | Met-MAb (Roche) | inhibitor, Daiichi Sankyo) |

SR-27897 (CCK A inhibitor, Sanofi-Synthelabo)
tocladesine (cyclic AMP agonist, Ribapharm)
alvocidib (CDK inhibitor, Aventis)
CV-247 (COX-2 inhibitor, Ivy Medical)
P54 (COX-2 inhibitor, Phytopharm)
CapCell ™ (CYP450 stimulant, Bavarian Nordic)
GCS-100 (gal3 antagonist, GlycoGenesys)

ceflatonin (apoptosis promotor, ChemGenex)
BCX-1777 (PNP inhibitor, BioCryst)
ranpirnase (ribonuclease stimulant, Alfacell)
galarubicin (RNA synthesis inhibitor, Dong-A)
tirapazamine (reducing agent, SRI
International)
N-acetylcysteine (reducing agent, Zambon)

TABLE 12-continued

| | |
|---|---|
| G17DT immunogen (gastrin inhibitor, Aphton) | R-flurbiprofen (NF-kappaB inhibitor, Encore) |
| efaproxiral (oxygenator, Allos Therapeutics) | 3CPA (NF-kappaB inhibitor, Active Biotech) |
| PI-88 (heparanase inhibitor, Progen) | seocalcitol (vitamin D receptor agonist, Leo) |
| tesmilifene (histamine antagonist, YM BioSciences) | 131-I-TM-601 (DNA antagonist, TransMolecular) |
| histamine (histamine H2 receptor agonist, Maxim) | eflornithine (ODC inhibitor, ILEX Oncology) |
| tiazofurin (IMPDH inhibitor, Ribapharm) | minodronic acid (osteoclast inhibitor, Yamanouchi) |
| cilengitide (integrin antagonist, Merck KGaA) | |
| SR-31747 (IL-1 antagonist, Sanofi-Synthelabo) | indisulam (p53 stimulant, Eisai) |
| CCI-779 (mTOR kinase inhibitor, Wyeth) | aplidine (PPT inhibitor, PharmaMar) |
| exisulind (PDE V inhibitor, Cell Pathways) | gemtuzumab (CD33 antibody, Wyeth Ayerst) |
| CP-461 (PDE V inhibitor, Cell Pathways) | PG2 (hematopoiesis enhancer, Pharmagenesis) |
| AG-2037 (GART inhibitor, Pfizer) | |
| WX-UK1 (plasminogen activator inhibitor, Wilex) | Immunol ™ (triclosan oral rinse, Endo) |
| PBI-1402 (PMN stimulant, ProMetic LifeSciences) | triacetyluridine (uridine prodrug, Wellstat) |
| bortezomib (proteasome inhibitor, Millennium) | SN-4071 (sarcoma agent, Signature BioScience) |
| SRL-172 (T cell stimulant, SR Pharma) | |
| TLK-286 (glutathione S transferase inhibitor, Telik) | TransMID-107 ™ (immunotoxin, KS Biomedix) |
| | PCK-3145 (apoptosis promotor, Procyon) |
| PT-100 (growth factor agonist, Point Therapeutics) | doranidazole (apoptosis promotor, Pola) |
| | cafestol |
| Chrysophanic acid | kahweol |
| Cesium oxides | caffeic acid |
| BRAF inhibitors, | Tyrphostin AG |
| PDL1 inhibitors | PD-1 inhibitors |
| MEK inhibitors | CTLA-4 inhibitors |
| bevacizumab | sorafenib |
| angiogenesis inhibitors | BRAF inhibitors |
| rituximab (CD20 antibody, Genentech | urocidin (apoptosis promotor, Bioniche) |
| carmustine | Ro-31-7453 (apoptosis promotor, La Roche) |
| Mitoxantrone | brostallicin (apoptosis promotor, Pharmacia) |
| Bleomycin | β-lapachone |
| Absinthin | gelonin |
| dabrafenib | CRS-207 |
| midostaurin (PKC inhibitor, Novartis) | CHS-828 (cytotoxic agent, Leo) |
| bryostatin-1 (PKC stimulant, GPC Biotech) | trans-retinoic acid (differentiator, NIH) |
| CDA-II (apoptosis promotor, Everlife) | MX6 (apoptosis promotor, MAXIA) |
| SDX-101 (apoptosis promotor, Salmedix) | apomine (apoptosis promotor, ILEX Oncology) |

The invention features the following numbered embodiments:

1. A compound having the structure:

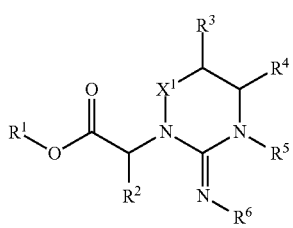

Formula I wherein $X^1$ is absent, NH, or $CH_2$;
$R^1$ is hydrogen, optionally substituted $C_1$-$C_6$ alkyl, or optionally substituted $C_6$-$C_{10}$ aryl $C_1$-$C_6$ alkyl;
$R^2$, $R^3$, and $R^4$ are independently hydrogen or optionally substituted $C_1$-$C_6$ alkyl; and
$R^5$ and $R^6$ are hydrogen or $NH_2$;
wherein if $R^5$ and $R^6$ are both hydrogen or $R^5$ is $NH_2$ and $R^6$ is hydrogen then $R^2$ is optionally substituted $C_1$-$C_6$ alkyl,
or a pharmaceutically acceptable salt thereof.

2. The compound of embodiment 1, wherein $R^1$ is hydrogen.

3. The compound of embodiments 1 or 2, wherein $R^3$ and $R^4$ are hydrogen.

4. The compound of any one of embodiments 1-3, wherein $R^2$ is hydrogen or optionally substituted $C_1$-$C_6$ alkyl, wherein said optionally substituted $C_1$-$C_6$ alkyl is methyl, ethyl, isopropyl, propyl, isobutyl, or optionally substituted $C_1$-$C_6$ haloalkyl.

5. The compound of embodiment 4, wherein said optionally substituted $C_1$-$C_6$ haloalkyl is trifluoromethyl.

6. The compound of any one of embodiments 1-5, wherein $R^5$ and $R^6$ are both hydrogen and $R^2$ is optionally substituted $C_1$-$C_6$ alkyl.

7. The compound of embodiment 6, wherein said optionally substituted $C_1$-$C_6$ alkyl is methyl, ethyl, isopropyl, or isobutyl.

8. The compound of any one of embodiments 1-5, wherein $R^5$ and $R^6$ are both $NH_2$.

9. The compound of embodiment 8, wherein $R^2$ is hydrogen.

10. The compound of embodiment 8, wherein $R^2$ is optionally substituted $C_1$-$C_6$ alkyl.

11. The compound of embodiment 10, wherein said optionally substituted $C_1$-$C_6$ alkyl is methyl or isopropyl.

12. The compound of any one of embodiments 1-5, wherein $R^5$ is $NH_2$, $R^6$ is hydrogen, and $R^2$ is optionally substituted $C_1$-$C_6$ alkyl.

13. The compound of embodiment 12, wherein said optionally substituted $C_1$-$C_6$ alkyl is methyl or isopropyl.

14. The compound of any one of embodiments 1-5, wherein $R^5$ is hydrogen and $R^6$ is $NH_2$.

15. The compound of embodiment 14, wherein $R^2$ is hydrogen.

16. The compound of embodiment 14, wherein $R^2$ is optionally substituted $C_1$-$C_6$ alkyl.

17. The compound of embodiment 16, wherein said optionally substituted $C_1$-$C_6$ alkyl is methyl or isopropyl.

18. The compound of any one of embodiments 1-17, wherein $X^1$ is absent.

19. The compound of any one of embodiments 1-17, wherein $X^1$ is $CH_2$.

20. The compound of any one of embodiments 1-17, wherein $X^1$ is $NH_2$.

21. The compound of embodiment 1, wherein said compound is any one of the compounds of Tables 1-3.

22. A compound having the structure:

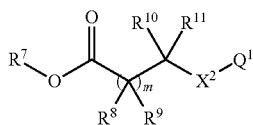

Formula II wherein $Q^1$ is optionally substituted amidino or optionally substituted 2-pyridyl;

$X^2$ is S or $NR^{12}$;

m is 0 or 1;

$R^7$ is hydrogen, optionally substituted $C_1$-$C_6$ alkyl, or optionally substituted $C_6$-$C_{10}$ aryl $C_1$-$C_6$ alkyl;

$R^8$ and $R^9$ are independently hydrogen, deuterium, halo, hydroxyl, $NH_2$, optionally substituted $C_1$-$C_6$ alkyl, or $R^8$ or $R^9$ can combine with $R^{10}$ or $R^{11}$ to form an optionally substituted $C_3$-$C_6$ cycloalkyl ring or with $R^{12}$ to form an optionally substituted $C_3$-$C_6$ heterocycle;

$R^{10}$ and $R^{11}$ are independently hydrogen, deuterium, optionally substituted $C_1$-$C_6$ alkyl, or $R^{10}$ or $R^{11}$ can combine with $R^8$ or $R^9$ to form an optionally substituted $C_3$-$C_6$ cycloalkyl ring;

$R^{12}$ is hydrogen, optionally substituted $C_1$-$C_6$ alkyl, or $R^{12}$ can combine with $R^8$ or $R^9$ to form an optionally substituted $C_3$-$C_6$ heterocycle, wherein if $Q^1$ is optionally substituted 2-pyridyl then $R^{12}$ is hydrogen, and wherein if $R^9$ is halo then $R^8$ is halo or optionally substituted $C_1$-$C_6$ alkyl, or a pharmaceutically acceptable salt thereof.

23. The compound of embodiment 22, wherein $R^7$ is hydrogen.

24. The compound of embodiments 22 or 23, wherein m is 1.

25. The compound of any one of embodiments 22-24, wherein $R^9$ is hydrogen, deuterium, or halo.

26. The compound of embodiment 25, wherein said halo is fluoro.

27. The compound of any one of embodiments 22-26, wherein $R^{11}$ is hydrogen or deuterium.

28. The compound of any one of embodiments 22-27, wherein $R^8$ and $R^{10}$ combine to form an optionally substituted $C_3$-$C_6$ cycloalkyl ring.

29. The compound of embodiment 28, wherein said optionally substituted $C_3$-$C_6$ cycloalkyl ring is cyclopropyl or cyclobutyl.

30. The compound of any one of embodiments 22-27, wherein both $R^{10}$ and $R^{11}$ are deuterium.

31. The compound of embodiment 30, wherein $R^8$ and $R^9$ are both deuterium.

32. The compound of any one of embodiments 22-27, wherein both $R^8$ and $R^9$ are halo.

33. The compound of embodiment 32, wherein said halo is fluoro.

34. The compound of any one of embodiments 22-27, wherein $R^{10}$ is optionally substituted $C_1$-$C_6$ alkyl.

35. The compound of embodiment 34, wherein said optionally substituted $C_1$-$C_6$ alkyl is optionally substituted $C_1$-$C_6$ haloalkyl.

36. The compound of embodiment 35, wherein said optionally substituted $C_1$-$C_6$ haloalkyl is trifluoromethyl.

37. The compound of embodiment 36, wherein $R^8$ is $NH_2$.

38. The compound of any one of embodiments 22-27, wherein $R^8$ is $NH_2$.

39. The compound of embodiment 38, wherein $R^{19}$ is optionally substituted $C_1$-$C_6$ alkyl.

40. The compound of embodiment 39, wherein said optionally substituted $C_1$-$C_6$ alkyl is methyl.

41. The compound of any one of embodiments 22-40, wherein $Q^1$ is optionally substituted amidino.

42. The compound of embodiment 41, wherein said optionally substituted amidino has the structure:

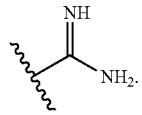 [SMILES: *C(=N)N]

43. The compound of embodiments 41 or 42, wherein $X^2$ is $NR^{12}$.

44. The compound of embodiment 43, wherein $R^8$ and $R^{12}$ combine to form an optionally substituted $C_3$-$C_6$ heterocycle.

45. The compound of embodiment 44, wherein said optionally substituted $C_3$-$C_6$ heterocycle is azetidine.

46. The compound of embodiment 43, wherein $R^{12}$ is hydrogen.

47. The compound of embodiments 41 or 42, wherein $X^2$ is S.

48. The compound of any one of embodiments 22-40, wherein $Q^1$ is optionally substituted 2-pyridyl.

49. The compound of embodiment 48, wherein said optionally substituted 2-pyridyl has the structure:

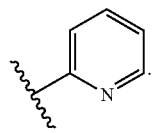

50. The compound of embodiments 48 or 49, wherein $X^2$ is $NR^{12}$ and $R^{12}$ is hydrogen.

51. The compound of embodiment 22, wherein said compound is any one of the compounds of Tables 4-6.

52. A compound having the structure:

A-B          Formula III wherein A is a inhibitor of creatine transport comprising an amidino group;

B has the structure:

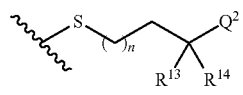

Formula IV wherein n is 0 or 1;

$Q^2$ is hydroxyl, optionally substituted amino, or —$SO_2OH$; and $R^{13}$ and $R^{14}$ are independently hydrogen, —$CO_2H$, or combine to form C=O;

wherein B is conjugated to A at one of the amidino nitrogens, or a pharmaceutically acceptable salt thereof.

53. The compound of embodiment 52, wherein $R^{14}$ is hydrogen.

54. The compound of embodiment 53, wherein $R^{13}$ is —$CO_2H$.

55. The compound of embodiment 53, wherein $R^{13}$ is hydrogen.

56. The compound of embodiments 52, wherein $R^{13}$ and $R^{14}$ combine to form C=O.

57. The compound of any one of embodiments 52-56, wherein n is 0.

58. The compound of any one of embodiments 52-56, wherein n is 1.

59. The compound of any one of embodiments 52-58, wherein $Q^2$ is optionally substituted amino.

60. The compound of embodiment 59, wherein said optionally substituted amino is —$NH_2$ or

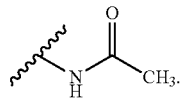 [SMILES: *NC(C)=O]

61. The compound of any one of embodiments 52-58, wherein $Q^2$ is hydroxyl.

62. The compound of any one of embodiments 52-58, wherein $Q^2$ is —$SO_2OH$.

63. The compound any one of embodiments 52-62, wherein said inhibitor of creatine transport has the structure of a compound of any one of embodiments 1-51 or any one of the compounds of Table 7 or Table 8.

64. The compound of embodiment 52, wherein said compound is any one of the compounds of Table 9 or Table 10.

65. A method for treating cancer, comprising administering to a subject in need thereof, a compound of any one of embodiments 1-64 in an amount sufficient to treat said cancer.

66. A method of slowing the spread of a migrating cancer, comprising administering to a subject in need thereof, a compound of any one of embodiments 1-64 in an amount sufficient to slow the spread of said migrating cancer.

67. The method of embodiment 66, wherein said method comprises the suppression of metastatic colonization of said migrating cancer in the liver.

68. The method of embodiment 67, wherein said migrating cancer is metastatic cancer.

69. The method of embodiment 68, wherein the metastatic cancer comprises cells exhibiting migration and/or invasion of migrating cells.

70. The method of embodiments 68 or 69, wherein said metastatic cancer comprises cells exhibiting endothelial recruitment and/or angiogenesis.

71. The method of any one of embodiments 67-70, wherein said migrating cancer spreads via seeding the surface of the peritoneal, pleural, pericardial, or subarachnoid spaces.

72. The method of any one of embodiments 67-70, wherein said migrating cancer spreads via the lymphatic system.

73. The method of any one of embodiments 67-70, wherein said migrating cancer spreads hematogenously.

74. The method of any one of embodiments 67-70, wherein said migrating cancer is a cell migration cancer.

75. The method of embodiment 74, wherein said cell migration cancer is a non-metastatic cell migration cancer.

76. The method of embodiment 75, where said cell migration cancer is ovarian cancer, mesothelioma, or primary lung cancer.

77. A method for inhibiting proliferation or growth of cancer stem cells or cancer initiating cells, comprising contacting the cell with a compound of any one of embodiments 1-64 in an amount sufficient to inhibit proliferation or growth of said cell.

78. A method of reducing the rate of tumor seeding of a cancer comprising administering to a subject in need thereof a compound of any one of embodiments 1-64 in an amount sufficient to reduce tumor seeding.

79. A method of reducing or treating metastatic nodule-forming of cancer comprising administering to a subject in need thereof a compound of any one of embodiments 1-64 in an amount sufficient to treat said metastatic nodule-forming of cancer.

80. The method of any one of embodiments 65-79, wherein said cancer is breast cancer, colon cancer, renal cell cancer, non-small cell lung cancer, hepatocellular carcinoma, gastric cancer, ovarian cancer, pancreatic cancer, esophageal cancer, prostate cancer, sarcoma, or melanoma.

81. The method of any one of embodiments 65-79, wherein said cancer is gastrointestinal cancer.

82. The method of embodiment 81, wherein said gastrointestinal cancer is esophageal cancer, stomach cancer, pancreatic cancer, liver cancer, gallbladder cancer, colorectal cancer, anal cancer, mucosa-associated lymphoid tissue cancer, gastrointestinal stromal tumors, a cancer of the biliary tree, or a gastrointestinal carcioid tumor.

83. The method of any one of embodiments 65-82, wherein said cancer is a drug resistant cancer.

84. The method of any one of embodiments 65-83 further comprising administering an additional antiproliferative agent.

85. The method of embodiment 84, wherein said additional antiproliferative agent is capecitabine, gemcitabine, fluorouracil, FOLFOX (5-FU, leucovorin, and Eloxatin), FOLFIRI (5-FU, leucovorin, and Camptosar), EOX (Epirubicin, Oxaliplatinum, and Xeloda), Taxotere, Erbitux, Zaltrap, Vectibix, Ramucirumab, Tivozanib, Stivarga, CRS-207, or a PD-1 or PDL-1 antibody.

86. A method of treating metastatic cancer in a subject in need thereof comprising:

(a) providing a subject identified to have, or to be at risk of having, metastatic cancer on the basis of the expression level of miR-483-5p and/or miR-551a is below a predetermined reference value or the expression level of CKB and/or SLC6a8 is above a predetermined reference value; and (b) administering to said subject an effective amount of a compound of any one of embodiments 1-64.

87. A method for treating metastatic cancer in a subject in need thereof, comprising contacting creatine transport channel SLC6a8 with a compound of any one of embodiments 1-64 in an amount effective to suppress metastatic colonization of said cancer.

EXAMPLES

Materials and Methods

Cell Culture

Indicated cell-lines were purchased from ATCC and cultured in DMEM media supplemented with 10% FBS, sodium pyruvate, L-glutamine and penicillin-streptomycin antibiotics. For drug pre-treatment, cells were treated with indicated amounts of drug for 24-48 hrs.

Animal Studies

All animal work was conducted in accordance with a protocol approved by the Institutional Animal Care and Use Committee (IACUC) at The Rockefeller University. 5-6 weeks old age-matched male NOD-SCID mice were used for intrahepatic colonization and liver metastasis assays.

Proliferation Assay in Hypoxic Conditions 100K cells were seeded in triplicates in 6 well plates and cells were counted 5 days after seeding. Cells were cultured in cell culture chamber containing 1% oxygen.

Primary Tumor Growth $1 \times 10^6$ cells were suspended in 100 µl of 1:1 PBS:Matrigel mixture and injected into the subcutaneous flanks of mice. Tumor growth was measured using digital calipers starting 7 days after injection when palpable tumors can be measured accurately. Volume of the tumors were calculated using the formula, Volume=(width)$^2$×(length)/2. When treated with drugs, mice were injected with indicated amounts of drug in 300 µl PBS daily until the mice were euthanized.

Metastasis Assay $5 \times 10^5$ highly metastatic cancer cells were injected into the portal circulation of immunodeficient mice. One day after inoculation of cancer cells, mice were injected indicated amounts of drug in 300 µL PBS. Treatment was continued daily and metastatic progression was monitored by bioluminescent imaging until the mice were euthanized at which point livers were excised for bioluminescent imaging and gross histology. Where indicated, cancer cells were pre-treated with indicated amounts of compound for 48 hrs before injection into immunodeficient mice.

In Vivo Creatine Transporter Inhibition Assay

Soluble compounds were formulated in saline solution (0.9% NaCl). Some compounds were first dissolved 1 N hydrochloric acid (1.0 equivalent) to make the HCl salt followed by addition of PBS to adjust to the final volume. Less soluble compounds were first dissolved 1 or 2 N hydrochloric acid (1.0 equivalent) to make the HCl salt followed by addition of DMSO and water to adjust to the final volume resulting in a 1:1 DMSO to aqueous ratio.

Studies were performed on 6-7 week old C57Bl6 male mice, receiving a regular diet (Purina 5001, Research Diet) and on a regular sleep rhythm (12 h night/day schedule). Experiments were performed ~6 h after exposing to daylight. Mice were weighed and randomly divided into groups of 3 mice per group and injected i.p. with 100-200 µL of dosing solution to deliver 250 mg/kg (50 mg/mL or 381 mM) β-GPA equivalent (i.e. 1.91 mmol/kg) along with a vehicle control. Creatine-(methyl-$d_3$) monohydrate (i.e. creatine-$d_3$, Cambridge Isotope Laboratories, Catalog DLM-1302) was dissolved in 100 µL 0.9% NaCl (0.2 mg/mL) and injected i.p. 7 minutes after drug injection. Volumes were adjusted based on the weight of the mice to reach a final dose of 1 mg/kg. After one hour, mice were euthanized, hearts were perfused with PBS, removed, snap-frozen in liquid nitrogen, and stored at −80° C. until further processing.

Mouse hearts were thawed and weighed into 1.5 mL Eppendorf conical tubes. Typical heart weights range from 800-1200 mg. Between six to twelve 1 mm zirconia/silica beads (BioSpec Products, Inc., Bartlesville, Okla.) were added to the tubes with sufficient volume of 70% 2-propanol in water to afford a 4-fold dilution. The samples were then placed in a MiniBeadBeater (BioSpec Products, Inc.) for 2 minutes to disrupt the tissue and homogenize the sample.

Aliqouts (20 µL) of the homogenized hearts were transferred to a 96-well microtiter plate. Samples were extracted by the addition of acetonitrile (1.0 mL) containing 0.25 µg/mL of creatine-$d_5$ (CDN Isotopes, Pointe-Claire, Quebec) as internal standard. Samples were mixed on a rotary shaker for 10 minutes then placed in a centrifuge to spin for 10 minutes at 3000 rpm at 4° C. Supernatant (900 µL) was transferred to 96-well deep well plate for analysis.

Calibration standards, blanks, and quality control samples are prepared from control mouse hearts homogenized as noted above. Aliquots of homogenate were then spiked with known quantities of creatine-$d_3$ (CDN Isotopes, Pointe-Claire, Quebec) or solvent, and processed along with the samples as noted above.

Analysis was conducted by LC-MS/MS using an Acquity UPLC (Waters Corp., Milford, Mass.)/Triple Quad 5500 (AB Sciex, Framingham, Mass.) system. Five microliters of sample are injected onto a HILIC column, 2.1×50 mm, 3 µm (Fortis Technologies, Cheshire, England) at a flow rate of 0.4 mL/min. A binary gradient of acetonitrile and 10 mM ammonium acetate was used to elute analytes from the column. The mass spectrometer was operated in positive ion electrospray in Multiple Reaction Monitoring mode for the following mass transitions:

Creatine-$d_5$: m/z 137.1/95.0
Creatine-$d_3$: m/z 135.1/93.0

Data were collected and processed using Analyst 1.6.2 (AB Sciex, Framingham, Mass.). A linear calibration of the creatine-$d_3$/creatine-$d_5$ peak area ratio ranged from 0.05 to 10 µg/mL. Data was report as µg of creatine-$d_3$ per gram of heart. Mean values and standard deviations were calculated from three heart samples and percent creatine-$d_3$ transport inhibition was reported relative to vehicle control.

TABLE 13

Percent Inhibition of Creatine-$d_3$ Transport in Heart Tissue.

| Compound | % Inhibition of Creatine-$d_3$ Transport |
|---|---|
| 219 | 79.0 (+/− 1.2) |
| 220 | 1.4 (+/− 8.2) |
| 258 | 71.8 (+/− 5.9) |
| 261 | 24.7 (+/− 12.6) |
| 358 | 11.1 (+/− 13.6) |
| 376 | 39.1 (+/− 25.2) |
| 125 | 4.5 (+/− 10.6) |
| 28 (β-GPA) | 73.4 (+/− 6.7) |

In Vivo Selection $1 \times 10^6$ LS174T cells expressing a luciferase reporter were suspended in a volume of 20 µl 1:1 PBS/Matrigel mixture and injected intra-hepatically into the livers of NOD-SCID mice. Metastatic nodules were allowed to develop over a period of 3-4 weeks and monitored by bioluminescence imaging. Nodules formed were excised and dissociated by collagenase and hyaluronidase digestion into single cell suspension. The cells were allowed to expand in in vitro before re-injection into mice. After three re-iterations of in vivo selection, highly metastatic LvM3a and LvM3b derivative cell-lines were established.

Lenti-miR Library Screening

Cells were transduced with a lentivirus Lenti-miR library of 611 miRNAs (System Biosciences) at a low multiplicity of infection (MOI) such that each cell over-expressed a single miRNA. The transduced population was then injected intra-hepatically into NOD-SCID mice for in vivo selection of miRNAs that when over-expressed, either promoted or suppressed metastatic liver colonization. Genomic DNA PCR amplication and recovery of lenti-viral miRNA inserts were performed on cells prior to injection and from liver nodules according to manufacturer's protocol. miRNA array profiling allowed for miRNA insert quantification prior to and after in vivo selection.

Organotypic Slice Culture System

Cells to be injected were labeled with cell-tracker red or green (Invitrogen) and inoculated into livers of NOD-SCID mice through intrasplenic injection. The livers were then extracted and cut into 150 um slices using a McIlwain tissue chopper (Ted Pella) and plated onto organotypic tissue culture inserts (Millipore) and cultured in William's E Medium supplemented with Hepatocyte Maintenance Supplement Pack (Invitrogen). After indicated time periods, the liver slices were fixed in paraformaldehyde and imaged using multi-photon microscopy.

In Vivo Caspase Activation Assay

To measure caspase activity in vivo, VivoGlo Caspase 3/7 Substrate (Z-DEVD-Aminoluciferin Sodium Salt, Promega) was used. The luciferin is inactive until the DEVD peptide is cleaved from by activated caspase-3 in apoptotic cells. DEVD-luciferin was injected into mice bearing colorectal cancer cells expressing luciferase. Upon activation by apoptotic cells, bioluminescence imaging can be performed to measure caspase activity in vivo. Five hours after in vivo caspase activity measurement, mice are injected with regular luciferin for normalization purposes.

Adeno-Associated Viral Therapy miR-483-5p and miR-551a were cloned as a polycistron consisting of both miRNA precursor with flanking genomic sequences in tandem into the BglII and NotI site of scAAV.GFP (Plasmid 21893, Addgene). Listed below are genomic sequences encoding for miR-483-5p and miR-551a (SEQ ID NOs: 5 and 6), corresponding precursor sequences (underlined, SEQ ID NOs: 3 and 4), and corresponding mature microRNA sequences (underlined and in bold, SEQ ID NOs: 1 and 2). Adeno-associated viruses were packaged, purified and titered using the AAV-DJ Helper Free expression system from Cell Biolabs.

miR-551a:
GGAGAACCTTCAGCTTCATGTGACCCAGAGACTCCTGTATGCCTGGCTC

TGGGAGTACAGAAGGGCCTAGAGCTGACCCCTGCCCTCCGAAGCCCCTG

GGGCACTAGATGGATGTGTGCCAGAGGGTAGTAGAGGCCTGGGGGTAGA

GCCCAGCACCCCCTTCGCGTAGAGACCTGGGGGACCAGCCAGCCCAGCA

ACCCCCTCGCGGCCGACGCCTGAGGCTGTTCCTGGCTGCTCCGGTGGCT

GCCAGA<u>GGGGACTGCCGGGTGACCCTGGAAATCCAGAGTGGGTGGGGCC

AGTCTGACCGTTTCTAGGCGACCCACTCTTGGTTTCCAGGGTTGCCCTG

GAAA</u>CCACAGATGGGGAGGGGTTGATGGCACCCAGCCTCCCCCAAGCCT

GGGAAGGGACCCC<u>GGATCCCC</u>AGAGCCTTTCCCTGCCTATGGAGCGTTT

CTCTTGGAGAACAGGGGGGCCTCTCAGCCCCTCAATGCAAGTTGCTGAG miR-483-5p:
CCTGCCCCATTTGGGGGTAGGAAGTGGCACTGCAGGGCCTGGTGCCAGC

CAGTCCTTGCCCAGGGAGAAGCTTCCCTGCACCAGGCTTTCCTGAGAGG

AGGGGAGGGCCAAGCCCCCACTTGGGGGACCCCCGTGATGGGGCTCCTG

CTCCCTCCTCCGGCTGATGGCACCTGCCCTTTGGCACCCCAAGGTGGAG

CCCCCAGCGACCTTCCCCTTCCAGCTGAGCATTGCTGTGGGGGA<u>GAGGG

GGAAGACGGGAGGAAAGAAGGGAGTGGTTCCATCACGCCTCCTCACTCC

TCTCCTCCCGTCTTCTCCTCTCCTGCCCTTGTCTCCCTGTCTCAGCAGC</u>

TCCAGGGGTGGTGTGGGCCCCTCCAGCCTCCTAGGTGGTGCCAGGCCAG

AGTCCAAGCTCAGGGACAGCAGTCCCTCCTGTGGGGGCCCCTGAACTGG

GCTCACATCCCACACATTTTCCAAACCACTCCCATTGTGAGCCTTTGGT

CCTGGTGGTGTCCCTCTGGTTGTGGGACCAAGAGCTTGTGCCCATTTTT

CATCTGAGGAAGGAGGCAGC

Listed below are the corresponding RNA sequences
for SEQ ID NOs: 1-4 (SEQ ID NOs: 7-10)

(SEQ ID NO: 7)
GACCCACUCUUGGUUUCCA (SEQ ID NO: 8)
GGGGACUGCCGGGUGACCCUGGAAAUCCAGAGUGGGUGGGGCCAGUCUG

ACCGUUUCUAGGCGACCCACUCUUGGUUUCCAGGGGUUGCCCUGGAAA (SEQ ID NO: 9)
GAAGACGGGAGGAAAGAAGGGAG (SEQ ID NO: 10)
GAGGGGGAAGACGGGAGGAAAGAAGGGAGUGGUUCCAUCACGCCUCCUC

ACUCCUCUCCUCCCGUCUUCUCCUCUC

CKB, SLC6a8 Knockdown pLKO vectors expressing shRNA hairpins targeting CKB and SLC6a8 were ordered from Sigma-Aldrich. Two independent hairpins that gave the best knockdown of transcript levels were used for all experiments. These hairpin DNA and RNA sequences are listed below in Table 14:

TABLE 14

Selected hairpin DNA and RNA sequences

| Name | DNA Sequences | SEQ ID NO | RNA Sequences | SEQ ID NO |
|---|---|---|---|---|
| CKB | CCGGCCCAGATTGAAACT CTCTTCACTCGAGTGAA GAGAGTTTCAATCTGGG TTTTT | 11 | CCGGCCCAGAUUGAAACUC UCUUCACUCGAGUGAAGAG AGUUUCAAUCUGGGUUUUU | 15 |
| CKB | CCGGCCGCGGTATCTGG CACAATGACTCGAGTCAT TGTGCCAGATACCGCGG TTTTTTG | 12 | CCGGCCGCGGUAUCUGGC ACAAUGACUCGAGUCAUUG UGCCAGAUACCGCGGUUUU UUG | 16 |
| shSLC 6a8 #2 | CCGGGCTGGTCTACAAC AACACCTACTCGAGTAGG TGTTGTTGTAGACCAGCT TTTTG | 19 | CCGGGCUGGUCUACAACAA CACCUACUCGAGUAGGUGU UGUUGUAGACCAGCUUUUU G | 20 |
| shSLC 6a8 #4 | CCGGCTTATTCCCTACGT CCTGATCCTCGAGGATCA GGACGTAGGGAATAAGTT TTTG | 13 | CCGGCUUAUUCCCUACGUC CUGAUCCUCGAGGAUCAGG ACGUAGGGAAUAAGUUUUU G | 17 |
| shSLC 6a8 #5 | CCGGATTACCTGGTCAAG TCCTTTACTCGAGTAAAG GACTTGACCAGGTAATTT TTTG | 14 | CCGGAUUACCUGGUCAAGU CCUUUACUCGAGUAAAGGA CUUGACCAGGUAAUUUUUU G | 18 |

The following primers were used for quantitative qRT-PCR of SLC6a8: Forward Primer: 5'-GGC AGC TAC AAC CGC TTC AAC A-3' and Reverse Primer: 5'-CAG GAT GGA GAA GAC CAC GAA G-3' (SEQ ID No. 21 and 22, respectively).

Cyclocreatine and Beta-Guanidiopropionic Acid Treatment

Mice were treated with 10 mg of cyclocreatine or saline vehicle, administered through intra-peritoneal injection. The treatment regime started one day after inoculation of tumor cells and continued until the mice were euthanized. Beta-guanidipropionic acid was administered at a dose of 200 µL of 0.5M solution through intra-peritoneal injection. Treatment regime were as that for cyclocreatine treatment.

Example 1. Synthesis of Creatine Transport Inhibitors and/or Creatine Kinase Inhibitors of the Invention Compounds of the invention may be synthesized using methods known in the art, for example using methods described in U.S. Pat. No. 5,321,030, 5,324,731, 5,955,617, 5,994,577, or 5,998,457 or methods described in *Metabolism* 1980, 29 (7), 686, *J. Med. Chem.* 2001, 44, 1231, *J. Biol. Chem.* 1972, 247, 4382, *J. Chem. Inf. Model.* 2008, 48 (3), 556, or *J. Med. Chem.* 2001, 44, 1217. Alternatively, the compounds of the invention may be synthesized using the methods described below.

Abbreviations
ACN acetonitrile
β-GPA 3-guanidinopropionic acid i.e. β-guanidinopropionic acid
BINAP racemic 2,2'-bis(diphenylphosphino)-1,1'-binaphthyl
BLQ below level of quantification
Boc tert-butyloxycarbonyl
$Br_2$ bromine
BrCN cyanogen bromide
° C. degrees Celcius
ca. circa or approximately
CAN ceric ammonium nitrate
Cbz carbobenzyloxy
$CH_2C_{12}$ dichloromethane
CuI copper (I) iodide
$Cs_2CO_3$ cesium carbonate
$D_2O$ deuterium oxide
DCC dicyclohexylcarbodiimide
DCI dicyclohexylcarbodiimide
DCM dichloromethane or methylenechloride
DIPEA diisopropylethylamine
DMAP 4-dimethylaminopyridine or N,N-dimethylaminopyridine
DME 1,2-dimethoxyethane
DMF N,N-dimethylformamide
DMSO dimethylsulfoxide
eq. equivalents
ES(pos)MS electrospray positive mode mass spectrometry
EtOAC ethyl acetate
EtOH ethanol
$Et_2O$ diethyl ether
Fmoc fluorenylmethyloxycarbonyl chloride
g gram(s)
HPLC high performance liquid chromatography
h hour
$H_2$ hydrogen gas
$K_2CO_3$ potassium carbonate
$K_3PO_4$ potassium phosphate tribasic
KOH potassium hydroxide
LC/MS liquid chromatography mass spectrometry
LC/MS/MS liquid chromatography tandem mass spectrometry
LiOH lithium hydroxide
M molar
MeI methyl iodide
MeOH methanol
mg milligram(s)
$MgSO_4$ magnesium sulfate
min. minute(s)
mL milliliters(s)
mm millimeter(s)
mmol millimole(s)
MTS 2-methyl-2-thiopseudourea sulfate
m/z mass to charge ratio
N normal
$Na_2S_2O_3$ sodium thiosulfate
$Na_2SO_4$ sodium sulfate
NaH sodium hydride
$NaHCO_3$ sodium bicarbonate
NaI sodium Iodide
$NaIO_4$ sodium periodate
$NaOCH_3$ sodium methoxide
NaOH sodium hydroxide
$NaNO_2$ sodium nitrite
NBS N-bromosuccinimide
NMR nuclear magnetic resonance
PhthNK potassium phthalimide
Pd/C palladium on carbon
$Pd(OAc)_2$ palladium (II) acetate
$PdCl_2$ palladium (II) chloride
psi pounds per square inch
PyBOP benzotriazole-1-yl-oxy-tris-(dimethylamino)-phosphonium hexafluorophosphate
$RuCl_3$ ruthenium trichloride hydrate
$SO_2Cl_2$ sulfuryl chloride
$SOCl_2$ thionyl chloride
TCI 1,1'-thiocarbonyldiimidazole
TEA triethylamine
TFA trifluoroacetic acid
THF tetrahydrofuran
TLC thin layer chromatography
TPP triphenylphosphine
TSA p-toluenesulfonic acid General Method to Make Cyclocreatine Analogs of the Invention

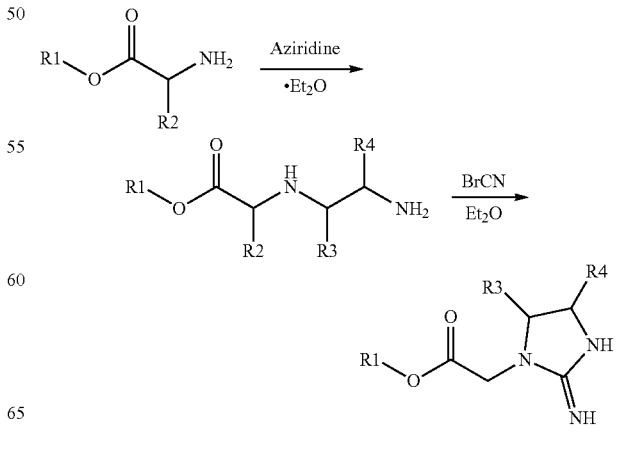

Cyclocreatine analogs may be made from amino carboxylic acids or esters and reaction with aziridines in inert solvents (e.g. diethyl ether, THF, DME, ethanol, DMF, THF, etc.). These diamine intermediates are then reacted with cyanogen bromide in inert solvent (e.g. diethyl ether, THF, DMF, etc.) to form iminoimidazolidine desired products.

General Method to Make 1-carboxymethyl-2-iminohexahydropyrimidine Analogs of the Invention

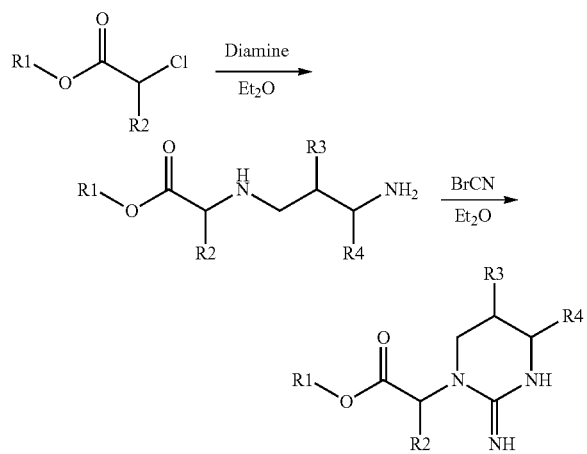

Iminohexahydropyrimidine analogs may be made from α-halo carboxylic acids or esters and reaction with 1,3-diaminopropanes. These diamine intermediates may be reacted with cyanogen bromide in inert solvent (e.g. diethyl ether, THF, DMF, etc.) to form iminohexahydropyrimidine desired products.

General Method to Make Dihydrazinylimidazolidine and Dihydrazinylhexahydropyrimidine Analogs of the Invention

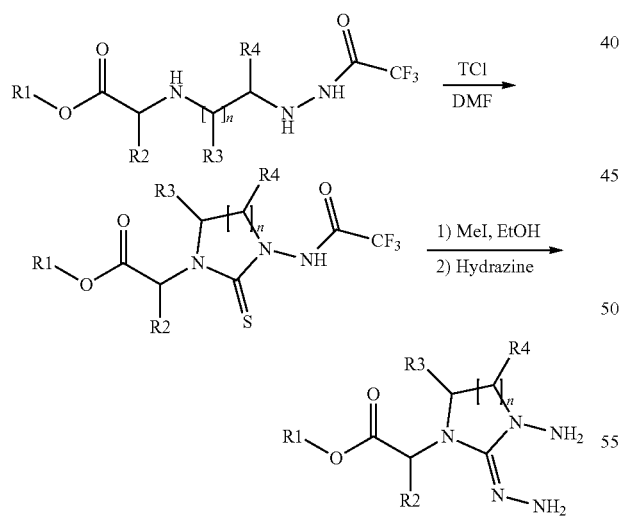

Dihydrazinyl analogs may be made from α-halo carboxylic acids or esters and reaction with protected hydrazinyl alkyl amino derivatives. Protected hydrazinyl alkyl amino derivatives may be made by reaction of trifluoroacetohydrazide with aziridines or 1-azido-3-halopropane followed by subsequent azide reduction under standard conditions (e.g. triphenylphosphine-acetone-water). These diamine intermediates may be reacted with 1,1'-thiocarbonyldiimidazole (TCI) in polar solvent (e.g. DMF, dioxane, etc.) to form imidazolidinethiones or tetrahydro-2-pyrimidinethiones. Activation with alkyl halide (e.g. methyl iodide) and subsequent reaction with hydrazine cleaves the trifluoroacetamide protecting group and would afford the desired products.

General Method to Make 2-hydrazinylimidazolidine and 2-hydrazinylhexahydropyrimidine Analogs of the Invention

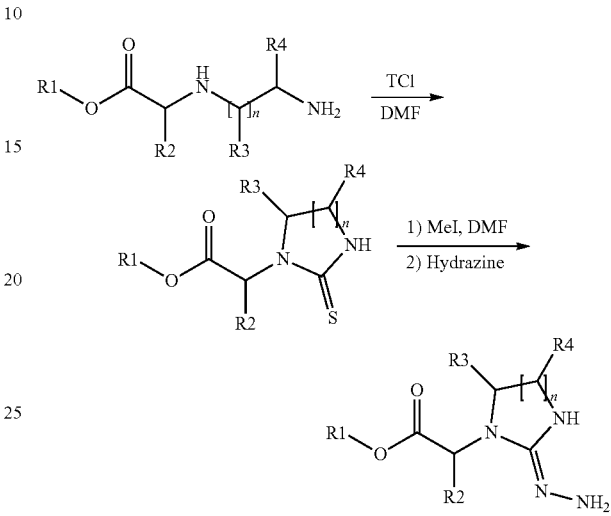

The diaminocarboxylic acid or ester intermediates generated above may be reacted with 1,1'-thiocarbonyldiimidazole (TCI) in polar solvent (e.g. DMF, dioxane, etc.) to form imidazolidinethiones or tetrahydro-2-pyrimidinethiones. Activation with alkyl halide (e.g. methyl iodide) and subsequent reaction with hydrazine would afford the desired products.

General Method to Make Aminoiminoimidazolidine and Aminoiminohexahydropyrimidine Analogs of the Invention

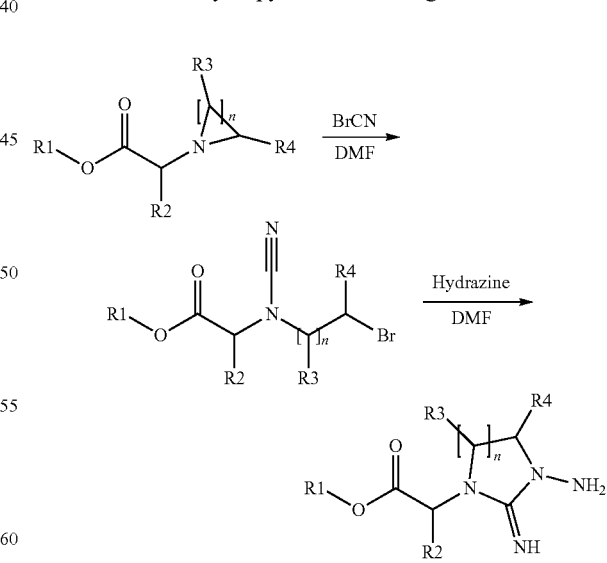

Aminoiminoimidazolidine and aminoiminohexahydropyrimidine analogs may be made from α-halo carboxylic acids or esters and reaction with azirindes or azetidines respectively. These α-carboxy aziridines or azetidines are opened with cyanogen bromide to form cyanamide alkyl bromide intermediates (see *J. Org. Chem.* 1949, 14, 605 and *J. Am. Chem. Soc.* 2013, 135(41), 15306). Reaction with hydrazine would afford the desired cyclic products.

General Method to Make imino-1,2,4-triazinanes Analogs of the Invention

Imino-1,2,4-triazinanes analogs may be made from α-halo carboxylic acids or esters and reaction with protected hydrazinyl alkyl azido derivatives. PMB-protected hydrazinyl alkyl azide

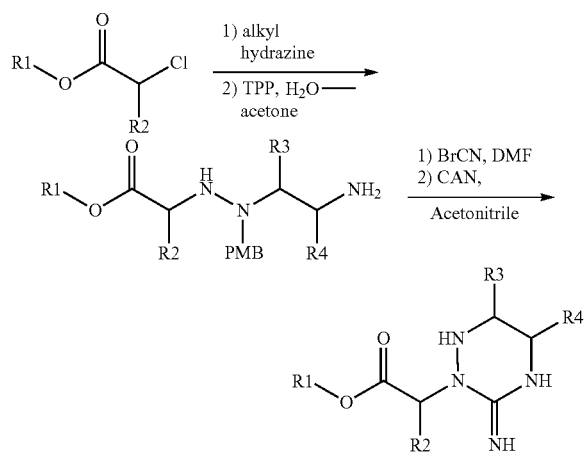

derivatives may be prepared as described in *Org. Biomol. Chem.* 2012, 10(30), 5811. The azide is reduced under standard conditions (e.g. triphenylphosphine-acetone-water) and the resulting diamine is treated with cyanogen bromide to form the cyclic core. Deprotection of the PMB hydrazine protecting group under standard conditions (e.g. CAN, strong acid, etc.) would afford the desired product.

Synthesis of Compound 225

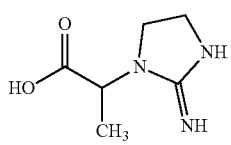

Alanine (2.0 mmol) is dissolved in diethyl ether (10 mL) and aziridine (2.0 mmol) is added. The mixture is heated to reflux for 2 h and cooled to room temperature. Cyanogen bromide (2.3 mmol) is added and the reaction is stirred at room temperature overnight. The precipitate is filtered and washed with diethyl ether to afford 2-(2-iminoimidazolidin-1-yl)propanoic acid (225).

Compounds 226-228 may be synthesized using similar methods as used to make compound 225 by replacing alanine with α-aminobutanoic acid, valine, or isoleucine.

Synthesis of Compound 237

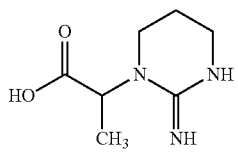

2-Chloropropionic acid (2.0 mmol) is dissolved in diethyl ether and 1,3-diaminopropane (2.0 mmol) is added. The reaction is stirred overnight at room temperature and the precipitate is filtered and washed with diethyl ether to afford the HCl salt of 2-[(3-aminopropyl)amino]propanoic acid. The salt is dissolved in water and sodium carbonate (2.5 mmol) is added followed by cyanogen bromide (2.3 mmol). The reaction is stirred at room temperature overnight. The reaction is quenched with trifluoroacetic acid and the mixture is concentrated under reduced pressure. The residue is purified by reverse phase chromatography (acetonitrile/water with 0.05% trifluoroacetic acid) and the product is collected and lyophilized to afford the trifluoroacetate salt of 2-(2-imino-1,3-diazinan-1-yl)propanoic acid (237).

Compounds 238-240 may be synthesized using similar methods as used to make compound 237 by replacing 2-chloropropanoic acid with 2-chlorobutanoic acid, 2-chloro-3-methylbutanoic acid, or 2-chloro-3-methylpentanoic acid.

Synthesis of Compound 229

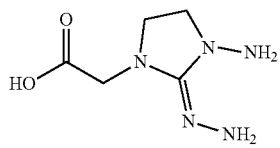 [SMILES: N/N=C1\N(N)CCN1CC(=O)O]

Step 1: 2-{[2-(trifluoroacetohydrazido)ethyl]amino}acetic acid (INT-1)

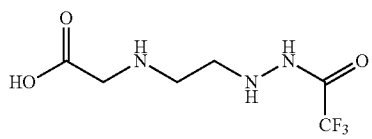

Trifluoroacetohydrazide (2.0 mmol) and aziridine (2.0 mmol) are dissolved in diethyl ether (5 mL) and stirred at room temperature overnight. 2-Chloroacetic acid (2.0 mmol) is added and the mixture stirred 3 h at room temperature. The precipitate is filtered and washed with diethyl ether to afford INT-1.

Step 2: 2-[2-sulfanylidene-3-(trifluoroacetamido)imidazolidin-1-yl]acetic acid (INT-2)

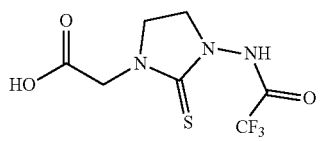

Diamine INT-1 (1.5 mmol) is dissolved in DMF (5 mL) and reacted with 1,1'-thiocarbonyldiimidazole (1.5 mmol) at room temperature for 3 h. The reaction is poured into 0.1 N aqueous HCl, the aqueous layer is extracted with ethyl acetate, the organic layer is dried over sodium sulfate, concentrated under reduced pressure, and purified by silica gel column chromatography (10-90 methanol-dichloromethane) to afford INT-2.

Step 3: 2-[3-amino-2-hydrazinylideneimidazolidin-1-yl]acetic acid (229)

INT-2 (1.0 mmol) is dissolved in ethanol (5 mL) and methyl iodide is added (1.0 mmol). The mixture is stirred for 1 h at room temperature. Upon completion, hydrazine (5 mmol) is added and the mixture is heated to reflux for 8 h. The mixture is concentrated to remove excess hydrazine, the residue is purified by reverse phase chromatography (acetonitrile/water with 0.05% trifluoroacetic acid), and the product is collected and lyophilized to afford the trifluoroacetate salt of 2-[3-amino-2-hydrazinylideneimidazolidin-1-yl]acetic acid (229).

Compounds 230-228 and 241-243 may be synthesized using similar methods as used to make compound 229 by replacing chloroacetic acid with 2-chloroacetic acid, 2-chloropropanoic acid, or 2-chloro-3-methylbutanoic acid. To synthesize compounds 241-243, aziridine may be replaced with 1,3-dibromopropane.

Synthesis of Compound 232

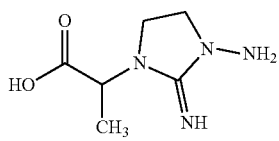

2-Chloropropionic acid (2.0 mmol) is dissolved in diethyl ether and aziridine (2.0 mmol) is added. The reaction is stirred overnight at room temperature and the precipitate is filtered and washed with diethyl ether to afford the HCl salt of 2-(aziridin-1-yl)propanoic acid. The salt is dissolved in water, sodium carbonate (2.5 mmol) is added followed by cyanogen bromide (2.3 mmol), and the reaction is stirred at room temperature overnight. The reaction is quenched with trifluoroacetic acid and the mixture is concentrated under reduced pressure. The residue is purified by reverse phase chromatography (acetonitrile/water with 0.05% trifluoroacetic acid) and the product is collected and lyophilized to afford the trifluoroacetate salt of 2-(3-amino-2-iminoimidazolidin-1-yl)propanoic acid (232).

Compounds 233 and 244-246 may be synthesized using similar methods to make compound 232 by replacing 2-chloropropanoic acid with 2-chloroacetic acid, or 2-chloro-3-methylbutanoic acid. To synthesize compounds 244-246, aziridine may be replaced with azetidine.

Synthesis of Compound 234

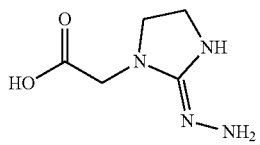

Step 1: 2-(2-sulfanylideneimidazolidin-1-yl)acetic acid (INT-3)

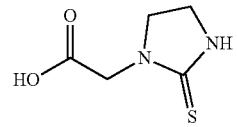

Glycine (2 mmol) is dissolved in diethyl ether (10 mL) and aziridine (2 mmol) is added. The mixture is heat is to reflux for 2 h and cooled to room temperature. The mixture is concentrated under reduced pressure, dissolved in DMF (5 mL), and reacted with 1,1'-thiocarbonyldiimidazole (1.5 mmol) at room temperature for 3 h. The reaction is poured into 0.1 N aqueous HCl, the aqueous layer is extracted with ethyl acetate, the organic layer is dried over sodium sulfate, concentrated under reduced pressure, and purified by silica gel column chromatography (10-90 methanol-dichloromethane) to afford INT-3.

Step 2: 2-[2-hydrazinylideneimidazolidin-1-yl]acetic acid (234)

INT-3 (1.0 mmol) is dissolved in ethanol (5 mL) and methyl iodide is added (1.0 mmol). The mixture is stirred for 1 h at room temperature. Upon completion, hydrazine (5 mmol) is added and the mixture is heated to reflux for 8 h. The mixture is concentrated to room excess hydrazine, the residue is purified by reverse phase chromatography (acetonitrile/water with 0.05% trifluoroacetic acid), and the product is collected and lyophilized to afford the trifluoroacetate salt of 2-[2-hydrazinylideneimidazolidin-1-yl]acetic acid (234).

Compounds 235-336 may be synthesized using similar methods to make compound 234 by replacing glycine with alanine or valine. Compounds 247-349 may be synthesized using similar methods to make the diamine intermediate for compound 237 and then following the protocol to make 234.

Synthesis of Compound 250

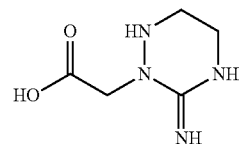

Step 1: 1-(2-azidoethyl)-1-[(4-methoxyphenyl)methyl]hydrazine (INT-4)

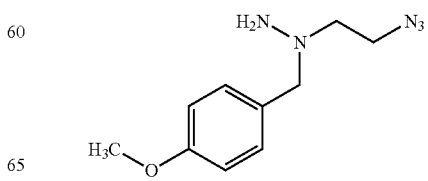

Synthesis of PMB-protected hydrazinyl ethyl azide is prepared as described in *Org. Biomol. Chem.* 2012, 10(30), 5811.

Step 2: 2-[2-(2-aminoethyl)-2-[(4-methoxyphenyl) methyl]hydrazine-1-yl]acetic acid (INT-5)

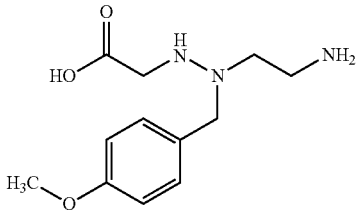 [SMILES: COc1ccc(CN(CCN)NCC(=O)O)cc1]

2-Chloropropionic acid (2.0 mmol) is dissolved in diethyl ether (5 mL) and INT-4 (2.0 mmol) is added. The reaction is stirred overnight at room temperature and the precipitate is filtered and washed with diethyl ether to afford the HCl salt. The salt is dissolved in water-acetone (1:10, 5 mL) and triphenylphosphine (TPP) is added. The mixture is heated to 50° C. for 14 hours.

Step 3: 2-(3-imino-1,2,4-triazinan-2-yl)acetic acid (250)

INT-5 (1.0 mmol) is dissolved in water, sodium carbonate (2.5 mmol) is added followed by cyanogen bromide (1.3 mmol), and the reaction is stirred at room temperature overnight. The reaction is quenched with trifluoroacetic acid and the mixture is concentrated under reduced pressure. The residue is purified by reverse phase chromatography (acetonitrile/water with 0.05% trifluoroacetic acid) and the product is collected and lyophilized to afford the trifluoroacetate salt of 2-(3-imino-1,2,4-triazinan-2-yl)acetic acid (250).

Compounds 251-252 may be synthesized using similar methods to make compound 250 by replacing 2-chloroacetic acid with 2-chloropropanoic acid or 2-chloro-3-methylbutanoic acid.

General Method to Make Guanidine Containing Compounds of the Invention

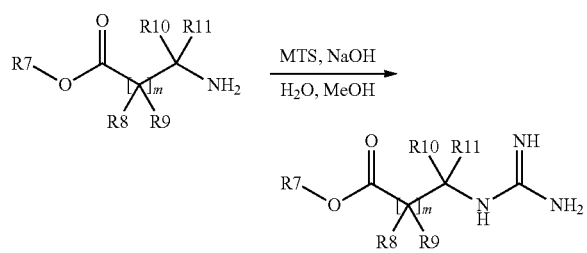

Guanidines are made from amines using standard guanylating agents (e.g. 2-methyl-2-thiopseudourea sulfate [MTS], cyanamide, N,N-di-Boc-1H-pyrazole-1-carboxamide, etc.). A preferred method using MTS is described in *J. Med. Chem.* 2001, 44, 1217, *J. Chem. Soc. C* 1971, 238 and *Tetrahedron Lett.* 1996, 37, 2483. Briefly, amines are dissolved or suspended in basic aqueous alcoholic solvent and reacted with 2-methyl-2-thiopseudourea sulfate (MTS) for 24-72 h or longer and precipitated products are isolated by filtration. If necessary, ester hydrolysis is done by treatment with hydroxide ion (e.g. LiOH, NaOH, KOH, etc) in aqueous alcoholic solvent or THF, to afford the desired product.

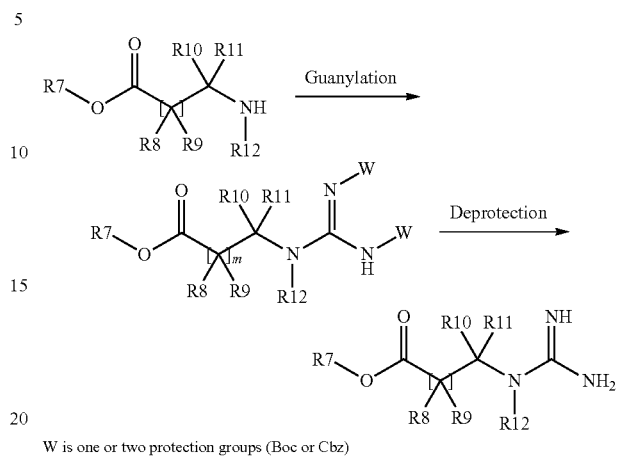

W is one or two protection groups (Boc or Cbz)

In some case, guanidines are made from amines under anhydrous conditions using pyrazole-activated guanylating agents (e.g. 1H-pyrazole-1-carboxamidine hydrochloride, 3,5-dimethyl-1-pyrazolylformaminidium nitrate, N-Boc-1H-pyrazole-1-carboxamidine, N,N-di-Boc-1H-pyrazole-1-carboxamidine, N-(benzyloxycarbonyl)-1H-pyrazole-1-carboxamidine, and N,N-bis(benzyloxycarbonyl)-1H-pyrazole-1-carboxamidine). Methods for

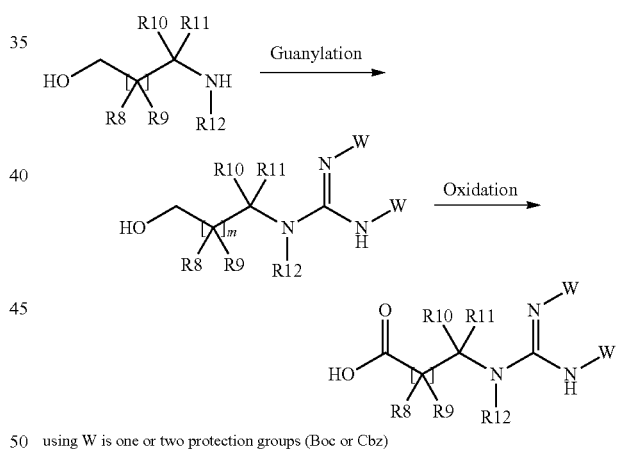

using W is one or two protection groups (Boc or Cbz)

pyrazole-activated guanylating agents are reviewed in *Eur. J. Org. Chem.* 2002, 3909. Briefly, amines are used in excess or with a base (e.g. triethylamine, diisopropylethylamine, etc.) and are dissolved in solvent (e.g. DMF, acetonitrile, THF, methanol, dichloromethane, etc.). The reaction is stirred for 4-72 h and at room temperature but in some cases heating is required. When protected pyrazole-activated guanylating agents are used (i.e. W=Boc or Cbz) products can be purified by normal phase silica gel column chromatography. If necessary, ester hydrolysis is done by treatment with hydroxide ion (e.g. LiOH, NaOH, KOH, etc) in aqueous alcoholic solvent or THF, to provide the carboxylic acid. Finally, standard deprotection conditions are used to remove the guanidine protecting groups (i.e. TFA removal of Boc or hydrogenation of Cbz) to afford the desired product.

In other cases, amino alcohols are used with the method above. After guanylation, the alcohol is oxidized to the carboxylic acid using sodium metaperiodate and ruthenium (III) chloride (catalytic) in acetonitrile, ethyl acetate and water (*Org. Lett.* 2008, 10, 5155). Finally, standard deprotection conditions are used to remove the guanidine protecting groups (i.e. TFA removal of Boc or hydrogenation of Cbz) to afford the desired product.

General Method to Make 2-aminopyridine Containing Compounds of the Invention

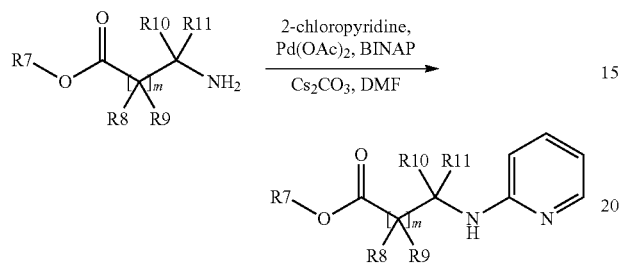

Aminopyridines may be made utilizing cross-coupling methods as described in *J. Am. Chem. Soc.* 2008, 130(20), 6586 and *J. Org. Chem.* 1996, 61(21), 7240. Briefly, amines, 2-halopyridines, and sufficient base (e.g. cesium carbonate, potassium tert-butoxide, etc.) are dissolved or suspended in polar solvent (e.g. DMF, dioxane), catalytic palladium (e.g. $PdCl_2$ or $Pd(OAc)_2$) and phosphine ligand (e.g. BINAP) are then be added and the reaction is heated to greater than 80° C. for 4-6 h. If necessary, ester hydrolysis by treatment with hydroxide ion (e.g. LiOH, NaOH, KOH, etc) in aqueous alcoholic solvent or THF, affords the desired product.

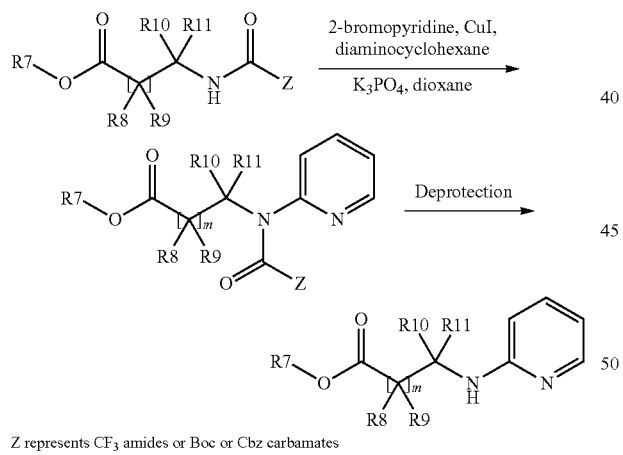

Z represents $CF_3$ amides or Boc or Cbz carbamates

Alternatively, Buchwald amide-cross-coupling methods are used to generate desired compounds as described in see *J. Am. Chem. Soc.* 2002, 124, 11684 and *J. Am. Chem. Soc.* 2001, 123, 7727. Briefly, amines are protected as amides or carbamates (e.g. trifluoroacetamide, Boc, Cbz, etc.) and reacted with 2-bromopyridine in polar solvent (e.g. dioxane, DMF) with base (e.g. potassium phosphate tribasic, cesium carbonate, potassium tert-butoxide, etc.), racemic trans-1,2-diaminocyclohexane ligand, and catalytic copper (I) iodide. The solution is degassed for 5 minutes by bubbling nitrogen gas directly into the solution and the mixture is heated at greater than 95° C. for 6-12 hours. Amine protecting groups are removed using standard conditions and, if necessary, ester hydrolysis by treatment with hydroxide ion (e.g. LiOH, NaOH, KOH, etc) in aqueous alcoholic solvent or THF, affords the desired product.

General Method to Make Pseudothiourea Containing Compounds of the Invention

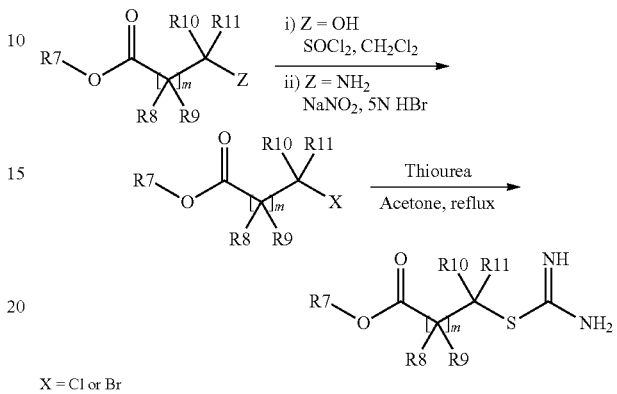

X = Cl or Br

Pseudothioureas may be made by reaction of a thiourea with alkylhalides as described in *J. Med. Chem.* 2001, 44, 1217. Briefly, 3-chloropropionic acids or esters may be reacted with thiourea in polar solvent (e.g. acetone) followed by refluxing the mixture for 48 h. 3-Chloropropionic acids or esters may be made by reaction of 3-hydroxypropionic acids with thionyl chloride as described in International Patent Publication No. WO9933785.

Alternatively, pseudothioureas may be made from amino compounds via alkyl bromides using methods as described in *Tetrahedron: Asymmetry* 1998, 9(10), 1641 and International Patent Publication No. WO2002009705. Briefly, 3-aminocarboxylic acids or esters may be converted to 3-bromocarboxylic acids or esters via activation with sodium nitrite in the presence of hydrobromic acid. The resulting bromo compound may be reacted with a thiourea in a suitable solvent (e.g. toluene or acetone) at greater than 60° C. for 4-24 h. If necessary, ester hydrolysis by treatment with hydroxide ion (e.g. LiOH, NaOH, KOH, etc) in aqueous alcoholic solvent, would afford the desired product.

General Method to Make 2-aminopseudothiourea Containing Compounds of the Invention

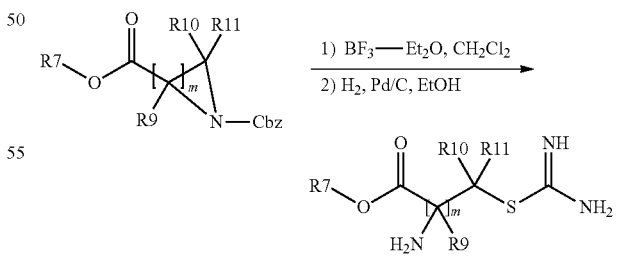

2-Aminopseudothioureas may be made from aziridines by methods similar to those described in Chem. Comm. 2000, 7, 619 and *Org. Biomol. Chem.* 2005, 3(18), 3357. Briefly, N-Cbz-2-carboxyaziridines may be reacted with thiourea and borontrifluoride-etherate in inert solvent (e.g. chloroform, dichloromethane, etc). Subsequent hydrogenation in the presence of palladium on carbon, and if necessary, ester hydrolysis by treatment with hydroxide ion (e.g. LiOH, NaOH, KOH, etc) in aqueous alcoholic solvent, would afford the desired product. 2-Carboxyaziridines may be made by methods as described in *Synlett* 2001, 5, 679 and *Tetrahedron Lett.* 2006, 47(13), 2065 and may be converted to Cbz-protected aziridines by standard methods.

Many starting materials for compounds of the invention are commercially available or methods for synthesis are known in the literature. Table 15 lists starting materials for synthesis of compounds of the invention and provides literature references for uncommon reagents.

TABLE 15

Starting materials for the synthesis of selected compounds

| # | Structure | Starting Material | CAS Number | Reference |
|---|---|---|---|---|
| SM01 | 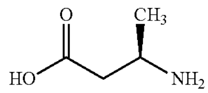 | (3R)-3-aminobutyric acid | 3775-73-3 | *Org. Process Res. Dev.* 2011, 15, 1130 |
| SM02 | 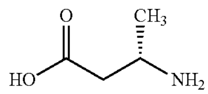 | (3S)-3-aminobutyric acid | 3775-72-2 | *Org. Process Res. Dev.* 2011, 15, 1130 |
| SM03 | 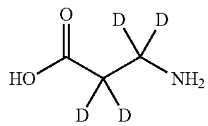 | β-alanine-2,2,3,3-$D_4$ | 116173-67-2 | *J. Labelled Compd. Ra.* 1988, 25(2), 217 |
| SM04 | 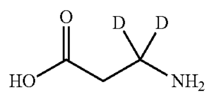 | β-alanine-3,3-$D_2$ | 116173-66-1 | *J. Labelled Compd. Ra.* 1988, 25(2), 217 |
| SM05 | 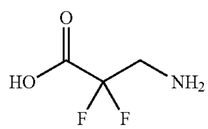 | 2,2-difluoro-3-amino-propanoic acid | 428452-49-7 | *Tetrahedron Lett.* 2003, 44(11), 2375; PCT Int. Appl., 2007062308 |
| SM06 | 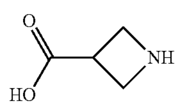 | 3-azetidinecarboxylic acid | 36476-78-5 | Commercially available |
| SM07 | 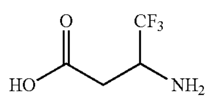 | 3-amino-4,4,4-trifluorobutanoic acids | 584-20-3 | Commercially available |
| SM08 | 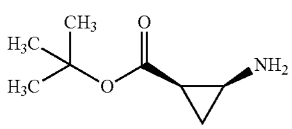 | tert-butyl (1R,2S)-2-aminocyclopropane-1-carboxylate | 150626-49-6 | JP 05155827 A 19930622 |
| SM09 | 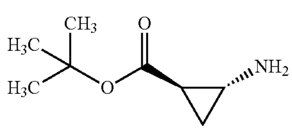 | tert-butyl (1S,2R)-2-aminocyclopropane-1-carboxylate | 150737-97-6 | JP 05155827 A 19930622; International Patent Publication No. WO 2008123207 |
| SM10 | 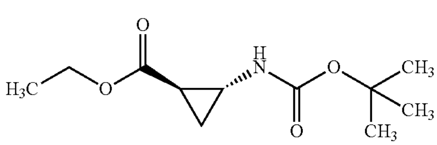 [SMILES: CCOC(=O)[C@@H]1C[C@H]1NC(=O)OC(C)(C)C] | ethyl (1R,2R)-2-{[(tert-butoxy)carbonyl]amino}cyclopropane-1-carboxylate | 613261-17-9 | *J. Org. Chem.* 2003, 68(20), 7884; *Org. Lett.* 2013, 15(4), 772; |
| SM11 | 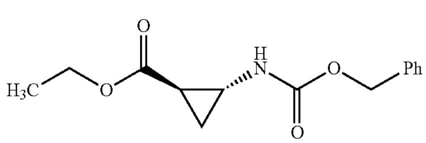 [SMILES: CCOC(=O)[C@@H]1C[C@H]1NC(=O)OCc1ccccc1] | ethyl (1R,2R)-2-{[(benzyloxy)carbonyl]amino}cyclopropane-1-carboxylate | 613261-16-8 | *J. Org. Chem.* 2003, 68(20), 7884; *Org. Lett.* 2013, 15(4), 772; in addition protocols as described in *Tetrahedron* 2012, 68(47), 9566 can also be used to generate useful starting materials |

TABLE 15-continued

Starting materials for the synthesis of selected compounds

| # | Structure | Starting Material | CAS Number | Reference |
|---|---|---|---|---|
| SM12 | 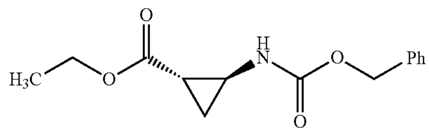 [SMILES: CCOC(=O)[C@H]1C[C@@H]1NC(=O)OCc1ccccc1] | ethyl (1S,2S)-2-[(methoxycarbonyl)amino]cyclopropane-1-carboxylate | 1356459-72-7 | J. Org. Chem. 2003, 68(20), 7884; Org. Lett. 2013, 15(4), 772; in addition protocols as described in Tetrahedron 2012, 68(47), 9566 can also be used to generate useful starting materials |
| SM13 | 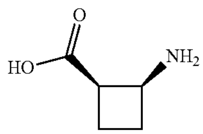 | (1R,2S)-2-aminocyclobutane-1-carboxylic acid | 221158-95-8 | J. Org. Chem. 2009, 74(8), 3217; J. Org. Chem. 2005, 70(20), 7963; Tetrahedron: Asymmetry 2000, 11(17), 3569 |
| SM14 | 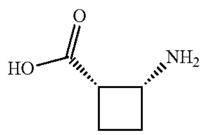 | (1S,2R)-2-aminocyclobutane-1-carboxylic acid | 648433-09-4 | J. Org. Chem. 2009, 74(8), 3217; J. Org. Chem. 2005, 70(20), 7963 |
| SM15 | 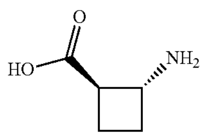 | (1R,2R)-2-aminocyclobutane-1-carboxylic acid | 951173-26-5 | J. Org. Chem. 2009, 74(8), 3217 |
| SM16 | 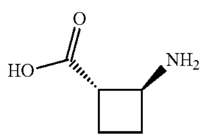 | (1S,2S)-2-aminocyclobutane-1-carboxylic acid | 951173-27-6 | J. Org. Chem. 2009, 74(8), 3217 |
| SM17 | 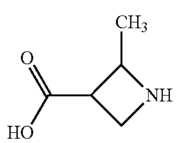 | 2-methyl-3-azetidinecarboxylic acid | 1638771-37-5 | Chiral trans isomers: Synthesis 2005, 20, 3508; Chiral cis isomers: J. Org. Chem. 2012, 77(17), 7212 |
| SM18 | 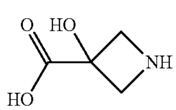 | 2-hydroxy-3-azetidinecarboxylic acid | 70807-37-3 | Commercially available; International Patent Publication No. WO2011043817 |
| SM19 | 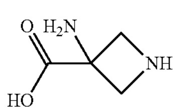 | 2-amino-3-azetidinecarboxylic acid | 138650-25-6 | Commercially available |
| SM20 | 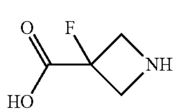 | 3-fluoro-3-azetidinecarboxylic acid | 1363380-85-1 | International Patent Publication No. WO2013019561; J. Org. Chem. 2009, 74(5), 2250; or made by deprotection of 1-[(tert-butoxy)carbonyl]-3-fluoroazetidine-3-carboxylic acid [1126650-67-6] |
| SM21 | 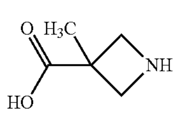 | 2-methyl-3-azetidinecarboxylic acid | 1213240-07-3 | Commercially available; or made by deprotection of 1-[(tert-butoxy)carbonyl]-3-methylazetidine-3-carboxylic acid [887591-62-0] |
| SM22 | 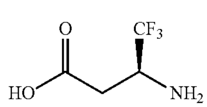 | (3S)-3-amino-4,4,4-trifluorobutanoic acids | 151871-99-7 | Chem. Comm. 2012, 48(34), 4124 |
| SM23 | 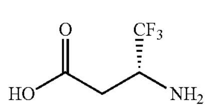 | (3R)-3-amino-4,4,4-trifluorobutanoic acids | 151911-19-2 | Chem. Comm. 2012, 48(34), 4124 |

TABLE 15-continued

Starting materials for the synthesis of selected compounds

| # | Structure | Starting Material | CAS Number | Reference |
|---|-----------|-------------------|------------|-----------|
| SM24 | 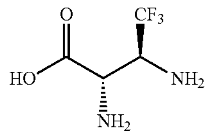 [SMILES: N[C@H](C(=O)O)[C@H](N)C(F)(F)F] | (2S,3S)-2,3-diamino-4,4,4-trifluorobutanoic acid | 1632315-15-1 | *J. Fluorine Chem.* 2015, 171, 67 |
| SM25 | 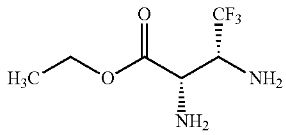 | ethyl (2S,3R)-2,3-diamino-4,4,4-trifluorobutanoate | 1219366-64-9 | International Patent Publication No. WO2010031750 |
| SM26 | 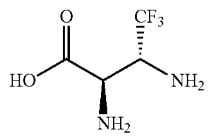 [SMILES: N[C@H]([C@@H](N)C(=O)O)C(F)(F)F] | (2R,3R)-2,3-diamino-4,4,4-trifluorobutanoic acid | NA | Made by a similar protocol as [1632315-15-1] above but using (R)-N-[(1E)-ethylidene]-2-methylpropane-2-sulfinamide [1219607-85-8] |
| SM27 | 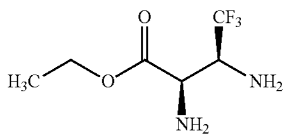 | ethyl (2R,3S)-2,3-diamino-4,4,4-trifluorobutanoate | NA | Made by a similar protocol as [1219366-64-9] above but using (R)-N-[(1E)-ethylidene]-2-methylpropane-2-sulfinamide [1219607-85-8] |
| SM28 | 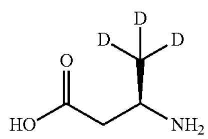 | (3R)-3-amino(4,4,4-$^2$H$_3$)butanoic acid | NA | Made according to procedures described for the synthesis of chiral 3-aminobutyric acid in *Helv. Chim. Acta* 1988, 71, 1824 and *Tetrahedron: Asymmetry* 1991, 3, 183, but replacing crotonic acid with 2-butenoic-4,4,4-d$_3$ acid [1375453-29-4] made according to *J. Magn. Reson.* 2011, 210(1), 107 |
| SM29 | 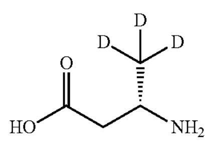 | (3S)-3-amino(4,4,4-$^2$H$_3$)butanoic acid | NA | As above |
| SM30 | 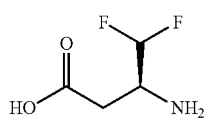 | (S)-3-amino-4,4-difluoro-butanoic acid | 111218-68-9 | *Tetrahedron Asymmetry* 1994, 5(6), 1119 |
| SM31 | 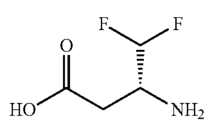 | (R)-3-amino-4,4-difluoro-butanoic acid | 109537-89-5 | *Tetrahedron Asymmetry* 1994, 5(6), 1119 |
| SM32 | 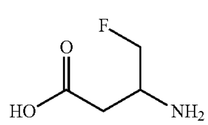 | 3-amino-4-fluorobutanoic acid | 77162-47-1 | *Syn. Comm.* 1985, 15(5), 377 |
| SM33 | 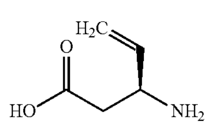 | (3S)-3-aminopent-4-enoic acid | 1389348-84-8 | Made by hydrogenation of ethyl (3S)-3-aminopent-4-ynoate [149251-15-0] at 1 atm using Lindlar's catalyst and then ester hydrolysis |
| SM34 | 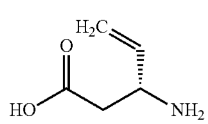 | (3R)-3-aminopent-4-enoic acid | 1388637-32-8 | Made by hydrogenation of ethyl (3R)-3-aminopent-4-ynoate [188853-28-3] at 1 atm using Lindlar's catalyst and then ester hydrolysis |

TABLE 15-continued

Starting materials for the synthesis of selected compounds

| # | Structure | Starting Material | CAS Number | Reference |
|---|---|---|---|---|
| SM35 | 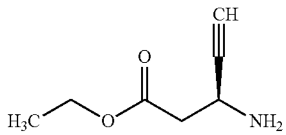 | ethyl (3S)-3-aminopent-4-ynoate | 149251-15-0 | *Bioorg. Med. Chem. Lett.* 1997, 7(13), 1699; U.S. Pat. No. 5,536,869; the ester can be hydrolyzed before or after the guanylation step |
| SM36 | 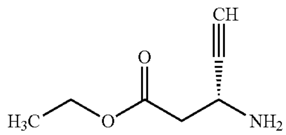 | ethyl (3R)-3-aminopent-4-ynoate | 188853-28-3 | *Bioorg. Med. Chem.* 1999, 7(10), 2221; the ester can be hydrolyzed before or after the guanylation step |
| SM37 | 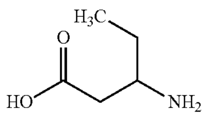 | 3-amino-pentanoic acid | 18664-78-3 | Commercially available |
| SM38 | 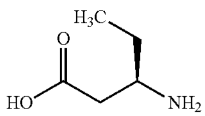 | (R)-3-amino-pentanoic acid | 131347-76-7 | Commercially available |
| SM39 | 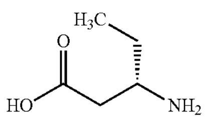 | (S)-3-aminopentanoic acid | 14389-77-6 | Commercially available |
| SM40 | 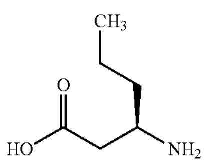 | (3R)-3-aminohexanoic acid | 775551-50-3 | *Synthesis* 2008, 7, 1153 & *Chem. Commun.* 2007, 8, 849 |
| SM41 | 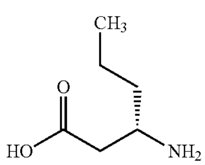 | (3S)-3-aminohexanoic acid | 91298-66-7 | *ChemBioChem* 2009, 10(9), 1558 & *Synlett* 1994, 10, 795 |
| SM42 | 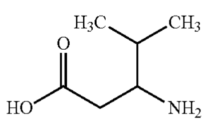 | 3-amino-4-methylpentanoic acid | 5699-54-7 | Commercially available |
| SM43 | 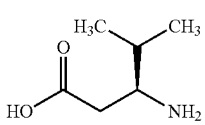 | (S)-3-amino-4-methylpentanoic acid | 40469-85-0 | Commercially available |
| SM44 | 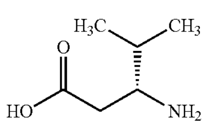 | (R)-3-amino-4-methylpentanoic acid | 75992-50-6 | Commercially available |
| SM45 | 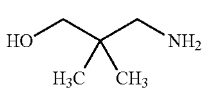 | 3-amino-2,2-dimethylpropan-1-ol | 26734-09-8 | Commercially available; requires oxidation of the alcohol after guanylation |
| SM46 | 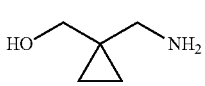 | [1-(aminomethyl)cyclopropyl]methanol | 45434-02-4 | Commercially available; requires oxidation of the alcohol after guanylation |

TABLE 15-continued

Starting materials for the synthesis of selected compounds

| # | Structure | Starting Material | CAS Number | Reference |
|---|---|---|---|---|
| SM47 | 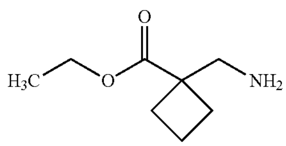 | ethyl 1-(aminomethyl)cyclobutane-1-carboxylate | 911060-83-8 | Commercially available; the ester can be hydrolyzed before or after the guanylation step |
| SM48 | 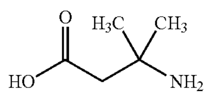 | 3-amino-3-methylbutanoic acid | 625-05-8 | Commercially available |
| SM49 | 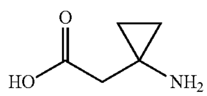 | 2-(1-aminocyclopropyl)acetic acid | 133616-20-3 | *Synlett* 1991, 2, 87 |
| SM50 | 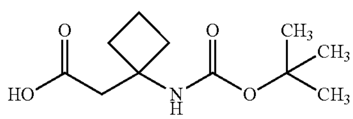 [SMILES: CC(C)(C)OC(=O)NC1(CC(=O)O)CCC1] | 2-(1-{[(tert-butoxy)carbonyl]amino}cyclobutyl)acetic acid | 249762-02-5 | Commercially available; requires hydrolysis of the Boc protecting group prior to guanylation |
| SM51 | 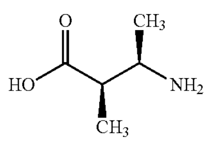 | (2R,3R)-3-amino-2-methylbutanoic acid | 139344-67-5 | U.S. Pat. Appl. Publ., 20110218342; *Tetrahedron*, 2007, 63(26), 5820 |
| SM52 | 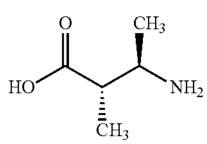 | (2S,3R)-3-amino-2-methylbutanoic acid | 863115-43-9 | Made by an analogous protocol described in *Heterocycles* 1999, 50(2), 677 for [39801-26-8] but using (R)-(-)-N-methoxy-2-pyrrolidine carboxamide |
| SM53 | 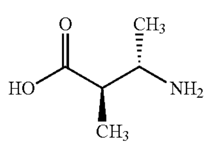 | (2R,3S)-3-amino-2-methylbutanoic acid | 39801-26-8 | *Heterocycles* 1999, 50(2), 677; *J. Org. Chem.* 1993, 58(8), 2282 |
| SM54 | 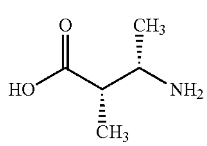 | (2S,3S)-3-amino-2-methylbutanoic acid | 139344-68-6 | *J. Am. Chem. Soc.* 2005, 127(32), 11252; *J. Org. Chem.* 1993, 58(8), 2282 |
| SM55 | 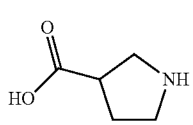 | pyrrolidine-3-carboxylic acid | 59378-87-9 | Commercially available |
| SM56 | 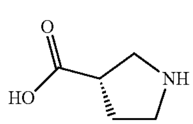 | (3S)-pyrrolidine-3-carboxylic acid | 72580-53-1 | Commercially available |
| SM57 | 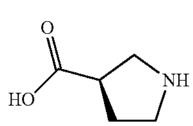 | (3R)-pyrrolidine-3-carboxylic acid | 72580-54-2 | Commercially available |

TABLE 15-continued

Starting materials for the synthesis of selected compounds

| # | Structure | Starting Material | CAS Number | Reference |
|---|---|---|---|---|
| SM58 | (structure) | 2-[(2S)-1-[(tert-butoxy)carbonyl]azetidin-2-yl]acetic acid | 1289384-58-2 | Made from (S)-(tert-butoxycarbonyl)azetidine-2-carboxylic acid according to the protocol described in International Patent Publication No. WO2011111875; requires hydrolysis of the Boc protecting group prior to guanylation |
| SM59 | (structure) | 2-[(2R)-1-[(tert-butoxy)carbonyl]azetidin-2-yl]acetic acid | 1369534-61-1 | Made from (R)-(tert-butoxycarbonyl)azetidine-2-carboxylic acid according to the protocol described in International Patent Publication No. WO2011111875; requires hydrolysis of the Boc protecting group prior to guanylation |
| SM60 | (structure) | cis-3-aminocyclobutane-1-carboxylic acid | 74316-27-1 | Commercially available |
| SM61 | (structure) | trans-3-aminocyclobutane-1-carboxylic acid | 74307-75-8 | Commercially available |
| SM62 | (structure) | 3-{[(tert-butoxy)carbonyl]amino}-1-hydroxycyclobutane-1-carboxylic acid | 1067239-17-1 | International Patent Publication No. WO2011044538 & WO2008124821; requires hydrolysis of the Boc protecting group prior to guanylation |
| SM63 | (structure) | ethyl 3-amino-1-{[(tert-butoxy)carbonyl]amino}cyclobutane-1-carboxylate | NA | ethyl 1-{[(tert-butoxy)carbonyl]amino}-3-hydroxycyclobutane-1-carboxylate [413597-67-8] (U.S. Pat. Appl. Publ., 20060292073) is converted to the amine by activation of the hydroxyl group (e.g. tosyl chloride and pyridine), displacement with lithium azide, and reduction to the amine (i.e. catalytic hydrogenation of Pd/C or with triphenylphosphine) |
| SM64 | (structure) | 2-(azetidin-3-yl)acetic acid | 183062-92-2 | Commercially available; or made by deprotection of 2-{1-[(tert-butoxy)carbonyl]azetidin-3-yl}acetic acid [183062-96-6] prior to guanylation |
| SM65 | (structure) | L-(2S)-2,3-diaminopropionic acid | 4033-39-0 | Commercially available |
| SM66 | (structure) | β-chloroalanine | 51887-88-8 (D) 13215-35-5 (D/L) | Org. Biomol. Chem. 2005, 3(18), 3357 |
| SM67 | (structure) | (2S,3R)-2-amino-3-chlorobutanoic acid | 64233-79-0 | Make desired stereoisomers from L-threonine and L-allo-threonine using a similar procedure described in: International Patent Publication No. WO9933785 |

TABLE 15-continued

Starting materials for the synthesis of selected compounds

| # | Structure | Starting Material | CAS Number | Reference |
|---|-----------|-------------------|------------|-----------|
| SM68 | 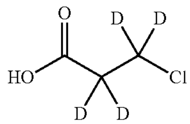 | 3-chloropropionic-2,2,3,3-$d_4$ acid | 1219802-17-1 | Commercially available |
| SM69 | 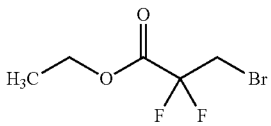 | ethyl 3-bromo-2,2-difluoropropionate | 111773-24-1 | Commercially available |
| SM70 | 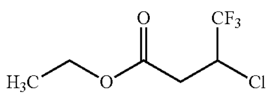 | ethyl 3-chloro-4,4,4-trifluorobutyrate | 1309602-63-8 | Commercially available |
| SM71 | 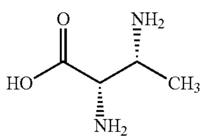 | (2S,3R)-2,3-diaminobutanoic acid | 25023-80-7 | Org. Biomol. Chem. 2003, 1(21), 3708; Synlett 1996, 7, 621; Tetrahedron 2001, 57(39), 8267 |
| SM72 | 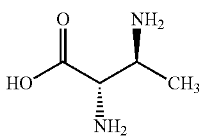 | (2S,3S)-2,3-diaminobutanoic acid | 80999-51-5 | Org. Biomol. Chem. 2003, 1(21), 3708; Synlett 1996, 7, 621; Tetrahedron 2001, 57(39), 8267 |
| SM73 | 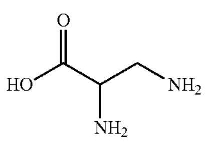 | 2,3-diaminopropionic acid | 54897-59-5 | Commercially available |

Synthesis of Compound 219

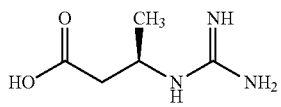

(R)-Aminobutyric acid SM01 (750 mg, 7.27 mmol) and 2-methyl-2-thiopseudourea sulfate (MTS, 1.21 g, 4.36 mmol) were suspended in methanol (4 mL). After addition of 3N sodium hydroxide in water (2.62 mL, 1.09 eq.), the clear solution was stirred for 3 days at room temperature. Subsequently, the white precipitate was filtered off and washed with water/methanol (15 mL, 1/2). The white powder was air dried for 1 hour and then put under high vacuum for 2 days to yield the (3R)-3-carbamimidamidobutanoic acid (219) as a white solid (879 mg, 83%); $^1$H-NMR (300 MHz, D$_2$O): δ 3.81 (m, 1H), 2.31 (m, 2H), 1.15 (d, 3H); ES(pos)MS m/z 146.1 (M+H$^+$).

Synthesis of Compound 220

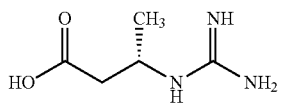

(S)-Aminobutyric acid SM02 (750 mg, 7.27 mmol) was converted into the corresponding (3S)-3-carbamimidamidobutanoic acid (220) according to the procedure for compound 219. The desired product was obtained as a white powder after high vacuum drying for 3 days (756 mg, 72%); $^1$H-NMR (300 MHz, D$_2$O): δ 3.84 (m, 1H), 2.35 (m, 2H), 1.18 (d, 3H). ES(pos) MS m/z 145.9 (M+H$^+$).

Synthesis of Compound 221

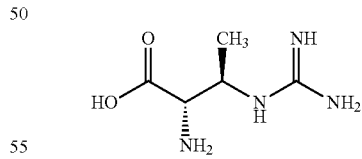

A suspension of (2S,3R)-2,3-diaminobutanoic acid SM71 (25 mmol) and 2-methyl-2-thiopseudourea sulfate (MTS, 25 mmol) in methanol (25 mL) is stirred for 5 days at room temperature under a nitrogen atmosphere. The reaction is then cooled to 0° C., filtered through a medium porosity glass frit, and the collected solid is washed with water and dried to provide compound 221 as a mixture of regioisomers. The material is purified by preparative HPLC chromatography and the product is collected and lyophilized to afford compound 221.

Synthesis of Compound 223

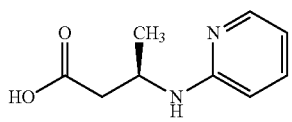

2-chloro-pyridine (25 mmol), palladium (II) acetate (2.5 mmol), racemic 2,2'-bis(diphenylphosphino)-1,1'-binaphthyl (2.5 mmol) and cesium carbonate (65 mmol) are dissolved in toluene (75 mL) in a previously degassed sealed vessel. The mixture is flushed with nitrogen gas. Methyl-(R)-3-aminobutyrate SM01 (20 mmol) is added to the solution under nitrogen and the sealed mixture is heated overnight at 100° C. The reaction is cooled to room temperature, diluted with diethyl ether and washed with pH 7 buffer and water. The organic layer is concentrated and purified by silica gel column chromatography (10:90 methanol-dichloromethane) to afford (3R)-3-[(pyridin-2-yl)amino]butanoic acid (223).

Synthesis of Compound 257

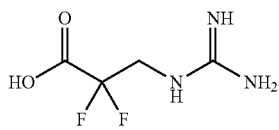

Step 1: (1H-1,2,3-benzotriazol-1-ylmethyl)dibenzylamine (INT-6)

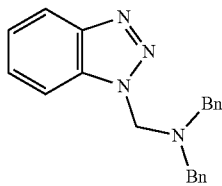 [SMILES: c1ccc(CN(Cc2ccccc2)Cn2nnc3ccccc32)cc1]

Hydroxymethylbenztriazol (10.4 g, 69.7 mmol) and dibenzylamine (13.4 mL, 69.7 mmol) were converted to INT-6 (95% yield) according to the protocol in US2009/054414.

Step 2: ethyl 3-(dibenzylamino)-2,2-difluoropropanoate (INT-7)

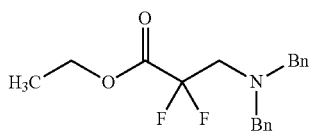

Ethyl bromodifluoro acetate (4.8 g, 23.65 mmol) and INT-6 (7.78 g, 23.7 mmol) were coupled according to the protocol in US2009/054414 to afford INT-7 (53% yield).

Step 3: ethyl 3-amino-2,2-difluoropropanoate TFA salt (INT-8)

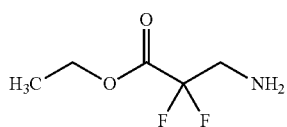

The INT-7 (1.52 g, 4.59 mmol) was dissolved in ethanol (25 mL). Trifluoroacetic acid (0.372 mL, 4.85 mL) and a catalytic amount of palladium hydroxide on carbon was added and the reaction was subjected to hydrogen under atmospheric pressure for 16 h. Subsequently, the catalyst was removed by filteration through celite and washed with ethanol. The resulting filtrate was evaporated under reduced pressure and the residue was treated with toluene (50 mL) and concentrated, this was repeated twice to remove residual solvent and excess water. The residue was dried under high vacuum overnight to afford the INT-8 as a yellowish oil (used as crude in the next step).

Step 4: ethyl 3-{[(1Z)-{[(tert-butoxy)carbonyl]amino}({[(tert-butoxy)carbonyl]imino})methyl]amino}-2,2-difluoropropanoate (INT-9)

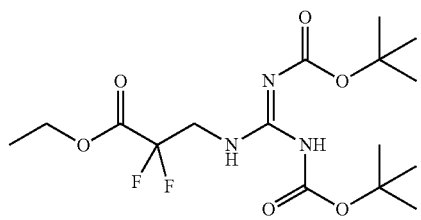 [SMILES: CCOC(=O)C(F)(F)CN/C(=N/C(=O)OC(C)(C)C)NC(=O)OC(C)(C)C]

The crude TFA salt of INT-8 was dissolved in dry THF (10 mL) and then treated with triethylamine (1.36 mL, 9.73 mmol) and N,N'-di-Boc-1H-pyrazole-1-carboxamidine (1.57 g, 5.05 mmol). After stirring overnight at room temperature, the reaction mixture was poured into ethyl acetate (200 mL) and then washed with water (2×100 mL) adjusting the pH of the aqueous layer to pH 1-2 using 1N HCl. The combined aqueous washes were then re-extracted with ethyl acetate (100 mL). The second organic phase was in turn washed with acidified water (100 mL) using 1N HCl to adjust the to pH 1-2. The combined organic phases were dried over magnesium sulfate, filtered, evaporated, and purified by silica gel column chromatography to afford INT-9 as a viscous oil that solidified upon standing (1.25 g, 70% for two steps); $^1$H-NMR (300 MHz, DMSO-$d_6$): δ 11.42 (s, 1H), 8.60 (t, 1H), 4.26 (q, 2H), 4.05 (td, 2H), 1.49 (s, 9H), 1.39 (s, 9H), 1.26 (t, 3H).

Step 5: Compound 257

INT-9 (0.5 g) is dissolved in THF (5 mL) and 1N LiOH is added (2.5 mL). Once ester hydrolysis is complete the mixture is concentrated under vacuum and the residue is dissolved in 1:4 trifluoroacetic acid-dichloromethane (5 mL). The mixture is stirred at room temperature overnight to remove the Boc-protecting groups. The mixture is concentrated under vacuum, the residue is purified by preparative HPLC chromatography, and the product is collected and lyophilized to afford compound 257. Alternatively, the ester in INT-8 is hydrolyzed using lithium hydroxide to make SM05 and the resulting amino acid is guanylated using 1H-pyrazole-1-carboxamidine hydrochloride and diisopropylethylamine in DMF as shown below for compound 261.

Synthesis of Compound 258

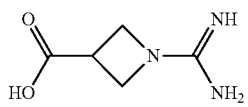

3-Azetidinecarboxylic acid SM06 (2.0 g, 19.8 mmol) was suspended in water (2 mL) and then treated with 10 N sodium hydroxide solution in water (1.96 mL, 19.6 mmol). The thick yellowish solution was then treated with solid cyanamide (1.01 g, 24 mmol) and the mixture turned solid instantly. More water (5 mL) was added to ensure adequate stirring and the slurry was then stirred at room temperature for 3 days. The white solid was subsequently filtered off, washed with cold water (10 mL, 0° C.) and then air dried for 2 hours. High vacuum drying for 2 days affords compound 258 as a white solid (1.48 g, 52%); $^1$H-NMR (300 MHz, D$_2$O): δ 4.19 (t, 2H), 4.07 (dd, 2H), 3.34 (m, 1H); ES(pos) MS m/z 143.9 (M+H$^+$).

Synthesis of Compound 261

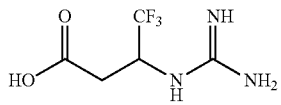

3-Amino-4,4,4-trifluorobutyric acid SM07 (500 mg, 3.18 mmol) and diisopropylethylamine (1.16 mL, 6.68 mmol) were dissolved in dry DMF (3 mL). After addition of 1H-pyrazole-1-carboxamidine hydrochloride (593 mg, 3.50 mmol), the reaction mixture was stirred for 20 days at room temperature. The precipitate was filtered off, washed with methanol/water (2/1, 15 mL) and air-dried. High vacuum drying overnight affords the desired compound 261 as a white powder (135 mg, 21%); $^1$H-NMR (300 MHz, D$_2$O): δ 4.09 (m, 1H), 2.47 (dd, 1H), 2.22 (dd, 1H); ES(pos) MS m/z 200.07 (M+H$^+$).

Synthesis of Compound 275

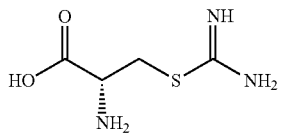

Thiourea (100 mmol) and β-chloro-D-alanine hydrochloride SM66 (100 mmol) in acetone (22 mL) is stirred at reflux for 48 h. Acetone (ca. 150 mL) is added, and the mixture is stirred vigorously to promote solidification. The solid is broken up, stirred until fine, filtered under nitrogen and washed with acetone. The crude solid is dissolved in warm 2-propanol (120 mL) and diluted with diethyl ether until cloudy (80 mL) and crystallization to afford (2R)-2-amino-3-(carbamimidoylsulfanyl)propanoic acid (275).

Synthesis of Compound 278

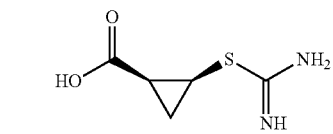

To a flask is added cis-2-aminocyclobutane-1-carboxylic acid (18.8 mmol) and 24.5 mL of 5 N hydrobromic acid. The reaction is cooled in an ice bath to 0-5° C., followed by drop-wise addition of sodium nitrite (30.1 mmol) in 7.5 mL of water over five hours. The temperature is maintained below 5° C. during the addition. After the addition is complete, the reaction is stirred for 12 hours at room temperature. The reaction is diluted with diethyl ether (15 mL), the aqueous layer is removed and the organic phase is washed with 1 N hydrochloric acid (15 mL). The combined aqueous layers are washed with ethyl acetate (10 mL) and the combined organic extracts are dried of magnesium sulfate, filtered and concentrated under reduced pressure. The solid is recrystallized from ethyl acetate (10 mL) and hexanes (10 mL) to obtain trans-2-bromocyclobutane-1-carboxylic acid.

To a suspension of thiourea (15 mmol) in toluene (50 mL) in an oil bath at 60° C. is added trans-2-bromocyclobutane-1-carboxylic acid (2.5 mmol). The reaction is stirred at 60° C. for 5 h. The toluene is then removed under reduced pressure and the resulting residue is diluted with water (25 mL) and 1 N hydrochloric acid (30 mL), to achieve pH of 1-1.5. The mixture is stirred at room temperature for 1-2 hours and then extracted with ethyl acetate (3×50 mL). The combined organic layers are dried over magnesium sulfate, filtered and concentrated under reduced pressure. The resulting solid is dissolved in water (3.0 mL) and filtered through a 0.2 μm nylon filter. The filtrate is purified by preparative HPLC (e.g. Waters PrepPak cartridge Delta-Pak C18 compression column, 15 μm 25×100 mm, 95:5 water-acetonitrile at 12.0 mL/min). The product is collected and lyophilized to afford the product cis-2-(carbamimidoylsulfanyl)cyclopropane-1-carboxylic acid (278).

Synthesis of Compound 286

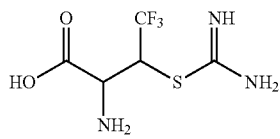 [SMILES: N=C(N)SC(C(N)C(=O)O)C(F)(F)F]

Step 1: 1-Benzyl 2-methyl 3-(trifluoromethyl)aziridine-1,2-dicarboxylate (INT-10)

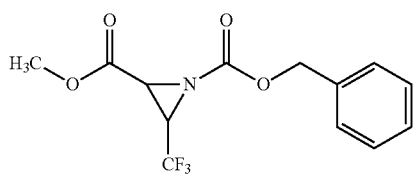

INT-10 may be made by methods as described in *Synlett* 2001, 5, 679 and *Tetrahedron Lett.* 2006, 47(13), 2065 and converted to a Cbz-protected aziridine by standard methods (see *Org. Biomol. Chem.* 2005, 3(18), 3357).

Step 2: methyl 2-{[(benzyloxy)carbonyl]amino}-3-(carbamimidoylsulfanyl)-4,4,4-trifluorobutanoate (INT-11)

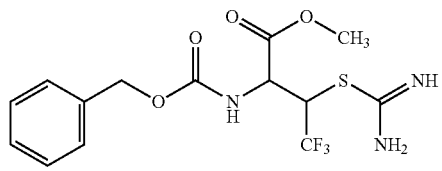 [SMILES: COC(=O)C(NC(=O)OCc1ccccc1)C(SC(=N)N)C(F)(F)F]

INT-10 (1.0 mmol) is dissolved in dichloromethane (10 mL) and the mixture is cooled to 0° C. Borontrifluoride-etherate (1.0 mmol, 1 M dichloromethane) is added dropwise and the reaction is warmed to room temperature. The reaction is poured into 0.1 N aqueous HCl, the aqueous layer is extracted with ethyl acetate, the organic layer is dried over sodium sulfate, concentrated under reduced pressure, and purified by silica gel column chromatography (10-90 methanol-dichloromethane) to afford INT-11.

Step 3: 2-amino-3-(carbamimidoylsulfanyl)-4,4,4-trifluorobutanoic acid (286)

INT-11 (0.5 mmol) is dissolved methanol, 10% palladium on carbon (Pd/C 10 mol %) is added and the flask is vacuum purged with hydrogen gas 5 times. The mixture is stirred vigorously at room temperature under a hydrogen atmosphere for 16 h. Nitrogen gas is used to purge the flask and the mixture is filtered through Celite to remove the Pd/C. The mixture is concentrated under reduced pressure, and the residue is treated with 1N sodium hydroxide in methanol. Once ester hydrolysis is complete, the mixture is concentrated again under reduced pressure, and the resulting residue is dissolved in water (3.0 mL) and filtered through a 0.2 µm nylon filter. The filtrate is purified by preparative HPLC (e.g. Waters PrepPak cartridge Delta-Pak C18 compression column, 15 µm 25×100 mm, 95:5 water-acetonitrile at 12.0 mL/min). The product is collected and lyophilized to afford the product 2-amino-3-(carbamimidoylsulfanyl)-4,4,4-trifluorobutanoic acid (286).

Synthesis of Compound 358

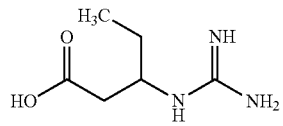

Aminopentanoic acid SM37 (500 mg, 4.27 mmol) was converted into the corresponding guanidino derivative according to the procedure for compound (219). The desired compound 358 was obtained as a white powder after high vacuum drying (291 mg, 43%); $^1$H-NMR (300 MHz, D$_2$O): δ 3.63 (m, 1H), 2.39 (dd, 1H), 2.29 (dd, 1H), 1.52 (m, 2H), 0.85 (t, 3H); ES(pos) MS m/z 160.11 (M+H$^+$).

Synthesis of Compound 376

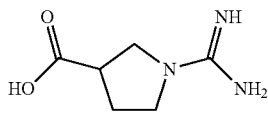 [SMILES: N=C(N)N1CCC(C(=O)O)C1]

Pyrrolidine-3-carboxylic acid hydrochloride (500 mg, 3.30 mmol) was converted into the desired derivative (376) according to a modified procedure described for compound 258 where the amount of base was increased to neutralize the HCl-salt of the starting material. The final material was isolated as a white powder (198 mg, 38%); $^1$H-NMR (300 MHz, D$_2$O): δ 3.4 (m, 4H), 2.99 (m, 1H), 2.17 (m, 1H), 2.03 (m, 1H); ES(pos) MS m/z 158.09 (M+H$^+$).

Synthesis of Compound 366

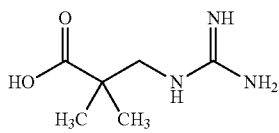

Step 1: tert-butyl N-[(1Z)-{[(tert-butoxy)carbonyl]imino}[(3-hydroxy-2,2-dimethylpropyl)amino]methyl]carbamate (INT-12)

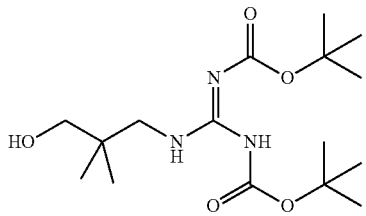 [SMILES: CC(C)(CO)CN/C(=N/C(=O)OC(C)(C)C)NC(=O)OC(C)(C)C]

3-Amino-2,2-dimethylpropanol SM45 (464 mg, 4.5 mmol) was dissolved in dry THF (7 mL) and then treated with N,N'-di-Boc-1H-pyrazole-1-carboxamidine (1.24 g, 4.0 mmol). After stirring for 72 hours at room temperature, the reaction mixture was poured into ethyl acetate (200 mL) and then washed with water (2×100 mL) adjusting the pH of the aqueous layer to pH 1-2 using 1N HCl. The combined aqueous washes were then re-extracted with ethyl acetate (100 mL). The second organic phase was in turn washed with acidified water (100 mL) using 1N HCl to adjust the to pH 1-2. The combined organic phases were dried over magnesium sulfate, filtered, evaporated, and purified by silica gel column chromatography to afford INT-12 as a viscous oil that solidified upon standing (1.32 g, 96%); $^1$H-NMR (300 MHz, DMSO-d6): δ 11.48 (s, 1H). 8.55 (t, 1H), 4.93 (t, 1H), 3.18 (d, 2H), 3.13 (d, 2H), 1.48 (s, 9H), 1.39 (s, 9H), 0.82 (s, 6H).

Step 2: 3-{[(1Z)-{[(tert-butoxy)carbonyl]amino}({[(tert-butoxy)carbonyl]imino})methyl]amino}-2,2-dimethylpropanoic acid (INT-13)

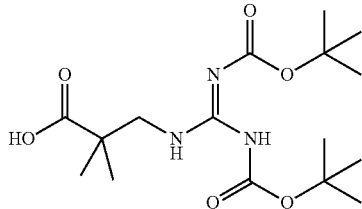 [SMILES: CC(C)(C)OC(=O)/N=C(/NCC(C)(C)C(=O)O)NC(=O)OC(C)(C)C]

INT-12 (1.30 g, 3.76 mmol) was dissolved in acetonitrile (25 mL), carbon tetrachloride (25 mL), and water (40 mL). Sodium periodate (4.83 g, 22.6 mmol) and ruthenium trichloride (50 mg, catalytic) were added and the mixture was stirred for 3 h at room temperature or until TLC showed starting material had been consumed. The resulting biphasic mixture was poured into ethyl acetate (200 mL) and then washed with water (2×100 mL) adjusting the pH of the aqueous layer to pH 1-2 using 1N HCl. The combined aqueous washes were then re-extracted with ethyl acetate (100 mL). The second organic phase was in turn washed with acidified water (100 mL) using 1N HCl to adjust the to pH 1-2. The combined organic phases were dried over magnesium sulfate, filtered, evaporated, and purified by silica gel column chromatography to afford INT-13 as a solid foam (1.05 g, 78%); $^1$H-NMR (300 MHz, DMSO-$d_6$): δ 11.47 (s, 1H), 8.53 (t, 1H), 3.42 (d, 2H), 1.47 (s, 9H), 1.39 (s, 9H), 1.13 (s, 6H).

Step 3: Compound 366

INT-14 is dissolved in 1:4 trifluoroacetic acid-dichloromethane (5 mL). The mixture is stirred at room temperature overnight to remove the Boc-protecting groups. The mixture is concentrated under vacuum and the residue is purified by preparative HPLC chromatography to afford compound 366.

In addition to the compounds described above, similar protocols are used to make numerous analogs shown in Table 16 from starting materials listed in Table 15.

TABLE 16

Starting materials for the synthesis of selected compounds

| Compound # | Table # | Starting Material | Protocol |
|---|---|---|---|
| 253 | 4 | SM08 or SM09 | See 261 |
| 254 | 4 | SM10-SM12 | See 261 |
| 255 | 4 | SM03 | See 219 |
| 256 | 4 | SM04 | See 219 |
| 257 | 4 | SM05 | See 257 |
| 258 | 4 | SM06 | See 258 |
| 259 | 4 | SM13 or SM14 | See 219 |
| 260 | 4 | SM15 or SM16 | See 219 |
| 261 | 4 | SM07 | See 261 |
| 262 | 4 | SM24-SM27 | See 261 |
| 327 | 4 | SM08 | See 261 |
| 328 | 4 | SM09 | See 261 |
| 329 | 4 | SM10 or SM11 | See 261 |
| 330 | 4 | SM12 | See 261 |
| 331 | 4 | SM13 | See 219 |
| 332 | 4 | SM14 | See 219 |
| 333 | 4 | SM15 | See 219 |
| 334 | 4 | SM16 | See 219 |
| 335 | 4 | SM17 | See 258 |
| 336 | 4 | SM17 | See 258 |
| 337 | 4 | SM17 | See 258 |
| 338 | 4 | SM17 | See 258 |
| 339 | 4 | SM18 | See 258 |
| 340 | 4 | SM19 | See 258 |
| 341 | 4 | SM20 | See 258 |
| 342 | 4 | SM21 | See 258 |
| 343 | 4 | SM22 | See 261 |
| 344 | 4 | SM23 | See 261 |
| 345 | 4 | SM24 | See 261 |
| 346 | 4 | SM25 | See 261 |
| 347 | 4 | SM26 | See 261 |
| 348 | 4 | SM27 | See 261 |
| 349 | 4 | SM28 | See 219 |
| 350 | 4 | SM29 | See 219 |
| 351 | 4 | SM30 | See 261 |
| 352 | 4 | SM31 | See 261 |
| 353 | 4 | SM32 | See 219 |
| 354 | 4 | SM33 | See 219 |
| 355 | 4 | SM34 | See 219 |
| 356 | 4 | SM35 | See 219 |
| 357 | 4 | SM36 | See 219 |
| 358 | 4 | SM37 | See 358 |
| 359 | 4 | SM38 | See 219 |
| 360 | 4 | SM39 | See 219 |
| 361 | 4 | SM40 | See 219 |
| 362 | 4 | SM41 | See 219 |
| 363 | 4 | SM42 | See 261 |
| 364 | 4 | SM43 | See 261 |
| 365 | 4 | SM44 | See 261 |
| 366 | 4 | SM45 | See 366 |
| 367 | 4 | SM46 | See 366 |
| 368 | 4 | SM47 | See 261 |
| 369 | 4 | SM48 | See 261 |
| 370 | 4 | SM49 | See 261 |
| 371 | 4 | SM50 | See 261 |
| 372 | 4 | SM51 | See 219 |
| 373 | 4 | SM52 | See 219 |
| 374 | 4 | SM53 | See 219 |
| 375 | 4 | SM54 | See 219 |
| 376 | 4 | SM55 | See 376 |
| 377 | 4 | SM56 | See 376 |
| 378 | 4 | SM57 | See 376 |
| 379 | 4 | SM59 | See 258 |
| 380 | 4 | SM58 | See 258 |
| 381 | 4 | SM60 | See 219 |
| 382 | 4 | SM61 | See 219 |
| 383 | 4 | SM62 | See 219 |
| 384 | 4 | SM63 | See 219 |
| 385 | 4 | SM64 | See 258 |
| 263 | 5 | SM65 | See 223 |
| 264 | 5 | SM72 | See 223 |
| 265 | 5 | SM71 | See 223 |
| 266 | 5 | SM08 or SM09 | See 223 |
| 267 | 5 | SM10-SM12 | See 223 |
| 268 | 5 | SM03 | See 223 |
| 269 | 5 | SM04 | See 223 |
| 270 | 5 | SM05 | See 223 |
| 271 | 5 | SM13 or SM14 | See 223 |
| 272 | 5 | SM15 or SM16 | See 223 |
| 273 | 5 | SM07 | See 223 |
| 274 | 5 | SM24-SM27 | See 223 |
| 386 | 5 | SM73 | See 223 |
| 387 | 5 | SM71 | See 223 |
| 388 | 5 | SM72 | See 223 |
| 389 | 5 | SM08 | See 223 |
| 390 | 5 | SM09 | See 223 |
| 391 | 5 | SM10 or SM11 | See 223 |
| 392 | 5 | SM12 | See 223 |
| 393 | 5 | SM13 | See 223 |
| 394 | 5 | SM14 | See 223 |
| 395 | 5 | SM15 | See 223 |
| 396 | 5 | SM16 | See 223 |
| 397 | 5 | SM17 | See 223 |
| 398 | 5 | SM17 | See 223 |
| 399 | 5 | SM17 | See 223 |
| 400 | 5 | SM17 | See 223 |

TABLE 16-continued

Starting materials for the synthesis of selected compounds

| Compound # | Table # | Starting Material | Protocol |
|---|---|---|---|
| 401 | 5 | SM18 | See 223 |
| 402 | 5 | SM19 | See 223 |
| 403 | 5 | SM20 | See 223 |
| 404 | 5 | SM21 | See 223 |
| 405 | 5 | SM22 | See 223 |
| 406 | 5 | SM23 | See 223 |
| 407 | 5 | SM24 | See 223 |
| 408 | 5 | SM25 | See 223 |
| 409 | 5 | SM26 | See 223 |
| 410 | 5 | SM27 | See 223 |
| 411 | 5 | SM28 | See 223 |
| 412 | 5 | SM29 | See 223 |
| 413 | 5 | SM30 | See 223 |
| 414 | 5 | SM31 | See 223 |
| 415 | 5 | SM32 | See 223 |
| 416 | 5 | SM33 | See 223 |
| 417 | 5 | SM34 | See 223 |
| 418 | 5 | SM35 | See 223 |
| 419 | 5 | SM36 | See 223 |
| 420 | 5 | SM38 | See 223 |
| 421 | 5 | SM39 | See 223 |
| 422 | 5 | SM45 | See 223 |
| 423 | 5 | SM46 | See 223 |
| 424 | 5 | SM47 | See 223 |
| 425 | 5 | SM48 | See 223 |
| 426 | 5 | SM49 | See 223 |
| 427 | 5 | SM50 | See 223 |
| 428 | 5 | SM51 | See 223 |
| 429 | 5 | SM52 | See 223 |
| 430 | 5 | SM53 | See 223 |
| 431 | 5 | SM54 | See 223 |
| 432 | 5 | SM58 | See 223 |
| 433 | 5 | SM59 | See 223 |
| 434 | 5 | SM60 | See 223 |
| 435 | 5 | SM61 | See 223 |
| 436 | 5 | SM62 | See 223 |
| 275 | 6 | SM66 | See 275 |
| 276 | 6 | SM67 | See 275 |
| 277 | 6 | SM67 | See 275 |
| 278 | 6 | SM08 or SM09 | See 278 |
| 279 | 6 | SM10-SM12 | See 278 |
| 280 | 6 | SM03 | See 278 |
| 281 | 6 | SM68 | See 275 |
| 282 | 6 | SM69 | See 275 |
| 283 | 6 | SM13 or SM14 | See 275 |
| 284 | 6 | SM15 or SM16 | See 278 |
| 285 | 6 | SM07 | See 278 |
| 286 | 6 | SM24-SM27 | See 286 |

Generic Scheme to Make Sulfanyl N-amidinoprodrugs

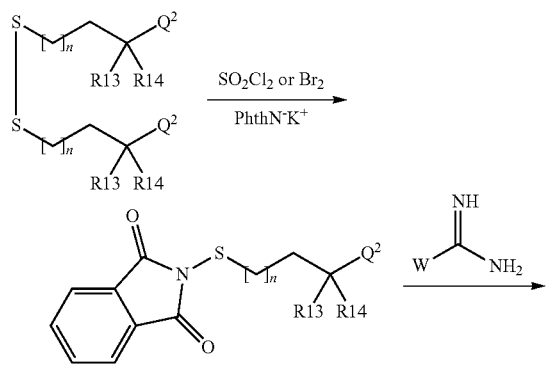

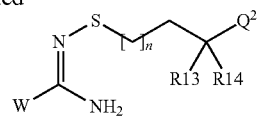

Sulfanyl N-amidino prodrugs may be synthesized in several steps from homodisulfides via N-alkylthiol-phthalimide. Disulfides are commercially available or easily prepared from sulfhydryls using standard conditions (e.g. iodine-water U.S. Pat. No. 6,025,488, sodium iodide-peroxide Synthesis, 2007, 3286-3289, etc.). In step 1, disulfides are reacted with bromine or sulfuryl chloride to generate sulfenyl bromides or sulfenyl chlorides in situ at −15° C. to 0° C. in inert solvent (e.g. dichloromethane, 1,2-dichloroethane, chloroform, etc.; see *J. Org. Chem.* 1971, 36, 3828; and *J. Org. Chem.* 1986, 51 (26), 5333). The resulting mixture is then agitated for 5 to 30 minutes and subsequently transferred drop-wise to a suspension of potassium phthalimide in a suitable solvent such as 1,2-dichloroethane at −15° C. to 0° C. (see *J. Med. Chem.* 2009, 52 (14), 4142 and *Bioorg. Med. Chem. Lett.* 2007, 17, 6629). In step 2, N-alkylthiol-phthalimides are reacted with amidino or guanidine compounds to afford the desired products (see *J. Med. Chem.* 2009, 52 (14), 4142 and International Patent Publication No. WO2010100337).

Synthesis of Compound 287

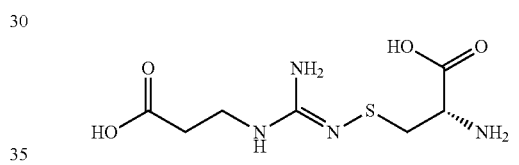

Step 1: (2S)-2-amino-3-[(1,3-dioxo-2,3-dihydro-1H-isoindol-2-yl)sulfanyl]propanoic acid (INT-15)

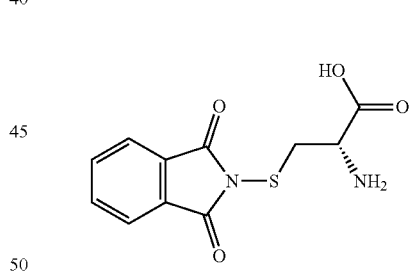

L-cystine (5 mmol), phthalimide (5 mmmol), pyridine (10 mmol) are dissolved in acetonitrile (10 mL). Bromine (5 mmol) is added drop-wise to the solution at 0° C. and the mixture is warmed to room temperature and stirred overnight. The reaction is concentrated under reduced pressure and the residue is then purified by reverse phase chromatography (acetonitrile/water with 0.05% trifluoroacetic acid). The product is collected and lyophilized to afford the trifluoroacetate salt of INT-15.

Step 2: (2S)-2-amino-3-{[{amino[(2-carboxyethyl)amino]methylidene}amino]sulfanyl}propanoic acid (287)

β-Guanidinopropionic acid (1.00 mmol), INT-15 (1.15 mmol) and potassium carbonate (1.15 mmol) are dissolved in anhydrous acetonitrile (10 ml) and stirred overnight. The reaction is concentrated under reduced pressure and the residue is then purified by reverse phase chromatography (acetonitrile/water with 0.05% trifluoroacetic acid). The product is collected and lyophilized to afford the trifluoroacetate salt of 287.

In addition to the synthesis of compound 287 described above, additional prodrugs may be made by combining different guanidine compounds (e.g. β-guanidinopropionic acid, β-guanidinobutanoic acid, 2-(2-iminoimidazolidin-1-yl)acetic acid, L-homocystine, etc.) with different activated thiols (e.g. derived from L-cystine, N,N-diacetyl-L-cystine, 2-(carboxymethyldisulfanyl)acetic acid, etc.) as listed in Table 17.

Synthesis of Compound 323

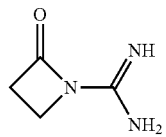

Step 1: N-benzyl-2-oxoazetidine-1-carbothioamide

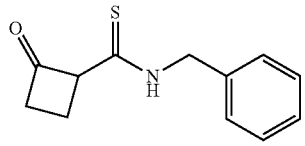 [SMILES: O=C1CCC1C(=S)NCc1ccccc1]

TABLE 17

Starting materials for the synthesis of selected compounds

| Compound # | Guanidine Compound | Disulfide Starting Material [CAS] |
|---|---|---|
| 288 | β-guanidinopropionic acid | N,N'-diacetyl-L-cystine [5545-17-5] |
| 289 | β-guanidinopropionic acid | 2-(carboxymethyldisulfanyl)acetic acid [505-73-7] |
| 290 | β-guanidinopropionic acid | 2,2'-Dithiobis(ethylammonium) sulphate [16214-16-7] |
| 291 | β-guanidinopropionic acid | L-homocystine [626-72-2] |
| 292 | β-guanidinopropionic acid | 2,2'-dithiodiethanesulfonic acid [45127-11-5] |
| 293 | β-guanidinobutanoic acid | L-cystine [56-89-3] |
| 294 | β-guanidinobutanoic acid | N,N'-diacetyl-L-cystine [5545-17-5] |
| 295 | β-guanidinobutanoic acid | 2-(carboxymethyldisulfanyl)acetic acid [505-73-7] |
| 296 | β-guanidinobutanoic acid | 2,2'-dithiobis(ethylammonium) sulphate [16214-16-7] |
| 297 | β-guanidinobutanoic acid | L-homocystine [626-72-2] |
| 298 | β-guanidinobutanoic acid | 2,2'-dithiodiethanesulfonic acid [45127-11-5] |
| 299 | 2-(2-iminoimidazolidin-1-yl)acetic acid | L-cystine [56-89-3] |
| 300 | 2-(2-iminoimidazolidin-1-yl)acetic acid | N,N'-diacetyl-L-cystine [5545-17-5] |
| 301 | 2-(2-iminoimidazolidin-1-yl)acetic acid | 2-(carboxymethyldisulfanyl)acetic acid [505-73-7] |
| 302 | 2-(2-iminoimidazolidin-1-yl)acetic acid | 2,2'-dithiobis(ethylammonium) sulphate [16214-16-7] |
| 303 | 2-(2-iminoimidazolidin-1-yl)acetic acid | L-homocystine [626-72-2] |
| 304 | 2-(2-iminoimidazolidin-1-yl)acetic acid | 2,2'-dithiodiethanesulfonic acid [45127-11-5] |
| 305 | 2-(2-imino-1,3-diazinan-1-yl)acetic acid | L-cystine [56-89-3] |
| 306 | 2-(2-imino-1,3-diazinan-1-yl)acetic acid | N,N'-diacetyl-L-cystine [5545-17-5] |
| 307 | 2-(2-imino-1,3-diazinan-1-yl)acetic acid | 2-(carboxymethyldisulfanyl)acetic acid [505-73-7] |
| 308 | 2-(2-imino-1,3-diazinan-1-yl)acetic acid | 2,2'-dithiobis(ethylammonium) sulphate [16214-16-7] |
| 309 | 2-(2-imino-1,3-diazinan-1-yl)acetic acid | L-homocystine [626-72-2] |
| 310 | 2-(2-imino-1,3-diazinan-1-yl)acetic acid | 2,2'-dithiodiethanesulfonic acid [45127-11-5] |
| 311 | 2-(1-methylguanidino)acetic acid | L-cystine [56-89-3] |
| 312 | 2-(1-methylguanidino)acetic acid | N,N'-diacetyl-L-cystine [5545-17-5] |
| 313 | 2-(1-methylguanidino)acetic acid | 2-(carboxymethyldisulfanyl)acetic acid [505-73-7] |
| 314 | 2-(1-methylguanidino)acetic acid | 2,2'-dithiobis(ethylammonium) sulphate [16214-16-7] |
| 315 | 2-(1-methylguanidino)acetic acid | L-homocystine [626-72-2] |
| 316 | 2-(1-methylguanidino)acetic acid | 2,2'-dithiodiethanesulfonic acid [45127-11-5] |
| 317 | 2-(1,3-dimethylguanidino)acetic acid | L-cystine [56-89-3] |
| 318 | 2-(1,3-dimethylguanidino)acetic acid | N,N'-diacetyl-L-cystine [5545-17-5] |
| 319 | 2-(1,3-dimethylguanidino)acetic acid | 2-(carboxymethyldisulfanyl)acetic acid [505-73-7] |
| 320 | 2-(1,3-dimethylguanidino)acetic acid | 2,2'-dithiobis(ethylammonium) sulphate [16214-16-7] |
| 321 | 2-(1,3-dimethylguanidino)acetic acid | L-homocystine [626-72-2] |
| 322 | 2-(1,3-dimethylguanidino)acetic acid | 2,2'-dithiodiethanesulfonic acid [45127-11-5] |

Azetidinone (5 mmol) is dissolved in tetrahydrofuran and the mixture is cooled in an ice bath. Sodium hydride (60% mineral oil dispersion, 6 mmol) is added followed by benzyl thioisocyanate (5 mmol) and the mixture is stirred to room temperature over 2 h. The reaction is poured into water, the aqueous layer is extracted with ethyl acetate, the organic layer is dried over sodium sulfate, concentrated under reduced pressure and purified by silica gel column chromatography (50-50 ethyl acetate-hexanes) to afford N-benzyl-2-oxoazetidine-1-carbothioamide.

Step 2: N,N'-dibenzyl-2-oxoazetidine-1-carboximidamide

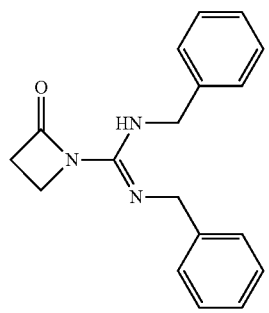 [SMILES: O=C1CCN1/C(=N/Cc1ccccc1)NCc1ccccc1]

To a stirring solution of N-benzyl-2-oxoazetidine-1-carbothioamide (2.5 mmol) in methanol (5 mL) is added methyl iodide (7.0 mmol). The solution is stirred for 2 h, and solvent is removed under reduced pressure. The residue is partitioned between ethyl acetate (15 mL) and saturated aqueous bicarbonate solution (15 mL), the mixture is shaken and the organic layer is dried over sodium sulfate, concentrated under reduced pressure and purified by silica gel column chromatography (50-50 ethyl acetate-hexanes) to afford the intermediate pseudothiourea.

To a stirring solution of this pseudothiourea (1 mmol) in methanol (3 mL) is added benzylamine (1 mmol). The resulting solution is heated to reflux for 12 h in a sealed tube, cooled to ambient temperature, the mixture is concentrated under reduced pressure and purified by silica gel column chromatography (50-50 ethyl acetate-hexanes) to afford N,N'-dibenzyl-2-oxoazetidine-1-carboximidamide.

Step 3: 2-oxoazetidine-1-carboximidamide

N,N'-Dibenzyl-2-oxoazetidine-1-carboximidamide (0.5 mmol) is dissolved methanol, 10% palladium on carbon (Pd/C 10 mol %) is added and the flask is vacuum purged with hydrogen gas 5 times. The mixture is stirred vigorously at room temperature under a hydrogen atmosphere for 16 h. Nitrogen gas is used to purge the flask and the mixture is filtered through Celite to remove the Pd/C. 1N Hydrochloric acid in methanol is added to precipitate the HCl salt of compound 323.

Synthesis of Compound 324

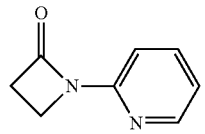 [SMILES: O=C1CCN1c1ccccn1]

2-chloro-pyridine (25 mmol), palladium (II) acetate (2.5 mmol), racemic 2,2'-bis(diphenylphosphino)-1,1'-binaphthyl (2.5 mmol) and cesium carbonate (65 mmol) is dissolved in toluene (75 mL) in a previously degassed sealed vessel. The mixture is flushed with nitrogen gas. Azetidinone (20 mmol) is added to the solution under nitrogen and the sealed mixture is heated overnight at 100° C. The reaction is cooled to room temperature, diluted with diethyl ether, and washed with saturated bicarbonate solution and water. The organic layer is concentrated and purified by silica gel column chromatography (2:98 methanol-dichloromethane) to afford 1-(pyridin-2-yl)azetidin-2-one.

Synthesis of Compound 325

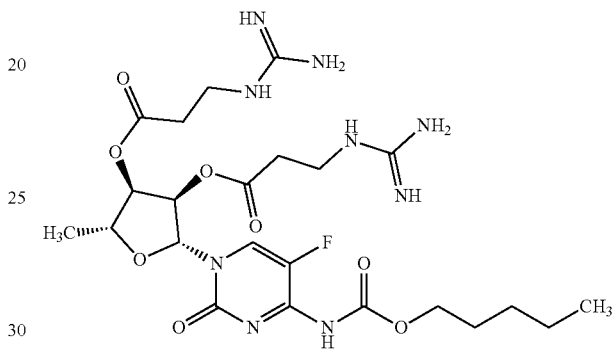

Step 1: 3-{[{[(tert-butoxy)carbonyl]amino}({[(tert-butoxy)carbonyl]imino})methyl]amino}propanoic acid (INT-16)

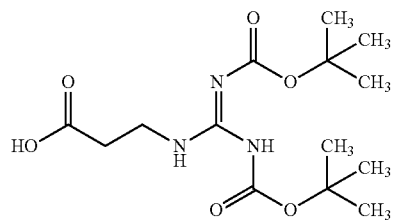 [SMILES: CC(C)(C)OC(=O)/N=C(/NCCC(=O)O)NC(=O)OC(C)(C)C]

β-alanine (1.0 mmol) and N,N-di-(Boc)-1H-pyrazole-1-carboxamide (1.0 mmol) are suspended in pyridine (2.0 mL) and stirred at 25° C. for 2 days. The homogenous reaction is treated with 1N NaOH and extracted into ethyl acetate. The aqueous layer is acidified (pH 3) with 1N HCl and then extracted into ethyl acetate. The combined organic layers are washed with brine, dried over sodium sulfate, filtered and concentrated under reduced pressure to provide 3-{[{[(tert-butoxy)carbonyl]amino}({[(tert-butoxy)carbonyl]imino}) methyl]amino}propanoic acid (INT-16).

Step 2: (2R,3R,4R,5R)-4-[(3-{[{[(tert-butoxy)carbonyl]amino}({[(tert-butoxy)carbonyl]imino})methyl]amino}propanoyl)oxy]-5-(5-fluoro-2-oxo-4-{[(pentyloxy)carbonyl]amino}-1,2-Dihydropyrimidin-1-yl)-2-methyloxolan-3-yl-3-{[{(tert-butoxy)carbonyl]amino}({[(tert-butoxy)carbonyl]imino})methyl]amino}propanoate (INT-17)

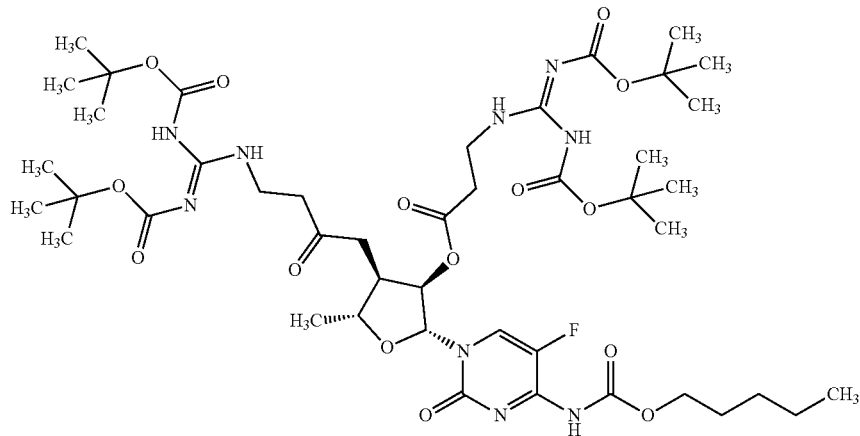 [SMILES: CCCCCOC(=O)Nc1nc(=O)n([C@@H]2O[C@H](C)[C@@H](CC(=O)CCN/C(=N/C(=O)OC(C)(C)C)NC(=O)OC(C)(C)C)[C@H]2OC(=O)CCN/C(=N/C(=O)OC(C)(C)C)NC(=O)OC(C)(C)C)cc1F]

INT-17 (0.7 mmol) and benzotriazole-1-yl-oxy-tris-(dimethylamino)-phosphonium hexafluorophosphate (PyBOP) (0.6 mmol) are added to a solution of capecitabine (0.30 mmol) in dichloromethane (2.0 mL). The resulting mixture is stirred at 25° C. overnight. The dichloromethane is removed under reduced pressure and the residue is taken up in ethyl acetate. The organic layer is washed with water, brine, dried over magnesium sulfate filtered, and concentrated under reduced pressure. The residue is purified by silica gel column chromatography (2:98 methanol-dichloromethane) to afford the Boc-protected coupled compound (INT-17).

Step 3: (2R,3R,4R,5R)-4-[(3-carbamimidamidopropanoyl)oxy]-5-(5-fluoro-2-oxo-4-{[(pentyloxy)carbonyl]amino}-1,2-dihydropyrimidin-1-yl)-2-methyloxolan-3-yl 3-carbamimidamidopropanoate (325)

Boc-Deprotection is accomplished by standard condition using neat trifluoroacetic acid, mixtures of trifluoroacetic acid (TFA) with methylene chloride, or hydrochloride acid (HCl) in dioxane. The material from the previous step INT-17 (0.20 mmol) is treated with 4N HCl/dioxane (2.0 mmol). The mixture is stirred at 25° C. overnight, concentrated under reduced pressure, and then subjected to reverse phase chromatography (acetonitrile/water with 0.05% trifluoroacetic acid) to afford the desired product 325.
Synthesis of Compound 326

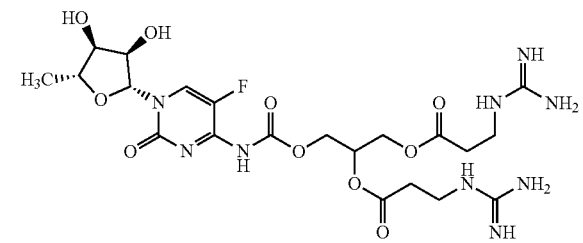 [SMILES: C[C@H]1O[C@@H](n2cc(F)c(NC(=O)OCC(COC(=O)CCNC(=N)N)OC(=O)CCNC(=N)N)nc2=O)[C@H](O)[C@@H]1O]

Step 1: 1-(benzyloxy)-3-[(3-{[bis({[(tert-butoxy)carbonyl]amino})methylidene]amino}propanoyl)oxy]propan-2-yl-3-{[bis({[(tert-butoxy)carbonyl]amino})methylidene]amino}propanoate (INT-18)

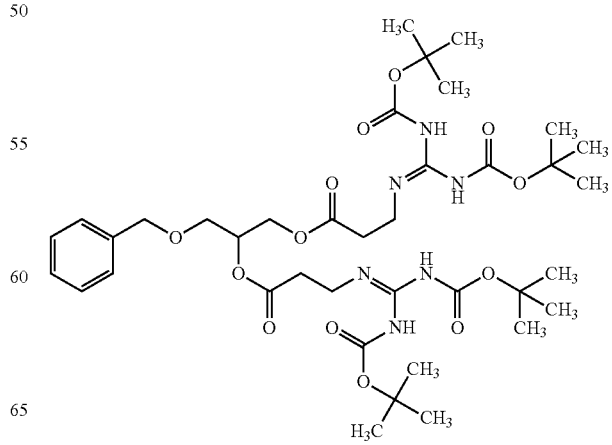

INT-17 (2.2 mmol) and benzotriazole-1-yl-oxy-tris-(dimethylamino)-phosphonium hexafluorophosphate (PyBOP) (2.1 mmol) are added to a solution of 3-(benzyloxy)propane-1,2-diol (1.0 mmol) in dichloromethane (10 mL). The resulting mixture is stirred at 25° C. overnight. The dichloromethane is removed under reduced pressure and the residue is taken up in ethyl acetate. The organic layer is washed with water, brine, dried over magnesium sulfate filtered, and concentrated under reduced pressure. The residue is purified by silica gel column chromatography (50:50 ethyl acetate-hexane) to afford the desired compound INT-18.

INT-18 (0.5 mmol) is dissolved methanol, 10% palladium on carbon (10% Pd/C, 0.05 mmol) is added, and the flask is vacuum purged with hydrogen gas 5 times. The mixture is stirred vigorously at room temperature under a hydrogen atmosphere for 16 h. Nitrogen gas is used to purge the flask and the mixture is filtered through Celite to remove the Pd/C and the solvent is concentrated under reduced pressure. The residue is used as is in the next reaction.

Step 2: 1-[(3-{[bis({[(tert-butoxy)carbonyl]amino}) methylidene]amino}propanoyl)oxy]-3-[(chlorocarbonyl)oxy]propan-2-yl-3-{[bis({[(tert-butoxy)carbonyl]amino})methylidene]amino}propanoate (INT-19)

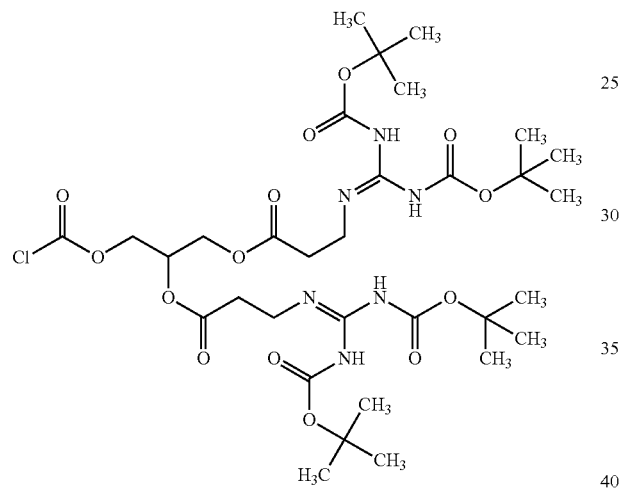

A mixture of triphosgene (0.25 mmol), sodium carbonate (0.5 mmol), and dimethylformamide (0.018 mmol) as a catalyst, in toluene (2 mL) is cooled to 0° C. and stirred at this temperature for 30 min. A solution of the residue from the previous reaction in toluene (2 mL) is added slowly over a period 30 min. The reaction mixture is stirred at 0° C. for 8 h. The solid sodium carbonate is removed by filtration and the solvent is concentrated under reduced pressure. The resulting residue INT-19 is used as-is in the next reaction.

Step 3: 1-[({1-[(4R,6R,6aS)-2,2,6-trimethyl-tetrahydro-2H-furo[3,4-d][1,3]dioxol-4-yl]-5-fluoro-2-oxo-1,2,3,4-tetrahydropyrimidin-4-yl}carbamoyl) oxy]-3-[(3-{[bis({[(tert-butoxy)carbonyl]amino}) methylidene]amino}propanoyl)oxy]propan-2-yl-3-{[bis({[(tert-butoxy)carbonyl]amino})methylidene] amino}propanoate (INT-20)

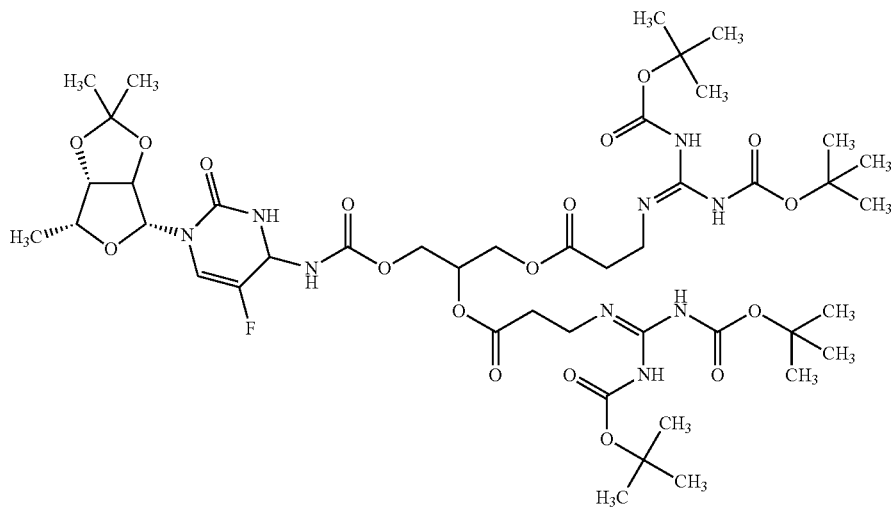

5-Fluoro-2',3'-o-isopropylidenecytidine (5-FI PC) is made according to protocols described in International Patent Publication Nos. WO2008144980 and WO2008131062. 5-FIPC (0.25 mmol) and pyridine (0.5 mmol) are dissolved in dichloromethane (5 mL) and INT-12 is added as a solution in dichloromethane (5 mL). The mixture is stirred at room temperature for 3 h. The reaction is poured into ethyl acetate (50 mL) and washed with water, brine, dried over magnesium sulfate filtered, and concentrated under reduced pressure. The residue is purified by silica gel column chromatography (50:50 ethyl acetate-hexane) to afford the desired compound INT-20.

Step 4: 1-[(3-carbamimidamidopropanoyl)oxy]-3-[({1-[(2R,3R,4S,5R)-3,4-dihydroxy-5-methyloxolan-2-yl]-5-fluoro-2-oxo-1,2-dihydropyrimidin-4-yl}carbamoyl)oxy]propan-2-yl 3-carbamimidamidopropanoate (326)

INT-20 (0.20 mmol) is treated with 4N HCl/dioxane (2.0 mmol). The mixture is stirred at room temperature overnight and then water is added and the mixture is stirred an additional 8 h. The reaction is concentrated under reduced pressure and the residue is then purified by reverse phase chromatography (acetonitrile/water with 0.05% trifluoroacetic acid) and the product is collected and lyophilized to afford the trifluoroacetate salt of compound 326.

Example 2. Determining Compound Activity

The invention provides compounds that are useful for treating cancer and/or for inhibiting cancer cell survival, hypoxic survival, metastatic survival, or metastatic colonization.

To determine the activity of a compound, one can contact the compound with a system containing test cells expressing a reporter gene encoded by a nucleic acid operatively liked to a promoter of a marker gene selected from the above-mentioned metastasis promoters or suppressors. The system can be an in vitro cell line model or an in vivo animal model. The cells can naturally express the gene, or can be modified to express a recombinant nucleic acid. The recombinant nucleic acid can contain a nucleic acid coding a reporter polypeptide to a heterologous promoter. One then measures the expression level of the miRNA, polypeptide, or reporter polypeptide.

For the polypeptide, the expression level can be determined at either the mRNA level or at the protein level. Methods of measuring mRNA levels in a cell, a tissue sample, or a body fluid are well known in the art. To measure mRNA levels, cells can be lysed and the levels of mRNA in the lysates or in RNA purified or semi-purified from the lysates can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out using tissue sections or unlysed cell suspensions, and detectably (e.g., fluorescent or enzyme) labeled DNA or RNA probes. Additional mRNA-quantifying methods include RNA protection assay (RPA) and SAGE. Methods of measuring protein levels in a cell or a tissue sample are also known in the art.

To determine the effectiveness of a compound to treat cancer and/or inhibiting cancer cell survival, hypoxic survival, metastatic survival, or metastatic colonization, one can compare the level obtained in the manner described above with a control level (e.g., one obtained in the absence of the candidate compound). The compound is identified as being effective if (i) a metastasis suppressor's level is higher than a control or reference value or (ii) a metastasis promoter's level is lower than the control or reference value. One can further verify the efficacy of a compound thus-identified using the in vitro cell culture model or an in vivo animal model as disclosed in the examples below.

The activity of compounds may also be determined by methods known in the art to determine CKB or creatine transport inhibition. For example, methods to determine inhibition of CKB are described in McLaughlin et al. J. Biol. Chem. 1972, 247:4382-4388, incorporated herein by reference. Methods to determine inhibition of creatine transport are described in Fitch et al. Metabolism, 1980, 29:686-690, Dodd et al. J. Biol. Chem. 2005, 280:32649-32654, and Dodd et al. J. Biol. Chem. 2007, 282:15528-15533, each of which is incorporated herein by reference.

Example 3. In Vivo Selection

As a first step to identify molecular regulators of liver colonization by colon cancer, an in vivo selection was performed on the LS-174T human colon cancer line for enhanced liver colonization through iterative intra-hepatic injection of cancer cells into immunodeficient mice followed by surgical resection of the liver colonies and dissociation of cells. More specifically, liver colonization by $5 \times 10^5$ LS-Parental, LvM3a and LvM3b cells was examined after direct intrahepatic injection by bioluminescence. Mice were imaged at day 21 after injection and livers extracted for ex vivo imaging and gross morphological examination. Photon flux ratios for the groups were obtained and compared. It was found that third-generation liver colonizers LS-LvM3a and LS-LvM3b displayed dramatically enhanced (>50 fold) capacity for liver colonization upon intra-hepatic injection relative to their parental line. Importantly, these derivatives also displayed significantly enhanced (>150 fold) liver metastatic capacity upon portal circulation injection in metastatic colonization assays—revealing liver colonization capacity to be a key step in colon cancer metastatic progression. For these bioluminescence assays, all P values for the groups' respective photon flux ratios were based on one-sided Student's t-tests and found to be less than 0.05, 0.001, or 0.0001.

In order to systematically identify microRNA regulators of metastatic progression, a library of lentiviral particles, each encoding one of 611 human microRNAs, was transduced into the LS-LvM3b colonizer population, the LS-174T parental line, as well as the SW620 colon cancer population. These cancer populations, containing cancer cells expressing each of 661 miRNAs, were then intra-hepatically injected into mice in order to allow for the selection of cells capable of colonizing the liver. Genomic PCR amplification of miRNA sequences, reverse-transcription, and miRNA profiling of miRNA inserts allowed for the quantification of miRNA insert representation. It was identified that several miRNAs displayed drop-out in the context of liver colonization in both colon cancer cell lines, consistent with the over-expression of these miRNAs suppressing liver colonization by colon cancer cells.

Example 4. Determination of Effect of Endogenous Levels of miRNAs

In this example, assays were carried out to examine whether endogenous levels of any of these miRNAs exhibit silencing in highly metastatic derivatives relative to isogenic poorly metastatic cells. Indeed, miR-483-5p and miR-551a were found to be silenced in highly metastatic LS-LVM3a and LS-LVM3b liver colonizers relative to their parental line and the metastatic SW620 derivative relative to its isogenic parental line. Consistent with a suppressive role for these miRNAs in liver colonization, over-expression of miR-483-5p or miR-551a robustly suppressed metastatic colonization by the LS-LvM3b cells, while inhibition of endogenous miR-483-5p or miR-551a in poorly metastatic parental lines LS-174T and SW480 significantly enhanced liver metastatic colonization.

Example 5. Investigation of the Mechanism of Action of miRNAs

In this example, assays were carried out to investigate the mechanism(s) by which these miRNAs exert their anti-metastatic effects. The effects of these miRNAs on metastatic progression were not secondary to modulation of proliferative capacity since miR-551a inhibition did not effect in vitro proliferation, while miR-483-5p inhibition increased proliferation. Additionally, over-expression of these miRNAs did not alter the invasive capacity or apoptotic rates of cancer cells. In order to determine the mechanism(s) by which these miRNAs impact metastasis, assays were performed to identify the time-point during the metastatic process when cells over-expressing these miRNAs display a defect in progression. Surprisingly, it was noted that as early as 24 hours after injection of cells into the portal circulation for hepatic metastatic colonization assays, cells over-expressing these miRNAs were out-competed in their representation relative to cells expressing a control hairpin.

Example 6. Organotypic Slice Culture System

To elucidate the mechanism(s) by which these miRNAs suppress liver metastatic colonization, an in vitro liver organotypic slice culture system was developed. This system allowed one to study early events during liver metastasis after single-cell dissemination of colon cancer cells in the liver microenvironment. Consistent with prior studies on a significant selection on cell survival during metastatic colonization, there was a large drop-off in the numbers of cells within the liver microenvironment as a function of time. Highly metastatic LvM3b colonizer cells were significantly better at persisting in the liver microenvironment than their poorly metastatic parental line—consistent with a positive role for intrahepatic persistence in metastatic progression.

Next, assays were carried out to investigate whether the effects of this miRNA regulatory network on cancer cell persistence are caused by diminished cancer cell survival during metastatic progression. To quantify cell death in vivo, a bioluminescence-based luciferin reporter of caspace-3/7 activity was utilized.

More specifically, SW480 cells whose endogenous miR-483-5p or miR-551a were inhibited and subsequently introduced into the liver of immunodeficient mice by intrasplenic injection. Then, relative in vivo caspase activity in these cells was monitored using a caspase-3 activated DEVD-luciferin. It was found that miRNA inhibition significantly reduced in vivo caspase activity in colon cancer cells during the early phase of hepatic colonization, revealing cancer survival to be the phenotype suppressed by these miRNAs.

These in vivo findings were corroborated by an organotypic slice culture system. Briefly, survival of the SW480 cells in organotypic cultures (n=8) whose endogenous miR-483-5p or miR-551a were inhibited by pre-treatment with LNAs. $5 \times 10^5$ cells were labeled with cell-tracker green (LS-Parental) or cell-tracker red (LvM3b) and introduced into the liver through intrasplenic injection. Immediately after injection, the liver was excised and 150-um slice cultures were made using a tissue chopper. Survival of the cells in organotypic cultures was monitored for up to 4 days with a multi-photon microscope. Dye-swap experiments were performed to exclude effects of dye bias. Representative images at day 0 and day 3 were shown. It was found that over-expression of both microRNAs in LS-LvM3b cells suppressed colon cancer persistence while inhibition of endogenous levels of both microRNAs enhanced persistence of poorly metastatic SW480 cells. The above findings reveal miR-483-5p and miR-551a to suppress liver metastatic colonization and metastatic cell survival in the liver—a phenotype exhibited by highly metastatic colon cancer cells.

Example 7. Investigation of Downstream Effectors

In this example, assays were carried out to identify the downstream effectors of these miRNAs. Through transcriptomic profiling, transcripts that were down-regulated by over-expression of each microRNA and which contained 3'-UTR or coding-sequence (CDS) elements complementary to the miRNAs were identified. Interestingly, Creatine Kinase Brain-type (CKB) was identified as a putative target of both miRNAs, suggesting that these miRNAs, which exhibit common in vivo and organotypic phenotypes might mediate their effects through a common target gene. Indeed, quantitative PCR validation revealed suppression of CKB transcript levels upon over-expression of the microRNAs. It was found that expression levels of CKB in highly metastatic LvM3b cells were suppressed by over-expressing miR-483-5p and miR-551a. Additionally, endogenous miR-483 and miR-551a were found to suppress endogenous CKB protein levels. For example, it was found that expression of CKB was up-regulated in poorly metastatic SW480 cells whose endogenous miR-483-5p and miR-551aa were inhibited with LNAs. Mutagenesis and luciferase-based reporter assays revealed miR-483-5p and miR-551a to directly target the 3'UTR or CDS of CKB. To that end, luciferase reporter assays of CKB coding sequence and 3'-UTR were carried out. It was found that miR-483-5p and miR-551a targeted complementary regions in the 3'-UTR and coding sequence of CKB respectively. The assays were performed with the complementary regions mutated as well and they were performed at least 3 times.

Example 8. Investigation of the Role of CKB in Liver Metastasis

In this example, assays were carried out to examine if CKB is sufficient and necessary for liver metastatic colonization by colon cancer.

Briefly, liver metastasis was examined in mice injected intrasplenically with $5 \times 10^5$ poorly metastatic SW480 cells and CKB over-expressing cells. The mice were euthanized at 28 days after injection and livers excised for bioluminescent imaging. Similarly, liver metastasis was also examined in mice injected intrasplenically with $5 \times 10^5$ highly aggressive LvM3b expressing a control hairpin or a hairpin targeting CKB. These mice were euthanized 21 days after injection as described above.

It was found that over-expression of CKB in poorly metastatic SW480 cells was sufficient to promote liver metastasis by more than 3-folds, while CKB knockdown in metastatic LS-LvM3b cells and SW480 cells, through independent hairpin knockdown in each line robustly suppressed liver metastasis by more than 5 folds. Consistent with the effects of the miRNAs, CKB over-expression was sufficient to significantly enhance the ability of colon cancer cells to persist in the liver micro-environment and enhanced their representation in the liver, while CKB knockdown significantly reduced intra-hepatic persistence. To that end, study was carried out to examine survival of control SW480 and CKB over-expressing SW480 cells in organotypic liver slices (n=8), and organotypic slice cultures of LvM3b cells expressing a control hairpin or hairpin targeting CKB (n=8). Images taken at day 0 and day 2 showed that CKB over-expression was sufficient to significantly enhance the ability of cancer cells. In these assays, P values were found to be less than 0.001 or 0.0001 based on one-sided Student's t-tests.

To investigate whether CKB acts directly downstream of miR-483-5p and miR-551a, the coding-sequence of CKB was over-expressed in cells over-expressing miR-483-5p or miR-551a. Briefly, assays were performed to examine metastatic progression in mice injected with $5 \times 10^5$ LvM3b cells over-expressing miR-483-5p and miR-551a, with and without CKB over-expression. Liver metastases were monitored by bioluminescent imaging and mice euthanized 35 days after injection. It was found that over-expression of CKB was sufficient to rescue the suppressed liver metastatic phenotypes of cells over-expressing miR-483-5p and miR-551a. Conversely, knockdown of CKB in cells displaying endogenous miR-483-5p or miR-551a inhibition prevented the enhanced metastasis effect seen with miR-483-5p or miR-551a inhibition. To that end, assays were performed to examine liver metastasis in mice injected with $5 \times 10^5$ SW480 cells whose endogenous miR-483-5p and miR-551a were inhibited by LNA, with and without CKB knockdown. The mice were euthanized after 28 days and liver excised for ex vivo bioluminescence imaging. The results of the above mutational, gain- and loss-of-function experiments, and epistasis analyses reveal CKB to be a direct target of miR-483-5p and miR-551a and to act as a downstream effector of these miRNAs in the regulation of colon cancer metastatic progression. In these assays, P values were found to be less than 0.05 or 0.001 based on one-sided Student's t-tests.

To further confirm the roles of CKB, relative in vivo caspase activities were examined in control SW480 and CKB over-expressing cells in livers of mice. The activities were measured by bioluminescence using a caspase-3 activated DEVD-luciferin and normalized to bioluminescence signal from regular luciferin (n=3). Similar relative in vivo caspase-3 activity were also examined in SW480 cells expressing a control hairpin or hairpin targeting CKB and introduced into the livers of mice through intrasplenic injection. Caspase activities were measured on day 1, day 4 and day 7 after injection. Consistent with the above findings, CKB over-expression significantly reduced, while CKB knockdown significantly enhanced, in vivo caspase-3/7 activity in colon cancer cells during the initial phase of hepatic colonization. In these assays, P values were found to be less than 0.05 or 0.001 based on one-sided Student's t-tests. These findings reveal CKB to be a promoter of colon cancer survival during hepatic metastatic colonization.

Example 9. CKB Knockdown Experiments

CKB is known to regulate the reservoir of rapidly mobilized high-energy phosphates in tissues such as the brain and kidneys by catalyzing the transfer of a high-energy phosphate group from phosphocreatine to ADP, yielding ATP and creatine. It was hypothesized that CKB generation of ATP from phosphocreatine might provide colon cancer cells with an energetic advantage during hepatic colonization. To determine if ATP, the end-product of CKB catalysis, could rescue metastasis suppression seen upon CKB knockdown, CKB knockdown cells were loaded with ATP prior to injection of cells in experimental metastasis assays. Briefly, liver metastasis was examined in mice injected with $5 \times 10^5$ LvM3b with or without CKB knockdown and pre-treated with 100 uM ATP or vehicle. Metastatic burden was monitored by bioluminescent imaging and mice euthanized 21 days after injection. It was found that ATP loading of cells was sufficient to significantly enhance the suppressed metastasis phenotype in cells depleted of CKB by more than 10 folds. The rescue by ATP was specific since ATP loading did not enhance the metastatic activity of cells expressing a short-hairpin control.

Similar studies were done to determine whether creatine and phosphocreatine could rescue the phenotype of seen upon CKB knock-down. More specifically, assays were performed to examine liver metastasis in mice injected with $5 \times 10^5$ LvM3b cells pre-treated with 10 uM creatine, in the background of CKB knockdown. The mice were then euthanized as described above and liver extracted for ex vivo bioluminescent imaging at day 21 after injection. Also, colorectal cancer metastasis was examined in mice injected with $5 \times 10^5$ LvM3b cells with CKB knockdown and pre-treated with 10 uM creatine-phosphate. Liver metastasis was monitored by bioluminescent imaging and mice were euthanized as described above. It was found that both creatine and creatine-phosphate rescued metastasis suppression.

In order to investigate whether colon cancer metastasis could be inhibited by blocking the transport of creatine into colon cancer cells, the creatine transporter channel SLC6a8 was inhibited in LvM3b cells by expressing short hairpin targeting SLC6a8. Then liver metastasis by LvM3b cells was examined in the same manner described above. It was found that knock-down of the creatine transporter channel SLC6a8 inhibited colon cancer metastasis. These findings reveal that colon cancer cells are dependent on CKB generated ATP for their survival during hepatic colonization.

Example 10. Analysis of miRNA and CKB Expression Levels in Primary Colon Cancers and Liver Metastases In order to determine if this cooperative miRNA regulatory network controlling colon cancer metastatic progression has human pathologic relevance, the expression levels of miR-483-5p and miR-551a were analyzed in a set of 67 primary colon cancers as well as liver metastases obtained from patients at MSKCC. More specifically, miR-483-5p and miR-551a levels in 37 primary tumor samples and 30 liver metastases samples were quantified by quantitative real-time PCR. Consistent with a metastasis-suppressive role for these miRNAs during metastatic progression, miR-483 and miR-551a both displayed significantly reduced expression levels in human liver metastases relative to primary colon cancers (FIG. 1a; $p<0.05$ for miR-483-5p and $p<0.05$ for miR-551a; N=67).

Figures 1A, 1B, 1C, 1D, 1E:
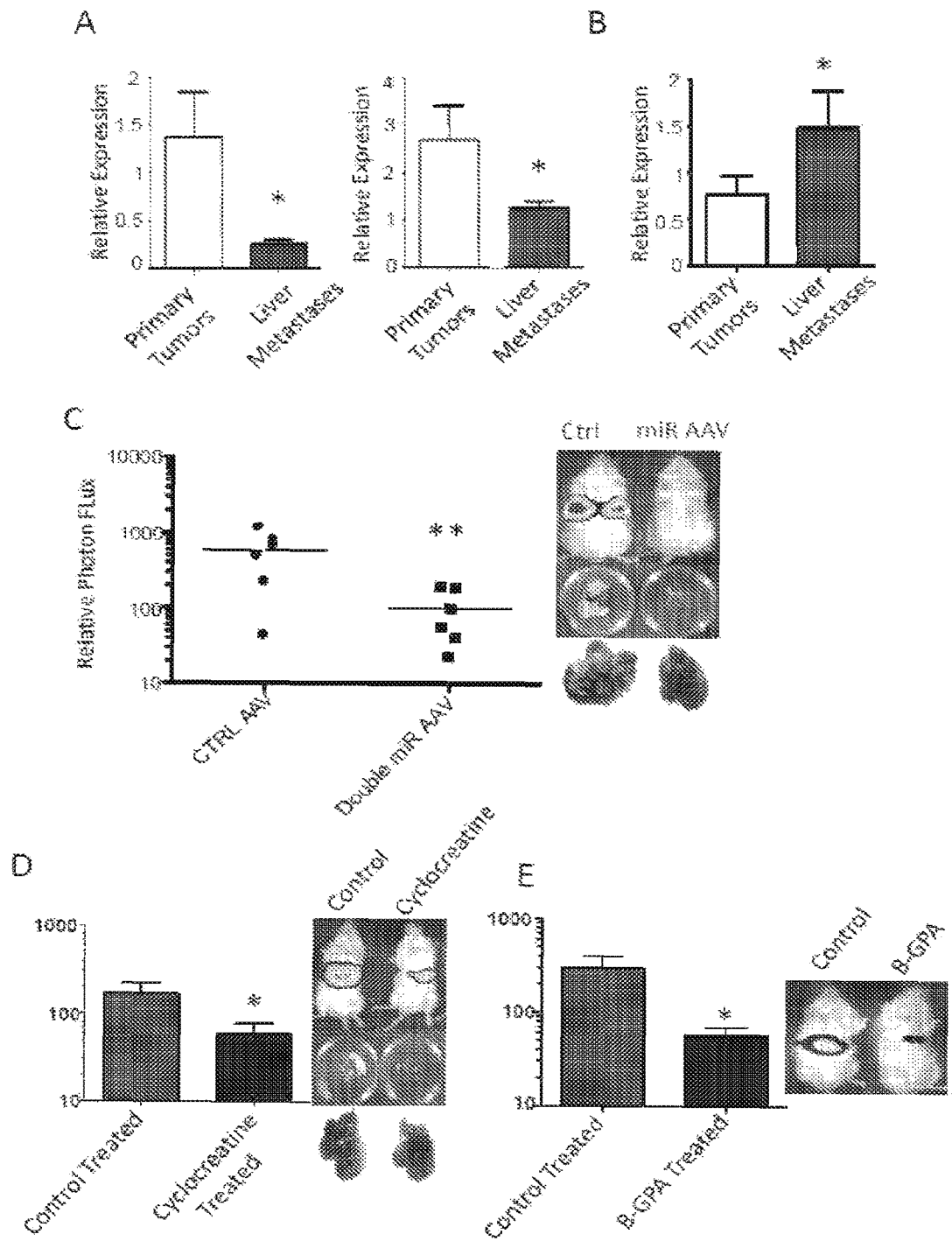
FIG. 1A-1E are a set of diagrams and photographs showing that miR-483-5p, miR-551a and CKB are clinically relevant and can be therapeutically inhibited. a, miR-483-5p and miR-551a levels in 37 primary tumor samples and 30 liver metastases samples were quantified by quantitative real-time PCR. b, CKB expression levels in 37 primary tumor samples and 30 liver metastases samples were measured by quantitative real-time PCR. c, Liver metastasis in mice injected with LvM3b cells and treated with a single dose of AAV doubly expressing miR-483-5p and miR-551a one day after injection cells. d, Bioluminescent measurements of liver metastasis in mice injected with $5 \times 10^5$ LvM3b cells and treated with cyclocreatine daily for two weeks. Mice were euthanized and livers excised for ex vivo imaging at the end of the treatment. e, Bioluminescent measurements of liver metastasis in mice injected with $5 \times 10^5$ LvM3b cells and treated with the creatine transporter inhibitor beta-guanidinopropionic acid (β-GPA) daily for two weeks. Error bars, s.e.m; all P values are based on one-sided Student's t-tests. *P<0.05; P<0.001; *P<0.0001.

CKB expression levels were also examined in the 37 primary tumor samples and 30 liver metastases samples by quantitative real-time PCR. Importantly, CKB expression was found to be significantly elevated in liver metastases relative to primary colon cancers ($p<0.05$) and its expression was significantly anti-correlated with the miRNAs—consistent with its direct targeting by these miRNAs in human colon cancer (FIG. 1b). These findings are consistent with previous clinical histologic analyses revealing elevated levels of CKB protein in advanced stage cancer.

Example 11. Investigation of miRNA Regulatory Network as a Therapeutic Target

In this example, assays were carried out to investigate the therapeutic potential of targeting this miRNA regulatory network. To this end, mice were injected with a high number (500k) of highly metastatic LvM3a cells and 24 hours later injected mice with a single intra-venous dose of adenoviral-associated virus (AAV) expressing miR-483-5p and miR-551a off a single transcript. It was found that a single therapeutic dose of adeno-associated virus (AAV) delivering both miRNAs dramatically and significantly reduced metastatic colonization by more than 5 fold (FIG. 1c).

Finally, assays were carried out to determine the impact of small-molecule inhibition of CKB and restriction of creatine availability on colon cancer metastasis. Cyclocreatine, which resembles phosphocreatine, is a transition-state analog for creatine kinases. To examine the effect of cyclocreatine, bioluminescent measurements of liver metastasis were carried out in mice injected with $5 \times 10^5$ LvM3b cells and treated with cyclocreatine daily for two weeks. The mice were then euthanized and livers excised for ex vivo imaging at the end of the treatment. It was found that, despite being a poor inhibitor of CKB (5000 uM ki), treatment of mice with cyclocreatine significantly reduced metastatic colonization and proved superior to the current standard-of-care FOLFOX chemotherapy (FIG. 1d).

Similar assays were carried out using a creatine transporter inhibitor beta-guanidinopropionic acid (β-GPA). Bioluminescent measurements were used to examine liver metastasis in mice injected with $5 \times 10^5$ LvM3b cells and treated with β-GPA daily for two weeks. It was found that treatment of mice with this competitive inhibitor of the creatine transporter channel also significantly reduced metastatic colonization (FIG. 1e).

Using a systematic approach, two miRNAs were identified to act as suppressors of liver metastatic colonization by colon cancer cells. It was found find that these miRNAs convergently target CKB—a key gene that endows cells encountering hepatic hypoxia with the ability to generate ATP from phosphocreatine reserves. The successful targeting of this pathway using 4 independent therapeutics that were more effective than the current clinical standard-of-care, and which displayed no apparent toxicity suggest promise for therapeutic targeting of this pathway in human colon cancer. The above-described combined in vivo selection/gene screening approach, which is designated as MUlti-Gene Screening of Human genes through intra-Organ Tandem Selection (MUGSHOTS) has efficiently identified robust and pathologically validated regulators of liver colonization and metastasis by colon cancer and has the potential to discover coding and non-coding regulators of metastatic colonization of any organ by any cancer type.

Example 12. Investigation of Creatine Transport as a Therapeutic Target

Figure 2:
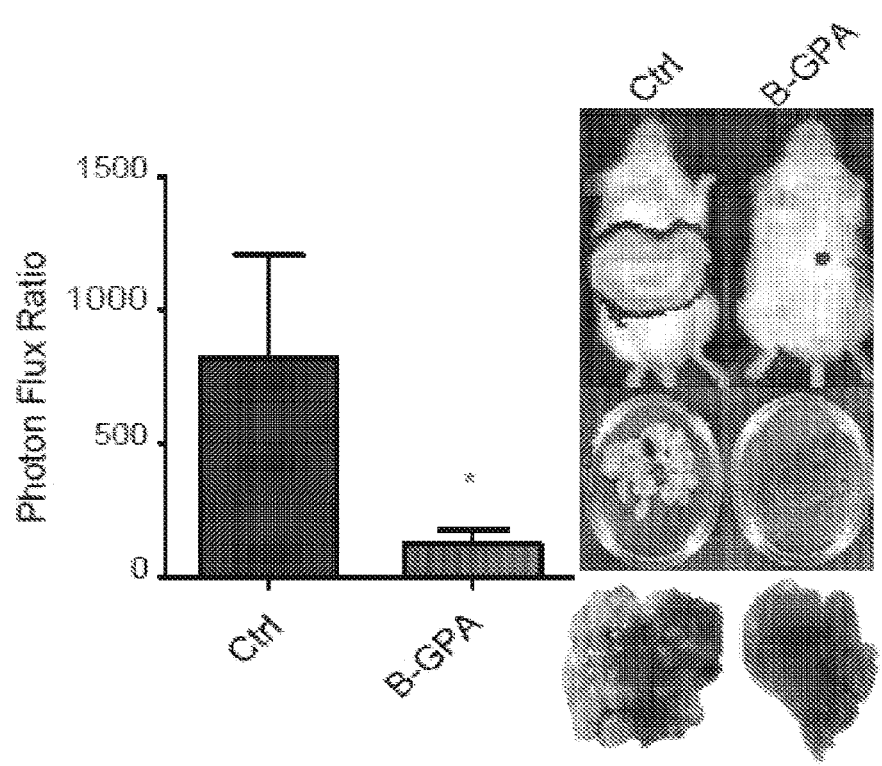
FIG. 2 is a diagram and a photograph showing that β-GPA treatment suppressed colorectal cancer metastasis. Bioluminescent measurements of liver metastasis in mice injected with $5 \times 10^5$ LvM3b cells and treated with β-GPA daily for three weeks. Mice were euthanized at three weeks and liver extracted for bioluminescent imaging and gross histology. Error bars represent the s.e.m; all P values are based on one-sided Student's t-tests. *P<0.05.

In this example, assays were carried out to confirm the therapeutic potential of targeting the creatine transporter channel SLC6a8 by administering the small molecule β-GPA, which is an inhibitor of SLC6a8. As mentioned above, administration of β-GPA to mice injected with LvM3b colon cancer cells resulted in inhibition of colon cancer metastasis to the liver after two weeks of treatment (FIG. 1e). To confirm this therapeutic effect, mice injected with LvM3b colon cancer cells we treated with either β-GPA or control vehicle (PBS) via intra-peritoneal injection daily for three weeks (FIG. 2). The mice were euthanized at three weeks and liver extracted for bioluminescent imaging and gross histology.

It was found that daily treatment with β-GPA led to a significant reduction in colon cancer metastasis to the liver, as assessed by in vivo bioluminescent imaging of in vivo mice, bioluminescent imaging of extracted liver, and by gross anatomical examination of extracted livers from treated mice (FIG. 2). More specifically, the average photon flux ratios as measure by the bioluminescence imaging for the control group (without treatment of β-GPA) and the treated groups were about 800 and 100, respectively. P values were found to be less than 0.05 based on one-sided Student's t-tests.

Example 13. Knockdown of SLC6a8

In this example assays were carried out to evaluate the therapeutic benefit of targeting the creatine transporter channel SLC6a8 with shRNA knockdown targeting SLC6a8.

Figures 3A, 3B, 3C:
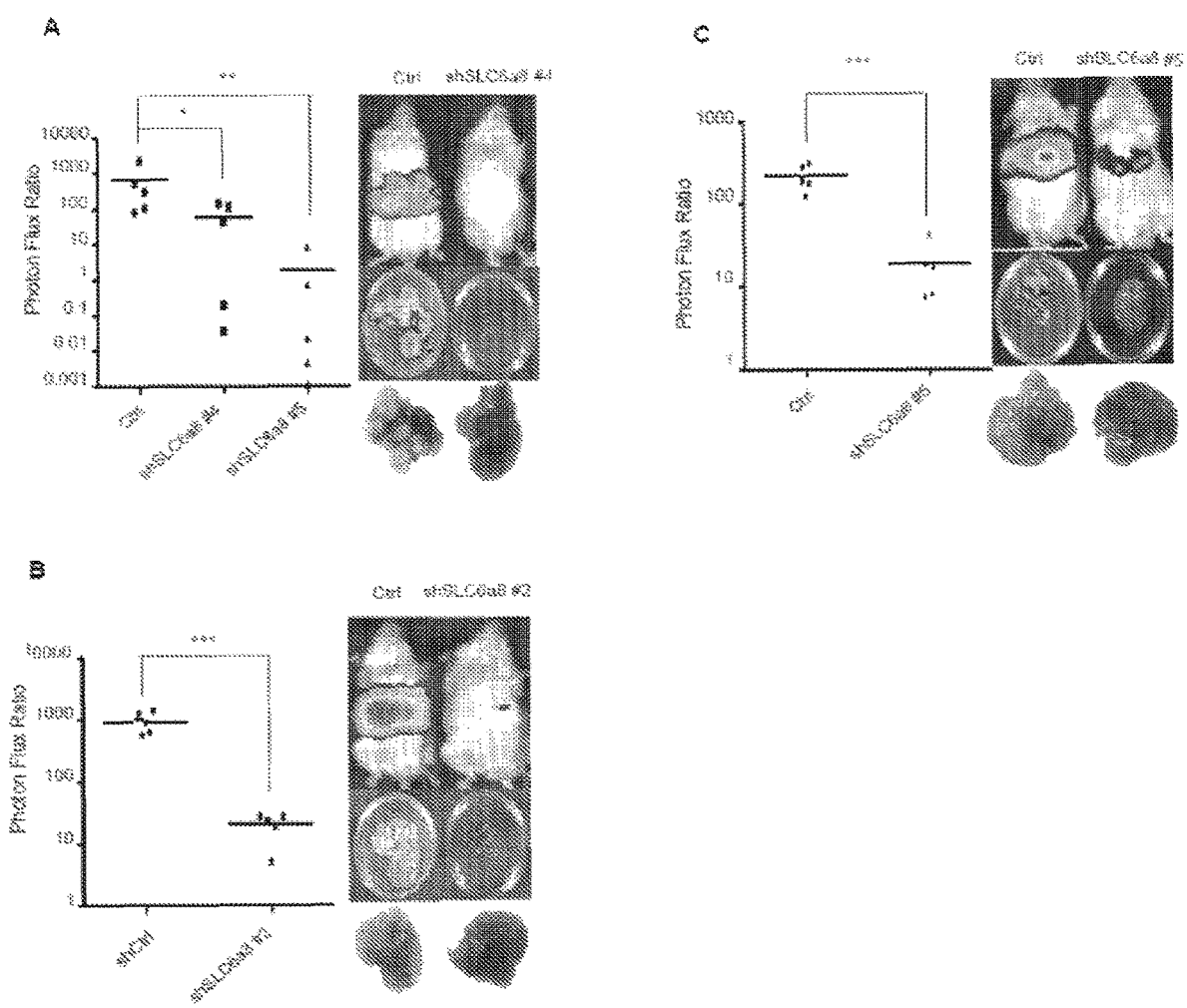
FIG. 3A-C are a set of diagrams and photographs showing that creatine transporter, SLC6a8 is required for colorectal and pancreatic cancer metastasis. a) Liver metastasis by highly aggressive LvM3b cells expressing short hairpins targeting the creatine transporter channel, SLC6a8. Liver metastasis were monitored by bioluminescent imaging and mice were euthanized three weeks after inoculation of cancer cells. Livers were extracted for gross histology. b) Liver metastasis in mice injected with $5 \times 10^5$ SW480 cells transduced with a shRNA targeting SLC6a8. Metastatic progression was monitored by bioluminescent imaging.

Briefly, mice were injected with LvM3b colon cancer cells expressing either of two independent short hairpin RNAs (shSLC6a8 #4 or shSLC6a8 #5) targeting the creatine transporter channel SLC6a8 or with control RNA (empty pLKO vector, ordered from Sigma Aldrich) (FIG. 3a). Again, liver metastasis was monitored by bioluminescent imaging and mice were euthanized three weeks after inoculation of cancer cells. Livers were extracted for gross histology. It was found that knockdown of SLC6a8 with two independent shRNAs resulted in inhibition of colon cancer metastasis (FIG. 3a).

To further confirm the therapeutic benefit of knockdown of SLC6a8, another independent colon cancer cell line (SW480 colon cancer cell line) expressing a short hairpin RNA targeting SLC6a8 (shSLC6a8 #2) was injected into mice (FIG. 3b). It was found that SLC6a8 knockdown significantly inhibited metastasis of SW480 colon cancer cells (FIG. 3b).

Lastly, the therapeutic benefit of targeting SLC6a8 was investigated in pancreatic cancer cells. To accomplish this, PANC1 pancreatic cancer cells expressing either an shRNA targeting SLC6a8 (shSLC6a8 #5) or a control RNA (empty pLKO vector) were injected into mice. Metastatic progression was monitored by bioluminescent imaging and mice were euthanized in the same manner described above. It was found that, at 28 days, there was a significant reduction in pancreatic cancer metastasis in the cells treated with shRNA targeting SLC6a8, revealing that SLC6a8 is a therapeutic target for pancreatic cancer.

Example 14. Correlation of Creatine Transport and Metastatic Progression

In this example, it was investigated whether expression of the creatine transporter SLC6a8 in human colon cancer tumors correlated with metastatic progression.

To accomplish this, quantitative real-time PCR was used to quantify the expression of SLC6a8 in 36 primary colon cancer tumors and 30 metastatic colon cancer tumors (FIG. 4). Indeed, expression of SLC6a8 was significantly higher in metastatic tumors (about 1.3) as compared with primary tumors (about 0.5), further confirming the central role of SLC6a8 in metastasis (FIG. 4). P values were found to be less than 0.05 based on one-sided Student's t-tests.

Example 15. Effect of β-GPA on Pancreatic Cancer

As mentioned above, it was demonstrated that inhibition of the creatine transporter SLC6a8 with shRNA mediated knock-down resulted in suppression of metastasis of both colon cancer as well as pancreatic cancer. It was also demonstrated that inhibition of SLC6a8 with the small molecule inhibitor 3-GPA resulted in therapeutic benefit for colon cancer metastasis in vivo. To evaluate if β-GPA treatment results in therapeutic benefit in pancreatic cancer, the ability of β-GPA treatment to inhibit the survival of human pancreatic cancer cells was assessed in vivo in mice.

Briefly, PANC1 pancreatic cancer cells were incubated for 48 hours with and without the presence of 10 mM of β-GPA, then injected into immunodeficient mice ($5 \times 10^5$ PANC1 cells each mouse; 4 mice each in the treated and untreated cohort). The mice were imaged with bioluminescence imaging on day 1 after injection and signal was normalized to day zero. Therapeutic benefit was observed as early as one day after the injections, with a significant reduction in the tumor burden of pancreatic cancer cells in vivo as assessed by bioluminescence imaging (FIG. 4) demonstrating therapeutic benefit of β-GPA treatment for pancreatic cancer. More specifically, the average photon flux ratios as measure by the bioluminescence imaging for the control group (without treatment of β-GPA) and the treated groups were about 2.7 and 1.6, respectively. P values were found to be less than 0.05 based on one-sided Student's t-tests.

Example 16. Combination of β-GPA and Fluorouracil or Gemcitabine

The above examples demonstrated that β-GPA treatment alone resulted in therapeutic benefit for colon cancer and pancreatic cancer. In this example it was investigated whether β-GPA treatment could enhance the therapeutic activity of the chemotherapy agents 5'-Fluorouracil and Gemcitabine. To accomplish this, cell viability was performed assays to compare the cytotoxic activity of 5'-Fluorouracil or Gemcitabine alone compared with combined therapy with β-GPA.

Briefly, 10 000 PANC1 cells were seeded in triplicate in 96-well plates and treated with various concentrations of Gemcitabine (1 nm, 10 nm, 100 nm, 1000 nm, 10000 nm, 100000 nm, and 1000000 nm) with or without 10 mM of β-GPA for 48 hours. Cell viability was then assayed using the WST-1 reagent (Roche Applied Science), with absorbance at 440 nm an indicator of the number of viable cells. As shown in FIG. 6, it was found that the addition of a therapeutic concentration of β-GPA enhanced the cytotoxic activity of Gemcitabine on PANC1 pancreatic cancer cells as assessed by a cell viability assay using the WST-1 reagent.

Likewise, the addition of a therapeutic concentration of β-GPA enhanced the cytotoxic activity of 5'-Fluorouracil on Ls-LvM3b colon cancer cells. To that end, 10,000 Ls-LvM3b cells were seeded in triplicate in 96-well plates and treated with various concentrations of 5'-Fluorouracil with or without 10 mM of β-GPA for 48 hours. Cell viability was assayed in the same manner described above with absorbance at 440 nm an indicator of the number of viable cells. As shown in FIG. 7, these results demonstrate that β-GPA enhance the therapeutic activity of commonly utilized chemotherapeutic agents for the treatment of colorectal and pancreatic cancer.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features herein before set forth.

All publications, patents and patent applications are herein incorporated by reference in their entirety to the same extent as if each individual publication, patent, or patent application was specifically and individually indicated to be incorporated by reference in its entirety.

What is claimed is:

1. A method for treating gastrointestinal cancer, comprising administering to a subject in need thereof, a compound having the structure:

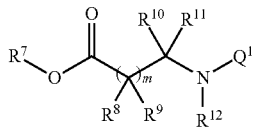

Formula V wherein $Q^1$ is optionally substituted amidino;

m is 1 or 2;

$R^7$ is hydrogen, optionally substituted $C_1$-$C_6$ alkyl, or optionally substituted $C_6$-$C_{10}$ aryl $C_1$-$C_6$ alkyl;

$R^8$ and $R^9$ are independently hydrogen, deuterium, halo, hydroxyl, $NH_2$, optionally substituted $C_1$-$C_3$ alkyl, or $R^8$ and $R^9$ combine with the atoms to which they are attached to form an optionally substituted $C_3$-$C_6$ cycloalkyl ring; or $R^8$ or $R^9$ combine with $R^{10}$ or $R^{11}$ with the atoms to which they are attached to form an optionally substituted $C_3$-$C_4$ cycloalkyl ring; or $R^8$ or $R^9$ combine with $R^{12}$ with the atoms to which they are attached to form an optionally substituted $C_3$-$C_5$ heterocycle;

$R^{10}$ and $R^{11}$ are independently hydrogen, deuterium, optionally substituted $C_1$-$C_4$ alkyl, optionally substituted $C_2$-$C_6$ alkenyl, optionally substituted $C_2$-$C_6$ alkynyl or $R^{10}$ and $R^{11}$ combine with the atoms to which they are attached to form an optionally substituted $C_3$-$C_6$ cycloalkyl ring; or $R^{10}$ or $R^{11}$ combine with $R^8$ or $R^9$ with the atoms to which they are attached to form an optionally substituted $C_3$-$C_4$ cycloalkyl ring; or $R^{10}$ or $R^{11}$ combine with $R^{12}$ with the atoms to which they are attached to form an optionally substituted $C_3$-$C_4$ heterocycle;

$R_{12}$ is hydrogen, $C_1$-$C_6$ alkyl, or $R^{12}$ combines with $R^8$ or $R^9$ with the atoms to which they are attached to form an optionally substituted $C_3$-$C_5$ heterocycle, or $R^{12}$ combines with $R^{10}$ or $R^{11}$ with the atoms to which they are attached to form an optionally substituted $C_3$-$C_4$ heterocycle;

or a pharmaceutically acceptable salt thereof, in an amount sufficient to treat said gastrointestinal cancer.

2. A method of slowing the spread of gastrointestinal cancer, comprising administering to a subject in need thereof, a compound having the structure:

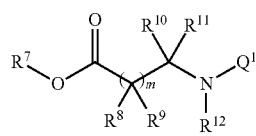

Formula V wherein $Q^1$ is optionally substituted amidino;

m is 1 or 2;

$R^7$ is hydrogen, optionally substituted $C_1$-$C_6$ alkyl, or optionally substituted $C_5$-$C_{10}$ aryl $C_1$-$C_6$ alkyl;

$R^8$ and $R^9$ are independently hydrogen, deuterium, halo, hydroxyl, $NH_2$, optionally substituted $C_1$-$C_3$ alkyl, or $R^8$ and $R^9$ combine with the atoms to which they are attached to form an optionally substituted $C_3$-$C_6$ cycloalkyl ring; or $R^8$ or $R^9$ combine with $R^{10}$ or $R^{11}$ with the atoms to which they are attached to form an optionally substituted $C_3$-$C_4$ cycloalkyl ring; or $R^8$ or $R^9$ combine with $R^{12}$ with the atoms to which they are attached to form an optionally substituted $C_3$-$C_5$ heterocycle;

$R^{10}$ and $R^{11}$ are independently hydrogen, deuterium, optionally substituted $C_1$-$C_4$ alkyl, optionally substituted $C_2$-$C_6$ alkenyl, optionally substituted $C_2$-$C_6$ alkynyl or $R^{10}$ and $R^{11}$ combine with the atoms to which they are attached to form an optionally substituted $C_3$-$C_6$ cycloalkyl ring; or $R^{10}$ or $R^{11}$ combine with $R^8$ or $R^9$ with the atoms to which they are attached to form an optionally substituted $C_3$-$C_4$ cycloalkyl ring; or $R^{10}$ or $R^{11}$ combine with $R^{12}$ with the atoms to which they are attached to form an optionally substituted $C_3$-$C_4$ heterocycle;

$R_{12}$ is hydrogen, $C_1$-$C_5$ alkyl, or $R^{12}$ combines with $R^8$ or $R^9$ with the atoms to which they are attached to form an optionally substituted $C_3$-$C_5$ heterocycle, or $R^{12}$ combines with $R^{10}$ or $R^{11}$ with the atoms to which they are attached to form an optionally substituted $C_3$-$C_4$ heterocycle;

or a pharmaceutically acceptable salt thereof, in an amount sufficient to slow the spread of said gastrointestinal cancer.

3. The method of claim 2, wherein said method comprises the suppression of metastatic colonization of said gastrointestinal cancer in the liver.

4. The method of claim 2, wherein said gastrointestinal cancer is metastatic gastrointestinal cancer.

5. The method of claim 4, wherein the metastatic gastrointestinal cancer comprises cells exhibiting migration and/or invasion of migrating cells.

6. The method of claim 4, wherein said metastatic gastrointestinal cancer comprises cells exhibiting endothelial recruitment and/or angiogenesis.

7. The method of claim 2, wherein said gastrointestinal cancer spreads via seeding the surface of the peritoneal, pleural, pericardial, or subarachnoid spaces.

8. The method of claim 2, wherein said gastrointestinal cancer spreads via the lymphatic system.

9. The method of claim 2, wherein said gastrointestinal cancer spreads hematogenously.

10. The method of claim 1, wherein said gastrointestinal cancer is a drug resistant gastrointestinal cancer.

11. The method of claim 1 further comprising administering an additional antiproliferative agent.

12. The method of claim 11, wherein said additional antiproliferative agent is capecitabine, gemcitabine, fluorouracil, FOLFOX (5-FU, leucovorin, and Eloxatin), FOLFIRI (5-FU, leucovorin, and Camptosar), EOX (Epirubicin, Oxaliplatinum, and Xeloda), Taxotere, Erbitux, Zaltrap, Vectibix, Ramucirumab, Tivozanib, Stivarga, CRS-207, or a PD-1 or PDL-1 antibody.

13. A method of treating metastatic gastrointestinal cancer in a subject in need thereof comprising:
(a) providing a subject identified as expressing CKB and/or SLC6a8; and
(b) administering to said subject an effective amount of a compound having the structure:

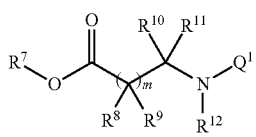

Formula V wherein $Q^1$ is optionally substituted amidino;
m is 1 or 2;
$R^7$ is hydrogen, optionally substituted $C_1$-$C_6$ alkyl, or optionally substituted $C_6$-$C_{10}$ aryl $C_1$-$C_6$ alkyl;
$R^8$ and $R^9$ are independently hydrogen, deuterium, halo, hydroxyl, $NH_2$, optionally substituted $C_1$-$C_3$ alkyl, or $R^8$ and $R^9$ combine with the atoms to which they are attached to form an optionally substituted $C_3$-$C_6$ cycloalkyl ring; or $R^8$ or $R^9$ combine with $R^{10}$ or $R^{11}$ with the atoms to which they are attached to form an optionally substituted $C_3$-$C_4$ cycloalkyl ring; or $R^8$ or $R^9$ combine with $R^{12}$ with the atoms to which they are attached to form an optionally substituted $C_3$-$C_5$ heterocycle;

$R^{10}$ and $R^{11}$ are independently hydrogen, deuterium, optionally substituted $C_1$-$C_4$ alkyl, optionally substituted $C_2$-$C_6$ alkenyl, optionally substituted $C_2$-$C_6$ alkynyl or $R^{10}$ and $R^{11}$ combine with the atoms to which they are attached to form an optionally substituted $C_3$-$C_6$ cycloalkyl ring; or $R^{10}$ or $R^{11}$ combine with $R^8$ or $R^9$ with the atoms to which they are attached to form an optionally substituted $C_3$-$C_4$ cycloalkyl ring; or $R^{10}$ or $R^{11}$ combine with $R^{12}$ with the atoms to which they are attached to form an optionally substituted $C_3$-$C_4$ heterocycle;

$R^{12}$ is hydrogen, $C_1$-$C_6$ alkyl, or $R^{12}$ combines with $R^8$ or $R^9$ with the atoms to which they are attached to form an optionally substituted $C_3$-$C_5$ heterocycle, or $R^{12}$ combines with $R^{10}$ or $R^{11}$ with the atoms to which they are attached to form an optionally substituted $C_3$-$C_4$ heterocycle;

or a pharmaceutically acceptable salt thereof.

14. A method for treating metastatic gastrointestinal cancer in a subject in need thereof, comprising contacting creatine transport channel SLC6a8 with a compound having the structure:

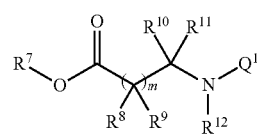

Formula V wherein $Q^1$ is optionally substituted amidino;
m is 1 or 2;
$R^7$ is hydrogen, optionally substituted $C_1$-$C_6$ alkyl, or optionally substituted $C_6$-$C_{10}$ aryl $C_1$-$C_6$ alkyl;
$R^8$ and $R^9$ are independently hydrogen, deuterium, halo, hydroxyl, $NH_2$, optionally substituted $C_1$-$C_3$ alkyl, or $R^8$ and $R^9$ combine with the atoms to which they are attached to form an optionally substituted $C_3$-$C_6$ cycloalkyl ring; or $R^8$ or $R^9$ combine with $R^{10}$ or $R^{11}$ with the atoms to which they are attached to form an optionally substituted $C_3$-$C_4$ cycloalkyl ring; or $R^8$ or $R^9$ combine with $R^{12}$ with the atoms to which they are attached to form an optionally substituted $C_3$-$C_5$ heterocycle;

$R^{10}$ and $R^{11}$ are independently hydrogen, deuterium, optionally substituted $C_1$-$C_4$ alkyl, optionally substituted $C_2$-$C_6$ alkenyl, optionally substituted $C_2$-$C_6$ alkynyl or $R^{10}$ and $R^{11}$ combine with the atoms to which they are attached to form an optionally substituted $C_3$-$C_6$ cycloalkyl ring; or $R^{10}$ or $R^{11}$ combine with $R^8$ or $R^9$ with the atoms to which they are attached to form an optionally substituted $C_3$-$C_4$ cycloalkyl ring; or $R^{10}$ or $R^{11}$ combine with $R^{12}$ with the atoms to which they are attached to form an optionally substituted $C_3$-$C_4$ heterocycle;

$R^{12}$ is hydrogen, $C_1$-$C_6$ alkyl, or $R^{12}$ combines with $R^8$ or $R^9$ with the atoms to which they are attached to form an optionally substituted $C_3$-$C_5$ heterocycle, or $R^{12}$ combines with $R^{10}$ or $R^{11}$ with the atoms to which they are attached to form an optionally substituted $C_3$-$C_4$ heterocycle;

or a pharmaceutically acceptable salt thereof, in an amount effective to suppress metastatic colonization of said gastrointestinal cancer.

* * * * *

SEQUENCE LISTING

<160> NUMBER OF SEQ ID NOS: 22

<210> SEQ ID NO 1
<211> LENGTH: 19
<212> TYPE: DNA
<213> ORGANISM: Homo sapiens

<400> SEQUENCE: 1
gacccactct tggtttcca                                                  19

<210> SEQ ID NO 2
<211> LENGTH: 23
<212> TYPE: DNA
<213> ORGANISM: Homo sapiens

```
<400> SEQUENCE: 2
gaagacggga ggaaagaagg gag                                           23

<210> SEQ ID NO 3
<211> LENGTH: 96
<212> TYPE: DNA
<213> ORGANISM: Homo sapiens

<400> SEQUENCE: 3
ggggactgcc gggtgaccct ggaaatccag agtgggtggg gccagtctga ccgtttctag   60
gcgacccact cttggtttcc agggttgccc tggaaa                             96

<210> SEQ ID NO 4
<211> LENGTH: 76
<212> TYPE: DNA
<213> ORGANISM: Homo sapiens

<400> SEQUENCE: 4 gaggggaag acgggaggaa agaagggagt ggttccatca cgcctcctca ctcctctcct    60
cccgtcttct cctctc                                                   76

<210> SEQ ID NO 5
<211> LENGTH: 559
<212> TYPE: DNA
<213> ORGANISM: Homo sapiens

<400> SEQUENCE: 5
cctgccccat ttgggggtag gaagtggcac tgcagggcct ggtgccagcc agtccttgcc   60
cagggagaag cttccctgca ccaggctttc ctgagaggag gggagggcca agcccccact  120
tgggggaccc ccgtgatggg gctcctgctc cctcctccgg ctgatggcac ctgcccttg   180 gcaccccaag gtggagcccc agcgaccttc cccttccag ctgagcattg ctgtggggga   240 gaggggaag acgggaggaa agaagggagt ggttccatca cgcctcctca ctcctctcct   300
cccgtcttct cctctcctgc ccttgtctcc ctgtctcagc agctccaggg gtggtgtggg  360
cccctccagc ctcctaggtg gtgccaggcc agagtccaag ctcagggaca gcagtccctc  420 ctgtggggc ccctgaactg ggctcacatc ccacacattt tccaaaccac tcccattgtg   480
agcctttggt cctggtggtg tccctctggt tgtgggacca agagcttgtg cccattttc   540 atctgaggaa ggaggcagc                                               559

<210> SEQ ID NO 6
<211> LENGTH: 490
<212> TYPE: DNA
<213> ORGANISM: Homo sapiens

<400> SEQUENCE: 6
ggagaacctt cagcttcatg tgacccagag actcctgtat gcctggctct gggagtacag   60
aagggcctag agctgacccc tgccctccga agccctggg gcactagatg gatgtgtgcc  120
agagggtagt agaggcctgg gggtagagcc cagcaccccc ttcgcgtaga gacctggggg  180
accagccagc ccagcaaccc cctcgcggcc gacgcctgag gctgttcctg gctgctccgg  240
tggctgccag aggggactgc cgggtgaccc tggaaatcca gagtgggtgg ggccagtctg  300
accgtttcta ggcgacccac tcttggtttc caggttgcc ctggaaacca cagatgggga   360 gggttgatg gcacccagcc tcccccaagc ctggaaggg accccggatc ccagagcct    420 ttccctgcct atggagcgtt tctcttggag aacaggggg cctctcagcc cctcaatgca   480
```
agttgctgag                                                                 490

<210> SEQ ID NO 7
<211> LENGTH: 19
<212> TYPE: RNA
<213> ORGANISM: Homo sapiens

<400> SEQUENCE: 7
gacccacucu ugguuucca                                                       19

<210> SEQ ID NO 8
<211> LENGTH: 96
<212> TYPE: RNA
<213> ORGANISM: Homo sapiens

<400> SEQUENCE: 8
ggggacugcc gggugacccu ggaaauccag aguggguggg gccagucuga ccguuucuag          60
gcgacccacu cuugguuucc aggguugccc uggaaa                                    96

<210> SEQ ID NO 9
<211> LENGTH: 23
<212> TYPE: RNA
<213> ORGANISM: Homo sapiens

<400> SEQUENCE: 9
gaagacggga ggaaagaagg gag                                                  23

<210> SEQ ID NO 10
<211> LENGTH: 76
<212> TYPE: RNA
<213> ORGANISM: Homo sapiens

<400> SEQUENCE: 10
gagggggaag acgggaggaa agaagggagu gguuccauca cgccuccuca cuccucuccu          60
cccgucuucu ccucuc                                                          76

<210> SEQ ID NO 11
<211> LENGTH: 57
<212> TYPE: DNA
<213> ORGANISM: Artificial Sequence
<220> FEATURE:
<223> OTHER INFORMATION: Synthetic Construct

<400> SEQUENCE: 11
ccggcccaga ttgaaactct cttcactcga gtgaagagag tttcaatctg ggtttttt            57

<210> SEQ ID NO 12
<211> LENGTH: 59
<212> TYPE: DNA
<213> ORGANISM: Artificial Sequence
<220> FEATURE:
<223> OTHER INFORMATION: Synthetic Construct

<400> SEQUENCE: 12
ccggccgcgg tatctggcac aatgactcga gtcattgtgc cagataccgc ggttttttg           59

<210> SEQ ID NO 13
<211> LENGTH: 58
<212> TYPE: DNA
<213> ORGANISM: Artificial Sequence
<220> FEATURE:
<223> OTHER INFORMATION: Synthetic Construct

```
<400> SEQUENCE: 13
ccggcttatt ccctacgtcc tgatcctcga ggatcaggac gtagggaata agtttttg         58

<210> SEQ ID NO 14
<211> LENGTH: 58
<212> TYPE: DNA
<213> ORGANISM: Artificial Sequence
<220> FEATURE:
<223> OTHER INFORMATION: Synthetic Construct

<400> SEQUENCE: 14
ccggattacc tggtcaagtc ctttactcga gtaaaggact tgaccaggta atttttg         58

<210> SEQ ID NO 15
<211> LENGTH: 57
<212> TYPE: RNA
<213> ORGANISM: Artificial Sequence
<220> FEATURE:
<223> OTHER INFORMATION: Synthetic Construct

<400> SEQUENCE: 15
ccggcccaga uugaaacucu cuucacucga gugaagagag uuucaaucug gguuuuu          57

<210> SEQ ID NO 16
<211> LENGTH: 59
<212> TYPE: RNA
<213> ORGANISM: Artificial Sequence
<220> FEATURE:
<223> OTHER INFORMATION: Synthetic Construct

<400> SEQUENCE: 16
ccggccgcgg uaucuggcac aaugacucga gucauguguc cagauaccgc gguuuuug        59

<210> SEQ ID NO 17
<211> LENGTH: 58
<212> TYPE: RNA
<213> ORGANISM: Artificial Sequence
<220> FEATURE:
<223> OTHER INFORMATION: Synthetic Construct

<400> SEQUENCE: 17
ccggcuuauu cccuacgucc ugauccucga ggaucaggac guagggaaua aguuuuug        58

<210> SEQ ID NO 18
<211> LENGTH: 58
<212> TYPE: RNA
<213> ORGANISM: Artificial Sequence
<220> FEATURE:
<223> OTHER INFORMATION: Synthetic Construct

<400> SEQUENCE: 18
ccggauuacc uggucaaguc cuuuacucga guaaaggacu ugaccaggua auuuuug         58

<210> SEQ ID NO 19
<211> LENGTH: 58
<212> TYPE: DNA
<213> ORGANISM: Artificial Sequence
<220> FEATURE:
<223> OTHER INFORMATION: Synthetic Construct

<400> SEQUENCE: 19
ccgggctggt ctacaacaac acctactcga gtaggtgttg ttgtagacca gctttttg        58

<210> SEQ ID NO 20
<211> LENGTH: 58
```

```
<212> TYPE: RNA
<213> ORGANISM: Artificial Sequence
<220> FEATURE:
<223> OTHER INFORMATION: Synthetic Construct

<400> SEQUENCE: 20
ccgggcuggu cuacaacaac accuacucga guagguguug uuguagacca gcuuuuug        58

<210> SEQ ID NO 21
<211> LENGTH: 22
<212> TYPE: DNA
<213> ORGANISM: Artificial Sequence
<220> FEATURE:
<223> OTHER INFORMATION: Synthetic Construct

<400> SEQUENCE: 21
ggcagctaca accgcttcaa ca                                               22

<210> SEQ ID NO 22
<211> LENGTH: 22
<212> TYPE: DNA
<213> ORGANISM: Artificial Sequence
<220> FEATURE:
<223> OTHER INFORMATION: Synthetic Construct

<400> SEQUENCE: 22
caggatggag aagaccacga ag                                               22
```